US011555078B2

(12) United States Patent
Campbell et al.

(10) Patent No.: US 11,555,078 B2
(45) Date of Patent: Jan. 17, 2023

(54) COMPOSITIONS AND METHODS RELATED TO TUMOR ACTIVATED ANTIBODIES TARGETING PSMA AND EFFECTOR CELL ANTIGENS

(71) Applicant: Janux Therapeutics, Inc., San Diego, CA (US)

(72) Inventors: David Campbell, San Diego, CA (US); Thomas R. DiRaimondo, San Diego, CA (US)

(73) Assignee: JANUX THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 17/544,539

(22) Filed: Dec. 7, 2021

(65) Prior Publication Data

US 2022/0177600 A1 Jun. 9, 2022

Related U.S. Application Data

(60) Provisional application No. 63/187,699, filed on May 12, 2021, provisional application No. 63/123,329, filed on Dec. 9, 2020.

(51) Int. Cl.

*C07K 16/28* (2006.01)
*C07K 16/30* (2006.01)
*C07K 14/765* (2006.01)

(52) U.S. Cl.

CPC ........ *C07K 16/3069* (2013.01); *C07K 14/765* (2013.01); *C07K 16/2809* (2013.01); *C07K 2317/565* (2013.01); *C07K 2317/569* (2013.01); *C07K 2317/622* (2013.01); *C07K 2317/92* (2013.01); *C07K 2319/30* (2013.01); *C07K 2319/31* (2013.01)

(58) Field of Classification Search

None

See application file for complete search history.

(56) References Cited

U.S. PATENT DOCUMENTS 7,850,971 B2 12/2010 Maddon et al.
8,114,965 B2 2/2012 Maddon et al.
8,470,330 B2 6/2013 Maddon et al.
8,784,821 B1 7/2014 Kufer et al.
9,249,211 B2 2/2016 Schellenberger et al.
9,453,078 B2 9/2016 Stagliano et al.
9,562,073 B2 2/2017 Moore et al.
9,650,445 B2 5/2017 Cobbold et al.
9,695,248 B2 7/2017 Maddon et al.
9,708,412 B2 7/2017 Baeuerle et al.
9,822,180 B2 11/2017 Cobbold et al.
9,856,314 B2 1/2018 Lowman et al.
9,889,211 B2 2/2018 Lowman et al.
9,976,166 B2 5/2018 Schellenberger et al.
10,066,016 B2 9/2018 Dubridge et al.
10,106,621 B2 10/2018 Cobbold et al.
10,118,961 B2 11/2018 Stagliano et al.
10,138,272 B2 11/2018 Moore et al.
10,544,221 B2 1/2020 Dubridge et al.
11,028,126 B2 6/2021 Moore et al.
2001/0031264 A1 10/2001 Segal
2010/0150918 A1 6/2010 Kufer et al.
2010/0189718 A1 7/2010 Dall'Acqua et al.
2014/0154253 A1* 6/2014 Ng .......................... A61P 35/02
435/69.6
2016/0122436 A1 5/2016 Kufer et al.
2016/0193332 A1 7/2016 Lowman et al.
2016/0194399 A1 7/2016 Irving et al.
2016/0355599 A1 12/2016 Sagert et al.
2017/0051074 A1 2/2017 Kirshner et al.
2017/0196996 A1 7/2017 Lowman et al.
2017/0247476 A1 8/2017 Yan et al.
2017/0349668 A1 12/2017 Rattel et al.
2017/0369563 A1 12/2017 Dubridge et al.
2018/0125988 A1 5/2018 Yang et al.
2018/0162949 A1 6/2018 Baeuerle et al.
2019/0040133 A1 2/2019 Kufer et al.
2019/0070248 A1 3/2019 Sahin et al.
2019/0153115 A1 5/2019 Schellenberger et al.
2019/0169295 A1 6/2019 Kufer et al.
2019/0169310 A1 6/2019 Kufer et al.
2019/0315863 A1 10/2019 Kim et al.
2019/0359714 A1 11/2019 Tipton et al.
2019/0381183 A1 12/2019 Ward Ober et al.
2020/0040099 A1 2/2020 Kufer et al.
2020/0181249 A1 6/2020 Curtis et al.
2021/0002343 A1 1/2021 Karow et al.

(Continued)

FOREIGN PATENT DOCUMENTS

EP 2155783 A2 2/2010
EP 3197916 A2 8/2017

(Continued)

OTHER PUBLICATIONS

Robert W. Bahr Memorandum of Feb. 22, 2018, 2 pages. (Year: 2018).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Chatalic et al., J Nucl Med 2015; 56:1094-1099 and Supplemental pp. 1-12. (Year: 2015).*
Geiger et al. Protease-activation using anti-idiotypic masks enables tumor specificity of a folate receptor 1-T cell bispecific antibody. Nat Commun 11(1):3196 (2020).

(Continued)

*Primary Examiner* — Zachary S Skelding
(74) *Attorney, Agent, or Firm* — Wilson Sonsini Goodrich & Rosati

(57) ABSTRACT

Provided herein are multispecific antibodies that selectively bind to PSMA and effector cell antigens such as CD3, pharmaceutical compositions thereof, as well as nucleic acids, and methods for making and discovering the same.

26 Claims, 46 Drawing Sheets

Specification includes a Sequence Listing.

(56) References Cited

U.S. PATENT DOCUMENTS

| | | | |
|---|---|---|---|
| 2021/0020264 A1 | 1/2021 | Stroh et al. |
| 2021/0054077 A1 | 2/2021 | Schellenberger et al. |
| 2022/0048949 A1 | 2/2022 | Campbell et al. |

FOREIGN PATENT DOCUMENTS

| | | | | |
|---|---|---|---|---|
| EP | 2820047 B1 | 4/2018 | |
| EP | 2819701 B1 | 7/2018 | |
| EP | 3174901 B1 | 6/2019 | |
| EP | 2970449 B1 | 9/2019 | |
| WO | WO-2007147001 A2 | 12/2007 | |
| WO | WO-2008119567 A2 | 10/2008 | |
| WO | WO-2009026303 A1 | 2/2009 | |
| WO | WO-2009040134 A1 | 4/2009 | |
| WO | WO-2011121110 A1 | 10/2011 | |
| WO | WO-2013128194 A1 | 9/2013 | |
| WO | WO-2014079000 A1 | 5/2014 | |
| WO | WO-2016118629 A1 | 7/2016 | |
| WO | WO-2017040344 A2 | 3/2017 | |
| WO | WO-2017156178 A1 | 9/2017 | |
| WO | WO-2017184619 A2 | 10/2017 | |
| WO | WO-2019051102 A2 | 3/2019 | |
| WO | WO-2019075405 A1 | 4/2019 | |
| WO | WO-2019096121 A1 | 5/2019 | |
| WO | WO-2019183218 A1 | 9/2019 | |
| WO | WO-2020033837 A1 | 2/2020 | |
| WO | WO-2020058762 A1 | 3/2020 | |
| WO | WO-2020069398 A1 | 4/2020 | |
| WO | WO-2020118109 A2 | 6/2020 | |
| WO | WO-2020150702 A1 | 7/2020 | |
| WO | WO-2020181140 A1 | 9/2020 | |
| WO | WO-2020181145 A1 | 9/2020 | |
| WO | WO-2020247867 A2 | 12/2020 | |
| WO | WO-2020247871 A2 | 12/2020 | |
| WO | WO-2022035866 A1 | 2/2022 | |
| WO | WO-2022081822 A1 | 4/2022 | |
| WO | WO2022098909 A1 * | 5/2022 | ......... C07K 16/2809 |
| WO | WO-2022125562 A1 | 6/2022 | |
| WO | WO-2022125566 A1 | 6/2022 | |
| WO | WO-2022125576 A1 | 6/2022 | |

OTHER PUBLICATIONS

Kinoshita et al. Expression of prostate-specific membrane antigen in normal and malignant human tissues. World J Surg 30:628-36 (2006).

Pan et al. Site-specific PEGylation of an anti-CEA/CD3 bispecific antibody improves its antitumor efficacy. Int. J. Nanomed 13:3189-3201 (2018).

PCT/US2021/062249 International Search Report and Written Opinion dated May 17, 2022.

PCT/US2021/062249 Invitation to Pay Additional Fees dated Mar. 15, 2022.

Altschul et al. Basic Local Alignment Search Tool. J. Mol. Biol. 215:403-410 (1990).

Altschul, et al. Gapped BLAST and PSI-BLAST: a new generation of protein database search programs. Nucleic Acids Res 25:3389-3402 (1997).

Bird et al. Single-chain antigen-binding proteins. Science 242:423-442 (1988).

Blumberg et al. Structure of the T-cell antigen receptor: evidence for two CD3 epsilon subunits in the T-cell receptor-CD3 complex. PNAS USA 87(18):7220-4 (1990).

Clackson et al. Making antibody fragments using phage display libraries. Nature 352(6336):624-628 (1991).

Colberre-Garapin et al. A new dominant hybrid selective marker for higher eukaryotic cells. J Mol Biol 150:1-14 (1981).

Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).

Courtenay-Luck. Genetic manipulation of monoclonal antibodies. Monoclonal Antibodies: Production, Engineering and Clinical Application pp. 166-179 (1995).

Crouse et al. Expression and amplification of engineered mouse dihydrofolate reductase minigenes. Mol Cell Biol 3(2):257-266 (1983).

Goldspiel et al. Human gene therapy. Clin Pharm 12:488-505 (1993).

Hanes et al. In vitro selection and evolution of functional proteins by using ribosome display. PNAS USA 94:4937-4942 (1997).

Huse et al. Generation of a large combinatorial library of the immunoglobulin repertoire in phage lambda. Science 246(4935):1275-1281 (1989).

Huston et al. Protein engineering of antibody binding sites: recovery of specific activity in an anti-digoxin single-chain Fv analogue produced in *Escherichia coli*. PNAS USA 85(16):5879-5883 (1988).

Karlin, et al. Applications and statistics for multiple high-scoring segments in molecular sequences. PNAS USA 90:5873-5877 (1993).

Karlin et al. Methods for assessing the statistical significance of molecular sequence features by using general scoring schemes. PNAS USA 87:2264-2268 (1990).

Kohler et al. Continuous cultures of fused cells secreting antibody of predefined specificity. Nature 256:495-497 (1975).

Kozbor et al. The production of monoclonal antibodies from human lymphocytes. Immunology Today 4:72-79 (1983).

Kutmeier et al. Assembly of humanized antibody genes from synthetic oligonucleotides using a single-round PCR. BioTechniques 17:242 (1994).

Larrick et al. PCR amplification of antibody genes. Methods 2:106-110 (1991).

Lowy et al., Isolation of transforming DNA: Cloning the hamster aprt gene. Cell 22:817-823 (1980).

Morgan et al. Human gene therapy. Ann RevBiochem 62:191-217 (1993).

Morrison et al. Chimeric human antibody molecules: mouse antigen-binding domains with human constant region domains. PNAS USA 81(21):6851-6855 (1984).

Mulligan et al. Selection for animal cells that express the *Escherichia coli* gene coding for xanthine-guanine phosphoribosyltransferase. PNAS USA 78(4):2072-2076 (1981).

Mulligan. The basic science of gene therapy. Science 260(5110):926-932 (1993).

Neuberger et al. Recombinant antibodies possessing novel effector functions. Nature 312(5995):604-608 (1984).

O'Hare et al. Transformation of mouse fibroblasts to methotrexate resistance by a recombinant plasmid expressing a prokaryotic dihydrofolate reductase. PNAS USA 78:1527-1531 (1981).

PCT/US2020/036493 International Invitation to Pay Additional Fees dated Sep. 15, 2020.

PCT/US2020/036493 International Search Report and Written Opinion dated Dec. 21, 2020.

Pessano et al. The T3/T cell receptor complex: antigenic distinction between the two 20-kd T3 (T3-delta and T3-epsilon) subunits. The EMBO Journal 4(2):337-344 (1985).

Santerre et al. Expression of prokaryotic genes for hygromycin B and G418 resistance as dominant-selection markers in mouse L cells. Gene 30(1-3):147-156 (1984).

Skerra et al. Assembly of a functional Immunoglobulin Fv fragment in *Escherichia coli*. Science 240(4855):1038-1041 (1988).

Szybalska et al. Genetics of human cell line. IV. DNA-mediated heritable transformation of a biochemical trait. PNAS USA 48:2026-2034 (1962).

Takeda et al. Construction of chimaeric processed immunoglobulin genes containing mouse variable and human constant region sequences. Nature 314(6010):452-454 (1985).

Tolstoshev. Gene Therapy, Concepts, Current Trials and Future Directions. Ann. Rev. Pharmacol. Toxicol. 32:573-596 (1993).

UniProt Accession No. A0A315V0J1 (A0A315V0J1_GAMAF) Gambusia affinis (Western mosquitofish) (*Heterandria affinis*) Phosphoinositide phospholipase C; retrieved from https://www.uniprot.org/uniprot/A0A315V0J1 (2018).

(56) References Cited

OTHER PUBLICATIONS

Ward et al. Binding activities of a repertoire of single immunoglobulin variable domains secreted from *Escherichia coli*. Nature 341(6242):544-546 (1989).
Ward et al. Genetic Manipulation and Expression of Antibodies. Monoclonal Antibodies: Principles and Applications, Wiley-Liss Inc., pp. 137-185 (1995).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wootton et al. Statistics of local complexity in amino acid sequences and sequence databases. Computers & Chemistry 17(2):149-163 (Jun. 1993).
Wu et al. Delivery systems for gene therapy. Biotherapy 3:87-95 (1991).
Zhao et al. High-efficiency transfection of primary human and mouse T lymphocytes using RNA electroporation. Mol. Ther. 13:151-159 (2006).
Kessenbrock et al. Matrix metalloproteinases: regulators of the tumor microenvironment. Cell 141(1):52-67 (2010).
Liao et al. Activation of lymphocytes by anti-CD3 single-chain antibody dinners expressed on the plasma membrane of tumor cells. Gene Therapy. 7:339-347 (2000).
MultiSpecies: sporulation protein [Methanosarcina], NCBI WP 048120037.1. https://www.ncbi.nlm.nih.gov/protein/WP048120037.1?report=genbank&log$=protalign . . . Jan. 22, 2022.
Olson et al. In vivo characterization of activatable cell penetrating peptides for targeting protease activity in cancer. Integr Biol (Camb) 1(5-6):382-393 (2009).
PCT/US2021/045395 International Search Report and Written Opinion dated Dec. 10, 2021.
PCT/US2021/054948 International Search Report and Written Opinion dated Feb. 25, 2022.
PCT/US2021/062233 International Search Report and Written Opinion dated Apr. 26, 2022.
PCT/US2021/062238 International Search Report and Written Opinion dated Apr. 26, 2022.
UniProtKB A0A1D2VVTX0. Sporulatioti protein [online] Dec. 11, 2019 [retrieved Nov. 2, 2021], Available on the internet: httias://www.uniprot.org/uniprot/A0A1D2VVIX0.
UniProtKB Accession No. A0A101XTH3_ 9BACL, Acidibacillus ferrooxidans ATVV55 _ 11625gene Uncharacterized protein. Apr. 13, 2016 [online], [Retrieved on Mar. 4, 2022], Retrieved from the internet: <url: <a=href=>https://www.uniprot.org/uniprot/A0A101XTH3.</url:>.
U.S. Appl. No. 17/398,500 Notice of Allowance dated Jul. 28, 2022.
U.S. Appl. No. 17/398,500 Office Action dated Feb. 18, 2022.

* cited by examiner

| Cytotox | PC2 | PC7 | PC7 + MTSP1 | PC8 |
|---|---|---|---|---|
| IC50 pM | 10.26 | 2,371 | 15.88 | 11,210 |

| Cytotox | PC2 | PC6 | PC6 + MTSP1 | PC8 |
|---|---|---|---|---|
| IC50 pM | 6.01 | 1,902 | 11.5 | 6,521 |

| | Peptide-AA | Peptide-AB | Peptide-AC | Peptide-AD | Peptide-AE | Peptide-AF | Peptide-B |
|---|---|---|---|---|---|---|---|
| EC50 nM | 2.163 | 1.564 | 2.035 | 1.713 | 2.174 | 2.752 | 1.972 |

| | Peptide-AG | Peptide-AH | Peptide-AI | Peptide-AJ | Peptide-AK | Peptide-AL | Peptide-B |
|---|---|---|---|---|---|---|---|
| EC50 nM | 2.804 | 2.695 | 344.3 | 1.652 | 1.286 | 1.895 | 1.623 |

| | Peptide-AA | Peptide-AB | Peptide-AC | Peptide-AD | Peptide-AE | Peptide-AF | Peptide-B |
|---|---|---|---|---|---|---|---|
| IC50 uM | 7.9 | 3.2 | 8.5 | 6.5 | 17.2 | 11.7 | 0.28 |

| | Peptide-AG | Peptide-AH | Peptide-AI | Peptide-AJ | Peptide-AK | Peptide-AL | Peptide-B |
|---|---|---|---|---|---|---|---|
| IC50 uM | 17.3 | 15.2 | >100 | 2.9 | 0.01 | 0.35 | 0.15 |

SEQUENCE LISTING

```
<160> NUMBER OF SEQ ID NOS: 966

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Asn Lys Tyr Ala
1               5


<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Arg Ser Lys Tyr Asn Asn Tyr Ala Thr
1               5                   10


<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Arg His Gly Asn Phe Gly Asn Ser Tyr Ile Ser Tyr Trp Ala Tyr
1               5                   10                  15


<210> SEQ ID NO 4
<211> LENGTH: 9
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 4

Thr Gly Ala Val Thr Ser Gly Asn Tyr
1               5

<210> SEQ ID NO 5
<211> LENGTH: 2
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Gly Thr
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Val Leu Trp Tyr Ser Asn Arg Trp Val
1               5

<210> SEQ ID NO 7
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
165 170 175

Trp Val Gln Gln Lys Pro Gly Gln Ala Pro Arg Gly Leu Ile Gly Gly
180 185 190

Thr Lys Phe Leu Ala Pro Gly Thr Pro Ala Arg Phe Ser Gly Ser Leu
195 200 205

Leu Gly Gly Lys Ala Ala Leu Thr Leu Ser Gly Val Gln Pro Glu Asp
210 215 220

Glu Ala Glu Tyr Tyr Cys Val Leu Trp Tyr Ser Asn Arg Trp Val Phe
225 230 235 240

Gly Gly Gly Thr Lys Leu Thr Val Leu
245

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gly Phe Ala Phe Ser Arg Tyr Gly
1 5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Ile Trp Tyr Asp Gly Ser Asn Lys
1 5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ala Arg Gly Gly Asp Phe Leu Tyr Tyr Tyr Tyr Tyr Gly Met Asp Val
1 5 10 15

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gln Gly Ile Ser Asn Tyr
1 5

<210> SEQ ID NO 12
<211> LENGTH: 2
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Glu Ala
1

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

```
Gln Asn Tyr Asn Ser Ala Pro Phe Thr
1               5
```

<210> SEQ ID NO 14
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Thr Gly Lys Val Pro Lys Phe Leu Ile
        35                  40                  45

Tyr Glu Ala Ser Thr Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 226

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

Gln Val Gln Leu Val Glu Ser Gly Gly Gly Val Val Gln Pro Gly Arg
1 5 10 15

Ser Leu Arg Leu Ser Cys Ala Ala Ser Gly Phe Ala Phe Ser Arg Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Gln Tyr
65 70 75 80

Leu Gln Met Asn Ser Leu Arg Ala Glu Asp Thr Ala Val Tyr Tyr Cys
85 90 95

Ala Arg Gly Gly Asp Phe Leu Tyr Tyr Tyr Tyr Tyr Gly Met Asp Val
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys
225

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gly Gly Gly Ser Gln Cys Leu Gly Pro Glu Trp Glu Val Cys Pro Tyr
1 5 10 15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Gly Gly Val Tyr Cys Gly Pro Glu Phe Asp Glu Ser Val Gly Cys Met
1 5 10 15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gly Ser Gln Cys Leu Gly Pro Glu Trp Glu Val Cys Pro Tyr
1 5 10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Val Tyr Cys Gly Pro Glu Phe Asp Glu Ser Val Gly Cys Met
1 5 10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gly Gly Gly Gly Ser Gly Gly Gly Gly Ser Gly Gly Gly Gly Ser
1 5 10 15

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Gly Gly Gly Gly Ser
1 5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Gly Gly Gly Gly Ser Gly Gly Gly Ser
1 5

<210> SEQ ID NO 23
<211> LENGTH: 28

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gly Gly Gly Gly Ser Gly Gly Gly Leu Ser Gly Arg Ser Asp Ala Gly
1 5 10 15

Ser Pro Leu Gly Leu Ala Gly Ser Gly Gly Gly Ser
20 25

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Gly Gly Gly Ser Leu Ser Gly Arg Ser Asp Asn His Gly Ser Ser
1 5 10 15

Gly Thr

<210> SEQ ID NO 25
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Gly Gly Gly Gly Ser Ser Gly Gly Ser Gly Gly Ser Gly Leu Ser Gly
1 5 10 15

Arg Ser Asp Asn His Gly Ser Ser Gly Thr
20 25

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Ala Ser Gly Arg Ser Asp Asn His
1 5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Leu Ala Gly Arg Ser Asp Asn His
1 5

<210> SEQ ID NO 28
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 28

Ile Ser Ser Gly Leu Ala Ser Gly Arg Ser Asp Asn His
1               5                   10


<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Ser Ser Gly Leu Leu Ala Gly Arg Ser Asp Asn His
1               5                   10


<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Ser Gly Arg Ser Asp Asn His
1               5


<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Ser Ser Gly Leu Leu Ser Gly Arg Ser Asp Asn Pro
1               5                   10


<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Ser Ser Gly Leu Leu Ser Gly Arg Ser Asp Asn His
1               5                   10


<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Ser Gly Arg Ser Asp Asn His Ser Pro Leu Gly Leu Ala Gly Ser
1               5                   10                  15
```

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Pro Leu Gly Leu Ala Gly Ser Leu Ser Gly Arg Ser Asp Asn His
1               5                   10                  15

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Pro Leu Gly Leu Ser Gly Arg Ser Asp Asn His
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Ala Gly Arg Ser Asp Asn His Ser Pro Leu Gly Leu Ala Gly Ser
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Ser Gly Arg Ser Asp Asn His Val Pro Leu Ser Leu Lys Met Gly
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Ser Gly Arg Ser Asp Asn His Val Pro Leu Ser Leu Ser Met Gly
1               5                   10                  15

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Ser Ser Gly Gly Ser Gly Gly Ser Gly Gly Ser Gly Ile Ser Ser
1 5 10 15

Gly Leu Leu Ser Gly Arg Ser Asp Asn His Gly Ser Ser Gly Thr
20 25 30

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gly Ser Ser Gly Gly Ser Gly Gly Ser Gly Gly Ile Ser Ser Gly Leu
1 5 10 15

Leu Ser Gly Arg Ser Asp Asn His Gly Gly Gly Ser
20 25

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ala Ser Gly Arg Ser Asp Asn His
1 5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Leu Ala Gly Arg Ser Asp Asn His
1 5

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Ile Ser Ser Gly Leu Ala Ser Gly Arg Ser Asp Asn His
1 5 10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Leu Ser Gly Arg Ser Asp Ala Gly
1               5

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Ser Ser Gly Leu Leu Ser Gly Arg Ser Asp Ala Gly
1               5                   10

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Gly Leu Leu Ala Pro Pro Gly Gly Leu Ser Gly Arg Ser Asp
1               5                   10                  15

Ala Gly

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Pro Leu Gly Leu Ser Gly Arg Ser Asp Ala Gly
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Ser Gly Arg Ser Asp Ala Gly Ser Pro Leu Gly Leu Ala Gly
1               5                   10                  15

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Ser Gly Gly Gly Ser Gly Gly Gly Gly Ser Gly Gly
1               5                   10                  15

Ala Ser Ser Gly Ala Gly Gly Ser Gly Gly Gly Ser
            20                  25

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Gly Gly Ser
1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Ser
1

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Ser Gly Gly Ser
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Thr Phe Tyr Thr Ala Val
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Ile Arg Trp Thr Ala Leu Thr Thr
1               5
```

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ala Ala Arg Gly Thr Leu Gly Leu Phe Thr Thr Ala Asp Ser Tyr Asp
1               5                   10                  15

Tyr
```

<210> SEQ ID NO 57
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Tyr Thr Ala
            20                  25                  30

Val Met Gly Trp Val Arg Gln Ala Pro Gly Lys Gly Leu Glu Trp Val
        35                  40                  45

Ala Ala Ile Arg Trp Thr Ala Leu Thr Thr Ser Tyr Ala Asp Ser Val
    50                  55                  60

Lys Gly Arg Phe Thr Ile Ser Arg Asp Gly Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Gly Thr Leu Gly Leu Phe Thr Thr Ala Asp Ser Tyr Asp
            100                 105                 110

Tyr Trp Gly Gln Gly Thr Leu Val Thr Val Ser Ser
        115                 120
```

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Gly Phe Thr Phe Ser Lys Phe Gly
1               5
```

-continued

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ile Ser Gly Ser Gly Arg Asp Thr
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Thr Ile Gly Gly Ser Leu Ser Val
1               5

<210> SEQ ID NO 61
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 62
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Thr Gly Lys Val Pro Lys Phe Leu Ile
35 40 45

Tyr Glu Ala Ser Thr Leu Gln Ser Gly Val Pro Ser Arg Phe Ser Gly
50 55 60

Gly Gly Ser Gly Thr Asp Phe Thr Leu Thr Ile Ser Ser Leu Gln Pro
65 70 75 80

Glu Asp Val Ala Thr Tyr Tyr Cys Gln Asn Tyr Asn Ser Ala Pro Phe
85 90 95

Thr Phe Gly Pro Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 63
<211> LENGTH: 480
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser Ser Gly Gly Gly
115 120 125

Gly Ser Gly Gly Gly Gly Ser Gly Gly Gly Gly Ser Gln Thr Val Val
130 135 140

Thr Gln Glu Pro Ser Leu Thr Val Ser Pro Gly Gly Thr Val Thr Leu
145 150 155 160

Thr Cys Gly Ser Ser Thr Gly Ala Val Thr Ser Gly Asn Tyr Pro Asn
165 170 175

Trp Val Gln Gln Lys Pro Gly Gln Ala Pro Arg Gly Leu Ile Gly Gly
180 185 190

Thr Lys Phe Leu Ala Pro Gly Thr Pro Ala Arg Phe Ser Gly Ser Leu
195 200 205

Leu Gly Gly Lys Ala Ala Leu Thr Leu Ser Gly Val Gln Pro Glu Asp
210 215 220

Glu Ala Glu Tyr Tyr Cys Val Leu Trp Tyr Ser Asn Arg Trp Val Phe
225 230 235 240

Gly Gly Gly Thr Lys Leu Thr Val Leu Gly Gly Gly Gly Ser Gln Val
245 250 255

Gln Leu Val Glu Ser Gly Gly Gly Val Val Gln Pro Gly Arg Ser Leu
260 265 270

Arg Leu Ser Cys Ala Ala Ser Gly Phe Ala Phe Ser Arg Tyr Gly Met
275 280 285

His Trp Val Arg Gln Ala Pro Gly Lys Gly Leu Glu Trp Val Ala Val
290 295 300

Ile Trp Tyr Asp Gly Ser Asn Lys Tyr Tyr Ala Asp Ser Val Lys Gly
305 310 315 320

Arg Phe Thr Ile Ser Arg Asp Asn Ser Lys Asn Thr Gln Tyr Leu Gln
325 330 335

Met Asn Ser Leu Arg Ala Glu Asp Thr Ala Val Tyr Tyr Cys Ala Arg
340 345 350

Gly Gly Asp Phe Leu Tyr Tyr Tyr Tyr Tyr Gly Met Asp Val Trp Gly
355 360 365

Gln Gly Thr Thr Val Thr Val Ser Ser Ala Ser Thr Lys Gly Pro Ser
370 375 380

Val Phe Pro Leu Ala Pro Ser Ser Lys Ser Thr Ser Gly Gly Thr Ala
385 390 395 400

Ala Leu Gly Cys Leu Val Lys Asp Tyr Phe Pro Glu Pro Val Thr Val
405 410 415

Ser Trp Asn Ser Gly Ala Leu Thr Ser Gly Val His Thr Phe Pro Ala
420 425 430

Val Leu Gln Ser Ser Gly Leu Tyr Ser Leu Ser Ser Val Val Thr Val
435 440 445

Pro Ser Ser Ser Leu Gly Thr Gln Thr Tyr Ile Cys Asn Val Asn His
450 455 460

Lys Pro Ser Asn Thr Lys Val Asp Lys Lys Val Glu Pro Lys Ser Cys
465 470 475 480

<210> SEQ ID NO 64
<211> LENGTH: 468
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

-continued

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Gly Ser Asp Ile
                245                 250                 255

Gln Met Thr Gln Ser Pro Ser Ser Leu Ser Ala Ser Val Gly Asp Arg
            260                 265                 270

Val Thr Ile Thr Cys Arg Ala Ser Gln Gly Ile Ser Asn Tyr Leu Ala
        275                 280                 285

Trp Tyr Gln Gln Lys Thr Gly Lys Val Pro Lys Phe Leu Ile Tyr Glu
    290                 295                 300

Ala Ser Thr Leu Gln Ser Gly Val Pro Ser Arg Phe Ser Gly Gly Gly
305                 310                 315                 320

Ser Gly Thr Asp Phe Thr Leu Thr Ile Ser Ser Leu Gln Pro Glu Asp
                325                 330                 335

Val Ala Thr Tyr Tyr Cys Gln Asn Tyr Asn Ser Ala Pro Phe Thr Phe
            340                 345                 350

Gly Pro Gly Thr Lys Val Asp Ile Lys Arg Thr Val Ala Ala Pro Ser
        355                 360                 365

Val Phe Ile Phe Pro Pro Ser Asp Glu Gln Leu Lys Ser Gly Thr Ala
    370                 375                 380

Ser Val Val Cys Leu Leu Asn Asn Phe Tyr Pro Arg Glu Ala Lys Val
385                 390                 395                 400

Gln Trp Lys Val Asp Asn Ala Leu Gln Ser Gly Asn Ser Gln Glu Ser
                405                 410                 415

Val Thr Glu Gln Asp Ser Lys Asp Ser Thr Tyr Ser Leu Ser Ser Thr
            420                 425                 430

Leu Thr Leu Ser Lys Ala Asp Tyr Glu Lys His Lys Val Tyr Ala Cys
        435                 440                 445
```

```
Glu Val Thr His Gln Gly Leu Ser Ser Pro Val Thr Lys Ser Phe Asn
    450                 455                 460

Arg Gly Glu Cys
465


<210> SEQ ID NO 65
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Phe Leu Tyr Tyr Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30
```

```
Leu Ala Trp Tyr Gln Gln Lys Thr Gly Lys Val Pro Lys Phe Leu Ile
        35                  40                  45

Tyr Glu Ala Ser Thr Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 67
<211> LENGTH: 657
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Tyr Thr Ala
            20                  25                  30

Val Met Gly Trp Val Arg Gln Ala Pro Gly Lys Gly Leu Glu Trp Val
        35                  40                  45

Ala Ala Ile Arg Trp Thr Ala Leu Thr Thr Ser Tyr Ala Asp Ser Val
    50                  55                  60

Lys Gly Arg Phe Thr Ile Ser Arg Asp Gly Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Gly Thr Leu Gly Leu Phe Thr Thr Ala Asp Ser Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Gly Gly Gly Ser Gln Cys Leu Gly Pro Glu Trp
    130                 135                 140

Glu Val Cys Pro Tyr Gly Gly Gly Gly Ser Gly Gly Gly Leu Ser Gly
145                 150                 155                 160

Arg Ser Asp Ala Gly Ser Pro Leu Gly Leu Ala Gly Ser Gly Gly Gly
                165                 170                 175
```

```
Ser Glu Val Gln Leu Val Glu Ser Gly Gly Gly Leu Val Gln Pro Gly
            180                 185                 190

Gly Ser Leu Lys Leu Ser Cys Ala Ala Ser Gly Phe Thr Phe Asn Lys
        195                 200                 205

Tyr Ala Met Asn Trp Val Arg Gln Ala Pro Gly Lys Gly Leu Glu Trp
    210                 215                 220

Val Ala Arg Ile Arg Ser Lys Tyr Asn Asn Tyr Ala Thr Tyr Tyr Ala
225                 230                 235                 240

Asp Ser Val Lys Asp Arg Phe Thr Ile Ser Arg Asp Asp Ser Lys Asn
                245                 250                 255

Thr Ala Tyr Leu Gln Met Asn Asn Leu Lys Thr Glu Asp Thr Ala Val
            260                 265                 270

Tyr Tyr Cys Val Arg His Gly Asn Phe Gly Asn Ser Tyr Ile Ser Tyr
        275                 280                 285

Trp Ala Tyr Trp Gly Gln Gly Thr Leu Val Thr Val Ser Ser Gly Gly
    290                 295                 300

Gly Gly Ser Gly Gly Gly Gly Ser Gly Gly Gly Gly Ser Gln Thr Val
305                 310                 315                 320

Val Thr Gln Glu Pro Ser Leu Thr Val Ser Pro Gly Gly Thr Val Thr
                325                 330                 335

Leu Thr Cys Gly Ser Ser Thr Gly Ala Val Thr Ser Gly Asn Tyr Pro
            340                 345                 350

Asn Trp Val Gln Gln Lys Pro Gly Gln Ala Pro Arg Gly Leu Ile Gly
        355                 360                 365

Gly Thr Lys Phe Leu Ala Pro Gly Thr Pro Ala Arg Phe Ser Gly Ser
    370                 375                 380

Leu Leu Gly Gly Lys Ala Ala Leu Thr Leu Ser Gly Val Gln Pro Glu
385                 390                 395                 400

Asp Glu Ala Glu Tyr Tyr Cys Val Leu Trp Tyr Ser Asn Arg Trp Val
                405                 410                 415

Phe Gly Gly Gly Thr Lys Leu Thr Val Leu Gly Gly Gly Gly Ser Gln
            420                 425                 430

Val Gln Leu Val Glu Ser Gly Gly Gly Val Val Gln Pro Gly Arg Ser
        435                 440                 445

Leu Arg Leu Ser Cys Ala Ala Ser Gly Phe Ala Phe Ser Arg Tyr Gly
    450                 455                 460

Met His Trp Val Arg Gln Ala Pro Gly Lys Gly Leu Glu Trp Val Ala
465                 470                 475                 480

Val Ile Trp Tyr Asp Gly Ser Asn Lys Tyr Tyr Ala Asp Ser Val Lys
                485                 490                 495

Gly Arg Phe Thr Ile Ser Arg Asp Asn Ser Lys Asn Thr Gln Tyr Leu
            500                 505                 510

Gln Met Asn Ser Leu Arg Ala Glu Asp Thr Ala Val Tyr Tyr Cys Ala
        515                 520                 525

Arg Gly Gly Asp Phe Leu Tyr Tyr Tyr Tyr Tyr Gly Met Asp Val Trp
    530                 535                 540

Gly Gln Gly Thr Thr Val Thr Val Ser Ser Ala Ser Thr Lys Gly Pro
545                 550                 555                 560

Ser Val Phe Pro Leu Ala Pro Ser Ser Lys Ser Thr Ser Gly Gly Thr
                565                 570                 575

Ala Ala Leu Gly Cys Leu Val Lys Asp Tyr Phe Pro Glu Pro Val Thr
            580                 585                 590
```

Val Ser Trp Asn Ser Gly Ala Leu Thr Ser Gly Val His Thr Phe Pro
595 600 605

Ala Val Leu Gln Ser Ser Gly Leu Tyr Ser Leu Ser Ser Val Val Thr
610 615 620

Val Pro Ser Ser Ser Leu Gly Thr Gln Thr Tyr Ile Cys Asn Val Asn
625 630 635 640

His Lys Pro Ser Asn Thr Lys Val Asp Lys Lys Val Glu Pro Lys Ser
645 650 655

Cys

<210> SEQ ID NO 68
<211> LENGTH: 645
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Glu Val Gln Leu Val Glu Ser Gly Gly Gly Leu Val Gln Pro Gly Gly
1 5 10 15

Ser Leu Arg Leu Ser Cys Ala Ala Ser Gly Ser Thr Phe Tyr Thr Ala
20 25 30

Val Met Gly Trp Val Arg Gln Ala Pro Gly Lys Gly Leu Glu Trp Val
35 40 45

Ala Ala Ile Arg Trp Thr Ala Leu Thr Thr Ser Tyr Ala Asp Ser Val
50 55 60

Lys Gly Arg Phe Thr Ile Ser Arg Asp Gly Ala Lys Thr Thr Leu Tyr
65 70 75 80

Leu Gln Met Asn Ser Leu Arg Pro Glu Asp Thr Ala Val Tyr Tyr Cys
85 90 95

Ala Ala Arg Gly Thr Leu Gly Leu Phe Thr Thr Ala Asp Ser Tyr Asp
100 105 110

Tyr Trp Gly Gln Gly Thr Leu Val Thr Val Ser Ser Gly Gly Gly Gly
115 120 125

Ser Gly Gly Gly Ser Gly Gly Gly Ser Gln Cys Leu Gly Pro Glu Trp
130 135 140

Glu Val Cys Pro Tyr Gly Gly Gly Gly Ser Gly Gly Gly Leu Ser Gly
145 150 155 160

Arg Ser Asp Ala Gly Ser Pro Leu Gly Leu Ala Gly Ser Gly Gly Gly
165 170 175

Ser Glu Val Gln Leu Val Glu Ser Gly Gly Gly Leu Val Gln Pro Gly
180 185 190

Gly Ser Leu Lys Leu Ser Cys Ala Ala Ser Gly Phe Thr Phe Asn Lys
195 200 205

Tyr Ala Met Asn Trp Val Arg Gln Ala Pro Gly Lys Gly Leu Glu Trp
210 215 220

Val Ala Arg Ile Arg Ser Lys Tyr Asn Asn Tyr Ala Thr Tyr Tyr Ala
225 230 235 240

Asp Ser Val Lys Asp Arg Phe Thr Ile Ser Arg Asp Asp Ser Lys Asn
245 250 255

Thr Ala Tyr Leu Gln Met Asn Asn Leu Lys Thr Glu Asp Thr Ala Val
260 265 270

Tyr Tyr Cys Val Arg His Gly Asn Phe Gly Asn Ser Tyr Ile Ser Tyr
275 280 285

```
Trp Ala Tyr Trp Gly Gln Gly Thr Leu Val Thr Val Ser Ser Gly Gly
    290                 295                 300

Gly Gly Ser Gly Gly Gly Gly Ser Gly Gly Gly Gly Ser Gln Thr Val
305                 310                 315                 320

Val Thr Gln Glu Pro Ser Leu Thr Val Ser Pro Gly Gly Thr Val Thr
                325                 330                 335

Leu Thr Cys Gly Ser Ser Thr Gly Ala Val Thr Ser Gly Asn Tyr Pro
            340                 345                 350

Asn Trp Val Gln Gln Lys Pro Gly Gln Ala Pro Arg Gly Leu Ile Gly
        355                 360                 365

Gly Thr Lys Phe Leu Ala Pro Gly Thr Pro Ala Arg Phe Ser Gly Ser
    370                 375                 380

Leu Leu Gly Gly Lys Ala Ala Leu Thr Leu Ser Gly Val Gln Pro Glu
385                 390                 395                 400

Asp Glu Ala Glu Tyr Tyr Cys Val Leu Trp Tyr Ser Asn Arg Trp Val
                405                 410                 415

Phe Gly Gly Gly Thr Lys Leu Thr Val Leu Gly Gly Gly Gly Ser Asp
            420                 425                 430

Ile Gln Met Thr Gln Ser Pro Ser Ser Leu Ser Ala Ser Val Gly Asp
        435                 440                 445

Arg Val Thr Ile Thr Cys Arg Ala Ser Gln Gly Ile Ser Asn Tyr Leu
    450                 455                 460

Ala Trp Tyr Gln Gln Lys Thr Gly Lys Val Pro Lys Phe Leu Ile Tyr
465                 470                 475                 480

Glu Ala Ser Thr Leu Gln Ser Gly Val Pro Ser Arg Phe Ser Gly Gly
                485                 490                 495

Gly Ser Gly Thr Asp Phe Thr Leu Thr Ile Ser Ser Leu Gln Pro Glu
            500                 505                 510

Asp Val Ala Thr Tyr Tyr Cys Gln Asn Tyr Asn Ser Ala Pro Phe Thr
        515                 520                 525

Phe Gly Pro Gly Thr Lys Val Asp Ile Lys Arg Thr Val Ala Ala Pro
    530                 535                 540

Ser Val Phe Ile Phe Pro Pro Ser Asp Glu Gln Leu Lys Ser Gly Thr
545                 550                 555                 560

Ala Ser Val Val Cys Leu Leu Asn Asn Phe Tyr Pro Arg Glu Ala Lys
                565                 570                 575

Val Gln Trp Lys Val Asp Asn Ala Leu Gln Ser Gly Asn Ser Gln Glu
            580                 585                 590

Ser Val Thr Glu Gln Asp Ser Lys Asp Ser Thr Tyr Ser Leu Ser Ser
        595                 600                 605

Thr Leu Thr Leu Ser Lys Ala Asp Tyr Glu Lys His Lys Val Tyr Ala
    610                 615                 620

Cys Glu Val Thr His Gln Gly Leu Ser Ser Pro Val Thr Lys Ser Phe
625                 630                 635                 640

Asn Arg Gly Glu Cys
                645
```

<210> SEQ ID NO 69
<211> LENGTH: 226
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Phe Leu Tyr Tyr Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 70
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Thr Gly Lys Val Pro Lys Phe Leu Ile
        35                  40                  45

Tyr Glu Ala Ser Thr Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 71
<211> LENGTH: 657
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Glu Val Gln Leu Val Glu Ser Gly Gly Gly Leu Val Gln Pro Gly Gly
1 5 10 15

Ser Leu Arg Leu Ser Cys Ala Ala Ser Gly Ser Thr Phe Tyr Thr Ala
20 25 30

Val Met Gly Trp Val Arg Gln Ala Pro Gly Lys Gly Leu Glu Trp Val
35 40 45

Ala Ala Ile Arg Trp Thr Ala Leu Thr Thr Ser Tyr Ala Asp Ser Val
50 55 60

Lys Gly Arg Phe Thr Ile Ser Arg Asp Gly Ala Lys Thr Thr Leu Tyr
65 70 75 80

Leu Gln Met Asn Ser Leu Arg Pro Glu Asp Thr Ala Val Tyr Tyr Cys
85 90 95

Ala Ala Arg Gly Thr Leu Gly Leu Phe Thr Thr Ala Asp Ser Tyr Asp
100 105 110

Tyr Trp Gly Gln Gly Thr Leu Val Thr Val Ser Ser Gly Gly Gly Gly
115 120 125

Ser Gly Gly Gly Ser Gly Gly Val Tyr Cys Gly Pro Glu Phe Asp Glu
130 135 140

Ser Val Gly Cys Met Gly Gly Gly Gly Ser Gly Gly Gly Leu Ser Gly
145 150 155 160

Arg Ser Asp Ala Gly Ser Pro Leu Gly Leu Ala Gly Ser Gly Gly Gly
165 170 175

Ser Glu Val Gln Leu Val Glu Ser Gly Gly Gly Leu Val Gln Pro Gly
180 185 190

Gly Ser Leu Lys Leu Ser Cys Ala Ala Ser Gly Phe Thr Phe Asn Lys
195 200 205

Tyr Ala Met Asn Trp Val Arg Gln Ala Pro Gly Lys Gly Leu Glu Trp
210 215 220

Val Ala Arg Ile Arg Ser Lys Tyr Asn Asn Tyr Ala Thr Tyr Tyr Ala
225 230 235 240

-continued

```
Asp Ser Val Lys Asp Arg Phe Thr Ile Ser Arg Asp Asp Ser Lys Asn
                245                 250                 255

Thr Ala Tyr Leu Gln Met Asn Asn Leu Lys Thr Glu Asp Thr Ala Val
            260                 265                 270

Tyr Tyr Cys Val Arg His Gly Asn Phe Gly Asn Ser Tyr Ile Ser Tyr
        275                 280                 285

Trp Ala Tyr Trp Gly Gln Gly Thr Leu Val Thr Val Ser Ser Gly Gly
    290                 295                 300

Gly Gly Ser Gly Gly Gly Gly Ser Gly Gly Gly Gly Ser Gln Thr Val
305                 310                 315                 320

Val Thr Gln Glu Pro Ser Leu Thr Val Ser Pro Gly Gly Thr Val Thr
                325                 330                 335

Leu Thr Cys Gly Ser Ser Thr Gly Ala Val Thr Ser Gly Asn Tyr Pro
            340                 345                 350

Asn Trp Val Gln Gln Lys Pro Gly Gln Ala Pro Arg Gly Leu Ile Gly
        355                 360                 365

Gly Thr Lys Phe Leu Ala Pro Gly Thr Pro Ala Arg Phe Ser Gly Ser
    370                 375                 380

Leu Leu Gly Gly Lys Ala Ala Leu Thr Leu Ser Gly Val Gln Pro Glu
385                 390                 395                 400

Asp Glu Ala Glu Tyr Tyr Cys Val Leu Trp Tyr Ser Asn Arg Trp Val
                405                 410                 415

Phe Gly Gly Gly Thr Lys Leu Thr Val Leu Gly Gly Gly Gly Ser Gln
            420                 425                 430

Val Gln Leu Val Glu Ser Gly Gly Gly Val Val Gln Pro Gly Arg Ser
        435                 440                 445

Leu Arg Leu Ser Cys Ala Ala Ser Gly Phe Ala Phe Ser Arg Tyr Gly
    450                 455                 460

Met His Trp Val Arg Gln Ala Pro Gly Lys Gly Leu Glu Trp Val Ala
465                 470                 475                 480

Val Ile Trp Tyr Asp Gly Ser Asn Lys Tyr Tyr Ala Asp Ser Val Lys
                485                 490                 495

Gly Arg Phe Thr Ile Ser Arg Asp Asn Ser Lys Asn Thr Gln Tyr Leu
            500                 505                 510

Gln Met Asn Ser Leu Arg Ala Glu Asp Thr Ala Val Tyr Tyr Cys Ala
        515                 520                 525

Arg Gly Gly Asp Phe Leu Tyr Tyr Tyr Tyr Tyr Gly Met Asp Val Trp
    530                 535                 540

Gly Gln Gly Thr Thr Val Thr Val Ser Ser Ala Ser Thr Lys Gly Pro
545                 550                 555                 560

Ser Val Phe Pro Leu Ala Pro Ser Ser Lys Ser Thr Ser Gly Gly Thr
                565                 570                 575

Ala Ala Leu Gly Cys Leu Val Lys Asp Tyr Phe Pro Glu Pro Val Thr
            580                 585                 590

Val Ser Trp Asn Ser Gly Ala Leu Thr Ser Gly Val His Thr Phe Pro
        595                 600                 605

Ala Val Leu Gln Ser Ser Gly Leu Tyr Ser Leu Ser Ser Val Val Thr
    610                 615                 620

Val Pro Ser Ser Ser Leu Gly Thr Gln Thr Tyr Ile Cys Asn Val Asn
625                 630                 635                 640
```

His Lys Pro Ser Asn Thr Lys Val Asp Lys Lys Val Glu Pro Lys Ser
645 650 655

Cys

<210> SEQ ID NO 72
<211> LENGTH: 645
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Glu Val Gln Leu Val Glu Ser Gly Gly Gly Leu Val Gln Pro Gly Gly
1 5 10 15

Ser Leu Arg Leu Ser Cys Ala Ala Ser Gly Ser Thr Phe Tyr Thr Ala
20 25 30

Val Met Gly Trp Val Arg Gln Ala Pro Gly Lys Gly Leu Glu Trp Val
35 40 45

Ala Ala Ile Arg Trp Thr Ala Leu Thr Thr Ser Tyr Ala Asp Ser Val
50 55 60

Lys Gly Arg Phe Thr Ile Ser Arg Asp Gly Ala Lys Thr Thr Leu Tyr
65 70 75 80

Leu Gln Met Asn Ser Leu Arg Pro Glu Asp Thr Ala Val Tyr Tyr Cys
85 90 95

Ala Ala Arg Gly Thr Leu Gly Leu Phe Thr Thr Ala Asp Ser Tyr Asp
100 105 110

Tyr Trp Gly Gln Gly Thr Leu Val Thr Val Ser Ser Gly Gly Gly Gly
115 120 125

Ser Gly Gly Gly Ser Gly Gly Val Tyr Cys Gly Pro Glu Phe Asp Glu
130 135 140

Ser Val Gly Cys Met Gly Gly Gly Gly Ser Gly Gly Gly Leu Ser Gly
145 150 155 160

Arg Ser Asp Ala Gly Ser Pro Leu Gly Leu Ala Gly Ser Gly Gly Gly
165 170 175

Ser Glu Val Gln Leu Val Glu Ser Gly Gly Gly Leu Val Gln Pro Gly
180 185 190

Gly Ser Leu Lys Leu Ser Cys Ala Ala Ser Gly Phe Thr Phe Asn Lys
195 200 205

Tyr Ala Met Asn Trp Val Arg Gln Ala Pro Gly Lys Gly Leu Glu Trp
210 215 220

Val Ala Arg Ile Arg Ser Lys Tyr Asn Asn Tyr Ala Thr Tyr Tyr Ala
225 230 235 240

Asp Ser Val Lys Asp Arg Phe Thr Ile Ser Arg Asp Asp Ser Lys Asn
245 250 255

Thr Ala Tyr Leu Gln Met Asn Asn Leu Lys Thr Glu Asp Thr Ala Val
260 265 270

Tyr Tyr Cys Val Arg His Gly Asn Phe Gly Asn Ser Tyr Ile Ser Tyr
275 280 285

Trp Ala Tyr Trp Gly Gln Gly Thr Leu Val Thr Val Ser Ser Gly Gly
290 295 300

Gly Gly Ser Gly Gly Gly Gly Ser Gly Gly Gly Gly Ser Gln Thr Val
305 310 315 320

Val Thr Gln Glu Pro Ser Leu Thr Val Ser Pro Gly Gly Thr Val Thr
325 330 335

Leu Thr Cys Gly Ser Ser Thr Gly Ala Val Thr Ser Gly Asn Tyr Pro
340 345 350

Asn Trp Val Gln Gln Lys Pro Gly Gln Ala Pro Arg Gly Leu Ile Gly
355 360 365

Gly Thr Lys Phe Leu Ala Pro Gly Thr Pro Ala Arg Phe Ser Gly Ser
370 375 380

Leu Leu Gly Gly Lys Ala Ala Leu Thr Leu Ser Gly Val Gln Pro Glu
385 390 395 400

Asp Glu Ala Glu Tyr Tyr Cys Val Leu Trp Tyr Ser Asn Arg Trp Val
405 410 415

Phe Gly Gly Gly Thr Lys Leu Thr Val Leu Gly Gly Gly Gly Ser Asp
420 425 430

Ile Gln Met Thr Gln Ser Pro Ser Ser Leu Ser Ala Ser Val Gly Asp
435 440 445

Arg Val Thr Ile Thr Cys Arg Ala Ser Gln Gly Ile Ser Asn Tyr Leu
450 455 460

Ala Trp Tyr Gln Gln Lys Thr Gly Lys Val Pro Lys Phe Leu Ile Tyr
465 470 475 480

Glu Ala Ser Thr Leu Gln Ser Gly Val Pro Ser Arg Phe Ser Gly Gly
485 490 495

Gly Ser Gly Thr Asp Phe Thr Leu Thr Ile Ser Ser Leu Gln Pro Glu
500 505 510

Asp Val Ala Thr Tyr Tyr Cys Gln Asn Tyr Asn Ser Ala Pro Phe Thr
515 520 525

Phe Gly Pro Gly Thr Lys Val Asp Ile Lys Arg Thr Val Ala Ala Pro
530 535 540

Ser Val Phe Ile Phe Pro Pro Ser Asp Glu Gln Leu Lys Ser Gly Thr
545 550 555 560

Ala Ser Val Val Cys Leu Leu Asn Asn Phe Tyr Pro Arg Glu Ala Lys
565 570 575

Val Gln Trp Lys Val Asp Asn Ala Leu Gln Ser Gly Asn Ser Gln Glu
580 585 590

Ser Val Thr Glu Gln Asp Ser Lys Asp Ser Thr Tyr Ser Leu Ser Ser
595 600 605

Thr Leu Thr Leu Ser Lys Ala Asp Tyr Glu Lys His Lys Val Tyr Ala
610 615 620

Cys Glu Val Thr His Gln Gly Leu Ser Ser Pro Val Thr Lys Ser Phe
625 630 635 640

Asn Arg Gly Glu Cys
645

<210> SEQ ID NO 73
<211> LENGTH: 226
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

Gln Val Gln Leu Val Glu Ser Gly Gly Gly Val Val Gln Pro Gly Arg
1 5 10 15

Ser Leu Arg Leu Ser Cys Ala Ala Ser Gly Phe Ala Phe Ser Arg Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Gln Tyr
65 70 75 80

Leu Gln Met Asn Ser Leu Arg Ala Glu Asp Thr Ala Val Tyr Tyr Cys
85 90 95

Ala Arg Gly Gly Asp Phe Leu Tyr Tyr Tyr Tyr Tyr Gly Met Asp Val
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys
225

<210> SEQ ID NO 74
<211> LENGTH: 636
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Ala Pro Gly Lys Gly Leu Glu Trp Val
35 40 45

Ser Ser Ile Ser Gly Ser Gly Arg Asp Thr Leu Tyr Ala Asp Ser Val
50 55 60

Lys Gly Arg Phe Thr Ile Ser Arg Asp Asn Ala Lys Thr Thr Leu Tyr
65 70 75 80

Leu Gln Met Asn Ser Leu Arg Pro Glu Asp Thr Ala Val Tyr Tyr Cys
85 90 95

Thr Ile Gly Gly Ser Leu Ser Val Ser Ser Gln Gly Thr Leu Val Thr
100 105 110

Val Ser Ser Gly Gly Gly Gly Ser Gly Gly Gly Ser Gly Gly Val Tyr
115 120 125

Cys Gly Pro Glu Phe Asp Glu Ser Val Gly Cys Met Gly Gly Gly Gly
130 135 140

```
Ser Gly Gly Gly Leu Ser Gly Arg Ser Asp Ala Gly Ser Pro Leu Gly
145                 150                 155                 160

Leu Ala Gly Ser Gly Gly Gly Ser Glu Val Gln Leu Val Glu Ser Gly
                165                 170                 175

Gly Gly Leu Val Gln Pro Gly Gly Ser Leu Lys Leu Ser Cys Ala Ala
            180                 185                 190

Ser Gly Phe Thr Phe Asn Lys Tyr Ala Met Asn Trp Val Arg Gln Ala
        195                 200                 205

Pro Gly Lys Gly Leu Glu Trp Val Ala Arg Ile Arg Ser Lys Tyr Asn
    210                 215                 220

Asn Tyr Ala Thr Tyr Tyr Ala Asp Ser Val Lys Asp Arg Phe Thr Ile
225                 230                 235                 240

Ser Arg Asp Asp Ser Lys Asn Thr Ala Tyr Leu Gln Met Asn Asn Leu
                245                 250                 255

Lys Thr Glu Asp Thr Ala Val Tyr Tyr Cys Val Arg His Gly Asn Phe
            260                 265                 270

Gly Asn Ser Tyr Ile Ser Tyr Trp Ala Tyr Trp Gly Gln Gly Thr Leu
        275                 280                 285

Val Thr Val Ser Ser Gly Gly Gly Gly Ser Gly Gly Gly Gly Ser Gly
    290                 295                 300

Gly Gly Gly Ser Gln Thr Val Val Thr Gln Glu Pro Ser Leu Thr Val
305                 310                 315                 320

Ser Pro Gly Gly Thr Val Thr Leu Thr Cys Gly Ser Ser Thr Gly Ala
                325                 330                 335

Val Thr Ser Gly Asn Tyr Pro Asn Trp Val Gln Gln Lys Pro Gly Gln
            340                 345                 350

Ala Pro Arg Gly Leu Ile Gly Gly Thr Lys Phe Leu Ala Pro Gly Thr
        355                 360                 365

Pro Ala Arg Phe Ser Gly Ser Leu Leu Gly Gly Lys Ala Ala Leu Thr
    370                 375                 380

Leu Ser Gly Val Gln Pro Glu Asp Glu Ala Glu Tyr Tyr Cys Val Leu
385                 390                 395                 400

Trp Tyr Ser Asn Arg Trp Val Phe Gly Gly Gly Thr Lys Leu Thr Val
                405                 410                 415

Leu Gly Gly Gly Gly Ser Asp Ile Gln Met Thr Gln Ser Pro Ser Ser
            420                 425                 430

Leu Ser Ala Ser Val Gly Asp Arg Val Thr Ile Thr Cys Arg Ala Ser
        435                 440                 445

Gln Gly Ile Ser Asn Tyr Leu Ala Trp Tyr Gln Gln Lys Thr Gly Lys
    450                 455                 460

Val Pro Lys Phe Leu Ile Tyr Glu Ala Ser Thr Leu Gln Ser Gly Val
465                 470                 475                 480

Pro Ser Arg Phe Ser Gly Gly Gly Ser Gly Thr Asp Phe Thr Leu Thr
                485                 490                 495

Ile Ser Ser Leu Gln Pro Glu Asp Val Ala Thr Tyr Tyr Cys Gln Asn
            500                 505                 510

Tyr Asn Ser Ala Pro Phe Thr Phe Gly Pro Gly Thr Lys Val Asp Ile
        515                 520                 525

Lys Arg Thr Val Ala Ala Pro Ser Val Phe Ile Phe Pro Pro Ser Asp
    530                 535                 540

Glu Gln Leu Lys Ser Gly Thr Ala Ser Val Val Cys Leu Leu Asn Asn
545                 550                 555                 560
```

```
Phe Tyr Pro Arg Glu Ala Lys Val Gln Trp Lys Val Asp Asn Ala Leu
                565                 570                 575

Gln Ser Gly Asn Ser Gln Glu Ser Val Thr Glu Gln Asp Ser Lys Asp
            580                 585                 590

Ser Thr Tyr Ser Leu Ser Ser Thr Leu Thr Leu Ser Lys Ala Asp Tyr
        595                 600                 605

Glu Lys His Lys Val Tyr Ala Cys Glu Val Thr His Gln Gly Leu Ser
    610                 615                 620

Ser Pro Val Thr Lys Ser Phe Asn Arg Gly Glu Cys
625                 630                 635


<210> SEQ ID NO 75
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Phe Leu Tyr Tyr Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 76
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 76

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Ala Pro Gly Lys Gly Leu Glu Trp Val
35 40 45

Ser Ser Ile Ser Gly Ser Gly Arg Asp Thr Leu Tyr Ala Asp Ser Val
50 55 60

Lys Gly Arg Phe Thr Ile Ser Arg Asp Asn Ala Lys Thr Thr Leu Tyr
65 70 75 80

Leu Gln Met Asn Ser Leu Arg Pro Glu Asp Thr Ala Val Tyr Tyr Cys
85 90 95

Thr Ile Gly Gly Ser Leu Ser Val Ser Ser Gln Gly Thr Leu Val Thr
100 105 110

Val Ser Ser Gly Gly Gly Gly Ser Gly Gly Gly Ser Gly Gly Val Tyr
115 120 125

Cys Gly Pro Glu Phe Asp Glu Ser Val Gly Cys Met Gly Gly Gly Gly
130 135 140

Ser Gly Gly Gly Ser Gly Gly Gly Gly Ser Gly Gly Ala Ser Ser Gly
145 150 155 160

Ala Gly Gly Ser Gly Gly Gly Ser Glu Val Gln Leu Val Glu Ser Gly
165 170 175

Gly Gly Leu Val Gln Pro Gly Gly Ser Leu Lys Leu Ser Cys Ala Ala
180 185 190

Ser Gly Phe Thr Phe Asn Lys Tyr Ala Met Asn Trp Val Arg Gln Ala
195 200 205

Pro Gly Lys Gly Leu Glu Trp Val Ala Arg Ile Arg Ser Lys Tyr Asn
210 215 220

Asn Tyr Ala Thr Tyr Tyr Ala Asp Ser Val Lys Asp Arg Phe Thr Ile
225 230 235 240

Ser Arg Asp Asp Ser Lys Asn Thr Ala Tyr Leu Gln Met Asn Asn Leu
245 250 255

Lys Thr Glu Asp Thr Ala Val Tyr Tyr Cys Val Arg His Gly Asn Phe
260 265 270

Gly Asn Ser Tyr Ile Ser Tyr Trp Ala Tyr Trp Gly Gln Gly Thr Leu
275 280 285

Val Thr Val Ser Ser Gly Gly Gly Gly Ser Gly Gly Gly Gly Ser Gly
290 295 300

Gly Gly Gly Ser Gln Thr Val Val Thr Gln Glu Pro Ser Leu Thr Val
305 310 315 320

Ser Pro Gly Gly Thr Val Thr Leu Thr Cys Gly Ser Ser Thr Gly Ala
325 330 335

Val Thr Ser Gly Asn Tyr Pro Asn Trp Val Gln Gln Lys Pro Gly Gln
340 345 350

Ala Pro Arg Gly Leu Ile Gly Gly Thr Lys Phe Leu Ala Pro Gly Thr
355 360 365

Pro Ala Arg Phe Ser Gly Ser Leu Leu Gly Gly Lys Ala Ala Leu Thr
370 375 380

Leu Ser Gly Val Gln Pro Glu Asp Glu Ala Glu Tyr Tyr Cys Val Leu
385 390 395 400

Trp Tyr Ser Asn Arg Trp Val Phe Gly Gly Gly Thr Lys Leu Thr Val
405 410 415

Leu Gly Gly Gly Gly Ser Asp Ile Gln Met Thr Gln Ser Pro Ser Ser
420 425 430

Leu Ser Ala Ser Val Gly Asp Arg Val Thr Ile Thr Cys Arg Ala Ser
435 440 445

Gln Gly Ile Ser Asn Tyr Leu Ala Trp Tyr Gln Gln Lys Thr Gly Lys
450 455 460

Val Pro Lys Phe Leu Ile Tyr Glu Ala Ser Thr Leu Gln Ser Gly Val
465 470 475 480

Pro Ser Arg Phe Ser Gly Gly Gly Ser Gly Thr Asp Phe Thr Leu Thr
485 490 495

Ile Ser Ser Leu Gln Pro Glu Asp Val Ala Thr Tyr Tyr Cys Gln Asn
500 505 510

Tyr Asn Ser Ala Pro Phe Thr Phe Gly Pro Gly Thr Lys Val Asp Ile
515 520 525

Lys Arg Thr Val Ala Ala Pro Ser Val Phe Ile Phe Pro Pro Ser Asp
530 535 540

Glu Gln Leu Lys Ser Gly Thr Ala Ser Val Val Cys Leu Leu Asn Asn
545 550 555 560

Phe Tyr Pro Arg Glu Ala Lys Val Gln Trp Lys Val Asp Asn Ala Leu
565 570 575

Gln Ser Gly Asn Ser Gln Glu Ser Val Thr Glu Gln Asp Ser Lys Asp
580 585 590

Ser Thr Tyr Ser Leu Ser Ser Thr Leu Thr Leu Ser Lys Ala Asp Tyr
595 600 605

Glu Lys His Lys Val Tyr Ala Cys Glu Val Thr His Gln Gly Leu Ser
610 615 620

Ser Pro Val Thr Lys Ser Phe Asn Arg Gly Glu Cys
625 630 635

<210> SEQ ID NO 77
<211> LENGTH: 226
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Gln Val Gln Leu Val Glu Ser Gly Gly Gly Val Val Gln Pro Gly Arg
1 5 10 15

Ser Leu Arg Leu Ser Cys Ala Ala Ser Gly Phe Ala Phe Ser Arg Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Gln Tyr
65 70 75 80

Leu Gln Met Asn Ser Leu Arg Ala Glu Asp Thr Ala Val Tyr Tyr Cys
85 90 95

Ala Arg Gly Gly Asp Phe Leu Tyr Tyr Tyr Tyr Tyr Gly Met Asp Val
100 105 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Leu Trp Gly Cys Glu Trp Asn Cys Ala Gly Ile Thr Thr
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ser Gln Cys Leu Gly Pro Glu Trp Glu Val Cys Pro Tyr
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ser Gln Cys Leu Gly Pro Glu Trp Glu Val Cys Pro Tyr
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ala Gln Cys Leu Gly Pro Glu Trp Glu Val Cys Pro Tyr
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Ala Cys Leu Gly Pro Glu Trp Glu Val Cys Pro Tyr
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Gln Cys Ala Gly Pro Glu Trp Glu Val Cys Pro Tyr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ser Gln Cys Leu Ala Pro Glu Trp Glu Val Cys Pro Tyr
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ser Gln Cys Leu Gly Ala Glu Trp Glu Val Cys Pro Tyr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ser Gln Cys Leu Gly Pro Ala Trp Glu Val Cys Pro Tyr
1               5                   10

<210> SEQ ID NO 87
<211> LENGTH: 14

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Gly Ser Gln Cys Leu Gly Pro Glu Ala Glu Val Cys Pro Tyr
1 5 10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Gly Ser Gln Cys Leu Gly Pro Glu Trp Ala Val Cys Pro Tyr
1 5 10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Gly Ser Gln Cys Leu Gly Pro Glu Trp Glu Ala Cys Pro Tyr
1 5 10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Gly Ser Gln Cys Leu Gly Pro Glu Trp Glu Val Cys Ala Tyr
1 5 10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Gly Ser Gln Cys Leu Gly Pro Glu Trp Glu Val Cys Pro Ala
1 5 10

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Gly Ser Gln Cys Leu Gly Pro Glu Trp Glu Val Cys Pro Tyr
1 5 10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Val Tyr Cys Gly Pro Glu Phe Asp Glu Ser Val Gly Cys Met
1 5 10

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Ala Tyr Cys Gly Pro Glu Phe Asp Glu Ser Val Gly Cys Met
1 5 10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Val Ala Cys Gly Pro Glu Phe Asp Glu Ser Val Gly Cys Met
1 5 10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Val Tyr Cys Ala Pro Glu Phe Asp Glu Ser Val Gly Cys Met
1 5 10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Val Tyr Cys Gly Ala Glu Phe Asp Glu Ser Val Gly Cys Met
1 5 10

<210> SEQ ID NO 98
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Val Tyr Cys Gly Pro Ala Phe Asp Glu Ser Val Gly Cys Met
1 5 10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Val Tyr Cys Gly Pro Glu Ala Asp Glu Ser Val Gly Cys Met
1 5 10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Val Tyr Cys Gly Pro Glu Phe Ala Glu Ser Val Gly Cys Met
1 5 10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Val Tyr Cys Gly Pro Glu Phe Asp Ala Ser Val Gly Cys Met
1 5 10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Val Tyr Cys Gly Pro Glu Phe Asp Glu Ala Val Gly Cys Met
1 5 10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Val Tyr Cys Gly Pro Glu Phe Asp Glu Ser Ala Gly Cys Met
1 5 10

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Val Tyr Cys Gly Pro Glu Phe Asp Glu Ser Val Ala Cys Met
1 5 10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Val Tyr Cys Gly Pro Glu Phe Asp Glu Ser Val Gly Cys Ala
1 5 10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Asp Asp Cys Trp Pro Asp Trp Glu Phe Asp Phe Ala Cys Ala
1 5 10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Tyr Ile Cys Gly Leu Asp Phe Pro Asp Phe Leu Tyr Cys Asp
1 5 10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Phe Asp Cys Trp Pro Asp Trp Glu Glu Tyr Phe Val Cys Asp
1 5 10

<210> SEQ ID NO 109
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Tyr Ile Cys Trp Pro Asp Trp Glu Glu Tyr Phe Asp Cys Asp
1 5 10

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Asn Ile Cys Trp Pro Asp Trp Glu Asp Asp Tyr Phe Cys Phe
1 5 10

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Asn Phe Cys Trp Pro Asp Trp Glu Tyr Ile Tyr Pro Cys Ile
1 5 10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Val Asp Cys Trp Pro Asp Trp Glu Glu Asp Phe Leu Cys Ile
1 5 10

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

His Ala Cys Trp Pro Asp Trp Glu Glu Tyr Phe Pro Cys Asn
1 5 10

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Tyr Asp Cys Gly Pro Asp Val Asp Glu Ser Tyr Val Cys Val
1 5 10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Ile Asp Cys Trp Pro Asp Trp Glu Asp Asp Thr Phe Cys Tyr
1 5 10

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Tyr Leu Cys Gly Pro Asp Gly Asp Glu Thr Leu Ala Cys Tyr
1 5 10

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Val Asp Cys Gly Pro Asp Gly Asp Glu Ser Ile Leu Cys Tyr
1 5 10

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(9)
<223> OTHER INFORMATION: This sequence may encompass 1-3 “Gly Gly Ser” repeating units

<400> SEQUENCE: 118

Gly Gly Ser Gly Gly Ser Gly Gly Ser
1 5

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Phe Ile Cys Trp Pro Asp Trp Glu Glu Asp Tyr Phe Cys Ala
1 5 10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Gly Asp Cys Trp Pro Asp Trp Glu Trp Asp Phe Tyr Cys Asp
1 5 10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Tyr Leu Cys Trp Pro Asp Trp Glu Tyr Ile Asp Leu Cys Asp
1 5 10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Ser Phe Cys Trp Pro Asp Trp Glu Glu Tyr Phe Asp Cys Asp
1 5 10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Asp Asp Cys Trp Pro Asp Trp Glu Glu Tyr Ala Ser Cys Asp
1 5 10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Asn Leu Cys Trp Pro Asp Trp Glu Tyr Pro Phe Phe Cys Asp
1 5 10

<210> SEQ ID NO 125
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Phe Asp Cys Trp Pro Asp Trp Glu Glu Ser Phe Val Cys Asp
1 5 10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Asp Ile Cys Gly Pro Asp Gly Asp Glu Thr Ile Ile Cys Asp
1 5 10

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Asp Asp Cys Trp Pro Asp Trp Glu Tyr Tyr Ala Val Cys Asp
1 5 10

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Tyr Asp Cys Trp Pro Asp Trp Glu Glu Tyr Ser Asn Cys Asp
1 5 10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Ile Asn Cys Trp Pro Asp Trp Glu Asp Tyr Phe Phe Cys Asp
1 5 10

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Asn Ile Cys Trp Pro Asp Trp Glu Asp Asp Thr Phe Cys Phe
1 5 10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Asn Ile Cys Trp Pro Asp Trp Glu Pro Asn Ser Phe Cys Phe
1 5 10

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Tyr Asp Cys Gly Pro Glu Met Asp Glu Ser Ile Asp Cys Phe
1 5 10

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Asp Phe Cys Trp Pro Asp Trp Glu Phe Pro Phe Ile Cys His
1 5 10

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Asp Phe Cys Gly Pro Glu Met Asp Glu Ser Ile Thr Cys Ile
1 5 10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Tyr Asp Cys Gly Pro Glu Phe Asp Glu Ser Thr Val Cys Ile
1 5 10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

His Asp Cys Trp Pro Asp Trp Glu Trp Asp Ile Phe Cys Ile
1 5 10

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

His Ala Cys Trp Pro Asp Trp Glu Glu Tyr Asn Pro Cys Asn
1 5 10

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Asp Val Cys Trp Pro Asp Trp Glu Trp Asp Phe Phe Cys Asn
1 5 10

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Asn Tyr Cys Trp Pro Asp Trp Glu Tyr Tyr Ile Pro Cys Asn
1 5 10

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Ile Ile Cys Trp Pro Asp Trp Glu Phe Ile Asp Tyr Cys Asn
1 5 10

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Ser Leu Cys Trp Pro Asp Trp Glu Tyr Asp Ile Ala Cys Pro
1 5 10

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Asp Leu Cys Gly Pro Glu Leu Asp Glu Ser Ile Phe Cys Pro
1 5 10

<210> SEQ ID NO 143
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Thr Asn Cys Trp Pro Asp Trp Glu Trp Val Leu Pro Cys Pro
1 5 10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Ile Glu Cys Trp Pro Asp Trp Glu Pro Asn Tyr Phe Cys Pro
1 5 10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Ile Phe Cys Trp Pro Asp Trp Glu Asp Tyr Val Asp Cys Pro
1 5 10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Ile Asp Cys Trp Pro Asp Trp Glu Tyr Asp Phe Phe Cys Pro
1 5 10

<210> SEQ ID NO 147
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Leu Phe Cys Trp Pro Asp Trp Glu Asp Ser Phe Phe Cys Pro
1 5 10

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Val Asp Cys Trp Pro Asp Trp Glu Asp Tyr Ala Asp Cys Thr
1 5 10

<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Val Ile Cys Trp Pro Asp Trp Glu Gln Tyr Phe Pro Cys Val
1 5 10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Ile Glu Cys Trp Pro Asp Trp Glu Pro Ile Tyr Pro Cys Tyr
1 5 10

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Ile Thr Cys Trp Pro Asp Trp Glu Val Tyr Phe Pro Cys Tyr
1 5 10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Ile Asp Cys Trp Pro Asp Trp Glu Tyr Ile His Pro Cys Tyr
1 5 10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Ile Asp Cys Trp Pro Asp Trp Glu Tyr Ile Asn Pro Cys Tyr
1 5 10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Ala Asp Cys Trp Pro Asp Trp Glu Glu Ala Phe Pro Cys Tyr
1 5 10

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Ile Asp Cys Trp Pro Asp Trp Glu Tyr Ile Tyr Pro Cys Tyr
1 5 10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Asn Ile Cys Trp Pro Asp Trp Glu Asp Asp Asn Phe Cys Phe
1 5 10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Tyr Asp Cys Trp Pro Asp Trp Glu Tyr Val Asp Ala Cys Tyr
1 5 10

<210> SEQ ID NO 158
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Phe Tyr Cys Gly Pro Asp Gly Asp Glu Ser Tyr Val Cys Asp
1 5 10

<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Asp Ile Cys Trp Pro Asp Trp Glu Tyr Ile Asn Ile Cys Ser
1 5 10

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Phe Val Cys Trp Pro Asp Trp Glu Asp Phe Asn Phe Cys Asp
1 5 10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Phe Ala Cys Trp Pro Asp Trp Glu Asp Tyr Val Ala Cys Asp
1 5 10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Asp Asn Cys Trp Pro Asp Trp Glu Tyr Asp Phe Phe Cys Val
1 5 10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Tyr Asp Cys Trp Pro Asp Trp Glu Glu Tyr Asn Asp Cys Ala
1 5 10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Asp Asp Cys Gly Pro Asp Gly Asp Glu Thr Ile Ile Cys Val
1 5 10

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Phe Pro Cys Trp Pro Asp Trp Glu Glu Tyr Ala Ile Cys Asp
1 5 10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Pro Asp Cys Gly Pro Asp Gly Asp Glu Ser Leu Phe Cys Thr
1 5 10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Asp Asn Cys Trp Pro Asp Trp Glu Tyr Asp Tyr Phe Cys Val
1 5 10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Ile Phe Cys Trp Pro Asp Trp Glu Glu Phe Tyr Asp Cys Tyr
1 5 10

<210> SEQ ID NO 169
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Ala Asp Cys Trp Pro Asp Trp Glu Glu Tyr Phe Pro Cys Asn
1 5 10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 170

His Thr Cys Trp Pro Asp Trp Glu Asp Asp Ile Phe Cys Asn
1 5 10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

Phe Ala Cys Trp Pro Asp Trp Glu Glu Ala Phe Leu Cys Leu
1 5 10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Tyr Asp Cys Gly Pro Glu Leu Asp Glu Ser Ile Ala Cys Asp
1 5 10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Asn Ser Cys Trp Pro Asp Trp Glu Tyr Asp Ile Ile Cys Asp
1 5 10

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Phe Ala Cys Trp Pro Asp Trp Glu Glu Val Ala Pro Cys Tyr
1 5 10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Leu Asp Cys Gly Pro Asp Gly Asp Glu Thr Leu Thr Cys Tyr
1 5 10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Val Leu Cys Trp Pro Asp Trp Glu Glu Phe Tyr Asp Cys Pro
1 5 10

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

His Ala Cys Trp Pro Val Trp Glu Glu Tyr Phe Pro Cys Asn
1 5 10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Asn Glu Cys Trp Pro Asn Gly Glu Pro Thr Phe Pro Cys Thr
1 5 10

<210> SEQ ID NO 179
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Leu Thr Cys Gly Pro Asp Gly Asp Glu Thr Leu Tyr Cys Asp
1 5 10

<210> SEQ ID NO 180
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Tyr Asp Cys Gly Pro Glu Tyr Asp Glu Ser Val Pro Cys Ile
1 5 10

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Ile Glu Cys Trp Pro Asp Trp Glu Pro Asn Ser Phe Cys Asp
1 5 10

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Tyr Asp Cys Gly Pro Glu Leu Asp Glu Ser Ile His Cys Tyr
1 5 10

<210> SEQ ID NO 183
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Ile Tyr Cys Gly Pro Glu Phe Asp Glu Ser Thr Ile Cys Asn
1 5 10

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Ile Tyr Cys Gly Pro Glu Val Glu Glu Ala Tyr Leu Cys Tyr
1 5 10

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Phe Asp Cys Gly Pro Asp Gly Asp Glu Thr Val Tyr Cys Asp
1 5 10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Ile Asp Cys Gly Pro Asp Gly Asp Glu Thr Ile Ser Cys Tyr
1 5 10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Asn Tyr Cys Gly Pro Glu Phe Asp Glu Ser Ser Thr Cys Leu
1 5 10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Tyr Asp Cys Gly Pro Asp Gly Asp Glu Ser Tyr Phe Cys Asp
1 5 10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Asn Phe Cys Trp Pro Asp Trp Glu Tyr Phe Asn Asp Cys Asn
1 5 10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Val Leu Cys Trp Pro Asp Trp Glu Ala Phe Phe Asp Cys Asp
1 5 10

<210> SEQ ID NO 191
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Ile Tyr Cys Gly Pro Glu Trp Glu Trp Pro Val Ala Cys Asn
1 5 10

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Val Phe Cys Trp Pro Asp Trp Glu Asp Asn Phe Phe Cys Asn
1 5 10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Val Val Cys Trp Pro Asp Trp Glu Thr Phe Phe Pro Cys Asp
1 5 10

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Asp Asn Cys Gly Pro Asp Gly Asp Glu Thr Tyr Ile Cys Asn
1 5 10

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Asp Asn Cys Trp Pro Asp Trp Glu Tyr Asn Phe Phe Cys Val
1 5 10

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Phe Tyr Cys Gly Pro Glu Val Glu Glu Asp Tyr Leu Cys Ile
1 5 10

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Asp Asn Cys Trp Pro Asp Trp Glu Tyr Asp Ile Phe Cys Val
1 5 10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Ile Asp Cys Gly Pro Glu Phe Asp Glu Ser Ile Ala Cys Pro
1 5 10

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Tyr Phe Cys Gly Pro Glu Val Glu Glu Tyr Thr Leu Cys Phe
1 5 10

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Phe Tyr Cys Gly Pro Glu Phe Asp Glu Ser Ala Pro Cys Asn
1 5 10

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Phe Asp Cys Gly Pro Glu Val Glu Glu Tyr Phe Tyr Cys Ala
1 5 10

<210> SEQ ID NO 202
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Asp Phe Cys Trp Pro Asp Trp Glu Asp Phe Phe Phe Cys Ala
1 5 10

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Phe Phe Cys Gly Pro Asp Gly Asp Glu Thr Leu Ser Cys Asn
1 5 10

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 204

Phe Ile Cys Gly Pro Glu Phe Asp Glu Ser Val Ala Cys Leu
1 5 10

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 205

Tyr Asp Cys Gly Pro Glu Phe Asp Glu Ala Ile Gly Cys Tyr
1 5 10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Tyr Ile Cys Trp Pro Asp Trp Glu Glu Tyr Leu Tyr Cys Pro
1 5 10

<210> SEQ ID NO 207
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 207

Phe Asp Cys Trp Pro Asp Trp Glu Glu Pro Thr Thr Cys His
1 5 10

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Tyr Asp Cys Trp Pro Asp Trp Glu Asp Phe Pro Ile Cys Asp
1 5 10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Val Val Cys Trp Pro Asp Trp Glu Tyr Ile Asp Asp Cys Ser
1 5 10

<210> SEQ ID NO 210
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Ile Asn Cys Trp Pro Asp Trp Glu Val Ile Ser Phe Cys Asp
1 5 10

<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Leu Ser Cys Trp Pro Asp Trp Glu Glu Val Thr Pro Cys Leu
1 5 10

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

Phe Ala Cys Trp Pro Asp Trp Glu Glu Val Asp Ile Cys Tyr
1 5 10

<210> SEQ ID NO 213
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Tyr Asp Cys Gly Pro Glu Met Asp Glu Ser Ile Val Cys Asp
1 5 10

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Tyr Asp Cys Trp Pro Asp Trp Glu Val Phe Ile Val Cys Asp
1 5 10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Asp Asn Cys Trp Pro Asp Trp Glu His Asn Phe Phe Cys Val
1 5 10

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Tyr Asp Cys Gly Pro Asp Gly Asp Glu Ser Ile Tyr Cys Pro
1 5 10

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Tyr Asp Cys Gly Pro Glu Phe Glu Phe Pro Tyr Tyr Cys Phe
1 5 10

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Ala Asp Cys Gly Pro Glu Tyr Asp Glu Ser Val Pro Cys Val
1 5 10

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Phe Leu Cys Gly Pro Glu Val Glu Glu Val His Tyr Cys Ser
1 5 10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Thr Asp Cys Trp Pro Asp Trp Glu Tyr Ile Thr Ser Cys Ser
1 5 10

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Ala Phe Cys Gly Pro Glu Leu Asp Glu Ser Ile Thr Cys Asp
1 5 10

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Asn Asp Cys Trp Pro Asp Trp Glu Glu Tyr Phe Ser Cys Tyr
1 5 10

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Phe Asp Cys Gly Pro Glu Trp Glu Ile Val Thr Asp Cys Tyr
1 5 10

<210> SEQ ID NO 224
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Asn Leu Cys Gly Pro Glu Met Asp Glu Ser Ile Ile Cys Pro
1 5 10

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Asp Leu Cys Gly Pro Glu Met Asp Glu Ser Ile Tyr Cys Asp
1 5 10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 226

Phe Asp Cys Gly Pro Asp Gly Val Glu Asp Tyr Ile Cys Asp
1 5 10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 227

Tyr Ala Cys Trp Pro Asp Trp Glu Glu Asp Phe Ala Cys Tyr
1 5 10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 228

His Asp Cys Gly Pro Glu Met Asp Glu Ser Ile Val Cys Val
1 5 10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Val Phe Cys Gly Pro Glu Phe Glu Phe Ile Phe Leu Cys Ala
1 5 10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Tyr Asp Cys Gly Pro Glu Leu Asp Glu Ser Ile Leu Cys Asp
1 5 10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Ser Val Cys Trp Pro Asp Trp Glu Glu Phe Tyr Ser Cys Asp
1 5 10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Pro Tyr Cys Gly Pro Asp Gly Asp Glu Thr Ala Ile Cys Thr
1 5 10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Asp Asp Cys Gly Pro Glu Leu Glu Trp Tyr Tyr Pro Cys Tyr
1 5 10

<210> SEQ ID NO 234
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 234

Phe Ile Cys Gly Pro Glu Phe Asp Glu Ser Leu Pro Cys Asn
1 5 10

<210> SEQ ID NO 235
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 235

Ile Asp Cys Gly Pro Glu Phe Asp Glu Ser Leu Pro Cys Asp
1 5 10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 236

Phe Leu Cys Gly Pro Glu Phe Glu Glu Asp Ala Pro Cys Tyr
1 5 10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

Ile Phe Cys Gly Pro Asp Gly Asp Glu Thr His Ile Cys His
1 5 10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Val Phe Cys Trp Pro Asp Trp Glu Tyr Ile Asp Phe Cys Asn
1 5 10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Ile Phe Cys Gly Pro Glu Tyr Asp Glu Ser Leu His Cys Ile
1 5 10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

His Leu Cys Trp Pro Asp Trp Glu Trp Tyr Val Asp Cys Pro
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Phe Ile Cys Gly Pro Glu Met Asp Glu Ser Ile Ala Cys Asn
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Ile Phe Cys Gly Pro Glu Val Glu Met Ile Phe Leu Cys Asn
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Tyr Asp Cys Gly Pro Glu Trp Glu Phe Pro Val Asp Cys Ile
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Asn Leu Cys Gly Pro Glu Leu Asp Glu Ser Ile Thr Cys Phe
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Phe Tyr Cys Gly Pro Glu Val Glu Asp Phe Tyr Phe Cys Tyr
1               5                   10

<210> SEQ ID NO 246
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Asp Tyr Cys Gly Pro Glu Phe Asp Glu Ser Leu Ile Cys Asn
1 5 10

<210> SEQ ID NO 247
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Asp Tyr Cys Gly Pro Glu Phe Asp Glu Ser Leu Pro Cys Asp
1 5 10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Ala Ile Cys Gly Pro Glu Leu Asp Glu Ser Ile Ala Cys Pro
1 5 10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 249

Val Ile Cys Gly Pro Glu Val Glu Asp Tyr Asn Leu Cys Tyr
1 5 10

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

His Thr Cys Trp Pro Asp Trp Glu Asp Tyr Thr Val Cys Pro
1 5 10

<210> SEQ ID NO 251
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Ser Asp Cys Trp Pro Asp Trp Glu Tyr Phe Tyr Asp Cys Asn
1 5 10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Val Phe Cys Gly Pro Asp Gly Asp Glu Thr Val His Cys Asp
1 5 10

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 253

Asp Tyr Cys Gly Pro Glu Tyr Asp Glu Ser Val His Cys Ile
1 5 10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Ala Asp Cys Gly Pro Asp Gly Asp Glu Ser Ile Ile Cys His
1 5 10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Phe Tyr Cys Gly Pro Glu Leu Asp Glu Ser Leu Thr Cys Val
1 5 10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Ile Leu Cys Gly Pro Glu Val Glu Glu Asp Tyr Tyr Cys Tyr
1 5 10

<210> SEQ ID NO 257
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 257

His Leu Cys Trp Pro Asp Trp Glu Glu Tyr His Ser Cys Asp
1 5 10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Ile Phe Cys Trp Pro Asp Trp Glu Asp Tyr Asn Phe Cys Thr
1 5 10

<210> SEQ ID NO 259
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Ile Val Cys Gly Pro Asp Gly Asp Glu Thr Leu Ile Cys His
1 5 10

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 260

Ala Asp Cys Trp Pro Asp Trp Glu Trp Asp Tyr Thr Cys Asp
1 5 10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 261

Ile Thr Cys Gly Pro Glu Phe Asp Glu Ser Thr Thr Cys Asn
1 5 10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

Tyr His Cys Trp Pro Asp Trp Glu Glu Tyr Thr Ser Cys Asp
1 5 10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

Asn Tyr Cys Gly Pro Glu Val Glu Glu Tyr Ala Leu Cys Thr
1 5 10

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Phe Ile Cys Gly Pro Glu Met Asp Glu Ser Ile His Cys Asp
1 5 10

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Asp Asn Cys Trp Pro Asp Trp Glu Glu Phe Ala Val Cys Pro
1 5 10

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Tyr Asp Cys Gly Pro Glu Leu Asp Glu Thr Val Val Cys Asp
1 5 10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Tyr Asp Cys Gly Pro Glu Phe Asp Glu Ser Ile Ala Cys Tyr
1 5 10

<210> SEQ ID NO 268
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 268

Ile Asp Cys Trp Pro Asp Trp Glu Tyr Thr Val His Cys Asp
1 5 10

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 269

Asp Asp Cys Gly Pro Glu Leu Asp Glu Ser Ile Ile Cys Ile
1 5 10

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 270

Val Tyr Cys Gly Pro Glu Tyr Asp Glu Ser Ser Phe Cys Phe
1 5 10

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 271

Phe Asn Cys Trp Pro Asp Trp Glu Asp Pro Tyr Phe Cys Val
1 5 10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 272

Tyr Asp Cys Gly Pro Glu Tyr Asp Glu Ser Ser Tyr Cys Ser
1 5 10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 273

Val Ala Cys Trp Pro Asp Trp Glu Tyr Thr Asp Ser Cys Phe
1 5 10

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Thr Asp Cys Gly Pro Glu Phe Asp Glu Ser Val Ala Cys Tyr
1 5 10

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Thr Asp Cys Trp Pro Asp Trp Glu Phe Tyr Ala Asp Cys Asp
1 5 10

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Tyr Asp Cys Gly Pro Glu Leu Asp Glu Ser Val Ile Cys His
1 5 10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Ser Asp Cys Gly Pro Asp Gly Asp Glu Ser Ile Ile Cys Thr
1 5 10

<210> SEQ ID NO 278
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Tyr Tyr Cys Gly Pro Glu Phe Asp Glu Ser Ile Asp Cys Asp
1 5 10

<210> SEQ ID NO 279
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 279

Phe Phe Cys Gly Pro Glu Ile Asp Glu Ser Ile Ala Cys Val
1 5 10

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 280

Asp Tyr Cys Gly Pro Glu Phe Asp Glu Ser Thr Phe Cys Asp
1 5 10

<210> SEQ ID NO 281
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 281

Tyr Asp Cys Gly Pro Glu Trp Glu Trp Pro Ile Asp Cys Val
1 5 10

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 282

Phe Tyr Cys Gly Pro Glu Ile Glu Leu Phe Ser Phe Cys Tyr
1 5 10

<210> SEQ ID NO 283
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Tyr Tyr Cys Gly Pro Glu Val Asp Glu Ser Ile Thr Cys Pro
1 5 10

<210> SEQ ID NO 284
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 284

Ile Leu Cys Gly Pro Glu Phe Asp Glu Ser Ile Asn Cys Asn
1 5 10

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Val Val Cys Gly Pro Ala Met Gly Gln His Tyr Leu Cys Asp
1 5 10

<210> SEQ ID NO 286
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Val Val Cys Gly Thr Lys Met Gly Glu His Tyr Leu Cys Ser
1 5 10

<210> SEQ ID NO 287
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Tyr Asp Cys Trp Pro Asp Trp Glu Tyr Val Tyr Ala Cys Tyr
1 5 10

<210> SEQ ID NO 288
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

Asp Leu Cys Gly Pro Glu Leu Asp Glu Ser Val Asn Cys Asp
1 5 10

<210> SEQ ID NO 289
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

Tyr Tyr Cys Gly Pro Glu Phe Asp Glu Ser Thr Val Cys Tyr
1 5 10

<210> SEQ ID NO 290
<211> LENGTH: 14

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 290

Leu Asp Cys Trp Pro Asp Trp Glu Trp Pro Tyr Ser Cys Asn
1 5 10

<210> SEQ ID NO 291
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 291

Phe Ile Cys Trp Pro Asp Trp Glu Asp Asp Phe Phe Cys Tyr
1 5 10

<210> SEQ ID NO 292
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 292

Asp Leu Cys Gly Pro Glu Val Glu Trp Tyr Phe Phe Cys Asn
1 5 10

<210> SEQ ID NO 293
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 293

Tyr Asp Cys Gly Pro Glu Leu Asp Glu Ser Ile Val Cys Phe
1 5 10

<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 294

Leu Asn Cys Trp Pro Val Trp Glu Asp Asp Val Phe Cys Tyr
1 5 10

<210> SEQ ID NO 295
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 295

Phe Asn Cys Trp Pro Asp Trp Glu Asp Pro Asn Phe Cys Val
1 5 10

<210> SEQ ID NO 296
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Val Ile Cys Trp Pro Asp Trp Glu Asp Asp Tyr Phe Cys Pro
1 5 10

<210> SEQ ID NO 297
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Phe Leu Cys Gly Pro Glu Phe Asp Glu Ser Ser Val Cys Tyr
1 5 10

<210> SEQ ID NO 298
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Tyr Asp Cys Gly Pro Glu Leu Asp Glu Ser Ile Phe Cys Tyr
1 5 10

<210> SEQ ID NO 299
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

His Leu Cys Gly Pro Asp Gly Asp Glu Ser Phe Thr Cys Phe
1 5 10

<210> SEQ ID NO 300
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Tyr Phe Cys Gly Pro Glu Met Asp Glu Ser Leu Tyr Cys Ile
1 5 10

<210> SEQ ID NO 301
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 301

Tyr Tyr Cys Gly Pro Glu Val Glu Glu Tyr Ala Asn Cys Tyr
1 5 10

<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Asn Thr Cys Gly Pro Glu Phe Asp Glu Ser Thr Ala Cys Tyr
1 5 10

<210> SEQ ID NO 303
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 303

Ile Asp Cys Trp Pro Asp Trp Glu Glu Ala Phe Asn Cys Tyr
1 5 10

<210> SEQ ID NO 304
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Ala Tyr Cys Gly Pro Glu Leu Glu Glu Phe Phe Leu Cys Thr
1 5 10

<210> SEQ ID NO 305
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Ile Tyr Cys Gly Pro Glu Val Glu Glu Val His His Cys Tyr
1 5 10

<210> SEQ ID NO 306
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Phe Phe Cys Gly Pro Glu Phe Asp Glu Ser Val Ala Cys Asp
1 5 10

<210> SEQ ID NO 307
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Tyr Asp Cys Gly Pro Glu Leu Asp Glu Thr Ile Ile Cys Ala
1 5 10

<210> SEQ ID NO 308
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Ile Leu Cys Gly Pro Glu Trp Glu Tyr Pro Leu Asp Cys Ser
1 5 10

<210> SEQ ID NO 309
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Phe Ile Cys Gly Pro Glu Phe Asp Glu Ser Thr Thr Cys Asn
1 5 10

<210> SEQ ID NO 310
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 310

Phe Tyr Cys Gly Pro Glu Leu Asp Glu Ser Val Ser Cys Asp
1 5 10

<210> SEQ ID NO 311
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

His Leu Cys Gly Pro Glu Leu Asp Glu Ser Val Thr Cys Phe
1 5 10

<210> SEQ ID NO 312
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 312

Leu Ile Cys Gly Pro Glu Val Glu Asp Tyr Ser Leu Cys His
1 5 10

<210> SEQ ID NO 313
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Tyr Phe Cys Gly Pro Glu Met Asp Glu Ser Val Tyr Cys Asp
1 5 10

<210> SEQ ID NO 314
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

His Tyr Cys Gly Pro Glu Met Asp Glu Ser Ile Tyr Cys Ile
1 5 10

<210> SEQ ID NO 315
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 315

Phe Asp Cys Gly Pro Glu Leu Asp Glu Ser Ile Asn Cys Asp
1 5 10

<210> SEQ ID NO 316
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Tyr Tyr Cys Gly Pro Glu Val Glu Glu Tyr Ile Tyr Cys Thr
1 5 10

<210> SEQ ID NO 317
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 317

Leu Ala Cys Trp Pro Val Arg Glu Glu Ile Asn Ala Cys Ile
1               5                   10

<210> SEQ ID NO 318
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ile Asp Cys Trp Pro Asp Trp Glu Asp Ile Thr Phe Cys Asp
1               5                   10

<210> SEQ ID NO 319
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ile Val Cys Gly Pro Glu Leu Asp Glu Ser Ile Thr Cys Pro
1               5                   10

<210> SEQ ID NO 320
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Phe Tyr Cys Gly Pro Glu Phe Glu Leu Pro Ala Asp Cys Asp
1               5                   10

<210> SEQ ID NO 321
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Phe Asp Cys Gly Pro Glu Phe Asp Glu Ser Asn Pro Cys Phe
1               5                   10

<210> SEQ ID NO 322
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Asp Ala Cys Trp Pro Asp Trp Glu Glu Tyr Ser Ser Cys Asp
1               5                   10

<210> SEQ ID NO 323
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Asp His Cys Trp Pro Asp Trp Glu Pro Asn Tyr Phe Cys Val
1 5 10

<210> SEQ ID NO 324
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Asp Tyr Cys Trp Pro Asp Trp Glu Ile Asn Tyr Ile Cys Phe
1 5 10

<210> SEQ ID NO 325
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Ile Tyr Cys Trp Pro Asp Trp Glu Tyr Val Tyr Ala Cys Asn
1 5 10

<210> SEQ ID NO 326
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 326

Asp Phe Cys Gly Pro Glu Val Glu Glu Asp Tyr Leu Cys Asp
1 5 10

<210> SEQ ID NO 327
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

His Asp Cys Gly Pro Asp Gly Arg Glu Asp Tyr Asp Cys Ala
1 5 10

<210> SEQ ID NO 328
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Leu Ala Cys Trp Pro Asp Trp Glu Asp Asp Tyr Phe Cys Val
1 5 10

<210> SEQ ID NO 329
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 329

Asp Ile Cys Trp Pro Asp Trp Glu Asp Tyr Leu Pro Cys Val
1 5 10

<210> SEQ ID NO 330
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Ile Leu Cys Gly Pro Glu Ile Glu Val Tyr Ala Leu Cys Pro
1 5 10

<210> SEQ ID NO 331
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Ile Phe Cys Gly Pro Glu Trp Glu Phe Ser Val Leu Cys Asn
1 5 10

<210> SEQ ID NO 332
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Thr Tyr Cys Gly Pro Glu Val Glu Asp Phe Ser Leu Cys Val
1 5 10

<210> SEQ ID NO 333
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Phe Ile Cys Gly Pro Glu Trp Glu Phe Val Asp Ala Cys Phe
1 5 10

<210> SEQ ID NO 334
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Phe Ala Cys Trp Pro Asp Trp Glu Glu Asp Ser Pro Cys Asp
1 5 10

<210> SEQ ID NO 335
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 335

Ile Leu Cys Gly Pro Glu Val Glu Glu Leu Ile Phe Cys Pro
1 5 10

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Phe Tyr Cys Gly Pro Glu Val Glu Glu Tyr Ile Tyr Cys Tyr
1 5 10

<210> SEQ ID NO 337
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Asp Ser Cys Gly Pro Glu Leu Asp Glu Ser Ile Ile Cys Asp
1 5 10

<210> SEQ ID NO 338
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Phe Leu Cys Gly Pro Asp Gly Asp Glu Thr Ser Val Cys Asp
1 5 10

<210> SEQ ID NO 339
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Phe Asn Cys Trp Pro Asn Gly Glu Pro Thr Tyr Phe Cys Val
1               5                   10

<210> SEQ ID NO 340
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Leu Ala Cys Trp Pro Val Trp Glu Tyr Pro Val Thr Cys Ile
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asp Tyr Cys Gly Pro Glu Val Glu Glu Asp Val Tyr Cys Tyr
1               5                   10

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ile Thr Cys Trp Pro Asp Trp Glu Glu Tyr Ala Asn Cys Thr
1               5                   10

<210> SEQ ID NO 343
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Phe Phe Cys Gly Pro Asp Gly Asp Glu Thr Tyr Ser Cys Ile
1               5                   10

<210> SEQ ID NO 344
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Thr Asp Cys Trp Pro Asp Trp Glu Tyr Ala Thr Ser Cys Asp
1               5                   10

<210> SEQ ID NO 345
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Phe Asn Cys Gly Pro Asp Gly Tyr Glu Asp Tyr Leu Cys Asp
1 5 10

<210> SEQ ID NO 346
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

Tyr Asp Cys Trp Pro Asp Trp Glu Val Asp Phe His Cys Pro
1 5 10

<210> SEQ ID NO 347
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

Asn Ile Cys Trp Pro Asp Trp Glu Asp Asp Ser Phe Cys Phe
1 5 10

<210> SEQ ID NO 348
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Ala Thr Cys Gly Pro Glu Phe Asp Glu Ser Ile Gly Cys Ser
1 5 10

<210> SEQ ID NO 349
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 349

Ser Tyr Cys Gly Pro Glu Phe Asp Glu Ser Thr Phe Cys Asp
1 5 10

<210> SEQ ID NO 350
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 350

Pro Ile Cys Gly Pro Glu Tyr Asp Glu Ser Asp Val Cys Ala
1 5 10

<210> SEQ ID NO 351
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Tyr Tyr Cys Gly Pro Asp Gly Asp Glu Tyr Asn Ser Cys Ile
1 5 10

<210> SEQ ID NO 352
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Val Asp Cys Trp Pro Asp Trp Glu Val Phe Ile Ala Cys Asp
1 5 10

<210> SEQ ID NO 353
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Asp Leu Cys Gly Pro Glu Val Glu Glu Val Asn Leu Cys Leu
1 5 10

<210> SEQ ID NO 354
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Phe Asp Cys Gly Pro Glu Met Asp Glu Ser Thr Thr Cys Phe
1 5 10

<210> SEQ ID NO 355
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

Asn Phe Cys Trp Pro Asp Trp Glu Pro Ile Tyr Phe Cys Thr
1 5 10

<210> SEQ ID NO 356
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Val Asp Cys Gly Pro Asp Gly Asp Glu Ser Phe Phe Cys Leu
1               5                   10

<210> SEQ ID NO 357
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Val Asp Cys Gly Pro Asp Gly Asp Glu Thr Ala Phe Cys Ile
1               5                   10

<210> SEQ ID NO 358
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Asn Ile Cys Gly Pro Glu Met Asp Glu Ser Leu Val Cys Ile
1               5                   10

<210> SEQ ID NO 359
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ile Ile Cys Gly Pro Glu Phe Asp Glu Ser Phe Phe Cys Phe
1               5                   10

<210> SEQ ID NO 360
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asn Phe Cys Gly Pro Glu Tyr Asp Glu Ser Ile Ser Cys Ile
1               5                   10

<210> SEQ ID NO 361
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

His Leu Cys Gly Pro Glu Ile Glu Glu Ala Asp Ile Cys Asn
1 5 10

<210> SEQ ID NO 362
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Asp Tyr Cys Gly Pro Glu Val Glu Glu Asp Tyr Leu Cys Asp
1 5 10

<210> SEQ ID NO 363
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 363

Asp Tyr Cys Gly Pro Glu Leu Asp Glu Ser Ile Asn Cys Asp
1 5 10

<210> SEQ ID NO 364
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Phe Tyr Cys Gly Pro Glu Leu Asp Glu Ser Leu Phe Cys Val
1 5 10

<210> SEQ ID NO 365
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Pro Asp Cys Gly Pro Glu Trp Glu Phe Tyr Val Thr Cys Asn
1 5 10

<210> SEQ ID NO 366
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 366

Phe Asp Cys Gly Pro Glu Phe Glu Tyr Ile Tyr Ala Cys Thr
1 5 10

<210> SEQ ID NO 367
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 367

Asp Tyr Cys Gly Pro Glu Phe Asp Glu Ser Ser Ile Cys Asn
1 5 10

<210> SEQ ID NO 368
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 368

Asp Phe Cys Gly Pro Glu Val Glu Glu Tyr Ile Phe Cys Phe
1 5 10

<210> SEQ ID NO 369
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 369

Pro Val Cys Trp Pro Asp Trp Glu Tyr Val Ser Ser Cys Asp
1 5 10

<210> SEQ ID NO 370
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 370

Tyr Ile Cys Gly Pro Glu Arg Asp Glu Ser Asn Leu Cys Leu
1 5 10

<210> SEQ ID NO 371
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 371

Tyr Asp Cys Gly Pro Glu Leu Asp Glu Ser Ile Val Cys Asp
1 5 10

<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 372

His Asp Cys Trp Pro Asp Trp Glu Asp Phe Tyr Phe Cys Val
1 5 10

<210> SEQ ID NO 373
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 373

His Tyr Cys Gly Pro Glu Tyr Asp Glu Ser Ile Asp Cys Tyr
1 5 10

<210> SEQ ID NO 374
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 374

Leu Phe Cys Gly Pro Glu Met Pro Glu Asp Ile Phe Cys Asn
1 5 10

<210> SEQ ID NO 375
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 375

His Asp Cys Gly Pro Glu Leu Glu Phe His Tyr Ala Cys Tyr
1 5 10

<210> SEQ ID NO 376
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 376

Asp Phe Cys Gly Pro Glu Leu Asp Glu Ser Ile Asn Cys Phe
1 5 10

<210> SEQ ID NO 377
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

Tyr Phe Cys Gly Pro Glu Leu Asp Glu Ser Ile Ala Cys Asn
1 5 10

<210> SEQ ID NO 378
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 378

Thr Asp Cys Trp Pro Asp Trp Glu Asp Asp Ile Ile Cys Asp
1 5 10

<210> SEQ ID NO 379
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 379

Tyr Asp Cys Gly Pro Glu Leu Asp Glu Ser Ile Tyr Cys Phe
1 5 10

<210> SEQ ID NO 380
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 380

Tyr Tyr Cys Trp Pro Asp Trp Trp Glu Tyr Val Thr Cys Asp
1 5 10

<210> SEQ ID NO 381
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 381

Pro Ile Cys Gly Pro Glu Leu Glu Glu Ser Tyr Leu Cys Asn
1 5 10

<210> SEQ ID NO 382
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 382

Phe Asp Cys Gly Pro Glu Phe Asp Glu Ser Ile Val Cys Tyr
1 5 10

<210> SEQ ID NO 383
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 383

Val Leu Cys Gly Pro Asp Gly Ile Glu Phe Phe Asp Cys Pro
1 5 10

<210> SEQ ID NO 384
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

Ala Tyr Cys Gly Pro Glu Tyr Asp Glu Ser Leu Thr Cys Val
1 5 10

<210> SEQ ID NO 385
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 385

Asp Phe Cys Gly Pro Glu Leu Asp Glu Ser Ile Ile Cys Ala
1 5 10

<210> SEQ ID NO 386
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 386

Tyr Asp Cys Gly Pro Glu Phe Asp Glu Ser Leu Asp Cys Asn
1 5 10

<210> SEQ ID NO 387
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Ala Ile Cys Gly Pro Glu Phe Asp Glu Ser Val Ala Cys Asp
1 5 10

<210> SEQ ID NO 388
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

Leu Leu Cys Gly Pro Asp Gly Val Glu Asp Phe Phe Cys Asp
1 5 10

<210> SEQ ID NO 389
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Asn Phe Cys Gly Pro Glu Leu Pro Glu Asp Ile Phe Cys Phe
1 5 10

<210> SEQ ID NO 390
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 390

Phe Tyr Cys Gly Pro Glu Val Glu Glu Val Ser Leu Cys Asn
1 5 10

<210> SEQ ID NO 391
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 391

Tyr Asp Cys Gly Pro Asp Gly Tyr Glu Ala Phe Tyr Cys His
1 5 10

<210> SEQ ID NO 392
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 392

Asn Phe Cys Gly Pro Glu Ile Glu Phe Asp Tyr Leu Cys Asp
1 5 10

<210> SEQ ID NO 393
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 393

Asp Tyr Cys Gly Pro Asp Gly Val Glu Asp Phe Ile Cys Asn
1 5 10

<210> SEQ ID NO 394
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 394

Thr Asp Cys Trp Pro Asp Trp Glu Tyr Ile Tyr Ser Cys Ser
1 5 10

<210> SEQ ID NO 395
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 395

Phe Tyr Cys Gly Pro Glu Phe Glu Glu Ile Thr Asn Cys Ile
1 5 10

<210> SEQ ID NO 396
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Phe Asp Cys Trp Pro Asp Trp Glu Glu Ser Phe Phe Cys His
1 5 10

<210> SEQ ID NO 397
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 397

Asp Phe Cys Gly Pro Asp Gly Asp Glu Ser Val Phe Cys Pro
1 5 10

<210> SEQ ID NO 398
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

His Asn Cys Gly Pro Glu Leu Asp Glu Ser Leu Val Cys Asp
1 5 10

<210> SEQ ID NO 399
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Ile Tyr Cys Gly Pro Asp Gly Ala Glu Asp Tyr Thr Cys Asp
1 5 10

<210> SEQ ID NO 400
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Phe Asp Cys Gly Pro Glu Phe Glu Phe Pro Val Ile Cys Phe
1               5                   10

<210> SEQ ID NO 401
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Tyr Asn Cys Gly Pro Glu Leu Asp Glu Ser Val Thr Cys Asp
1               5                   10

<210> SEQ ID NO 402
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Phe Asp Cys Gly Pro Glu Leu Asp Glu Ser Ile His Cys Ala
1               5                   10

<210> SEQ ID NO 403
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Asp Ile Cys Gly Pro Glu Val Glu Glu Tyr Phe Leu Cys Phe
1               5                   10

<210> SEQ ID NO 404
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Phe Asp Cys Gly Pro Glu Val Asp Glu Ser Leu Thr Cys Phe
1               5                   10

<210> SEQ ID NO 405
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Phe Asp Cys Gly Pro Glu Ile Glu Glu Phe His Leu Cys Phe
1 5 10

<210> SEQ ID NO 406
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 406

Ala Tyr Cys Gly Pro Glu Leu Asp Glu Ser Ile Ile Cys Asp
1 5 10

<210> SEQ ID NO 407
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 407

Tyr Asn Cys Gly Pro Glu Leu Asp Glu Ser Ile Thr Cys Asn
1 5 10

<210> SEQ ID NO 408
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 408

Phe Asp Cys Trp Pro Asp Trp Glu Glu Pro Val Asp Cys Leu
1 5 10

<210> SEQ ID NO 409
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 409

Asp Val Cys Gly Pro Glu Leu Asp Glu Ser Val Leu Cys Pro
1 5 10

<210> SEQ ID NO 410
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 410

Asn Tyr Cys Gly Pro Glu Leu Asp Glu Ser Leu Pro Cys Pro
1 5 10

<210> SEQ ID NO 411
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Tyr Tyr Cys Trp Pro Asp Trp Glu Tyr Asp Ile Phe Cys Ser
1 5 10

<210> SEQ ID NO 412
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Asp Asp Cys Gly Pro Glu Phe Asp Glu Ser Thr Tyr Cys Asn
1 5 10

<210> SEQ ID NO 413
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 413

Phe Tyr Cys Gly Pro Glu Phe Glu Glu Val Phe His Cys Tyr
1 5 10

<210> SEQ ID NO 414
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 414

Thr Asp Cys Trp Pro Asp Trp Glu Glu Tyr Phe Leu Cys Asp
1 5 10

<210> SEQ ID NO 415
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 415

Val Tyr Cys Gly Pro Glu Trp Glu Glu Ser Tyr Leu Cys Pro
1 5 10

<210> SEQ ID NO 416
<211> LENGTH: 14
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 416

Asp Asp Cys Gly Pro Asn Gly Tyr Ala Thr Phe Ile Cys Tyr
1 5 10

<210> SEQ ID NO 417
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Phe Leu Cys Gly Pro Glu Ile Glu Asp Asp Thr His Cys Tyr
1 5 10

<210> SEQ ID NO 418
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Phe Ala Cys Trp Pro Asp Trp Glu Glu Thr Ile Pro Cys His
1 5 10

<210> SEQ ID NO 419
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 419

Val Leu Cys Gly Pro Glu Phe Asp Glu Ser Tyr Asn Cys Tyr
1 5 10

<210> SEQ ID NO 420
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 420

Tyr Asp Cys Gly Pro Glu Phe Asp Glu Ser Ile Ser Cys Ile
1 5 10

<210> SEQ ID NO 421
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 421

Tyr Asp Cys Gly Pro Glu Phe Asp Glu Ser Val Asn Cys Tyr
1 5 10

<210> SEQ ID NO 422
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 422

Ala Ile Cys Trp Pro Asp Trp Glu Glu Phe Val Asp Cys Tyr
1 5 10

<210> SEQ ID NO 423
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 423

Leu Thr Cys Trp Pro Val Arg Glu Glu Ile Phe Ala Cys Asp
1 5 10

<210> SEQ ID NO 424
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Val Leu Cys Gly Pro Glu Phe Asp Glu Ser Tyr Tyr Cys Asn
1 5 10

<210> SEQ ID NO 425
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 425

Asn Val Cys Gly Pro Glu Tyr Asp Glu Ser Ala Pro Cys Asn
1 5 10

<210> SEQ ID NO 426
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 426

His Asp Cys Gly Pro Glu Phe Asp Glu Ser Ile Ser Cys Val
1 5 10

<210> SEQ ID NO 427
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 427

Phe Asp Cys Gly Pro Glu Leu Asp Glu Thr Val Asp Cys Asn
1 5 10

<210> SEQ ID NO 428
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

Tyr Phe Cys Gly Pro Glu Val Glu Glu His Phe Tyr Cys Tyr
1 5 10

<210> SEQ ID NO 429
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 429

Asp Tyr Cys Gly Pro Glu Leu Asp Glu Ser Ile Ile Cys His
1 5 10

<210> SEQ ID NO 430
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 430

Asp Asp Cys Gly Pro Glu Val Pro Glu Asp Ile Thr Cys Tyr
1 5 10

<210> SEQ ID NO 431
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 431

Asp Asn Cys Gly Pro Glu Leu Asp Glu Ser Val Val Cys Asp
1 5 10

<210> SEQ ID NO 432
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 432

Val His Cys Trp Pro Asp Trp Glu Pro Asn Tyr Val Cys Asp
1 5 10

<210> SEQ ID NO 433
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 433

Asp Tyr Cys Gly Pro Glu Leu Asp Glu Ser Leu Phe Cys Leu
1 5 10

<210> SEQ ID NO 434
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 434

Asp Asp Cys Gly Pro Glu Leu Asp Glu Ser Val Val Cys Ala
1 5 10

<210> SEQ ID NO 435
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 435

Ala Ala Cys Gly Pro Glu Leu Asp Glu Ser Ile Val Cys Asp
1 5 10

<210> SEQ ID NO 436
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 436

Asp Phe Cys Gly Pro Glu Phe Glu Glu Ile Asn Asn Cys Phe
1 5 10

<210> SEQ ID NO 437
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 437

Tyr Tyr Cys Gly Pro Glu Phe Asp Glu Ser Asn Ala Cys Tyr
1 5 10

<210> SEQ ID NO 438
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 438

Val Leu Cys Gly Pro Glu Phe Asp Glu Ser Asn Ser Cys Tyr
1 5 10

<210> SEQ ID NO 439
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 439

Tyr Asp Cys Gly Pro Glu Phe Asp Glu Ser Ile Asp Cys Asp
1 5 10

<210> SEQ ID NO 440
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 440

Asp Ser Cys Gly Pro Glu Phe Glu Phe Tyr Tyr Val Cys Phe
1 5 10

<210> SEQ ID NO 441
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 441

Tyr Ile Cys Gly Pro Glu Leu Asp Glu Ser Leu Ile Cys His
1 5 10

<210> SEQ ID NO 442
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Phe Asp Cys Gly Pro Glu Val Glu Glu Asp Tyr Phe Cys Tyr
1 5 10

<210> SEQ ID NO 443
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 443

Phe Asp Cys Gly Pro Glu Tyr Asp Glu Ser Leu Tyr Cys Phe
1 5 10

<210> SEQ ID NO 444
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 444

Val Leu Cys Gly Pro Asp Gly Asp Glu Tyr Ser Phe Cys His
1 5 10

<210> SEQ ID NO 445
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 445

Ile Pro Cys Gly Pro Glu Met Asp Glu Ser Val Val Cys Asn
1 5 10

<210> SEQ ID NO 446
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 446

Ile Ile Cys Gly Pro Asp Gly Tyr Glu Asp Phe Thr Cys Asp
1 5 10

<210> SEQ ID NO 447
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 447

Ile Phe Cys Gly Pro Glu Leu Asp Glu Ser Ile Ile Cys Tyr
1 5 10

<210> SEQ ID NO 448
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 448

Val Asp Cys Gly Pro Glu Phe Asp Glu Ser Tyr Asp Cys Tyr
1 5 10

<210> SEQ ID NO 449
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 449

Leu Ser Cys Gly Pro Glu Met Asp Glu Ser Leu Tyr Cys Asp
1 5 10

<210> SEQ ID NO 450
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 450

Tyr Asp Cys Trp Pro Asp Trp Glu Tyr Asn Ile Asp Cys Thr
1 5 10

<210> SEQ ID NO 451
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 451

Asn His Cys Gly Pro Asp Gly Asp Glu Thr Ile Val Cys Phe
1 5 10

<210> SEQ ID NO 452
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 452

Asn Phe Cys Gly Pro Glu Leu Asp Glu Ser Ile Pro Cys His
1 5 10

<210> SEQ ID NO 453
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 453

Phe His Cys Gly Pro Glu Ile Glu Glu Tyr Ala Leu Cys Asp
1 5 10

<210> SEQ ID NO 454
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 454

Val Tyr Cys Gly Pro Glu Val Glu Asp Tyr Asn Leu Cys Tyr
1 5 10

<210> SEQ ID NO 455
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 455

Val Tyr Cys Gly Pro Asp Gly Asp Glu Leu Ala Asn Cys Tyr
1               5                   10

<210> SEQ ID NO 456
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 456

Leu Ile Cys Gly Pro Val Ile Ala Glu Asp Leu Pro Cys Asn
1               5                   10

<210> SEQ ID NO 457
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 457

Asp Ile Cys Gly Pro Glu Ile Pro Glu Asp Val Ser Cys Asp
1               5                   10

<210> SEQ ID NO 458
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 458

Ile Tyr Cys Gly Pro Glu Trp Glu Glu Ala Asp Tyr Cys Asp
1               5                   10

<210> SEQ ID NO 459
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 459

Ile Asp Cys Trp Pro Asp Trp Glu Asp Asp Ser Ile Cys Tyr
1               5                   10

<210> SEQ ID NO 460
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 460

Val Leu Cys Gly Pro Glu Val Glu Asp Phe Thr Leu Cys Asp
1 5 10

<210> SEQ ID NO 461
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 461

Leu Tyr Cys Gly Pro Val Ile Glu Glu Ile Tyr Tyr Cys Tyr
1 5 10

<210> SEQ ID NO 462
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 462

Phe Phe Cys Gly Pro Glu Phe Glu Val His Ser Asp Cys Asn
1 5 10

<210> SEQ ID NO 463
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 463

Asn Asp Cys Gly Pro Glu Val Glu Leu Val Ser Asp Cys Asn
1 5 10

<210> SEQ ID NO 464
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 464

Asp Leu Cys Gly Pro Glu Leu Asp Glu Ser Thr Val Cys Asp
1 5 10

<210> SEQ ID NO 465
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 465

Ile Pro Cys Gly Pro Glu Val Glu Asp Tyr Asn Leu Cys Asn
1 5 10

<210> SEQ ID NO 466
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 466

Tyr Tyr Cys Gly Pro Glu Leu Glu Trp Pro Val Val Cys Asn
1 5 10

<210> SEQ ID NO 467
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 467

Tyr Asp Cys Gly Pro Glu Leu Asp Glu Ser Val Ile Cys Asn
1 5 10

<210> SEQ ID NO 468
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 468

Val Tyr Cys Gly Pro Asp Gly Asp Glu Ser Phe Asp Cys Ala
1 5 10

<210> SEQ ID NO 469
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Asn Asp Cys Gly Pro Glu Trp Glu Asp Thr Tyr Phe Cys Leu
1 5 10

<210> SEQ ID NO 470
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 470

Pro Tyr Cys Gly Pro Glu Met Glu Glu Leu Ser Asn Cys Ser
1 5 10

<210> SEQ ID NO 471
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 471

Asp Asp Cys Gly Pro Glu Phe Glu Val Ile Ser Asp Cys Tyr
1 5 10

<210> SEQ ID NO 472
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 472

Asp Leu Cys Gly Pro Glu Phe Pro Glu Asp Val Pro Cys Asp
1 5 10

<210> SEQ ID NO 473
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 473

Ile Tyr Cys Gly Pro Glu Phe Asp Glu Ser Phe Val Cys Tyr
1 5 10

<210> SEQ ID NO 474
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

Ala Tyr Cys Gly Pro Glu Tyr Glu Val Phe Ala Asp Cys Asn
1 5 10

<210> SEQ ID NO 475
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

Ile Asp Cys Gly Pro Glu Tyr Asp Glu Ser Val Asp Cys Leu
1 5 10

<210> SEQ ID NO 476
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

His Ile Cys Trp Pro Asp Trp Glu Glu Phe His Asp Cys Asn
1 5 10

<210> SEQ ID NO 477
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 477

Tyr Asp Cys Gly Pro Glu Leu Asp Glu Thr Ile Thr Cys Leu
1 5 10

<210> SEQ ID NO 478
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 478

Tyr Leu Cys Gly Pro Glu Leu Asp Glu Thr Ile Leu Cys Asn
1 5 10

<210> SEQ ID NO 479
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 479

Phe Phe Cys Gly Pro Glu Phe Glu Glu Ala Phe Leu Cys Phe
1 5 10

<210> SEQ ID NO 480
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 480

Ile Leu Cys Gly Pro Glu Leu Asp Glu Ser Phe Thr Cys Ala
1 5 10

<210> SEQ ID NO 481
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 481

Phe His Cys Gly Pro Glu Val Glu Leu Tyr Thr Asp Cys Asn
1 5 10

<210> SEQ ID NO 482
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 482

Asn Leu Cys Gly Pro Glu Val Glu Glu Tyr Asn Phe Cys Tyr
1 5 10

<210> SEQ ID NO 483
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 483

Phe Asp Cys Gly Pro Glu Val Glu Glu Thr Tyr Tyr Cys Phe
1 5 10

<210> SEQ ID NO 484
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 484

Val Phe Cys Gly Pro Glu Phe Glu Glu Asp His Tyr Cys Tyr
1 5 10

<210> SEQ ID NO 485
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 485

Ala Ile Cys Gly Pro Glu Trp Glu Val Val Ala Asp Cys Asn
1 5 10

<210> SEQ ID NO 486
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 486

Phe Ile Cys Trp Pro Asp Trp Glu Glu Asp Asn Tyr Cys Asn
1 5 10

<210> SEQ ID NO 487
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 487

Ile Tyr Cys Gly Pro Glu Phe Asp Glu Ser Phe Ile Cys Asp
1 5 10

<210> SEQ ID NO 488
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 488

Asn Leu Cys Gly Pro Glu Val Glu Asp Val Tyr Asp Cys His
1 5 10

<210> SEQ ID NO 489
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 489

His Tyr Cys Gly Pro Glu Val Glu Glu Tyr His Asn Cys Asn
1 5 10

<210> SEQ ID NO 490
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 490

Asp Ile Cys Gly Pro Glu Tyr Asp Glu Ser Tyr Ser Cys Thr
1 5 10

<210> SEQ ID NO 491
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 491

Asp Tyr Cys Gly Pro Glu Leu Asp Glu Thr Leu Ile Cys Ala
1 5 10

<210> SEQ ID NO 492
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 492

Ile Ala Cys Gly Pro Glu Met Pro Glu Asp Ile Asp Cys Tyr
1 5 10

<210> SEQ ID NO 493
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 493

Ile Asp Cys Gly Pro Glu Leu Asp Glu Ser Ile Phe Cys Asp
1 5 10

<210> SEQ ID NO 494
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 494

Tyr Phe Cys Gly Pro Asp Val Glu Glu Asp Phe Ala Cys Asp
1 5 10

<210> SEQ ID NO 495
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 495

Tyr Asn Cys Gly Pro Glu Trp Glu Tyr Ala Ile Leu Cys Asp
1 5 10

<210> SEQ ID NO 496
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 496

Ile Tyr Cys Gly Pro Glu Val Glu Asp Tyr Ile Val Cys Asn
1 5 10

<210> SEQ ID NO 497
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 497

Tyr Asp Cys Gly Pro Glu Ile Asp Glu Ser Thr Pro Cys Ala
1 5 10

<210> SEQ ID NO 498
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 498

Asp Thr Cys Trp Pro Asp Trp Glu His Ile Tyr Ala Cys Asp
1 5 10

<210> SEQ ID NO 499
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 499

Asp Ile Cys Gly Pro Glu Met Asp Glu Ser Val Thr Cys Asn
1 5 10

<210> SEQ ID NO 500
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 500

Tyr Asp Cys Trp Pro Asp Trp Glu Arg Tyr Phe Pro Cys Ile
1 5 10

<210> SEQ ID NO 501
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 501

His Leu Cys Gly Pro Glu Leu Asp Glu Ser Val Ala Cys Ser
1 5 10

<210> SEQ ID NO 502
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 502

Tyr Asp Cys Gly Pro Asp Gly Asp Glu Thr Thr Ile Cys Ala
1 5 10

<210> SEQ ID NO 503
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 503

Tyr Tyr Cys Gly Pro Glu Tyr Glu Asp Val Leu Asp Cys Phe
1 5 10

<210> SEQ ID NO 504
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 504

Asp Phe Cys Gly Pro Glu Met Asp Glu Thr Ile Ser Cys Asp
1 5 10

<210> SEQ ID NO 505
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Ile Leu Cys Gly Pro Glu Leu Asp Glu Ser Leu Val Cys Asp
1 5 10

<210> SEQ ID NO 506
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 506

Leu Ile Cys Gly Pro Glu Trp Glu Val Ile Thr Asn Cys Asp
1 5 10

<210> SEQ ID NO 507
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 507

Tyr Asp Cys Gly Pro Glu Phe Asp Glu Tyr Phe Gly Cys Pro
1 5 10

<210> SEQ ID NO 508
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 508

Ala Leu Cys Gly Pro Glu Val Glu Val Tyr Asp Val Cys Val
1 5 10

<210> SEQ ID NO 509
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 509

Tyr His Cys Trp Pro Asp Trp Glu Asp Val Asn Phe Cys Tyr
1 5 10

<210> SEQ ID NO 510
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 510

Phe Leu Cys Gly Pro Met Gly Gly Leu Thr Phe Tyr Cys Tyr
1 5 10

<210> SEQ ID NO 511
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 511

Ile Ile Cys Gly Pro Glu Phe Asp Glu Tyr Val Gly Cys Phe
1 5 10

<210> SEQ ID NO 512
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 512

Phe Phe Cys Gly Pro Glu Met Asp Glu Ser Val His Cys Phe
1 5 10

<210> SEQ ID NO 513
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 513

Ala Phe Cys Gly Pro Glu Phe Asp Glu Ser Leu Phe Cys Ala
1 5 10

<210> SEQ ID NO 514
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 514

Asn Tyr Cys Gly Pro Asp Gly Asp Glu Thr Asn Ile Cys Asp
1 5 10

<210> SEQ ID NO 515
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 515

Tyr Leu Cys Gly Pro Glu Trp Glu Trp Val His Asn Cys Leu
1 5 10

<210> SEQ ID NO 516
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 516

Ala Thr Cys Gly Pro Asp Gly Asp Glu Ser His Ile Cys Ala
1 5 10

<210> SEQ ID NO 517
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 517

Val Tyr Cys Gly Pro Glu Val Glu Val Leu Asp Tyr Cys Asp
1 5 10

<210> SEQ ID NO 518
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 518

Ile His Cys Gly Pro Glu Trp Glu Phe Tyr Thr Asp Cys Asp
1 5 10

<210> SEQ ID NO 519
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 519

Asp Asp Cys Gly Pro Glu Leu Asp Glu Thr Val Ala Cys Asp
1 5 10

<210> SEQ ID NO 520
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 520

Tyr Leu Cys Gly Pro Glu Phe Asp Glu Ser Ile Asp Cys Asn
1 5 10

<210> SEQ ID NO 521
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 521

Leu Leu Cys Gly Pro Glu Val Glu Asp Val Phe Ala Cys Tyr
1 5 10

<210> SEQ ID NO 522
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 522

Tyr Asp Cys Gly Pro Glu Leu Asp Glu Ser Leu Thr Cys Asp
1 5 10

<210> SEQ ID NO 523
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 523

Phe Asp Cys Gly Pro Glu Leu Asp Glu Thr Val Asn Cys Tyr
1 5 10

<210> SEQ ID NO 524
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 524

Phe Ala Cys Trp Pro Asp Trp Glu Glu Ile Asn Asp Cys His
1 5 10

<210> SEQ ID NO 525
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 525

Tyr Tyr Cys Gly Pro Glu Tyr Glu Glu Asp Ile Tyr Cys Asn
1 5 10

<210> SEQ ID NO 526
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 526

Asn Val Cys Gly Pro Glu Val Glu Asp Tyr Thr Phe Cys Tyr
1 5 10

<210> SEQ ID NO 527
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 527

Ala Tyr Cys Gly Pro Glu Leu Glu Glu Tyr Asp Phe Cys Thr
1 5 10

<210> SEQ ID NO 528
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 528

Phe Asp Cys Gly Pro Glu Ile Asp Glu Ser Thr Ile Cys Thr
1 5 10

<210> SEQ ID NO 529
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Asn Leu Cys Gly Pro Glu Leu Asp Glu Thr Leu Val Cys Ala
1 5 10

<210> SEQ ID NO 530
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 530

Tyr Ser Cys Trp Pro Asp Trp Glu Glu Tyr Leu Ala Cys Asn
1 5 10

<210> SEQ ID NO 531
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

Gly Ile Cys Gly Pro Glu Val Glu Asp Tyr Asn Tyr Cys Asp
1 5 10

<210> SEQ ID NO 532
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 532

Phe Phe Cys Gly Pro Glu Leu Asp Glu Ser Val Asn Cys His
1 5 10

<210> SEQ ID NO 533
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 533

Tyr Tyr Cys Gly Pro Glu Tyr Glu Glu Asp Phe Tyr Cys Phe
1 5 10

<210> SEQ ID NO 534
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 534

Leu Tyr Cys Gly Pro Glu Tyr Asp Glu Ser Thr Asp Cys Tyr
1 5 10

<210> SEQ ID NO 535
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 535

Asp Tyr Cys Gly Pro Glu Val Glu Glu Asp Phe Leu Cys Tyr
1 5 10

<210> SEQ ID NO 536
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 536

Thr Leu Cys Gly Pro Glu Val Glu Leu Tyr Ile Phe Cys Asp
1 5 10

<210> SEQ ID NO 537
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 537

Phe Tyr Cys Gly Pro Glu Phe Glu Gln Ile Ala Asp Cys Tyr
1 5 10

<210> SEQ ID NO 538
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 538

Asp Asp Cys Gly Pro Glu Val Glu Glu Tyr His Leu Cys Asp
1 5 10

<210> SEQ ID NO 539
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 539

Asp Tyr Cys Gly Pro Glu Leu Glu Asp Val Thr Leu Cys His
1 5 10

<210> SEQ ID NO 540
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 540

Val Leu Cys Gly Pro Glu Val Glu Asp Val Asn Leu Cys Tyr
1 5 10

<210> SEQ ID NO 541
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 541

Asp Ile Cys Gly Pro Glu Leu Asp Glu Thr Ile Asp Cys Tyr
1 5 10

<210> SEQ ID NO 542
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 542

Thr Tyr Cys Gly Pro Glu Val Glu Glu Asp Ile Asn Cys Tyr
1 5 10

<210> SEQ ID NO 543
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 543

Ile Val Cys Trp Pro Asp Trp Glu Glu Tyr Pro Asn Cys Asp
1 5 10

<210> SEQ ID NO 544
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 544

Ser Asp Cys Gly Pro Glu Leu Asp Glu Ser Ile Ile Cys Thr
1 5 10

<210> SEQ ID NO 545
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 545

Tyr Asp Cys Gly Pro Glu Leu Pro Glu Asp Tyr Asp Cys Asn
1 5 10

<210> SEQ ID NO 546
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 546

Asn Leu Cys Trp Pro Asp Trp Glu Glu Tyr Tyr Ala Cys Asp
1 5 10

<210> SEQ ID NO 547
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 547

Asp Asp Cys Gly Pro Glu Leu Asp Glu Ser Leu Pro Cys His
1 5 10

<210> SEQ ID NO 548
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 548

Ser Leu Cys Gly Pro Asp Gly Gln Glu Asp Tyr Thr Cys Phe
1 5 10

<210> SEQ ID NO 549
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 549

Leu Ile Cys Trp Pro Asp Trp Glu Glu Tyr Asn Phe Cys Thr
1 5 10

<210> SEQ ID NO 550
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 550

Phe His Cys Gly Pro Asp Gly Asp Glu Thr Val Pro Cys Ile
1 5 10

<210> SEQ ID NO 551
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 551

Phe Asp Cys Gly Pro Glu Trp Glu Trp Ile Tyr Asp Cys Phe
1 5 10

<210> SEQ ID NO 552
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 552

Ile Tyr Cys Gly Pro Glu Trp Asp Glu Ser Leu Asp Cys Asp
1 5 10

<210> SEQ ID NO 553
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 553

Leu Ile Cys Gly Pro Glu Ile Asp Glu Ser Ala Ser Cys Asn
1 5 10

<210> SEQ ID NO 554
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 554

Thr Ser Cys Trp Val Asp Trp Glu Glu Phe Ser Asp Cys Ile
1 5 10

<210> SEQ ID NO 555
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 555

Tyr Tyr Cys Gly Pro Glu Val Glu Glu Asp Tyr Val Cys Asp
1 5 10

<210> SEQ ID NO 556
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 556

Asp Asp Cys Gly Pro Glu Gln Glu Phe Ile Tyr Ala Cys Ile
1 5 10

<210> SEQ ID NO 557
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 557

Ala Asp Cys Trp Pro Asp Trp Glu Glu Tyr Ala Asp Cys Tyr
1 5 10

<210> SEQ ID NO 558
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 558

Tyr Tyr Cys Gly Pro Glu Phe Asp Glu Ser Ile His Cys Ile
1 5 10

<210> SEQ ID NO 559
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 559

Ser Glu Cys Trp Pro Asp Trp Glu Pro Phe Phe Asp Cys Asn
1 5 10

<210> SEQ ID NO 560
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 560

Tyr His Cys Gly Pro Glu Met Asp Glu Ser Leu Ile Cys Thr
1 5 10

<210> SEQ ID NO 561
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 561

Ser Asp Cys Trp Pro Asp Trp Glu Asp Ala Tyr Phe Cys Ile
1 5 10

<210> SEQ ID NO 562
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 562

Val Asp Cys Gly Pro Glu Val Glu Glu Tyr Tyr His Cys Asp
1 5 10

<210> SEQ ID NO 563
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 563

Asp Asn Cys Gly Pro Glu Tyr Asp Glu Ser Ile Ala Cys Asn
1 5 10

<210> SEQ ID NO 564
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 564

Leu Tyr Cys Gly Pro Val Phe Glu Phe Tyr Asp Tyr Cys Tyr
1 5 10

<210> SEQ ID NO 565
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 565

Tyr Thr Cys Gly Pro Glu Met Asp Glu Ser Val Thr Cys Ile
1 5 10

<210> SEQ ID NO 566
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 566

Asn Phe Cys Trp Pro Asp Trp Glu Val Asn Ser Phe Cys Asp
1 5 10

<210> SEQ ID NO 567
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 567

Asn Ala Cys Trp Pro Asp Trp Glu Tyr Ile Asp Phe Cys Asn
1 5 10

<210> SEQ ID NO 568
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 568

Tyr Asn Cys Gly Pro Glu Met Asp Glu Ser Ile Phe Cys Ser
1 5 10

<210> SEQ ID NO 569
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 569

Leu Asp Cys Gly Pro Glu Leu Asp Glu Ser Ile Thr Cys Tyr
1 5 10

<210> SEQ ID NO 570
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 570

His Tyr Cys Gly Pro Glu Phe Asp Glu Ser Ile Asn Cys Asp
1 5 10

<210> SEQ ID NO 571
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 571

Ile Ile Cys Gly Pro Glu Leu Pro Glu Asp Tyr Val Cys Thr
1 5 10

<210> SEQ ID NO 572
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 572

Asp Ile Cys Gly Pro Glu Phe Asp Glu Ser Ile Asp Cys Ser
1 5 10

<210> SEQ ID NO 573
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 573

Pro Tyr Cys Gly Pro Glu Phe Asp Glu Ser Val Leu Cys Phe
1 5 10

<210> SEQ ID NO 574
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 574

Val Phe Cys Gly Pro Glu Phe Asp Glu Ser Val Asp Cys Tyr
1 5 10

<210> SEQ ID NO 575
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 575

Tyr Asp Cys Trp Pro Asp Trp Glu Glu Ala Leu Pro Cys Ala
1 5 10

<210> SEQ ID NO 576
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 576

Asp Asp Cys Trp Pro Asp Trp Glu Asp Tyr Val Phe Cys Phe
1 5 10

<210> SEQ ID NO 577
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 577

His Phe Cys Gly Pro Glu Trp Glu Leu Phe Ser Asp Cys Tyr
1 5 10

<210> SEQ ID NO 578
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 578

Ile Thr Cys Trp Pro Asp Trp Glu Val Asn Phe Pro Cys Tyr
1 5 10

<210> SEQ ID NO 579
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 579

Pro Asp Cys Gly Pro Glu Leu Asp Glu Ser Ile Thr Cys Asn
1 5 10

<210> SEQ ID NO 580
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 580

Asn Leu Cys Trp Pro Asp Trp Glu Ala Phe Phe Pro Cys Tyr
1 5 10

<210> SEQ ID NO 581
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 581

Phe Tyr Cys Gly Pro Glu Phe Glu Tyr Ile Arg Asp Cys Tyr
1 5 10

<210> SEQ ID NO 582
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 582

Phe Phe Cys Gly Pro Glu Phe Asp Glu Ser Ile Ile Cys Asp
1 5 10

<210> SEQ ID NO 583
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 583

Val Leu Cys Gly Pro Lys Gly Gly Pro Thr Tyr Asn Cys Ser
1 5 10

<210> SEQ ID NO 584
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 584

Leu Ala Cys Trp Pro Val Trp Glu Glu Pro Gly His Cys Asp
1 5 10

<210> SEQ ID NO 585
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 585

Asp Tyr Cys Gly Pro Glu Val Glu Asp Val Asn Asp Cys Tyr
1 5 10

<210> SEQ ID NO 586
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 586

Asp Tyr Cys Gly Pro Glu Phe Glu Glu Ala His Tyr Cys Asn
1 5 10

<210> SEQ ID NO 587
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 587

Val Leu Cys Gly Pro Glu Leu Asp Glu Thr Leu Thr Cys Ile
1 5 10

<210> SEQ ID NO 588
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 588

Tyr Tyr Cys Gly Pro Glu Ile Glu Asp Tyr Asn Leu Cys Asn
1 5 10

<210> SEQ ID NO 589
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 589

Tyr Ile Cys Gly Pro Glu Val Glu Glu Tyr Tyr Asn Cys Phe
1 5 10

<210> SEQ ID NO 590
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 590

Asp Ile Cys Gly Pro Glu Leu Asp Glu Ser Ile Phe Cys Phe
1 5 10

<210> SEQ ID NO 591
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 591

Asp Ile Cys Gly Pro Glu Val Glu Glu Asp Tyr Leu Cys Tyr
1 5 10

<210> SEQ ID NO 592
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 592

Thr Leu Cys Gly Pro Glu Phe Glu Glu Asp Ala Pro Cys Ile
1 5 10

<210> SEQ ID NO 593
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 593

Asn Tyr Cys Trp Pro Asp Trp Glu Tyr Ile Asn Ser Cys Val
1 5 10

<210> SEQ ID NO 594
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 594

Asn Asp Cys Gly Pro Glu Val Glu Glu Tyr Tyr Tyr Cys Thr
1 5 10

<210> SEQ ID NO 595
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 595

Ile Thr Cys Gly Pro Glu Met Asp Glu Ser Ile Asp Cys Asn
1 5 10

<210> SEQ ID NO 596
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 596

Tyr Tyr Cys Gly Pro Glu Met Ala Glu Asp Leu Ile Cys Asp
1 5 10

<210> SEQ ID NO 597
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 597

Ile Asp Cys Gly Pro Glu Leu Asp Glu Ser Ile Val Cys Thr
1 5 10

<210> SEQ ID NO 598
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 598

His Thr Cys Trp Pro Asp Trp Glu Trp Asp Val Tyr Cys Asp
1 5 10

<210> SEQ ID NO 599
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 599

Ile His Cys Gly Pro Glu Trp Glu Leu Ile Asp Asp Cys Leu
1 5 10

<210> SEQ ID NO 600
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 600

Tyr Thr Cys Gly Pro Glu Leu Asp Glu Ser Ile Thr Cys Thr
1 5 10

<210> SEQ ID NO 601
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 601

Phe His Cys Gly Pro Glu Val Glu Glu Thr Val Tyr Cys Phe
1 5 10

<210> SEQ ID NO 602
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 602

Asp Tyr Cys Gly Pro Glu Leu Asp Glu Ser Leu Ile Cys Asn
1 5 10

<210> SEQ ID NO 603
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 603

Ile Tyr Cys Gly Pro Glu Phe Asp Glu Ser Asp Tyr Cys Ile
1 5 10

<210> SEQ ID NO 604
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 604

Asp Leu Cys Gly Pro Glu Ile Glu Glu Asp Leu Val Cys Thr
1 5 10

<210> SEQ ID NO 605
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 605

Asn Ile Cys Gly Pro Glu Leu Gln Glu Asp Ile Val Cys Pro
1 5 10

<210> SEQ ID NO 606
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 606

Asn Asn Cys Gly Pro Glu Met Asp Glu Ser Ile Thr Cys Tyr
1 5 10

<210> SEQ ID NO 607
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 607

His Thr Cys Gly Pro Glu Leu Asp Glu Ser Ile Val Cys Val
1 5 10

<210> SEQ ID NO 608
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 608

Tyr Tyr Cys Gly Pro Glu Ile Glu Asp Ile Leu Val Cys Thr
1 5 10

<210> SEQ ID NO 609
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 609

Asn Thr Cys Gly Pro Glu Phe Glu Phe Val His Leu Cys Pro
1 5 10

<210> SEQ ID NO 610
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 610

Asp Ile Cys Gly Pro Glu Met Asp Glu Ser Thr Val Cys Asp
1 5 10

<210> SEQ ID NO 611
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 611

Ala Ile Cys Gly Pro Glu Val Glu Ile Val Asn Tyr Cys Tyr
1 5 10

<210> SEQ ID NO 612
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 612

His Leu Cys Gly Pro Glu Val Glu Asp Pro Thr Ala Cys Val
1 5 10

<210> SEQ ID NO 613
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 613

Ala Asp Cys Gly Pro Glu Leu Asp Glu Ser Ile Ser Cys Thr
1 5 10

<210> SEQ ID NO 614
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 614

Phe Asp Cys Gly Pro Glu Leu Asp Glu Ser Val Ile Cys Asp
1 5 10

<210> SEQ ID NO 615
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 615

Asp Val Cys Gly Pro Glu Phe Asp Glu Ser Ile Asp Cys Asn
1 5 10

<210> SEQ ID NO 616
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 616

Tyr Leu Cys Gly Pro Glu Val Glu Glu Ile Ser Ile Cys Phe
1 5 10

<210> SEQ ID NO 617
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 617

Ser Ala Cys Gly Pro Glu Phe Asp Glu Ser Leu His Cys Val
1 5 10

<210> SEQ ID NO 618
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 618

His Leu Cys Trp Pro Asp Trp Glu Glu Asp Ser Ala Cys Asn
1 5 10

<210> SEQ ID NO 619
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 619

His Thr Cys Trp Pro Asp Trp Glu Tyr Asp Tyr Asp Cys Phe
1 5 10

<210> SEQ ID NO 620
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 620

Tyr Asp Cys Gly Pro Glu Trp Glu Glu Val Ala Leu Cys Asn
1 5 10

<210> SEQ ID NO 621
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 621

Thr Leu Cys Gly Pro Glu Ile Glu Glu Tyr Ile Val Cys Tyr
1 5 10

<210> SEQ ID NO 622
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 622

Ser Tyr Cys Gly Pro Glu Phe Asp Glu Ser Ile Phe Cys Thr
1 5 10

<210> SEQ ID NO 623
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 623

Asp Ile Cys Gly Pro Glu Phe Asp Glu Ser Leu His Cys Tyr
1 5 10

<210> SEQ ID NO 624
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 624

Leu Phe Cys Gly Pro Glu Phe Glu Glu Ala Tyr Leu Cys Ile
1 5 10

<210> SEQ ID NO 625
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 625

Ile Phe Cys Gly Pro Glu Ile Glu Glu Asp Phe Val Cys Thr
1 5 10

<210> SEQ ID NO 626
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 626

Asp Asp Cys Gly Pro Glu Trp Glu Tyr Tyr Val Ala Cys Val
1 5 10

<210> SEQ ID NO 627
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 627

Asp Asp Cys Gly Pro Glu Leu Asp Glu Thr Thr Ile Cys Tyr
1 5 10

<210> SEQ ID NO 628
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 628

Ala Ser Cys Gly Pro Glu Leu Asp Glu Ser Ile Ala Cys Asp
1 5 10

<210> SEQ ID NO 629
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 629

Tyr Leu Cys Gly Pro Glu Val Glu Asp Tyr Asp Tyr Cys Tyr
1 5 10

<210> SEQ ID NO 630
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 630

Asp Leu Cys Gly Pro Glu Trp Glu Glu Thr Ile Phe Cys Ala
1 5 10

<210> SEQ ID NO 631
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 631

Asp Phe Cys Gly Pro Asp Gly Glu Glu Phe Tyr Ile Cys Pro
1 5 10

<210> SEQ ID NO 632
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 632

Val Tyr Cys Gly Pro Glu Val Glu Glu Asn Ile Leu Cys His
1 5 10

<210> SEQ ID NO 633
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 633

Asp Tyr Cys Gly Pro Glu Val Glu Glu Asn Tyr Phe Cys Phe
1 5 10

<210> SEQ ID NO 634
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 634

Asn Asp Cys Trp Pro Asp Trp Tyr Glu Phe Leu Ser Cys Asp
1 5 10

<210> SEQ ID NO 635
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 635

Arg Asp Cys Trp Pro Asp Trp Glu Val Pro Tyr Phe Cys Asp
1 5 10

<210> SEQ ID NO 636
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 636

Asn Leu Cys Gly Pro Glu Val Glu Glu Ala Val Tyr Cys Tyr
1 5 10

<210> SEQ ID NO 637
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 637

Phe Asp Cys Trp Pro Asp Gly Glu Leu Asn Tyr Leu Cys Thr
1 5 10

<210> SEQ ID NO 638
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 638

Tyr Tyr Cys Gly Pro Glu Val Glu Asp Val Asn Leu Cys Ile
1 5 10

<210> SEQ ID NO 639
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 639

Asp Asn Cys Gly Pro Glu Tyr Asp Glu Ser Ile Thr Cys Leu
1 5 10

<210> SEQ ID NO 640
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 640

Leu Asn Cys Trp Pro Asp Trp Glu Glu Asp Tyr Ser Cys Asn
1 5 10

<210> SEQ ID NO 641
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 641

Pro Thr Cys Gly Pro Glu Val Glu Glu Leu Leu Ser Cys Asn
1 5 10

<210> SEQ ID NO 642
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 642

Asp His Cys Gly Pro Glu Val Glu Leu Ile Phe Tyr Cys His
1 5 10

<210> SEQ ID NO 643
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 643

Phe His Cys Gly Pro Glu Leu Asp Glu Ser Ile Phe Cys Tyr
1 5 10

<210> SEQ ID NO 644
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 644

Phe Asp Cys Gly Pro Glu Leu Glu Glu Thr Val Val Cys Pro
1 5 10

<210> SEQ ID NO 645
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 645

Asp Phe Cys Gly Pro Glu Leu Asp Glu Ser Leu Pro Cys Ala
1 5 10

<210> SEQ ID NO 646
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 646

Asp Ser Cys Gly Pro Glu Leu Asp Glu Ser Ile Tyr Cys Asp
1 5 10

<210> SEQ ID NO 647
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 647

Ala Asp Cys Trp Pro Asp Trp Glu Glu Phe Leu Leu Cys Phe
1 5 10

<210> SEQ ID NO 648
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 648

Ile Leu Cys Gly Pro Glu Val Glu Glu Leu Asp Phe Cys Asn
1 5 10

<210> SEQ ID NO 649
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 649

Phe Phe Cys Gly Pro Glu Phe Glu Glu Ile Phe Leu Cys Tyr
1 5 10

<210> SEQ ID NO 650
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 650

Tyr Asn Cys Gly Pro Asp Gly Asp Glu Ser Tyr Asp Cys His
1 5 10

<210> SEQ ID NO 651
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 651

Asp Asn Cys Gly Pro Glu Leu Asp Glu Thr Ile Thr Cys Phe
1 5 10

<210> SEQ ID NO 652
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 652

His Asn Cys Gly Pro Asp Gly Asp Glu Ala Phe Ile Cys Asn
1 5 10

<210> SEQ ID NO 653
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 653

Asp Tyr Cys Gly Pro Glu Val Glu Glu Asp Leu Val Cys Pro
1 5 10

<210> SEQ ID NO 654
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 654

Asp Tyr Cys Gly Pro Glu Leu Asp Glu Ser Leu Asn Cys Phe
1 5 10

<210> SEQ ID NO 655
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 655

Asp Tyr Cys Gly Pro Glu Phe Gln Glu Asp Phe His Cys His
1 5 10

<210> SEQ ID NO 656
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 656

Tyr Asp Cys Gly Pro Glu Trp Glu Phe Thr Asp Asp Cys Ile
1 5 10

<210> SEQ ID NO 657
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 657

Asp Ile Cys Gly Pro Glu Tyr Glu Glu Asp Ile Ile Cys Tyr
1 5 10

<210> SEQ ID NO 658
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 658

Phe Asp Cys Gly Pro Glu Leu Asp Glu Thr Val Pro Cys Pro
1 5 10

<210> SEQ ID NO 659
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 659

Asn Tyr Cys Gly Pro Glu Leu Asp Glu Thr Ser Val Cys Asp
1 5 10

<210> SEQ ID NO 660
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 660

Tyr Tyr Cys Gly Pro Glu Trp Glu Phe Ser Phe Asp Cys Asp
1 5 10

<210> SEQ ID NO 661
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 661

Tyr Ala Cys Gly Pro Glu Leu Asp Glu Ser Val Thr Cys Asp
1 5 10

<210> SEQ ID NO 662
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 662

Phe Leu Cys Gly Pro Glu Val Glu Gln Asp Tyr Phe Cys Val
1 5 10

<210> SEQ ID NO 663
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 663

Asp Asn Cys Gly Pro Glu Phe Asp Glu Ser Val Arg Cys Asp
1 5 10

<210> SEQ ID NO 664
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 664

Asn Asp Cys Gly Pro Asp Gly Ile Glu Thr Val Asp Cys Tyr
1 5 10

<210> SEQ ID NO 665
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 665

Tyr Phe Cys Gly Pro Glu Val Glu Asp Tyr Asn Asp Cys Phe
1 5 10

<210> SEQ ID NO 666
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 666

Asn Leu Cys Gly Pro Glu Phe Asp Glu Ser Ile Phe Cys Tyr
1 5 10

<210> SEQ ID NO 667
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 667

Ile Asp Cys Trp Pro Asp Trp Glu Glu Tyr Ile Pro Cys Thr
1 5 10

<210> SEQ ID NO 668
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 668

Ile Tyr Cys Gly Pro Asp Gly Asp Glu Ser Phe Ile Cys Ala
1 5 10

<210> SEQ ID NO 669
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 669

Asp Tyr Cys Gly Pro Glu Phe Asp Glu Ser Val Val Cys Tyr
1 5 10

<210> SEQ ID NO 670
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 670

Val Phe Cys Gly Pro Glu Trp Glu Asp Ile Thr Asp Cys Asp
1 5 10

<210> SEQ ID NO 671
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 671

Leu Asp Cys Gly Pro Glu Val Asp Glu Thr Phe Thr Cys His
1 5 10

<210> SEQ ID NO 672
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 672

Asp Asp Cys Gly Pro Glu Tyr Asp Glu Ser Phe Ala Cys His
1 5 10

<210> SEQ ID NO 673
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 673

Ile Tyr Cys Gly Pro Glu Tyr Gln Glu Asp Leu Pro Cys Asn
1 5 10

<210> SEQ ID NO 674
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 674

Leu Asp Cys Gly Pro Glu Val Glu Glu Tyr Asn Tyr Cys Val
1 5 10

<210> SEQ ID NO 675
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 675

Tyr Val Cys Gly Pro Glu Phe Asp Glu Ser Ser Ala Cys Asn
1 5 10

<210> SEQ ID NO 676
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 676

Thr Pro Cys Gly Pro Glu Leu Glu Glu Ala Ile Gly Cys Tyr
1 5 10

<210> SEQ ID NO 677
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 677

Tyr Phe Cys Gly Pro Glu Phe Asp Glu Ser Ala Asp Cys Asn
1 5 10

<210> SEQ ID NO 678
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 678

Asp Asp Cys Gly Pro Glu Phe Glu Glu Asp Ile Ile Cys Asp
1 5 10

<210> SEQ ID NO 679
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 679

Leu Tyr Cys Gly Pro Val Val Glu Glu Leu Asn His Cys Asn
1 5 10

<210> SEQ ID NO 680
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 680

Val Ile Cys Gly Pro Asp Gly Glu Glu Leu Ile Ala Cys Ala
1               5                   10

<210> SEQ ID NO 681
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Phe Ala Cys Trp Pro Asp Trp Gln Glu Thr Tyr Val Cys Asn
1               5                   10

<210> SEQ ID NO 682
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Tyr Ile Cys Gly Pro Glu Val Glu Phe Leu Phe Phe Cys Asn
1               5                   10

<210> SEQ ID NO 683
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Thr Gln Cys Gly Pro Lys Gly Glu Pro Thr Tyr His Cys Tyr
1               5                   10

<210> SEQ ID NO 684
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Asn Tyr Cys Gly Pro Glu Val Glu Glu Tyr His Asn Cys Asp
1               5                   10

<210> SEQ ID NO 685
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Val Tyr Cys Gly Pro Glu Trp Glu Phe Phe Ser Asp Cys Ala
1               5                   10

<210> SEQ ID NO 686
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 686

Phe Tyr Cys Gly Pro Glu Leu Glu Glu Ser Phe Phe Cys Tyr
1 5 10

<210> SEQ ID NO 687
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 687

Asp Tyr Cys Gly Pro Glu Ile Glu Glu Asn Phe Tyr Cys Tyr
1 5 10

<210> SEQ ID NO 688
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 688

Tyr Ala Cys Gly Pro Glu Val Glu Glu Tyr Val Tyr Cys Ala
1 5 10

<210> SEQ ID NO 689
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 689

Val Asp Cys Gly Pro Glu Leu Asp Glu Ser Ile Ile Cys Asp
1 5 10

<210> SEQ ID NO 690
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 690

Asn Asp Cys Gly Pro Glu Met Asp Glu Ser Ile Ala Cys Tyr
1 5 10

<210> SEQ ID NO 691
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 691

Val Tyr Cys Gly Pro Glu Phe Asp Glu Tyr Leu Ala Cys Ala
1 5 10

<210> SEQ ID NO 692
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 692

Val Ile Cys Gly Pro Glu Phe Asp Glu Ser Ala Asn Cys Asp
1 5 10

<210> SEQ ID NO 693
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 693

Leu Thr Cys Trp Pro Asp Trp Glu Glu Asp Phe Phe Cys Asn
1 5 10

<210> SEQ ID NO 694
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 694

Phe Tyr Cys Gly Pro Glu Gln Glu Glu Ile Asn Tyr Cys Tyr
1 5 10

<210> SEQ ID NO 695
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 695

Thr Tyr Cys Gly Pro Glu Leu Glu Glu Phe Phe Leu Cys Tyr
1 5 10

<210> SEQ ID NO 696
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 696

Pro Asp Cys Gly Pro Glu Leu Asp Glu Ser Val Ala Cys His
1 5 10

<210> SEQ ID NO 697
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 697

Asn Asp Cys Gly Pro Glu Phe Glu Glu Ile Ile Phe Cys Val
1 5 10

<210> SEQ ID NO 698
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 698

Tyr Ile Cys Gly Pro Glu Phe Asp Glu Ser Phe Tyr Cys Asn
1 5 10

<210> SEQ ID NO 699
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 699

His Ala Cys Gly Pro Glu Leu Asp Glu Ser Leu Leu Cys Asn
1 5 10

<210> SEQ ID NO 700
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 700

Tyr Tyr Cys Gly Pro Glu Trp Glu Glu Ala Val Leu Cys Ala
1 5 10

<210> SEQ ID NO 701
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 701

Ala Phe Cys Gly Pro Glu Val Glu Glu Tyr Asp Leu Cys Asn
1 5 10

<210> SEQ ID NO 702
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 702

Tyr Asn Cys Gly Pro Glu Phe Asp Glu Ser Val Ala Cys Ser
1 5 10

<210> SEQ ID NO 703
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 703

Tyr Leu Cys Gly Pro Glu Val Glu Asp Asp Thr Leu Cys Ala
1 5 10

<210> SEQ ID NO 704
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 704

Ala Val Cys Gly Pro Glu Phe Asp Glu Ser Val Asn Cys Asp
1 5 10

<210> SEQ ID NO 705
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 705

Asn Tyr Cys Gly Pro Glu Trp Glu Val Tyr Ser Leu Cys Pro
1 5 10

<210> SEQ ID NO 706
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 706

Asp Phe Cys Gly Pro Glu Val Glu Glu Asp Thr Tyr Cys His
1 5 10

<210> SEQ ID NO 707
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 707

Ile Ser Cys Gly Pro Glu Tyr Glu Trp Asp Tyr Ala Cys Asn
1 5 10

<210> SEQ ID NO 708
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 708

Val Asn Cys Gly Pro Glu Leu Asp Glu Ser Ile Ile Cys Tyr
1 5 10

<210> SEQ ID NO 709
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 709

Tyr Asp Cys Gly Pro Glu Phe Asp Glu Thr Ala Pro Cys Tyr
1 5 10

<210> SEQ ID NO 710
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 710

Tyr Leu Cys Gly Pro Glu Phe Glu Glu Asn Phe Leu Cys Thr
1 5 10

<210> SEQ ID NO 711
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 711

Phe Asp Cys Gly Pro Glu Val Asp Glu Ser Val Asp Cys Ala
1 5 10

<210> SEQ ID NO 712
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 712

Tyr Asp Cys Gly Pro Glu Gln Glu Glu Ile Ser Phe Cys Asn
1 5 10

<210> SEQ ID NO 713
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 713

Ile Asp Cys Gly Pro Glu Ile Glu Leu Tyr Asp Asp Cys Phe
1 5 10

<210> SEQ ID NO 714
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 714

Thr Phe Cys Gly Pro Glu Leu Asp Glu Ser Val Tyr Cys Tyr
1 5 10

<210> SEQ ID NO 715
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 715

Phe Phe Cys Gly Pro Glu Ile Asp Glu Ser Asn Ala Cys Val
1 5 10

<210> SEQ ID NO 716
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 716

Tyr His Cys Trp Pro Asp Trp Glu Pro Ile Tyr Ile Cys Ile
1 5 10

<210> SEQ ID NO 717
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 717

Ala Ile Cys Gly Pro Glu Tyr Glu Glu Asp His Tyr Cys Tyr
1 5 10

<210> SEQ ID NO 718
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 718

Pro Leu Cys Gly Pro Asp Gly Phe Glu Asn Tyr Asn Cys Phe
1 5 10

<210> SEQ ID NO 719
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 719

Phe Pro Cys Trp Pro Asp Trp Glu Trp Asp Asn Asn Cys His
1 5 10

<210> SEQ ID NO 720
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 720

Val Asp Cys Gly Pro Asp Gly Asp Glu Leu Ala Ala Cys His
1 5 10

<210> SEQ ID NO 721
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 721

Val Asp Cys Trp Pro Asp Trp Glu Glu Tyr Tyr Ser Cys Asp
1 5 10

<210> SEQ ID NO 722
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 722

Val Tyr Cys Gly Pro Glu Tyr Asp Glu Ser Tyr Asp Cys Thr
1 5 10

<210> SEQ ID NO 723
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 723

Asn Leu Cys Gly Pro Glu Trp Glu Asn Phe Ala Asp Cys Phe
1 5 10

<210> SEQ ID NO 724
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 724

Tyr Leu Cys Gly Pro Glu Leu Glu Val Phe Phe Val Cys Asp
1 5 10

<210> SEQ ID NO 725
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 725

Ile Phe Cys Gly Pro Glu Leu Glu Asp Tyr Ser Ile Cys Phe
1 5 10

<210> SEQ ID NO 726
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 726

Asp Tyr Cys Gly Pro Glu Leu Glu Gln Tyr Asp Leu Cys Phe
1 5 10

<210> SEQ ID NO 727
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 727

Leu Leu Cys Gly Pro Val Asn Glu Asp Pro Leu Asp Cys Tyr
1 5 10

<210> SEQ ID NO 728
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 728

Ile Asp Cys Gly Pro Glu Phe Asp Glu Ser Val Phe Cys Tyr
1 5 10

<210> SEQ ID NO 729
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 729

Ile Ile Cys Gly Pro Glu Val Glu Glu Ile Asp Ile Cys Ser
1 5 10

<210> SEQ ID NO 730
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 730

Ile Ala Cys Trp Pro Asp Trp Glu Asp Tyr Ser Ser Cys Pro
1 5 10

<210> SEQ ID NO 731
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 731

Tyr Tyr Cys Gly Pro Glu Val Glu Asp Ile Asn Asp Cys Ile
1 5 10

<210> SEQ ID NO 732
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 732

Asn Ile Cys Gly Pro Glu Met Asp Glu Ser Ile Asp Cys Ile
1 5 10

<210> SEQ ID NO 733
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 733

Phe Asp Cys Trp Pro Asp Trp Glu Glu Leu Val Ser Cys Tyr
1 5 10

<210> SEQ ID NO 734
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 734

Tyr Phe Cys Gly Pro Glu Trp Glu Asp His Phe Phe Cys Asp
1 5 10

<210> SEQ ID NO 735
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 735

Thr Tyr Cys Gly Pro Glu Phe Glu Glu Asp Ser Tyr Cys Asp
1 5 10

<210> SEQ ID NO 736
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 736

Asn Leu Cys Gly Pro Glu Val Glu Leu Ile Asp Ile Cys Ser
1 5 10

<210> SEQ ID NO 737
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 737

Asp Asn Cys Gly Pro Glu Trp Glu Glu Val Tyr Leu Cys Asn
1 5 10

<210> SEQ ID NO 738
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 738

Phe Leu Cys Gly Pro Glu Phe Asp Glu Ser Asp Leu Cys Phe
1 5 10

<210> SEQ ID NO 739
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 739

His Ile Cys Gly Pro Glu Gln Asp Glu Ser Ile Gly Cys Thr
1 5 10

<210> SEQ ID NO 740
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 740

Phe Asp Cys Trp Pro Asp Trp Glu Asp Asn Ser Tyr Cys Asp
1 5 10

<210> SEQ ID NO 741
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 741

Thr Ala Cys Gly Pro Glu Trp Glu Phe Asp Phe Asn Cys Asp
1 5 10

<210> SEQ ID NO 742
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 742

His His Cys Trp Pro Asp Trp Glu Asp Tyr Ser Thr Cys Pro
1 5 10

<210> SEQ ID NO 743
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 743

Tyr Tyr Cys Gly Pro Glu Phe Asp Glu Ser Val Asn Cys Phe
1 5 10

<210> SEQ ID NO 744
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 744

Leu His Cys Trp Pro Asp Trp Glu Glu Ile Asp Ile Cys Asp
1 5 10

<210> SEQ ID NO 745
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 745

Asp Ile Cys Gly Pro Asp Gly Gln Glu Asp Phe Val Cys Ser
1 5 10

<210> SEQ ID NO 746
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 746

Asp Val Cys Trp Pro Asp Trp Glu Val Asn Tyr Phe Cys Asp
1 5 10

<210> SEQ ID NO 747
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 747

Val Asn Cys Gly Pro Glu Met Asp Glu Ser Ile Asp Cys Ala
1 5 10

<210> SEQ ID NO 748
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 748

Asp Asn Cys Gly Pro Glu Phe Asp Glu Ala Thr Val Cys Asn
1 5 10

<210> SEQ ID NO 749
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 749

Asp Leu Cys Gly Pro Glu Phe Glu Glu Val His Asn Cys Asn
1 5 10

<210> SEQ ID NO 750
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 750

Val Asn Cys Gly Pro Glu Phe Asp Glu Ser Ser Tyr Cys Phe
1 5 10

<210> SEQ ID NO 751
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 751

Asn Ile Cys Trp Pro Asp Trp Glu Glu Asp Asn Phe Cys Ser
1 5 10

<210> SEQ ID NO 752
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Phe Val Cys Gly Pro Glu Trp Glu Val Tyr Asp Asp Cys Asp
1               5                   10

<210> SEQ ID NO 753
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Ala Tyr Cys Gly Pro Glu Leu Glu Val Val His Leu Cys Val
1               5                   10

<210> SEQ ID NO 754
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Pro Phe Cys Gly Pro Glu Met Asp Glu Thr Ile Asp Cys Tyr
1               5                   10

<210> SEQ ID NO 755
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Leu Leu Cys Gly Pro Val Met Glu Asp Val Phe Ala Cys Tyr
1               5                   10

<210> SEQ ID NO 756
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Asp Leu Cys Gly Pro Glu Phe Asp Glu Ser Thr Asn Cys Tyr
1               5                   10

<210> SEQ ID NO 757
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

His Asp Cys Gly Pro Glu Met Glu Glu Tyr Tyr Leu Cys Pro
1 5 10

<210> SEQ ID NO 758
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 758

Thr Asp Cys Gly Pro Glu Tyr Asp Glu Ser Ile Ile Cys Pro
1 5 10

<210> SEQ ID NO 759
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 759

Val Leu Cys Trp Pro Asp Trp Glu Asp Tyr Ala Asp Cys Asn
1 5 10

<210> SEQ ID NO 760
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 760

Asn Asp Cys Gly Pro Glu Leu Asp Glu Ser Leu Thr Cys Asp
1 5 10

<210> SEQ ID NO 761
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 761

Ile Tyr Cys Gly Pro Glu Leu Asp Glu Ser Ile Ala Cys Tyr
1 5 10

<210> SEQ ID NO 762
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 762

Asn Tyr Cys Gly Pro Glu Val Glu Glu Phe Asn Phe Cys His
1 5 10

<210> SEQ ID NO 763
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 763

Asp Val Cys Gly Pro Glu Ile Glu Glu Tyr Ser Phe Cys Ile
1 5 10

<210> SEQ ID NO 764
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 764

Asp Leu Cys Gly Pro Glu Val Glu Glu Ile Thr Asp Cys Ala
1 5 10

<210> SEQ ID NO 765
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 765

His Asp Cys Gly Pro Glu Phe Asp Glu Ser Val Phe Cys Ile
1 5 10

<210> SEQ ID NO 766
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 766

Pro Leu Cys Gly Pro Val Leu Glu Glu Asp Ile Tyr Cys Tyr
1 5 10

<210> SEQ ID NO 767
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 767

Asp Leu Cys Gly Pro Glu Phe Glu Asp Ile Ile Asp Cys Asn
1 5 10

<210> SEQ ID NO 768
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 768

Asp Tyr Cys Gly Pro Glu Val Glu Val Pro Ser Asn Cys Asn
1 5 10

<210> SEQ ID NO 769
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 769

Ile Ile Cys Gly Pro Glu Leu Asp Glu Ser Thr Ala Cys Asp
1 5 10

<210> SEQ ID NO 770
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 770

Asp His Cys Gly Pro Glu Phe Asp Glu Ser Val Asn Cys Asp
1 5 10

<210> SEQ ID NO 771
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 771

Phe Asp Cys Gly Pro Glu Phe Asp Glu Ser Leu Tyr Cys Ser
1 5 10

<210> SEQ ID NO 772
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 772

Phe Ala Cys Trp Pro Asp Trp Glu Glu Val Tyr Ile Cys Tyr
1 5 10

<210> SEQ ID NO 773
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 773

Leu Tyr Cys Gly Pro Glu Phe Asp Glu Ser Leu Asp Cys Ser
1 5 10

<210> SEQ ID NO 774
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 774

Asp Leu Cys Gly Pro Glu Leu Glu Glu Ala Phe Leu Cys Ala
1 5 10

<210> SEQ ID NO 775
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 775

Phe Ala Cys Gly Pro Glu Leu Asp Glu Thr Leu Thr Cys Leu
1 5 10

<210> SEQ ID NO 776
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 776

Phe Asp Cys Gly Pro Glu Val Glu Glu Ile Ser Asn Cys Asp
1 5 10

<210> SEQ ID NO 777
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 777

Val His Cys Gly Pro Glu Leu Glu Tyr Pro Phe Asp Cys Asn
1 5 10

<210> SEQ ID NO 778
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 778

Ala Tyr Cys Gly Pro Glu Phe Glu Glu His Thr Thr Cys Asn
1 5 10

<210> SEQ ID NO 779
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 779

Leu Tyr Cys Gly Pro Val Ser Glu Gln Phe Thr Phe Cys Ile
1 5 10

<210> SEQ ID NO 780
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 780

Asp Tyr Cys Gly Pro Glu Leu Asp Glu Ser Tyr Asp Cys Asn
1 5 10

<210> SEQ ID NO 781
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 781

Phe Tyr Cys Gly Pro Glu Trp Glu Glu Phe Asp Val Cys Ile
1 5 10

<210> SEQ ID NO 782
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 782

Phe Thr Cys Gly Pro Glu Val Glu Glu Tyr Asp His Cys Ile
1 5 10

<210> SEQ ID NO 783
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 783

Tyr Asn Cys Gly Pro Glu Phe Asp Glu Ser Val Thr Cys Phe
1 5 10

<210> SEQ ID NO 784
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 784

Ala Val Cys Gly Pro Glu Asn Asp Glu Ser Asn Ser Cys Ala
1 5 10

<210> SEQ ID NO 785
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 785

Ile Tyr Cys Trp Pro Asp Trp Glu Val Pro Asn Asp Cys Ala
1 5 10

<210> SEQ ID NO 786
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 786

Tyr Phe Cys Gly Pro Glu Phe Glu Glu Phe Phe His Cys Tyr
1 5 10

<210> SEQ ID NO 787
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 787

Tyr Val Cys Gly Pro Asp Gly Asp Glu Ser Ser Phe Cys Asp
1 5 10

<210> SEQ ID NO 788
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 788

Ile Ser Cys Gly Pro Glu Val Glu Glu Phe Phe Tyr Cys Tyr
1 5 10

<210> SEQ ID NO 789
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 789

Leu Ile Cys Gly Pro Val Phe Glu Glu Asp Val Tyr Cys Asp
1 5 10

<210> SEQ ID NO 790
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 790

Val Tyr Cys Gly Pro Glu Val Glu Asp His Asn Tyr Cys Ala
1 5 10

<210> SEQ ID NO 791
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 791

Leu Asp Cys Gly Pro Glu Phe Glu Phe Val Tyr Ile Cys Ala
1 5 10

<210> SEQ ID NO 792
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 792

Tyr Asp Cys Gly Pro Glu Phe Glu Glu Asp Leu Pro Cys Ile
1 5 10

<210> SEQ ID NO 793
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 793

Asp Val Cys Gly Pro Glu Val Glu Glu Asp Tyr Tyr Cys Asp
1 5 10

<210> SEQ ID NO 794
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 794

Asn Asp Cys Trp Pro Asp Trp Glu Tyr Asp Asn Val Cys Val
1 5 10

<210> SEQ ID NO 795
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 795

Asp Leu Cys Gly Pro Glu Phe Glu Val Ala Asn Asp Cys Asn
1 5 10

<210> SEQ ID NO 796
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

His Asp Cys Gly Pro Glu Leu Asp Glu Ser Ile Ser Cys Asn
1               5                   10

<210> SEQ ID NO 797
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

Leu Asp Cys Trp Pro Asp Trp Glu Glu Thr Thr His Cys Asp
1               5                   10

<210> SEQ ID NO 798
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Ile Ile Cys Gly Pro Glu Val Glu Glu Asp Asp Tyr Cys Leu
1               5                   10

<210> SEQ ID NO 799
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

Tyr Tyr Cys Trp Pro Asp Trp Glu Glu Val Ile Ile Cys Asp
1               5                   10

<210> SEQ ID NO 800
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Phe Asp Cys Gly Pro Glu Ile Asp Glu Tyr Thr Asn Cys Asn
1               5                   10

<210> SEQ ID NO 801
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Ile Thr Cys Gly Pro Glu Leu Asp Glu Thr Ile Asn Cys Asp
1 5 10

<210> SEQ ID NO 802
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 802

Asp Ser Cys Gly Pro Glu Val Glu Glu Asp Ile Tyr Cys Ile
1 5 10

<210> SEQ ID NO 803
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 803

Tyr Leu Cys Gly Pro Glu Phe Asp Glu Ser Gly Asn Cys His
1 5 10

<210> SEQ ID NO 804
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 804

Asp Asn Cys Gly Pro Glu Leu Pro Glu Asp Tyr Phe Cys Asp
1 5 10

<210> SEQ ID NO 805
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 805

Val Leu Cys Gly Pro Glu Phe Glu Glu Val Ser Asn Cys Asn
1 5 10

<210> SEQ ID NO 806
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 806

Val Asp Cys Trp Pro Asp Trp Glu Glu Asp Ile Val Cys Asp
1 5 10

<210> SEQ ID NO 807
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 807

Val Tyr Cys Trp Pro Asp Trp Glu Asp Asn Phe Pro Cys Tyr
1 5 10

<210> SEQ ID NO 808
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 808

Asp Tyr Cys Gly Pro Glu Val Glu Glu His Phe Asn Cys His
1 5 10

<210> SEQ ID NO 809
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 809

Ala Asp Cys Gly Pro Glu Ile Glu Glu Asp Ala Tyr Cys Tyr
1 5 10

<210> SEQ ID NO 810
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 810

Ile Leu Cys Trp Pro Asp Trp Glu Asp Ala Thr Phe Cys Tyr
1 5 10

<210> SEQ ID NO 811
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 811

Ile His Cys Trp Pro Asp Trp Glu Asp Phe Asn Ile Cys Pro
1 5 10

<210> SEQ ID NO 812
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 812

Thr Ile Cys Gly Pro Glu Val Glu Asp Tyr Asn Asp Cys Ile
1 5 10

<210> SEQ ID NO 813
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 813

Asp Asp Cys Gly Pro Glu Leu Asp Glu Ser Val Ala Cys Ile
1 5 10

<210> SEQ ID NO 814
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 814

Asp Asp Cys Trp Pro Asp Trp Glu Asp His Ile Phe Cys Phe
1 5 10

<210> SEQ ID NO 815
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 815

Val Asn Cys Gly Pro Glu Val Glu Glu Ile Ile Phe Cys Asp
1 5 10

<210> SEQ ID NO 816
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 816

Ile Phe Cys Trp Pro Asp Trp Glu Asp Asp Thr Val Cys Ile
1 5 10

<210> SEQ ID NO 817
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 817

Ile Ile Cys Gly Pro Glu Phe Glu Glu Ile Ser Asp Cys Leu
1 5 10

<210> SEQ ID NO 818
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 818

Phe Asp Cys Gly Pro Glu Val Glu Glu Tyr Asn Asp Cys Asp
1 5 10

<210> SEQ ID NO 819
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 819

Asn Asp Cys Gly Pro Glu Leu Asp Glu Thr Leu Tyr Cys Ile
1 5 10

<210> SEQ ID NO 820
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 820

Ala Ile Cys Gly Pro Glu Leu Glu Glu Asp Ile Ser Cys Asn
1 5 10

<210> SEQ ID NO 821
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 821

His Leu Cys Gly Pro Glu Phe Asp Glu Ser Thr Asn Cys Tyr
1 5 10

<210> SEQ ID NO 822
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 822

Ser Tyr Cys Gly Pro Glu Leu Asp Glu Ser Val Ala Cys Ile
1 5 10

<210> SEQ ID NO 823
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 823

Leu Tyr Cys Gly Pro Glu Phe Glu Gln Leu Ala Asp Cys Thr
1 5 10

<210> SEQ ID NO 824
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 824

Ile Asp Cys Gly Pro Glu Leu Asp Glu Ser Ile Ala Cys Asn
1 5 10

<210> SEQ ID NO 825
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 825

Phe Asp Cys Gly Pro Asp Gly Gln Glu Asp Leu Val Cys Asn
1 5 10

<210> SEQ ID NO 826
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 826

Asn Leu Cys Gly Pro Glu Phe Glu Glu Phe Phe Asp Cys Tyr
1 5 10

<210> SEQ ID NO 827
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 827

Ser Ile Cys Gly Pro Glu Leu Gln Glu Asp Ile Val Cys Pro
1 5 10

<210> SEQ ID NO 828
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 828

Asn Pro Cys Gly Pro Glu Tyr Asp Glu Ser Ala His Cys Asp
1 5 10

<210> SEQ ID NO 829
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 829

Tyr Asp Cys Gly Pro Glu Leu Asp Glu Tyr Tyr Asn Cys Asn
1 5 10

<210> SEQ ID NO 830
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 830

Val Asp Cys Gly Pro Glu Leu Asp Glu Thr Ile Phe Cys Asp
1 5 10

<210> SEQ ID NO 831
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 831

Asp Asn Cys Gly Pro Glu Leu Asp Glu Ser Val Thr Cys Thr
1 5 10

<210> SEQ ID NO 832
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 832

Val Asp Cys Gly Pro Glu Leu Asp Glu Ser Ser Tyr Cys Asp
1 5 10

<210> SEQ ID NO 833
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 833

Tyr Tyr Cys Gly Pro Glu Phe Glu Phe Ile Asp Phe Cys Phe
1 5 10

<210> SEQ ID NO 834
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 834

Tyr Asp Cys Trp Pro Asp Trp Glu Val Ile Thr Tyr Cys Asn
1 5 10

<210> SEQ ID NO 835
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 835

Phe Asp Cys Gly Pro Glu Ile Glu Glu Asp Phe Phe Cys Val
1 5 10

<210> SEQ ID NO 836
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 836

Ile Phe Cys Trp Pro Asp Trp Asp Asp Ile Asn Phe Cys Asp
1 5 10

<210> SEQ ID NO 837
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 837

Asn Phe Cys Gly Pro Glu Leu Pro Glu Asp Ile Thr Cys Tyr
1 5 10

<210> SEQ ID NO 838
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 838

Ser Leu Cys Gly Pro Glu Phe Glu Glu Tyr Tyr His Cys Leu
1 5 10

<210> SEQ ID NO 839
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 839

Ala Ser Cys Gly Pro Glu Leu Asp Glu Ser Leu Asp Cys Leu
1 5 10

<210> SEQ ID NO 840
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 840

Ser Phe Cys Gly Pro Glu Arg Glu Trp Asp Leu Ala Cys Tyr
1 5 10

<210> SEQ ID NO 841
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 841

His Leu Cys Gly Pro Glu Phe Glu Asp Val Leu Asp Cys Ile
1 5 10

<210> SEQ ID NO 842
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 842

Leu Asp Cys Gly Pro Asp Gly Asp Glu Phe Tyr Tyr Cys Leu
1 5 10

<210> SEQ ID NO 843
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 843

Asp Asn Cys Trp Pro Asp Trp Glu Glu Asp Ile Ala Cys Thr
1 5 10

<210> SEQ ID NO 844
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 844

Ser Asp Cys Gly Pro Glu Leu Asp Glu Thr Ile His Cys Ile
1 5 10

<210> SEQ ID NO 845
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 845

Asn Ser Cys Gly Pro Asp Gly Asp Glu Ser Val Asp Cys Leu
1 5 10

<210> SEQ ID NO 846
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 846

Asp Leu Cys Gly Pro Glu Leu Asp Glu Ser Thr Leu Cys Ile
1 5 10

<210> SEQ ID NO 847
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 847

Phe Asp Cys Gly Pro Glu Ser Asp Glu Ser Phe Asn Cys Tyr
1 5 10

<210> SEQ ID NO 848
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 848

Asp Leu Cys Gly Pro Glu Phe Glu Glu Asp Asp Ile Cys Tyr
1 5 10

<210> SEQ ID NO 849
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 849

His Ala Cys Gly Pro Glu Phe Glu Glu Asp Thr Tyr Cys Phe
1 5 10

<210> SEQ ID NO 850
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 850

Ser Asp Cys Gly Pro Glu Leu Asp Glu Ser Val Ala Cys Ile
1 5 10

<210> SEQ ID NO 851
<211> LENGTH: 14

<212> TYPE: PRT
<213> ORGANISM: Artificial Sequence
<220> FEATURE:
<223> OTHER INFORMATION: Description of Artificial Sequence: Synthetic peptide

<400> SEQUENCE: 851

Ile Val Cys Gly Pro Glu Leu Pro Glu Asp Tyr Asn Cys Tyr
1 5 10

<210> SEQ ID NO 852
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 852

Asp Leu Cys Gly Pro Glu Phe Asp Glu Ser Phe Ile Cys Phe
1 5 10

<210> SEQ ID NO 853
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 853

Tyr Asp Cys Gly Pro Glu Phe Asp Glu Thr Leu Thr Cys Asn
1 5 10

<210> SEQ ID NO 854
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 854

Tyr Asp Cys Gly Pro Glu Val Glu Glu Ile Val Asn Cys Asp
1 5 10

<210> SEQ ID NO 855
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 855

Val Phe Cys Gly Pro Glu Ile Glu Asp Asp His Val Cys Ile
1 5 10

<210> SEQ ID NO 856
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 856

Phe Ile Cys Gly Pro Glu Trp Glu Asp Asp Tyr Ala Cys Ser
1 5 10

<210> SEQ ID NO 857
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 857

Asn Phe Cys Gly Pro Glu Phe Asp Glu Ser Val Gly Cys Asn
1 5 10

<210> SEQ ID NO 858
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 858

Asn Leu Cys Gly Pro Glu Val Glu Glu Ile Leu Ile Cys Asp
1 5 10

<210> SEQ ID NO 859
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 859

Asp Ser Cys Gly Pro Glu Val Glu Glu Tyr Asp Leu Cys Asn
1 5 10

<210> SEQ ID NO 860
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 860

Thr Leu Cys Gly Pro Glu Phe Glu Glu Ile Thr Asp Cys Asn
1 5 10

<210> SEQ ID NO 861
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 861

Thr Val Cys Gly Pro Lys Met Glu Met Asn Ser Thr Cys Asp
1 5 10

<210> SEQ ID NO 862
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 862

Val His Cys Trp Pro Asp Trp Glu Asp Ala Val Ser Cys Asn
1 5 10

<210> SEQ ID NO 863
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 863

Asp Leu Cys Gly Pro Asp Gly Asn Glu Leu Asp Phe Cys Phe
1 5 10

<210> SEQ ID NO 864
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 864

Asp Leu Cys Gly Pro Asp Gly Glu Glu His Tyr Tyr Cys Asp
1 5 10

<210> SEQ ID NO 865
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 865

Phe Asn Cys Gly Pro Glu Val Glu Glu Ile Leu Leu Cys Thr
1 5 10

<210> SEQ ID NO 866
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 866

His Tyr Cys Gly Pro Glu Val Glu Asn Ile Asn Asp Cys Ile
1 5 10

<210> SEQ ID NO 867
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 867

Ile Asp Cys Gly Pro Glu Leu Asp Glu Ser Val Ile Cys Asp
1               5                   10

<210> SEQ ID NO 868
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Ile Phe Cys Gly Pro Glu Ile Glu Gln Pro Ala Leu Cys Tyr
1               5                   10

<210> SEQ ID NO 869
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Tyr Asp Cys Gly Pro Glu Phe Gln Glu Asp Leu Val Cys Pro
1               5                   10

<210> SEQ ID NO 870
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 870

His Ala Cys Trp Pro Asp Trp Glu Glu Pro Asn Tyr Cys Asp
1               5                   10

<210> SEQ ID NO 871
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 871

Asn Val Cys Trp Pro Asp Trp Glu Glu Asp Tyr Asn Cys Tyr
1               5                   10

<210> SEQ ID NO 872
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Ser Phe Cys Gly Gln Glu Leu Gly Asp Asn Tyr Asp Cys Ile
1               5                   10

<210> SEQ ID NO 873
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 873

Asp Asp Cys Gly Pro Glu Leu Asp Glu Thr Thr Val Cys Tyr
1 5 10

<210> SEQ ID NO 874
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 874

Asn Phe Cys Gly Pro Glu Trp Glu Val Ala Thr Leu Cys Leu
1 5 10

<210> SEQ ID NO 875
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 875

Asp Leu Cys Gly Pro Glu Val Glu Glu Asp Thr Tyr Cys Asn
1 5 10

<210> SEQ ID NO 876
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 876

Ala Leu Cys Gly Pro Glu Val Glu Gln Val Asp Leu Cys Thr
1 5 10

<210> SEQ ID NO 877
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 877

Asp Asp Cys Gly Pro Glu Leu Asp Glu Ser Val Asn Cys Asn
1 5 10

<210> SEQ ID NO 878
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 878

Ile Phe Cys Gly Pro Glu Phe Glu Gln Ile Ile Tyr Cys Asp
1 5 10

<210> SEQ ID NO 879
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 879

Ser Asp Cys Trp Pro Asp Trp Glu Glu Val Tyr Tyr Cys Ser
1 5 10

<210> SEQ ID NO 880
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 880

Phe Phe Cys Gly Pro Asp Gly Asp Glu Val Ala Ile Cys Asp
1 5 10

<210> SEQ ID NO 881
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 881

Asp Asp Cys Trp Pro Asp Trp Glu Asp Asp Val Tyr Cys Tyr
1 5 10

<210> SEQ ID NO 882
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 882

Tyr Asp Cys Gly Pro Glu Phe Asp Glu Thr Val Val Cys Pro
1 5 10

<210> SEQ ID NO 883
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 883

Ser Tyr Cys Gly Pro Glu Leu Asp Glu Ser Val Asn Cys Val
1 5 10

<210> SEQ ID NO 884
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 884

Ala Phe Cys Val Ser Phe Gln Gln Ser Leu Pro His Cys Asp
1 5 10

<210> SEQ ID NO 885
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 885

Val Asn Cys Gly Pro Glu Val Glu Glu Tyr Phe Val Cys Phe
1 5 10

<210> SEQ ID NO 886
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 886

Thr Asn Cys Trp Pro Asp Trp Glu Glu Asp Phe Ala Cys Val
1 5 10

<210> SEQ ID NO 887
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 887

Asp Asp Cys Gly Pro Glu Phe Glu Glu Ile Ile Leu Cys Phe
1 5 10

<210> SEQ ID NO 888
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 888

Asn Ser Cys Gly Pro Glu Leu Glu Asp Tyr His Leu Cys Pro
1 5 10

<210> SEQ ID NO 889
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 889

Ile His Cys Gly Pro Asp Ser Asp Gly Phe Asp Phe Cys Asp
1 5 10

<210> SEQ ID NO 890
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 890

Phe Asp Cys Gly Pro Glu Leu Glu Glu Asp His Leu Cys Phe
1 5 10

<210> SEQ ID NO 891
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 891

Thr Val Cys Trp Pro Asp Phe Glu Glu Tyr Ala Asp Cys Asp
1 5 10

<210> SEQ ID NO 892
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 892

Tyr Phe Cys Trp Pro Asp Trp Glu Glu Ala Ala Asp Cys Leu
1 5 10

<210> SEQ ID NO 893
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 893

Val Ser Cys Gly Pro Glu Phe Asp Glu Ser Val Asp Cys Ile
1 5 10

<210> SEQ ID NO 894
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 894

Ala Val Cys Gly Pro Glu Leu Pro Glu Asp Ile Val Cys Tyr
1 5 10

<210> SEQ ID NO 895
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 895

Val Leu Cys Gly Pro Glu Val Glu Glu Tyr His Leu Cys Ala
1 5 10

<210> SEQ ID NO 896
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 896

Ser Leu Cys Trp Pro Asp Trp Glu Glu Val Asp Asn Cys Phe
1 5 10

<210> SEQ ID NO 897
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 897

Thr Ile Cys Gly Pro Asp Gly Gln Glu Asp Tyr Asn Cys His
1 5 10

<210> SEQ ID NO 898
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 898

Phe Leu Cys Gly Pro Glu Gly Glu Pro Thr Tyr Leu Cys Thr
1 5 10

<210> SEQ ID NO 899
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 899

Asp Asp Cys Trp Leu Glu Gln His Asp Ile Tyr Val Cys Ala
1 5 10

<210> SEQ ID NO 900
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 900

Ile Phe Cys Gly Pro Glu Val Glu Glu Val Ala Phe Cys Phe
1 5 10

<210> SEQ ID NO 901
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 901

Ala Leu Cys Gly Pro Glu Val Glu Asp Asp Tyr Asp Cys Leu
1 5 10

<210> SEQ ID NO 902
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 902

Asp Asp Cys Gly Pro Glu Ile Glu Leu Tyr Leu Thr Cys Ala
1 5 10

<210> SEQ ID NO 903
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 903

Thr Asp Cys Trp Pro Asp Trp Glu Asp Asp Ser Ile Cys Asp
1 5 10

<210> SEQ ID NO 904
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 904

Ser Ile Cys Gly Pro Glu Leu Glu Glu Ile Phe Leu Cys Asn
1 5 10

<210> SEQ ID NO 905
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 905

Asn Asp Cys Gly Pro Glu Leu Glu Glu Asp Ile Leu Cys Phe
1 5 10

<210> SEQ ID NO 906
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 906

Asp Asp Cys Gly Pro Glu Leu Asp Glu Thr Tyr Ser Cys Tyr
1 5 10

<210> SEQ ID NO 907
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 907

Phe Val Cys Gly Pro Glu Trp Glu Glu Ile Asp Leu Cys Ile
1 5 10

<210> SEQ ID NO 908
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 908

Tyr Asp Cys Gly Pro Glu Leu Asp Glu Ser Leu Ser Cys Pro
1 5 10

<210> SEQ ID NO 909
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 909

Asn Leu Cys Gly Pro Glu Leu Asp Glu Ser Ile Ile Cys Pro
1 5 10

<210> SEQ ID NO 910
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 910

Ile Asp Cys Trp Pro Asp Trp Glu Glu Phe Asn Asn Cys Phe
1 5 10

<210> SEQ ID NO 911
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 911

Ala Tyr Cys Gly Pro Glu Leu Glu Glu His Asp Tyr Cys Tyr
1 5 10

<210> SEQ ID NO 912
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 912

Asp Asp Cys Ser Pro Gln Phe Asp Gln Ile Asp Leu Cys Asp
1 5 10

<210> SEQ ID NO 913
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 913

Ser Tyr Cys Gly Pro Glu Ser Asp Glu Ser Ile Tyr Cys Tyr
1 5 10

<210> SEQ ID NO 914
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 914

Ser Leu Cys Gly Pro Glu Phe Gln Glu Asp Ala Pro Cys Asn
1 5 10

<210> SEQ ID NO 915
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 915

Asp Ala Cys Gly Pro Glu Leu Asp Glu Thr Thr His Cys Asp
1 5 10

<210> SEQ ID NO 916
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 916

Asn Asp Cys Gly Pro Glu Val Glu Glu Val Ala Asp Cys Phe
1 5 10

<210> SEQ ID NO 917
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 917

Tyr Ile Cys Gly Pro Glu Phe Glu Gln Asp Tyr Phe Cys Phe
1 5 10

<210> SEQ ID NO 918
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 918

Thr Asp Cys Gly Pro Asp Gly Asp Glu Thr Asn Tyr Cys Phe
1 5 10

<210> SEQ ID NO 919
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 919

Tyr Asp Cys Gly Pro Glu Val Asp Glu Ser Val Leu Cys Pro
1 5 10

<210> SEQ ID NO 920
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 920

Ile Asp Cys Gly Pro Glu Phe Asp Glu Ser Ala Tyr Cys Thr
1 5 10

<210> SEQ ID NO 921
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 921

Phe Asp Cys Gly Pro Glu Phe Glu Glu Phe Phe His Cys Tyr
1 5 10

<210> SEQ ID NO 922
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 922

Phe Pro Cys Gly Pro Glu Ile Glu Glu Tyr Asp Tyr Cys Val
1               5                   10

<210> SEQ ID NO 923
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 923

Ala Asp Cys Gly Pro Ile Phe Glu Ser Ile Asp Ile Cys Val
1               5                   10

<210> SEQ ID NO 924
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 924

Ile Ser Cys Gly Pro Asp Leu Trp Pro Thr Asp Ile Cys Thr
1               5                   10

<210> SEQ ID NO 925
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 925

Asp Asp Cys Gly Pro Asp Gly Asp Glu Val His Thr Cys Asn
1               5                   10

<210> SEQ ID NO 926
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 926

Ile Asp Cys Trp Pro Asp Trp Glu Gly Ser Phe Ala Cys Asn
1               5                   10

<210> SEQ ID NO 927
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 927

Leu Asn Cys Gly Pro Asp Gly Asp Glu Thr Phe Tyr Cys Asp
1               5                   10

<210> SEQ ID NO 928
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 928

Ile His Cys Gly Pro Glu Leu Gly Ala Tyr Ile Ser Cys Ser
1 5 10

<210> SEQ ID NO 929
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 929

Thr Ile Cys Trp Pro Asp Trp Glu Glu Asp Tyr Phe Cys Tyr
1 5 10

<210> SEQ ID NO 930
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 930

His Ser Cys Leu Ala Gln Phe Asp Gln Asp Leu Val Cys Ile
1 5 10

<210> SEQ ID NO 931
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 931

Asn Asn Cys Ala Ser Asp Leu Ser Glu Asp Asn Ser Cys Ile
1 5 10

<210> SEQ ID NO 932
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 932

Val Asn Cys Trp Pro Asp Trp Glu Glu Asp Val Ala Cys Asn
1 5 10

<210> SEQ ID NO 933
<211> LENGTH: 14
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 933

Val Tyr Cys Gly Pro Glu Leu Asp Glu Ser Phe Tyr Cys Phe
1 5 10

<210> SEQ ID NO 934
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 934

Leu Phe Cys Gly Thr Val Leu Asp Glu Phe Phe Asp Cys Asp
1 5 10

<210> SEQ ID NO 935
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 935

Phe Asp Cys Gly Pro Glu Leu Asp Glu Ser Val Ser Cys Ala
1 5 10

<210> SEQ ID NO 936
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 936

Tyr Tyr Cys Gly Pro Glu Val Glu Glu Asn Val Tyr Cys Ile
1 5 10

<210> SEQ ID NO 937
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 937

Asp Tyr Cys Gly Pro Glu Leu Asp Asp Ser Thr Ile Cys His
1 5 10

<210> SEQ ID NO 938
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 938

Val Phe Cys Gly Pro Gln Trp Ala Glu Ala Asn Ala Cys Phe
1 5 10

<210> SEQ ID NO 939
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 939

Phe Thr Cys Gly Pro Glu Tyr Asp Glu Ser Ile Thr Cys Pro
1 5 10

<210> SEQ ID NO 940
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 940

Leu Asn Cys Gly Pro Val Asn Asp Glu Ser Ser Val Cys Ile
1 5 10

<210> SEQ ID NO 941
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 941

Ala Ile Cys Trp Pro Asp Trp Glu Glu Phe Ser Asp Cys His
1 5 10

<210> SEQ ID NO 942
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 942

Tyr Tyr Cys Gly Val Asp Leu Gly Ala Asn Val Tyr Cys Tyr
1 5 10

<210> SEQ ID NO 943
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 943

His Tyr Cys Gly Pro Glu Val Glu Glu Asp Tyr His Cys Asp
1 5 10

<210> SEQ ID NO 944
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 944

Asn Asp Cys Gly Ser Leu Gln Tyr Asp Ile Pro Thr Cys Val
1 5 10

<210> SEQ ID NO 945
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 945

Tyr Val Cys Arg Pro Gln Leu Asp Val Tyr His Tyr Cys Asn
1 5 10

<210> SEQ ID NO 946
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 946

His Asp Cys Gly Pro Asp Gly Asp Glu Ser Ile Ile Cys Ser
1 5 10

<210> SEQ ID NO 947
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 947

Phe Asp Cys Gly Pro Glu Leu Asp Glu Thr Ile Ile Cys Pro
1 5 10

<210> SEQ ID NO 948
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 948

Val Asp Cys Gly Ser Asp Arg Gly Glu Asn Ala Ala Cys His
1 5 10

<210> SEQ ID NO 949
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 949

Asn Ile Cys Leu Ala Gln Phe Asn Glu Asp Pro Thr Cys Asn
1 5 10

<210> SEQ ID NO 950
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 950

Thr Asn Cys Gly Ser Lys Ser Gln Val Ser Asp His Cys Ile
1 5 10

<210> SEQ ID NO 951
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 951

Asn His Cys His Pro Gln Phe Trp Glu Leu Thr Asn Cys Asn
1 5 10

<210> SEQ ID NO 952
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 952

Leu Leu Cys His Pro Gln Gly Asp Leu Tyr His Leu Cys His
1 5 10

<210> SEQ ID NO 953
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 953

Thr Asn Cys Asp Ser Lys Leu Glu Gly Asp Asp Asn Cys Phe
1 5 10

<210> SEQ ID NO 954
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 954

Asn Asp Cys Gly Pro Glu Met Asp Glu Ser Leu Leu Cys Asp
1 5 10

<210> SEQ ID NO 955
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 955

Phe His Cys Gly Pro Glu Val Asp Glu Ser Ile Asn Cys Asn
1 5 10

<210> SEQ ID NO 956
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 956

Asp Phe Cys Gly Pro Asp Gly Asp Glu Thr Tyr Val Cys Ser
1 5 10

<210> SEQ ID NO 957
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 957

Val Ser Cys Gly Pro Gln Phe Asp Glu Asn Asn Thr Cys Asn
1 5 10

<210> SEQ ID NO 958
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 958

Val Tyr Cys His Leu Glu Ser Glu Gln Phe Asp Ile Cys Ile
1 5 10

<210> SEQ ID NO 959
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 959

Asp Asp Cys Gly Pro Glu Trp Glu Phe Val Phe Phe Cys Asp
1 5 10

<210> SEQ ID NO 960
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 960

Tyr Asn Cys Glu Gln Gln Gln Asp Glu Asp Pro Ser Cys Ile
1 5 10

<210> SEQ ID NO 961
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Asn Thr Cys Gly Thr Glu Gln His Glu Phe Asn Gly Cys Leu
1               5                   10

<210> SEQ ID NO 962
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 962

His Pro Cys Gln Pro Gly Phe Glu Glu Val Asp Tyr Cys Val
1               5                   10

<210> SEQ ID NO 963
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 963

Val Ala Cys Ser Arg Gln Leu Gly Glu Asp Ala Tyr Cys Asn
1               5                   10

<210> SEQ ID NO 964
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Asp Ile Cys Gly Ala Gln Glu Val His Val Tyr Thr Cys Pro
1               5                   10

<210> SEQ ID NO 965
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Phe Phe Cys Glu Gly Asn Leu Asp Ala Tyr Leu Leu Cys Leu
1               5                   10

<210> SEQ ID NO 966
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 966

```
Tyr Tyr Cys Gly Pro Asp Gly Glu Glu Asn Ile Val Cys Asp
1               5                   10
```

COMPOSITIONS AND METHODS RELATED TO TUMOR ACTIVATED ANTIBODIES TARGETING PSMA AND EFFECTOR CELL ANTIGENS

CROSS-REFERENCE

The present application claims the benefit of U.S. Provisional Application No. 63/123,329, filed Dec. 9, 2020, and U.S. Provisional Application No. 63/187,699, filed May 12, 2021, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 30, 2021, is named 52426-730_201_SL.txt and is 321,031 bytes in size.

SUMMARY

Disclosed herein, in certain embodiments, are isolated polypeptides or polypeptide complexes according to Formula I:

$$A_2\text{-}A_1\text{-}L_1\text{-}P_1\text{-}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA). In some embodiments, the first antigen recognizing molecule comprises an antibody or antibody fragment. In some embodiments, first antigen recognizing molecule comprises an antibody or antibody fragment that is human or humanized. In some embodiments, $L_1$ is bound to a N-terminus of the first antigen recognizing molecule. In some embodiments, $A_2$ is bound to a C-terminus of the first antigen recognizing molecule. In some embodiments, $L_1$ is bound to a C-terminus of the first antigen recognizing molecule. In some embodiments, $A_2$ is bound to a N-terminus of the first antigen recognizing molecule. In some embodiments, the antibody or antibody fragment comprises a single chain variable fragment, a single domain antibody, or a Fab fragment. In some embodiments, $A_1$ is the single chain variable fragment (scFv). In some embodiments, the scFv comprises a scFv heavy chain polypeptide and a scFv light chain polypeptide. In some embodiments, $A_1$ is the single domain antibody, In some embodiments, the antibody or antibody fragment comprises a single chain variable fragment (scFv), a heavy chain variable domain (VH domain), a light chain variable domain (VL domain), or a variable domain (VHH) of a camelid derived single domain antibody. In some embodiments, $A_1$ comprises an anti-CD3e single chain variable fragment. In some embodiments, $A_1$ comprises an anti-CD3e single chain variable fragment that has a $K_D$ binding of 1 μM or less to CD3 on CD3 expressing cells. In some embodiments, the effector cell antigen comprises CD3. In some embodiments, $A_1$ comprises a variable light chain and variable heavy chain each of which is capable of specifically binding to human CD3. In some embodiments, $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19. In some embodiments, the polypeptide or polypeptide complex of Formula I binds to an effector cell when $L_1$ is cleaved by the tumor specific protease. In some embodiments, the polypeptide or polypeptide complex of Formula I binds to an effector cell when $L_1$ is cleaved by the tumor specific protease and $A_1$ binds to the effector cell. In some embodiments, the effector cell is a T cell. In some embodiments, $A_1$ binds to a polypeptide that is part of a TCR-CD3 complex on the effector cell. In some embodiments, the polypeptide that is part of the TCR-CD3 complex is human CD3s. In some embodiments, the effector cell antigen comprises CD3, wherein the scFv comprises complementarity determining regions (CDRs): HC-CDR1, HC-CDR2, and HC-CDR3, wherein the HC-CDR1, the HC-CDR2, and the HC-CDR3 of the scFv comprise: HC-CDR1: SEQ ID NO: 1, HC-CDR2: SEQ ID NO: 2, and HC-CDR3: SEQ ID NO: 3; and the scFv comprises CDRs: LC-CDR1, LC-CDR2, and LC-CDR3, wherein the LC-CDR1, the LC-CDR2, and the LC-CDR3 of the scFv comprises: LC-CDR1: SEQ ID NO: 4, LC-CDR2: SEQ ID NO:5, and LC-CDR3: SEQ ID NO: 6. In some embodiments, the effector cell antigen comprises CD3, and the scFv comprises an amino acid sequence according to SEQ ID NO: 7. In some embodiments, second antigen recognizing molecule comprises an antibody or antibody fragment. In some embodiments, the antibody or antibody fragment thereof comprises a single chain variable fragment, a single domain antibody, or a Fab. In some embodiments, the antibody or antibody fragment thereof comprises a single chain variable fragment (scFv), a heavy chain variable domain (VH domain), a light chain variable domain (VL domain), or a variable domain (VHH) of a camelid derived single domain antibody. In some embodiments, the antibody or antibody fragment thereof is humanized or human. In some embodiments, $A_2$ is the Fab. In some embodiments, the Fab comprises (a) a Fab light chain polypeptide and (b) a Fab heavy chain polypeptide. In some embodiments, the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10; and the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 11, LC-CDR2: SEQ ID NO:12, and LC-CDR3: SEQ ID NO: 13. In some embodiments, the Fab light chain polypeptide comprises an amino acid sequence according to SEQ ID NO: 14. In some embodiments, the Fab heavy chain polypeptide comprises an amino acid sequence according to SEQ ID NO: 15. In some embodiments, the Fab light chain polypeptide of $A_2$ is bound to a C-terminus of the single chain variable fragment (scFv) of $A_1$. In some embodiments, the Fab heavy chain polypeptide of $A_2$ is bound to a C-terminus of the single chain variable fragment (scFv) $A_1$. In some embodiments, the Fab light chain polypeptide of $A_2$ is bound to a N-terminus of the single chain variable fragment (scFv) of $A_1$. In some embodiments, the Fab heavy chain polypeptide of $A_2$ is bound to a N-terminus of the single chain variable fragment (scFv) $A_1$. In some embodiments, the Fab heavy chain polypeptide of $A_2$ is bound to the scFv heavy chain polypeptide of $A_1$. In some embodiments, the Fab light chain polypeptide of $A_2$ is bound to the scFv heavy chain polypeptide of $A_1$. In some embodiments, the Fab heavy chain polypeptide of $A_2$ is bound to the scFv light chain polypeptide of $A_1$. In some embodiments, the Fab light chain polypeptide of $A_2$ is bound to the scFv light chain polypeptide of $A_1$. In some embodiments, $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease. In some embodiments, the polypeptide or polypeptide complex is according to Formula Ia:

$$P_2\text{-}L_2\text{-}A_2\text{-}A_1\text{-}L_1\text{-}P_1\text{—}H_1 \quad \text{(Formula Ia)}$$

In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$. In some embodiments, $P_1$ impairs binding of $A_1$ to the effector cell antigen. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ has less than 70% sequence homology to the effector cell antigen. In some embodiments, $P_2$ impairs binding of $A_2$ to PSMA. In some embodiments, $P_2$ is bound to $A_2$ through ionic interactions, electrostatic interactions, hydrophobic interactions, Pi-stacking interactions, and H-bonding interactions, or a combination thereof. In some embodiments, $P_2$ is bound to $A_2$ at or near an antigen binding site. In some embodiments, $P_2$ has less than 70% sequence homology to PSMA. In some embodiments, $P_1$ or $P_2$ comprises a peptide sequence of at least 10 amino acids in length. In some embodiments, $P_1$ or $P_2$ comprises a peptide sequence of at least 10 amino acids in length and no more than 20 amino acids in length. In some embodiments, $P_1$ or $P_2$ comprises a peptide sequence of at least 16 amino acids in length. In some embodiments, $P_1$ or $P_2$ comprises a peptide sequence of no more than 40 amino acids in length. In some embodiments, $P_1$ or $P_2$ comprises at least two cysteine amino acid residues. In some embodiments, $P_1$ or $P_2$ comprises a cyclic peptide or a linear peptide. In some embodiments, $P_1$ or $P_2$ comprises a cyclic peptide. In some embodiments, $P_1$ or $P_2$ comprises a linear peptide In some embodiments, $P_1$ comprises at least two cysteine amino acid residues. In some embodiments, $P_1$ comprises an amino acid sequence according to any one of SEQ ID NOs: 16-19 or 78. In some embodiments, $L_1$ is bound to a N-terminus of $A_1$. In some embodiments, $L_1$ is bound to a C-terminus of $A_1$. In some embodiments, $L_2$ is bound to a N-terminus of $A_2$. In some embodiments, $L_2$ is bound to a C-terminus of $A_2$. In some embodiments, $L_1$ or $L_2$ is a peptide sequence having at least 5 to no more than 50 amino acids. In some embodiments, $L_1$ or $L_2$ is a peptide sequence having at least 10 to no more than 30 amino acids. In some embodiments, $L_1$ or $L_2$ is a peptide sequence having at least 10 amino acids. In some embodiments, $L_1$ or $L_2$ is a peptide sequence having at least 18 amino acids. In some embodiments, $L_1$ or $L_2$ is a peptide sequence having at least 26 amino acids. In some embodiments, $L_1$ or $L_2$ has a formula comprising $(G_2S)_n$, wherein n is an integer from 1 to 3 (SEQ ID NO: 118). In some embodiments, $L_1$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, $P_1$ becomes unbound from $A_1$ when $L_1$ is cleaved by the tumor specific protease thereby exposing $A_1$ to the effector cell antigen. In some embodiments, $P_2$ becomes unbound from $A_2$ when $L_2$ is cleaved by the tumor specific protease thereby exposing $A_2$ to PSMA. In some embodiments, the tumor specific protease is selected from the group consisting of a matrix metalloprotease (MMP), serine protease, cysteine protease, threonine protease, and aspartic protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $L_1$ or $L_2$ comprises a urokinase cleavable amino acid sequence, a matriptase cleavable amino acid sequence, a matrix metalloprotease cleavable amino acid sequence, or a legumain cleavable amino acid sequence. In some embodiments, $L_1$ or $L_2$ comprises an amino acid sequence according to SEQ ID NO: 23. In some embodiments, $L_1$ or $L_2$ comprises an amino acid sequence according to any one of SEQ ID NOs: 20-49. In some embodiments, $L_1$ or $L_2$ comprises an amino acid sequence of Linker 25 (ISSGLLSGRSDAG) (SEQ ID NO: 45), Linker 26 (AAGLLAPPGGLSGRSDAG) (SEQ ID NO: 46), Linker 27 (SPLGLSGRSDAG) (SEQ ID NO: 47), or Linker 28 (LSGRSDAGSPLGLAG) (SEQ ID NO: 48), or an amino acid sequence that has 1, 2, or 3 amino acid substitutions, additions, or deletions relative to the amino acid sequence of Linker 25, Linker 26, Linker 27, or Linker 28. In some embodiments, $H_1$ comprises a polymer. In some embodiments, the polymer is polyethylene glycol (PEG). In some embodiments, $H_1$ comprises albumin. In some embodiments, $H_1$ comprises an Fe domain. In some embodiments, the albumin is serum albumin. In some embodiments, the albumin is human serum albumin. In some embodiments, $H_1$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, slgA, IgM or IgD. In some embodiments, the serum protein is albumin. In some embodiments, the polypeptide is an antibody. In some embodiments, the antibody comprises a single domain antibody, a single chain variable fragment, or a Fab. In some embodiments, the single domain antibody comprises a single domain antibody that binds to albumin. In some embodiments, the single domain antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A10m3 or a fragment thereof. In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10E. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60. In some embodiments, the single domain antibody is SA21. In some embodiments, the polypeptide or polypeptide complex comprises a modified amino acid, a non-natural amino acid, a modified non-natural amino acid, or a combination thereof. In some embodiments, the modified amino acid or modified non-natural amino acid comprises a post-translational modification. In some embodiments, $H_1$ comprises a linking moiety ($L_3$) that connects $H_1$ to $P_1$. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1. In some embodiments, $L_3$ comprises an amino acid sequence according to SEQ ID NO: 22. In some embodiments, the polypeptide or polypeptide complex comprises an amino acid sequence with at least 95% sequence identity to SEQ ID NOs: 62-77. In some embodiments, the polypeptide or polypeptide complex comprises an amino acid sequence with at least 95% sequence identity to SEQ ID NO: 72. In some embodiments, the polypeptide or polypeptide complex comprises an amino acid sequence with at least 95% sequence identity to SEQ ID NO: 73. In some embodiments, the polypeptide or polypeptide complex comprises an amino acid sequence with at least 95% sequence identity to SEQ ID NO: 62 and SEQ ID NO: 63. In some embodiments, the polypeptide or polypeptide complex comprises an amino acid sequence with at least 95% sequence identity to SEQ ID NO: 64 and SEQ ID NO: 65. In some embodiments, the polypeptide or polypeptide complex comprises an amino acid sequence with at least 95% sequence identity to SEQ ID NO: 66 and SEQ ID NO: 67. In some embodiments, the polypeptide or polypeptide complex comprises an amino acid sequence with at least 95% sequence identity to SEQ ID NO: 68 and SEQ ID NO: 69. In some embodiments, the polypeptide or polypeptide complex comprises an amino acid sequence with at least 95% sequence identity to SEQ ID NO: 70 and SEQ ID NO: 71. In some embodiments, the polypeptide or polypeptide complex comprises an amino acid sequence with at least 95% sequence identity to SEQ ID NO: 72 and SEQ ID NO: 73. In some embodiments, the polypeptide or polypeptide complex comprises an amino acid sequence with at least 95% sequence identity to SEQ ID NO: 74 and SEQ ID NO: 75. In some embodiments, the polypeptide or polypeptide complex comprises an amino acid sequence with at least 95% sequence identity to SEQ ID NO: 76 and SEQ ID NO: 77.

Disclosed herein, in certain embodiments, are pharmaceutical compositions comprising: (a) the polypeptide or polypeptide complex described herein; and (b) a pharmaceutically acceptable excipient.

Disclosed herein, in certain embodiments, are isolated recombinant nucleic acid molecules encoding the polypeptide or polypeptide complex described herein.

Disclosed herein, in certain embodiments, are isolated polypeptides or polypeptide complexes according to Formula II:

$$L_{1a}\text{-}P_{1a}\text{-}H_{1a} \tag{Formula II}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to PSMA; $P_{1a}$ comprises a peptide that binds to the first antigen recognizing molecule when $L_{1a}$ is uncleaved; and $H_{1a}$ comprises a half-life extending molecule. In some embodiments, $P_{1a}$ when $L_{1a}$ is uncleaved impairs binding of the first antigen recognizing molecule to the effector cell antigen. In some embodiments, the first antigen recognizing molecule comprises an antibody or antibody fragment. In some embodiments, the effector cell antigen is an anti-CD3 effector cell antigen. In some embodiments, $P_{1a}$ has less than 70% sequence homology to the effector cell antigen. In some embodiments, $P_{1a}$ comprises a peptide sequence of at least 10 amino acids in length. In some embodiments, $P_{1a}$ comprises a peptide sequence of at least 10 amino acids in length and no more than 20 amino acids in length. In some embodiments, $P_{1a}$ comprises a peptide sequence of at least 16 amino acids in length. In some embodiments, $P_{1a}$ comprises a peptide sequence of no more than 40 amino acids in length. In some embodiments, $P_{1a}$ comprises at least two cysteine amino acid residues. In some embodiments, $P_{1a}$ comprises a cyclic peptide or a linear peptide. In some embodiments, $P_{1a}$ comprises a cyclic peptide. In some embodiments, $P_{1a}$ comprises a linear peptide. In some embodiments, $P_{1a}$ comprises an amino acid sequence selected from the group consisting of any one of SEQ ID NOs: 16-19. In some embodiments, $H_{1a}$ comprises a polymer. In some embodiments, the polymer is polyethylene glycol (PEG). In some embodiments, $H_{1a}$ comprises albumin. In some embodiments, $H_{1a}$ comprises an Fc domain. In some embodiments, the albumin is serum albumin. In some embodiments, the albumin is human serum albumin. In some embodiments, $H_{1a}$ comprises a polypeptide, a ligand, or a small molecule. In some embodiments, the polypeptide, the ligand or the small molecule binds a serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the antibody comprises a single domain antibody that binds to albumin. In some embodiments, the antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A10m3 or a fragment thereof.

In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10E. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60. In some embodiments, the single domain antibody is SA21. In some embodiments, $H_{1a}$ comprises a linking moiety ($L_{1a}$) that connects $H_{1a}$ to $P_{1a}$. In some embodiments, $L_{1a}$ is a peptide sequence having at least 5 to no more than 50 amino acids. In some embodiments, $L_{1a}$ is a peptide sequence having at least 10 to no more than 30 amino acids. In some embodiments, $L_{1a}$ is a peptide sequence having at least 10 amino acids. In some embodiments, $L_{1a}$ is a peptide sequence having at least 18 amino acids. In some embodiments, $L_{1a}$ is a peptide sequence having at least 26 amino acids. In some embodiments, $L_{1a}$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1. In some embodiments, $L_{1a}$ comprises an amino acid sequence according to SEQ ID NO: 23. Disclosed herein some embodiments are polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv. Disclosed herein in some embodiments are polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1A:
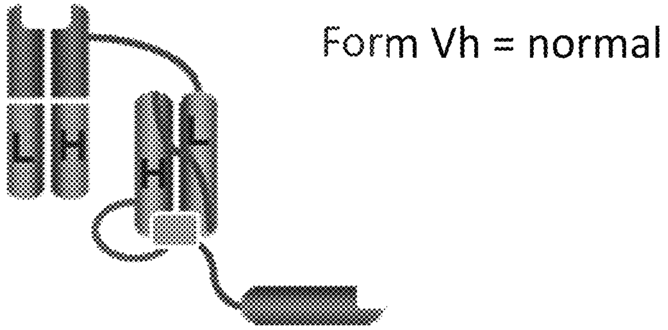
FIGS. 1A-1R illustrate polypeptide complexes of this disclosure in a normal orientation (FIG. 1A), flipped orientation (FIG. 1B), and in several structural arrangements (FIGS. 1C-1R).
Figure 1B:
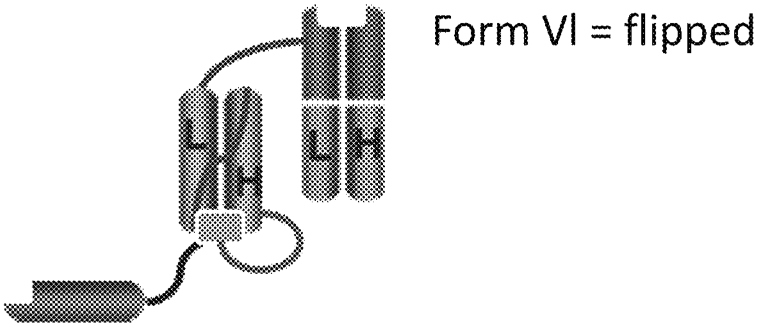

Multispecific antibodies combine the benefits of different binding specificities derived from two or more antibodies into a single composition. Multispecific antibodies for redirecting T cells to cancers have shown promise in both pre-clinical and clinical studies. This approach relies on binding of one antigen interacting portion of the antibody to a tumor-associated antigen or marker, while a second antigen interacting portion can bind to an effector cell antigen on a T cell, such as CD3, which then triggers cytotoxic activity.

One such tumor-associated antigen is PSMA. Prostate-specific membrane antigen (PSMA), also known as glutamate carboxypeptidase II (GCPII), N-acetyl-L-aspartyl-L-glutamate peptidase I (NAALADase I), or NAAG peptidase is an enzyme that in humans is encoded by the FOLH1 (folate hydrolase 1) gene. PSMA is a zinc metalloenzyme that resides in membranes. Most of the enzyme resides in the extracellular space. Human PSMA is highly expressed in the prostate, roughly a hundred times greater than in most other tissues. In some prostate cancers, PSMA is the second-most upregulated gene product, with an 8- to 12-fold increase over levels in noncancerous prostate cells.

T cell engagers (TCEs) therapeutics have several benefits including they are not cell therapies and thus can be offered as off-the-shelf therapies as opposed to chimeric antigen receptor T cell (CAR T cell) therapies. While TCE therapeutics have displayed potent anti-tumor activity in hematological cancers, developing TCEs to treat solid tumors has faced challenges due to the limitations of prior TCE technologies, namely (i) overactivation of the immune system leading to cytokine release syndrome (CRS), (ii) on-target, healthy tissue toxicities and (iii) poor pharmacokinetics (PK) leading to short half-life. CRS arises from the systemic activation of T cells and can result in life-threatening elevations in inflammatory cytokines such as interleukin-6 (IL-6). Severe and acute CRS leading to dose limited toxicities and deaths have been observed upon the dosing of T cell engagers develop using other platforms to treat cancer patients in poor clinical studies. This toxicity restricts the maximum blood levels of T cell engagers that can be safely dosed. T cell engager effectiveness has also been limited because of on-target, healthy tissue toxicity. T cell engagers developed using a platform not designed for tumor-specification activation have resulted in clinicals holds and dose-limiting toxicities resulting from target expression in healthy tissues. T cell engagers have also been limited by short half-lives. T cell engagers quickly reach sub-therapeutic levels after being administered as they are quickly eliminated from the body due to their short exposure half-lives. For this reason, T cell engagers such as blinatumomab are typically administered by a low-dose, continuous infusion pump over a period of weeks to overcome the challenge of a short half-life and to maintain therapeutic levels of drug in the body. A continuous dosing regimen represents a significant burden for patients.

To overcome these challenges associated with the effectiveness of T cell engagers, described herein, are polypeptide or polypeptide complexes that comprise binding domains that selectively bind to an effector cell antigen and PSMA, in which one or more of the binding domains is selectively activated in the tumor microenvironment and the polypeptide or polypeptide complex comprises a half-life extending molecule. Such modifications reduce CRS and on-target healthy tissue toxicity risk, improves stability in the bloodstream and serum half-life prior to activation. The polypeptide or polypeptide complexes described herein have activity at low levels of target expression, and are easily manufactured.

In some embodiments, the polypeptides or polypeptide complexes described herein are used in a method of treating cancer. In some embodiments, the cancer has cells that express PSMA. In some embodiments, the polypeptides or polypeptide complexes described herein are used in a method of treating prostate cancer. In some embodiments, the prostate cancer is metastatic castrate resistant prostate cancer (mCRPC). Prostate cancer is the second most common cancer in men worldwide with over 3 million men living with prostate cancer in the United States alone. Early diagnoses and effective therapies mean that most prostate cancer patients have a prognosis with a mean five-year survival rate of approximately 98 percent. However, an estimated six percent of prostate cancer patients develop metastatic disease, which is associated with a five-year survival rate of approximately 30 percent. There were an estimated 33,000 deaths in the United States due to prostate cancer in 2020.

In some instances, the polypeptides or polypeptide complexes described herein are used to treat a solid tumor cancer. In some embodiments, the cancer is lung, breast (e.g. HER2+; ER/PR+; TNBC), cervical, ovarian, colorectal, pancreatic or gastric. In some embodiments, are methods of treating cancer comprising administering to a subject in need thereof an isolated polypeptide or polypeptide complex according to Formula I:

$$A_2\text{-}A_1\text{-}L_1\text{-}P_1\text{-}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to PSMA.

Disclosed herein, in some embodiments, are isolated polypeptides or polypeptide complexes according to Formula I:

$$A_2\text{-}A_1\text{-}L_1\text{-}P_1\text{-}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Disclosed herein, in some embodiments, are isolated polypeptides or polypeptide complexes according to Formula I:

$$A_2\text{-}A_1\text{-}L_1\text{-}P_1\text{-}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA).

Disclosed herein, in some embodiments, are isolated polypeptides or polypeptide complexes comprising Formula I:

$$A_2\text{-}A_1\text{-}L_1\text{-}P_1\text{-}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Disclosed herein, in some embodiments, are isolated polypeptides or polypeptide complexes comprising Formula I:

$$A_2\text{-}A_1\text{-}L_1\text{-}P_1\text{-}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA).

Disclosed herein, in some embodiments, are isolated polypeptides or polypeptide complexes according to Formula I:

$$A_2\text{-}A_1\text{-}L_1\text{-}P_1\text{-}H_1 \quad \text{(Formula I)}$$

wherein: $A_1$ comprises a first antigen recognizing molecule that binds to prostate-specific membrane antigen (PSMA); $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to an effector cell antigen.

Disclosed herein, in some embodiments, are isolated polypeptides or polypeptide complexes according to Formula I:

$$A_2\text{-}A_1\text{-}L_1\text{-}P_1\text{-}H_1 \quad \text{(Formula I)}$$

wherein: $A_1$ is a first antigen recognizing molecule that binds to prostate-specific membrane antigen (PSMA); $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to effector cell antigen.

Disclosed herein, in some embodiments, are isolated polypeptides or polypeptide complexes comprising Formula I:

$$A_2\text{-}A_1\text{-}L_1\text{-}P_1\text{-}H_1 \quad \text{(Formula I)}$$

wherein: $A_1$ comprises a first antigen recognizing molecule that binds to prostate-specific membrane antigen (PSMA); $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to an effector cell antigen.

Disclosed herein, in some embodiments, are isolated polypeptides or polypeptide complexes comprising Formula I:

$$A_2\text{-}A_1\text{-}L_1\text{-}P_1\text{-}H_1 \quad \text{(Formula I)}$$

wherein: $A_1$ is a first antigen recognizing molecule that binds to prostate-specific membrane antigen (PSMA); $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to an effector cell antigen.

Disclosed herein, in some embodiments, are isolated polypeptides or polypeptide complexes according to Formula Ia:

$$P_2\text{-}L_2\text{-}A_2\text{-}A_1\text{-}L_1\text{-}P_1\text{-}H_1 \quad \text{(Formula Ia)}$$

wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Disclosed herein, in some embodiments, are isolated polypeptides or polypeptide complexes according to Formula Ia:

$$P_2\text{-}L_2\text{-}A_2\text{-}A_1\text{-}L_1\text{-}P_1\text{-}H_1 \quad \text{(Formula Ia)}$$

wherein $A_2$ further comprises $P_2$ and $L_2$, wherein $P_2$ is a peptide that binds to $A_2$; and $L_2$ is a linking moiety that connects $A_2$ to $P_2$ and is a substrate for a tumor specific protease.

Disclosed herein, in some embodiments, are isolated polypeptides or polypeptide complexes comprising Formula Ia:

$$P_2\text{-}L_2\text{-}A_2\text{-}A_1\text{-}L_1\text{-}P_1\text{-}H_1 \quad \text{(Formula Ia)}$$

wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Disclosed herein, in some embodiments, are isolated polypeptides or polypeptide complexes comprising Formula Ia:

$$P_2\text{-}L_2\text{-}A_2\text{-}A_1\text{-}L_1\text{-}P_1\text{-}H_1 \quad \text{(Formula Ia)}$$

wherein $A_2$ further comprises $P_2$ and $L_2$, wherein $P_2$ is a peptide that binds to $A_2$; and $L_2$ is a linking moiety that connects $A_2$ to $P_2$ and is a substrate for a tumor specific protease.

Disclosed herein, in some embodiments, are isolated polypeptides or polypeptide complexes according to Formula II:

$$L_{1a}\text{-}P_{1a}\text{-}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated polypeptides or polypeptide complexes comprising Formula II:

$$L_{1a}\text{-}P_{1a}\text{-}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated polypeptides or polypeptide complexes according to Formula II:

$$L_{1a}\text{-}P_{1a}\text{-}H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

Disclosed herein, in some embodiments, are isolated polypeptides or polypeptide complexes comprising Formula II:

$$L_{1a}\text{-}P_{1a}\text{-}H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

First Antigen Recognizing Molecule (A)

Disclosed herein, in some embodiments, are isolated polypeptides or polypeptide complexes, wherein the first antigen recognizing molecule binds to an effector cell antigen and the second antigen recognizing molecule binds to PSMA. In some embodiments, the effector cell antigen comprises CD3. In some embodiments, $A_1$ comprises a first antigen recognizing molecule that binds to an effector cell antigen.

In some embodiments, $A_1$ comprises an antibody or antibody fragment. In some embodiments, $A_1$ comprises an antibody or antibody fragment that is human or humanized. In some embodiments, $L_1$ is bound to a N-terminus of the antibody or antibody fragment. In some embodiments, $L_1$ is bound to a N-terminus of the antibody or antibody fragment and $A_2$ is bound to the other N-terminus of the antibody or antibody fragment. In some embodiments, $A_2$ is bound to a C-terminus of the antibody or antibody fragment. In some embodiments, $L_1$ is bound to a C-terminus of the antibody or antibody fragment. In some embodiments, $A_2$ is bound to a N-terminus of the antibody or antibody fragment. In some embodiments, the antibody or antibody fragment comprises a single chain variable fragment, a single domain antibody, or a Fab fragment. In some embodiments, $A_1$ is the single chain variable fragment (scFv). In some embodiments, the scFv comprises a scFv heavy chain polypeptide and a scFv light chain polypeptide. In some embodiments, $A_1$ is the single domain antibody. In some embodiments, $A_1$ comprises a variable light chain and variable heavy chain each of which is capable of specifically binding to human CD3. In some embodiments, the effector cell antigen comprises CD3. In some embodiments, $A_1$ comprises an anti-CD3e single chain variable fragment. In some embodiments, $A_1$ comprises an anti-CD3e single chain variable fragment that has a $K_D$ binding of 1 μM or less to CD3 on CD3 expressing cells. In some embodiments, $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

In some embodiments, $A_1$ comprises a first antigen recognizing molecule that binds PSMA. In some embodiments, $A_1$ comprises a variable light chain and variable heavy chain each of which is capable of specifically binding to human PSMA.

In some embodiments, the scFv that binds to CD3 comprises a scFv light chain variable domain and a scFv heavy chain variable domain. In some embodiments, the scFv heavy chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity). In some embodiments, the scFv light chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity).

In some embodiments, the scFv heavy chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity); and the scFv light chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity).

TABLE 1 anti-CD3 amino acid sequences (CDRs as determined by IMGT numbering system)

| Construct Description | Amino Acid Sequence (N to C) | SEQ ID NO: |
|---|---|---|
| SP34.185 CD3: HC: CDR1 | GFTFNKYA | 1 |
| SP34.185 CD3: HC: CDR2 | IRSKYNNYAT | 2 |
| SP34.185 CD3: HC: CDR3 | VRHGNFGNSYISYWAY | 3 |
| SP34.185 CD3: LC: CDR1 | TGAVTSGNY | 4 |
| SP34.185 CD3: LC: CDR2 | GT | 5 |
| SP34.185 CD3: LC: CDR3 | VLWYSNRWV | 6 |
| SP34.185 scFv VH-linker 1-VL | EVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTWTQEPSLTVSPGGTVTLTCGSS**TGAVTSGNY**PNWVQQKPGQAPRGLIG**GT**KFLAPGTPARFSGSLLGGKAALTLSGVQPEDEAEYYC**VLWYSNRWV**FGGGTKLTVL | 7 |

In some embodiments, the scFv heavy chain variable domain comprises complementarity determining regions (CDRs): HC-CDR1, HC-CDR2, and HC-CDR3, wherein the HC-CDR1, the HC-CDR2, and the HC-CDR3 of the scFv heavy chain variable domain comprise: HC-CDR1: SEQ ID NO: 1; HC-CDR2: SEQ ID NO: 2; HC-CDR3: SEQ ID NO: 3, and wherein the CDRs comprise from 0-2 amino acid modifications in at least one of the HC-CDR1, HC-CDR2, or HC-CDR3. In some embodiments, the scFv light chain variable domain comprises complementarity determining regions (CDRs): LC-CDR1, LC-CDR2, and LC-CDR3, wherein the LC-CDR1, the LC-CDR2, and the LC-CDR3 of the scFv light chain variable domain comprise: LC-CDR1: SEQ ID NO: 4; LC-CDR2: SEQ ID NO: 5; and LC-CDR3: SEQ ID NO: 6, and wherein the CDRs comprise from 0-2 amino acid modifications in at least one of the LC-CDR1, LC-CDR2, or LC-CDR3.

In some embodiments, the polypeptide or polypeptide complex of Formula I binds to an effector cell when $L_1$ is cleaved by the tumor specific protease. In some embodiments, the polypeptide or polypeptide complex of Formula I binds to an effector cell when $L_1$ is cleaved by the tumor specific protease and $A_1$ binds to the effector cell. In some embodiments, the effector cell is a T cell. In some embodiments, $A_1$ binds to a polypeptide that is part of a TCR-CD3 complex on the effector cell. In some embodiments, the polypeptide that is part of the TCR-CD3 complex is human CD3R. In some embodiments, the effector cell antigen comprises CD3, wherein the scFv comprises complementarity determining regions (CDRs): HC-CDR1, HC-CDR2, and HC-CDR3, wherein the HC-CDR1, the HC-CDR2, and the HC-CDR3 of the scFv comprise: HC-CDR1: SEQ ID NO: 1, HC-CDR2: SEQ ID NO: 2, and HC-CDR3: SEQ ID NO: 3; and the scFv comprises CDRs: LC-CDR1, LC-CDR2, and LC-CDR3, wherein the LC-CDR1, the LC-CDR2, and the LC-CDR3 of the scFv comprise: LC-CDR1: SEQ ID NO: 4, LC-CDR2: SEQ ID NO:5, and LC-CDR3: SEQ ID NO: 6. In some embodiments, the effector cell antigen comprises CD3, and the scFv comprises an amino acid sequence according to SEQ ID NO: 7.

In some embodiments, the effector cell antigen comprises CD3, and wherein $A_1$ comprises complementarity determining regions (CDRs): HC-CDR1, HC-CDR2, and HC-CDR3, wherein the HC-CDR1, the HC-CDR2, and the HC-CDR3 of $A_1$ comprises: HC-CDR1: SEQ ID NO: 1, HC-CDR2: SEQ ID NO: 2, and HC-CDR3: SEQ ID NO: 3; and $A_1$ comprises CDRs: LC-CDR1, LC-CDR2, and LC-CDR3, wherein the LC-CDR1, the LC-CDR2, and the LC-CDR3 of $A_1$ comprise: LC-CDR1: SEQ ID NO: 4, LC-CDR2: SEQ ID NO:5, and LC-CDR3: SEQ ID NO: 6. In some embodiments, the effector cell antigen comprises CD3, and $A_1$ comprises an amino acid sequence according to SEQ ID NO: 7.

In some embodiments, $A_1$ comprises an amino acid sequence according to SEQ ID NO: 7. In some embodiments, $A_1$ comprises an amino acid sequence that has at least 80% sequence identity to SEQ ID NO: 7. In some embodiments, $A_1$ comprises an amino acid sequence that has at least 85% sequence identity to SEQ ID NO: 7. In some embodiments, $A_1$ comprises an amino acid sequence that has at least 90% sequence identity to SEQ ID NO: 7. In some embodiments, $A_1$ comprises an amino acid sequence that has at least 95% sequence identity to SEQ ID NO: 7. In some embodiments, $A_1$ comprises an amino acid sequence that has at least 99% sequence identity to SEQ ID NO: 7.

In some embodiments, the polypeptide or polypeptide complex has weaker binding affinity for the tumor cell antigen as compared to the binding affinity for the tumor cell antigen of an isolated polypeptide or polypeptide complex that does not have $P_1$ or $L_1$. In some embodiments, the polypeptide or polypeptide complex has weaker binding affinity for the tumor cell antigen that is at least 5× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 8× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 10× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 15× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 20× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 25× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 30× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 35× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 40× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 45× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 50× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 55× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 60× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 65× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 70× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 75× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 80× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 85× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 90× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 95× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 100× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 120× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 1000× higher than the binding affinity for the tumor cell antigen of a form of the polypeptide or polypeptide complex that does not have $P_1$ or $L_1$.

In some embodiments, the polypeptide or polypeptide complex has weaker binding affinity for the tumor cell antigen as compared to the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 5× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 8× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 10× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 15× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 20× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 25× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 30× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 35× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 40× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 45× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 50× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 55× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 60× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 65× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 70× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 75× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 80× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 85× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 90× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 95× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 100× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 120× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 1000× higher than the binding affinity for the tumor cell antigen of the polypeptide or polypeptide complex in which $L_1$ has been cleaved by the tumor specific protease.

In some embodiments, the polypeptide or polypeptide complex has an increased $EC_{50}$ in an IFNγ release T-cell activation assay as compared to the $EC_{50}$ in an IFNγ release T-cell activation assay of an isolated polypeptide or polypeptide complex that does not have $P_1$ or $L_1$. In some embodiments, the polypeptide or polypeptide complex has an increased $EC_{50}$ in an IFNγ release T-cell activation assay that is at least 10× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 20× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 30× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 40× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 50× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 60× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 70× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 80× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 90× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 100× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 1000× higher than the $EC_{50}$ in an IFNγ release T-cell activation assay of a form of the polypeptide or polypeptide complex that does not have $P_1$ or $L_1$.

In some embodiments, the polypeptide or polypeptide complex has an increased $EC_{50}$ in an IFNγ release T-cell activation assay as compared to the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 10× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 20× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 30× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 40× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 50× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 60× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 70× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 80× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 90× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 100× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 1000× higher than the $EC_{50}$ in an IFNγ release T-cell activation assay of the polypeptide or polypeptide complex in which $L_1$ has been cleaved by the tumor specific protease.

In some embodiments, the polypeptide or polypeptide complex has an increased $EC_{50}$ in a T-cell cytolysis assay as compared to the $EC_{50}$ in a T-cell cytolysis assay of an isolated polypeptide or polypeptide complex that does not have $P_1$ or $L_1$. In some embodiments, the polypeptide or polypeptide complex has an increased $EC_{50}$ in a T-cell cytolysis assay that is at least 10× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 20× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 30× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 40× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 50× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 60× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 70× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 80× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 90× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 100× higher than the $EC_{50}$ in a T-cell cytolysis assay of an isolated polypeptide or polypeptide complex that does not have $P_1$ or $L_1$. In some embodiments, the polypeptide or polypeptide complex has an increased $EC_{50}$ in a T-cell cytolysis assay that is at least 1000× higher than the $EC_{50}$ in a T-cell cytolysis assay of an isolated polypeptide or polypeptide complex that does not have $P_1$ or $L_1$.

In some embodiments, the polypeptide or polypeptide complex has an increased $EC_{50}$ in a T-cell cytolysis assay as compared to the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 10× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 20× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 30× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 40× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 50× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 60× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{5}s$ in a T-cell cytolysis assay that is at least 70× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 80× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 90× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 100× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 1,000× higher than the $EC_{50}$ in a T-cell cytolysis assay of the polypeptide or polypeptide complex in which $L_1$ has been cleaved by the tumor specific protease.

In some embodiments, the polypeptide or polypeptide complex $P_2$-$L_2$-$A_2$-$A_2$-$L_1$-$P_1$-$H_1$ (Formula Ia) has weaker binding affinity for the tumor cell antigen as compared to the binding affinity for the tumor cell antigen of an isolated polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 10× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 50× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 75× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 100× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 120× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 200× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 300× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 400× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 500× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 600× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 700× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 800× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 900× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 1000× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 10,000× higher than the binding affinity for the tumor cell antigen of a form of the polypeptide or polypeptide complex of Formula Ia that does not have $P_1$, $L_1$, $P_2$, or $L_2$.

In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen as compared to the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 10× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 50× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 75× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 100× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 120× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 200× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 300× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 400× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 500× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 600× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 700× higher than the binding affinity for the tumor cell antigen of the polypeptide or polypeptide complex of Formula Ia in which $L_1$, and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 800× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 900× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 100× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has weaker binding affinity for the tumor cell antigen that is at least 10,000× higher than the binding affinity for the tumor cell antigen of the polypeptide or polypeptide complex of Formula Ia in which $L_1$ and $L_2$ have been cleaved by the tumor specific proteases.

In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay as compared to the $EC_{50}$ in an IFNγ release T-cell activation assay of an isolated polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 10× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 50× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 75× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 100× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 200× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 300× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 400× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 500× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 600× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 700× higher than the $EC_{50}$ in an IFNγ release T-cell activation assay of a form of the polypeptide or polypeptide complex of Formula Ia that does not $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 800× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 900× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 1000× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in an IFNγ release T-cell activation assay that is at least 10,000× higher than the $EC_{50}$ in an IFNγ release T-cell activation assay of a form of the polypeptide or polypeptide complex of Formula Ia that does not have $P_1$, $L_1$, $P_2$, or $L_2$.

In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay as compared to the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 10× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 50× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_j$(Formula Ia) has an increased $EC_{50}$ in a T-cell cytolysis assay that is at least 75× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 100× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 200× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 300× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 400× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 500× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 600× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 700× higher than the ECao in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 800× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 900× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 1000× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 10,000× higher than the $EC_{50}$ in a T-cell cytolysis assay of the polypeptide or polypeptide complex of Formula Ia in which $L_1$ and $L_2$ have been cleaved by the tumor specific proteases.

In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay as compared to the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 10× higher than the $EC_{50}$ in a T-cell cytolysis assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 50× higher than the $EC_{50}$ in a T-cell cytolysis assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 75× higher than the $EC_{50}$ in a T-cell cytolysis assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 100× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 200× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 300× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 400× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 500× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 600× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 700× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 800× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 900× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 1000× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 10,000× higher than the $EC_{50}$ in a T-cell cytolysis assay of an isolated polypeptide or polypeptide complex that does not have $P_1$, $L_1$, $P_2$, or $L_2$.

In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay as compared to the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 10× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 50× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-L-$P_1$-$H_1$ (Formula Ia) has an increased $EC_{50}$ in a T-cell cytolysis assay that is at least 75× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 100× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 200× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 300× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 400× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_j$(Formula Ia) has an increased $EC_{50}$ in a T-cell cytolysis assay that is at least 500× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 600× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 700× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 800× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 900× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 1000× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$-$H_1$ (Formula Ia) has an increased $EC_{50}$ in a T-cell cytolysis assay that is at least 10,000× higher than the $EC_{50}$ in a T-cell cytolysis assay of the polypeptide or polypeptide complex of Formula Ia in which $L_1$ and $L_2$ have been cleaved by the tumor specific proteases.

Second Antigen Recognizing Molecule ($A_2$)

In some embodiments, $A_2$ comprises an antibody or antibody fragment. In some embodiments, the antibody or antibody fragment thereof comprises a single chain variable fragment, a single domain antibody, a Fab, or a Fab'. In some embodiments, the antibody or antibody fragment thereof comprises a single chain variable fragment (scFv), a heavy chain variable domain (VH domain), a light chain variable domain (VL domain), or a variable domain (VHH) of a camelid derived single domain antibody. In some embodiments, the antibody or antibody fragment thereof is humanized or human. In some embodiments, $A_2$ is the Fab or Fab'. In some embodiments, the Fab or Fab' comprises (a) a Fab light chain polypeptide and (b) a Fab heavy chain polypeptide. In some embodiments, the antibody or antibody fragment thereof comprises a PSMA binding domain.

In some embodiments, the antigen binding fragment (Fab) or Fab' that binds to PSMA comprises a Fab light chain polypeptide chain and a Fab heavy chain polypeptide. In some embodiments, the Fab light chain polypeptide comprises a Fab light chain variable domain. In some embodiments, the Fab heavy chain polypeptide comprises a Fab heavy chain variable domain. In some embodiments, the Fab heavy chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity). In some embodiments, the Fab light chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity).

In some embodiments, the Fab heavy chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity); and the Fab light chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity).

TABLE 2 anti-PSMA amino acid sequences (CDRs as determined by IMGT numbering system)

| Construct Description | Amino Acid Sequence (N to C) | SEQ ID NO: |
|---|---|---|
| PSMA: HC: CDR1 | GFAFSRYG | 8 |
| PSMA: HC: CDR2 | IWYDGSNK | 9 |
| PSMA: HC: CDR3 | ARGGDFLYYYYGMDV | 10 |
| PSMA: LC: CDR1 | QGISNY | 11 |
| PSMA: LC: CDR2 | EA | 12 |
| PSMA: LC: CDR3 | QNYNSAPFT | 13 |

TABLE 2-continued anti-PSMA amino acid sequences (CDRs as determined by IMGT numbering system)

| Construct Description | Amino Acid Sequence (N to C) | SEQ ID NO: |
|---|---|---|
| 006 PSMA Fab LC | DIQMTQSPSSLSASVGDRVTITCRASQGISNYLAWYQQKTGKVPKFLIYEASTLQSGVPSRFSGGGSGTDFTLTISSLQPEDVATYYCQNYNSAPFTFGPGTKVDIKRTVAAPSVFIFPPSDEQLKSGTASVVCLLNNFYPREAKVQWKVDNALQSGNSQESV1EQDSKDSTYSLSSTLTLSKADYEKHKVYACEVTHQGLSSPVTKSFNRGEC | 14 |
| 006 PSMA Fab HC | QVQLVESGGGVVQSCAPGRSLRLASGFAFSRYGMHWVRQAPGKGLEWVAVIWYDGSNKYYADSVKGRFTISRDNSKNTQYLQMNSLRAEDTAVYYCARGGDFLYYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 15 |

In some embodiments, the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10; and the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 11, LC-CDR2: SEQ ID NO:12, and LC-CDR3: SEQ ID NO: 13. In some embodiments, the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10 and wherein the CDRs comprise from 0-2 amino acid modifications in at least one of the HC-CDR1, HC-CDR2, or HC-CDR3; and the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 11, LC-CDR2: SEQ ID NO:12, and LC-CDR3: SEQ ID NO: 13 and wherein the CDRs comprise from 0-2 amino acid modifications in at least one of the LC-CDR1, LC-CDR2, or LC-CDR3.

In some embodiments, $A_2$ comprises complementarity determining regions (CDRs): HC-CDR1, HC-CDR2, and HC-CDR3, wherein the HC-CDR1, the HC-CDR2, and the HC-CDR3 of $A_2$ comprise: HC-CDR1: SEQ ID NO: 8, HC-CDR2: SEQ ID NO: 9, and HC-CDR3: SEQ ID NO: 10;

and $A_2$ comprises CDRs: LC-CDR1, LC-CDR2, and LC-CDR3, wherein the LC-CDR1, the LC-CDR2, and the LC-CDR3 of $A_2$ comprise LC-CDR1: SEQ ID NO: 11, LC-CDR2: SEQ ID NO:12, and LC-CDR3: SEQ ID NO: 13. In some embodiments, $A_2$ comprises complementarity determining regions (CDRs): HC-CDR1, HC-CDR2, and HC-CDR3, wherein the HC-CDR1, the HC-CDR2, and the HC-CDR3 of $A_2$ comprise: HC-CDR1: SEQ ID NO: 8, HC-CDR2: SEQ ID NO: 9, and HC-CDR3: SEQ ID NO: 10 and wherein the CDRs comprise from 0-2 amino acid modifications in at least one of the HC-CDR1, HC-CDR2, or HC-CDR3; and $A_2$ comprises CDRs: LC-CDR1, LC-CDR2, and LC-CDR3, wherein the LC-CDR1, the LC-CDR2, and the LC-CDR3 of $A_2$ comprise LC-CDR1: SEQ ID NO: 11, LC-CDR2: SEQ ID NO:12, and LC-CDR3: SEQ ID NO: 13 and wherein the CDRs comprise from 0-2 amino acid modifications in at least one of the LC-CDR1, LC-CDR2, or LC-CDR3.

In some embodiments, the Fab light chain polypeptide comprises an amino acid sequence according to SEQ ID NO: 14. In some embodiments, the Fab light chain polypeptide comprises an amino acid sequence that has at least 80% sequence identity according to SEQ ID NO: 14. In some embodiments, the Fab light chain polypeptide comprises an amino acid sequence that has at least 85% sequence identity according to SEQ ID NO: 14. In some embodiments, the Fab light chain polypeptide comprises an amino acid sequence that has at least 90% sequence identity according to SEQ ID NO: 14. In some embodiments, the Fab light chain polypeptide comprises an amino acid sequence that has at least 95% sequence identity according to SEQ ID NO: 14. In some embodiments, the Fab light chain polypeptide comprises an amino acid sequence that has at least 99% sequence identity according to SEQ ID NO: 14.

In some embodiments, the Fab heavy chain polypeptide comprises an amino acid sequence according to SEQ ID NO: 15. In some embodiments, the Fab heavy chain polypeptide comprises an amino acid sequence that has at least 80% sequence identity according to SEQ ID NO: 15. In some embodiments, the Fab heavy chain polypeptide comprises an amino acid sequence that has at least 85% sequence identity according to SEQ ID NO: 15. In some embodiments, the Fab heavy chain polypeptide comprises an amino acid sequence that has at least 90% sequence identity according to SEQ ID NO: 15. In some embodiments, the Fab heavy chain polypeptide comprises an amino acid sequence that has at least 95% sequence identity according to SEQ ID NO: 15. In some embodiments, the Fab heavy chain polypeptide comprises an amino acid sequence that has at least 99% sequence identity according to SEQ ID NO: 15.

In some embodiments, the Fab light chain polypeptide of $A_2$ is bound to a C-terminus of the single chain variable fragment (scFv) of $A_1$. In some embodiments, the Fab heavy chain polypeptide of $A_2$ is bound to a C-terminus of the single chain variable fragment (scFv) $A_1$. In some embodiments, the Fab light chain polypeptide of $A_2$ is bound to a N-terminus of the single chain variable fragment (scFv) of $A_1$. In some embodiments, the Fab heavy chain polypeptide of $A_2$ is bound to a N-terminus of the single chain variable fragment (scFv) $A_1$. In some embodiments, the Fab heavy chain polypeptide of $A_2$ is bound to the scFv heavy chain polypeptide of $A_1$. In some embodiments, the Fab light chain polypeptide of $A_2$ is bound to the scFv heavy chain polypeptide of $A_1$. In some embodiments, the Fab heavy chain polypeptide of $A_2$ is bound to the scFv light chain polypeptide of $A_1$. In some embodiments, the Fab light chain polypeptide of $A_2$ is bound to the scFv light chain polypeptide of $A_1$.

In some embodiments, $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease. In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$.

In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$.

Peptide ($P_1$ and $P_2$ and $P_{1a}$)

In some embodiments, $P_1$, $P_2$, or $P_{1a}$ comprises a sequence as disclosed in Table 3 or a sequence substantially identical thereto (e.g., a sequence that has 0, 1, or 2 amino acid modifications).

TABLE 3

$P_1$ and $P_2$ and $P_{1a}$ Sequences

| Construct Description | Amino Acid Sequence (N to C) | SEQ ID NO: |
|---|---|---|
| SP34.185 scFv mask | GGGSQCLGPEWEVCPY | 16 |
| SP34.185 scFv mask | GGVYCGPEFDESVGCM | 17 |
| SP34.185 scFv mask Peptide-A | GSQCLGPEWEVCPY | 18 |
| SP34.185 scFv mask Peptide-B | VYCGPEFDESVGCM | 19 |
| SP34.194 scFv mask Peptide-AM | YLWGCEWNCAGITT | 78 |

In some embodiments, $P_1$ impairs binding of $A_1$ to a first target antigen. In some embodiments, $P_1$ impairs binding of $A_1$ to the effector cell antigen. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ is bound to $A_1$ at or near an antigen binding site. In some embodiments, $P_1$ becomes unbound from $A_1$ when $L_1$ is cleaved by the tumor specific protease thereby exposing $A_1$ to the effector cell antigen. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $P_1$ has less than 70% sequence identity to the effector cell antigen. In some embodiments, $P_1$ has less than 75% sequence identity to the effector cell antigen. In some embodiments, $P_1$ has less than 80% sequence identity to the effector cell antigen. In some embodiments, $P_1$ has less than 85% sequence identity to the effector cell antigen. In some embodiments, $P_1$ has less than 90% sequence identity to the effector cell antigen. In some embodiments, $P_1$ has less than 95% sequence identity to the effector cell antigen. In some embodiments, $P_1$ has less than 98% sequence identity to the effector cell antigen. In some embodiments, $P_1$ has less than 99% sequence identity to the effector cell antigen. In some embodiments, $P_1$ comprises a de novo amino acid sequence that shares less than 10% sequence identity to the effector cell antigen. In some embodiments, $P_1$ comprises an amino acid sequence according to any one of SEQ ID NOs: 16-19. In some embodiments, $P_1$ comprises the amino acid sequence of SEQ ID NO: 16. In some embodiments, $P_1$ comprises the amino acid sequence of SEQ ID NO: 17. In some embodiments, $P_1$ comprises the amino acid sequence of SEQ ID NO: 18. In some embodiments, $P_1$ comprises the amino acid sequence of SEQ ID NO: 19. In some embodiments, $P_1$ comprises the amino acid sequence of SEQ ID NO: 78.

In some embodiments, $P_1$ comprises an amino acid sequence according to $Z_1$-$Z_2$-C-$Z_4$-P-$Z_6$-$Z_7$-$Z_8$-$Z_9$-$Z_{10}$-$Z_{11}$-$Z_{12}$-C-$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_5$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; $Z_{14}$ is selected from D, Y, N, F, I, P, V, A, T, H, L and S. In some embodiments, $Z_1$ is selected from D, Y, F, I, and N; $Z_2$ is selected from D, Y, L, F, I, and N; $Z_4$ is selected from G and W; $Z_6$ is selected from E and D; Z, is selected from W, L, F, and V; $Z_5$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; $Z_{14}$ is selected from D, Y, N, F, I, and P. In some embodiments, $Z_1$ is selected from D, Y, and F; $Z_2$ is selected from D, Y, L, and F; $Z_4$ is selected from G and W; $Z_6$ is selected from E and D; $Z_7$ is selected from W, $L_1$ and F; $Z_5$ is selected from E and D; $Z_9$ is selected from E and D; $Z_{10}$ is selected from S, D, and Y; Zn is selected from I, Y, and F; $Z_{12}$ is selected from F, D, Y, and L; and $Z_{14}$ is selected from D, Y, and N.

In some embodiments, $P_1$ comprises an amino acid sequence according to $U_1$-$U_2$-C-$U_4$-P-$U_6$-$U_7$-$U_8$-$U_9$-$U_{10}$-$U_{11}$-$U_{12}$-C-$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S. In some embodiments, $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P. In some embodiments, $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_1$ is selected from I, Y, V, L, and F; $U_{12}$ is selected from F, D, Y, G, A, and L; and $U_{14}$ is selected from D, Y, M, and N.

In some embodiments, $P_1$ comprises the amino acid sequences according to any one of SEQ ID NOs: 79-105. In some embodiments, $P_1$ comprises an amino acid sequences according to any of the sequences of Table 20. In some embodiments, $P_1$ comprises the amino acid sequences according to any one of SEQ ID NOs: 106-117.

In some embodiments, $P_1$ comprises the amino acid sequence according to SEQ ID NO: 18 or a peptide sequence that has 1, 2, or 3, amino acid substitutions, additions, or deletions relative to the amino acid sequence of SEQ ID NO: 18.

In some embodiments, $P_1$ comprises the amino acid sequence according to SEQ ID NO: 19 or a peptide sequence that has 1, 2, or 3, amino acid substitutions, additions, or deletions relative to the amino acid sequence of SEQ ID NO: 19.

In some embodiments, $P_1$ comprises the amino acid sequence according to SEQ ID NO: 116 or a peptide sequence that has 1, 2, or 3, amino acid substitutions, additions, or deletions relative to the amino acid sequence of SEQ ID NO: 116.

In some embodiments, $P_1$ comprises the amino acid sequence according to SEQ ID NO: 18.

In some embodiments, $P_1$ comprises the amino acid sequence according to SEQ ID NO: 19.

In some embodiments, $P_1$ comprises the amino acid sequence according to SEQ ID NO: 116.

In some embodiments, $P_2$ impairs binding of $A_2$ to the second target antigen. In some embodiments, wherein $P_2$ impairs binding of $A_2$ to PSMA. In some embodiments, $P_2$ is bound to $A_2$ through ionic interactions, electrostatic interactions, hydrophobic interactions, Pi-stacking interactions, and H-bonding interactions, or a combination thereof. In some embodiments, $P_2$ is bound to $A_2$ at or near an antigen binding site. In some embodiments, $P_2$ becomes unbound from $A_2$ when $L_2$ is cleaved by the tumor specific protease thereby exposing $A_2$ to the PSMA. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $P_2$ has less than 70% sequence identity to the PSMA. In some embodiments, $P_2$ has less than 75% sequence identity to the PSMA. In some embodiments, $P_2$ has less than 80% sequence identity to the PSMA. In some embodiments, $P_2$ has less than 85% sequence identity to the PSMA. In some embodiments, $P_2$ has less than 90% sequence identity to the PSMA. In some embodiments, $P_2$ has less than 95% sequence identity to the PSMA. In some embodiments, $P_2$ has less than 98% sequence identity to the PSMA. In some embodiments, $P_2$ has less than 99% sequence identity to the PSMA. In some embodiments, $P_2$ comprises a de novo amino acid sequence that shares less than 10% sequence identity to the PSMA.

In some embodiments, $P_{1a}$ when $L_{1a}$ is uncleaved impairs binding of the antigen recognizing molecule to the target antigen. In some embodiments, the antigen recognizing molecule comprises an antibody or antibody fragment. In some embodiments, the target antigen is an anti-CD3 effector cell antigen. In some embodiments, the target antigen is prostate-specific membrane antigen (PSMA). In some embodiments, $P_{1a}$ has less than 70% sequence identity to the target antigen. In some embodiments, $P_{1a}$ has less than 75% sequence identity to the target antigen. In some embodiments, $P_{1a}$ has less than 80% sequence identity to the target antigen. In some embodiments, $P_{1a}$ has less than 85% sequence identity to the target antigen. In some embodiments, $P_{1a}$ has less than 90% sequence identity to the target antigen. In some embodiments, $P_{1a}$ has less than 95% sequence identity to the target antigen. In some embodiments, $P_{1a}$ has less than 98% sequence identity to the target antigen. In some embodiments, $P_{1a}$ has less than 99% sequence identity to the target antigen. In some embodiments, $P_{1a}$ comprises a de novo amino acid sequence that shares less than 10% sequence identity to the second target antigen.

In some embodiments, $P_{1a}$ comprises an amino acid sequence according to $Z_1$-$Z_2$-C-$Z_4$-P-$Z_6$-$Z_7$-$Z_8$-$Z_9$-$Z_{10}$-$Z_{11}$-$Z_{12}$-C-$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S. In some embodiments, $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_5$ is selected from E and D; $Z_9$ is selected from E, D, Y, and V; $Z_{10}$ is selected from S, D, Y, T, and I; $Z_u$ is selected from I, Y, F, V, L, and T; $Z_{12}$ is selected from F, D, Y, L, I, V, A, and N; and $Z_{14}$ is selected from D, Y, N, F, I, and P. In some embodiments, $Z_1$ is selected from D, Y, and F; $Z_2$ is selected from D, Y, L, and F; $Z_4$ is selected from G and W; $Z_6$ is selected from E and D; $Z_7$ is selected from W, $L_1$ and F; $Z_8$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N.

In some embodiments, $P_{1a}$ comprises an amino acid sequence according to $U_1$-$U_2$-C-$U_4$-P-$U_6$-$U_7$-$U_8$-$U_9$-$U_{10}$-$U_{11}$-$U_{12}$-C-$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S. In some embodiments, U, is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P. In some embodiments, U, is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

In some embodiments, $P_{1a}$ comprises the amino acid sequences according to any one of SEQ ID NOs: 79-105.

In some embodiments, $P_{1a}$ comprises an amino acid sequences according to any of the sequences of Table 20.

In some embodiments, $P_{1a}$ comprises the amino acid sequences according to any one of SEQ ID NOs: 106-117.

In some embodiments, $P_{1a}$ comprises the amino acid sequence according to SEQ ID NO: 18 or a peptide sequence that has 1, 2, or 3, amino acid substitutions, additions, or deletions relative to the amino acid sequence of SEQ ID NO: 18.

In some embodiments, $P_{1a}$ comprises the amino acid sequence according to SEQ ID NO: 19 or a peptide sequence that has 1, 2, or 3, amino acid substitutions, additions, or deletions relative to the amino acid sequence of SEQ ID NO: 19.

In some embodiments, $P_{1a}$ comprises the amino acid sequence according to SEQ ID NO: 116 or a peptide sequence that has 1, 2, or 3, amino acid substitutions, additions, or deletions relative to the amino acid sequence of SEQ ID NO: 116.

In some embodiments, $P_{1a}$ comprises the amino acid sequence according to SEQ ID NO: 18.

In some embodiments, $P_{1a}$ comprises the amino acid sequence according to SEQ ID NO: 19.

In some embodiments, $P_{1a}$ comprises the amino acid sequence according to SEQ ID NO: 116.

In some embodiments, $P_1$, $P_2$, or $P_{1a}$ comprises a peptide sequence of at least 5 amino acids in length. In some embodiments, $P_1$, $P_2$, or $P_{1a}$ comprises a peptide sequence of at least 6 amino acids in length. In some embodiments, $P_1$, $P_2$, or $P_{1a}$ comprises a peptide sequence of at least 10 amino acids in length. In some embodiments, $P_1$, $P_2$, or $P_{1a}$ comprises a peptide sequence of at least 10 amino acids in length and no more than 20 amino acids in length. In some embodiments, $P_1$, $P_2$, or $P_{1a}$ comprises a peptide sequence of at least 16 amino acids in length. In some embodiments, $P_1$, $P_2$, or $P_{1a}$ comprises a peptide sequence of no more than 40 amino acids in length. In some embodiments, $P_1$, $P_2$, or $P_{1a}$ comprises at least two cysteine amino acid residues. In some embodiments, $P_1$, $P_2$, or $P_{1a}$ comprises a cyclic peptide or a linear peptide. In some embodiments, $P_1$, $P_2$, or $P_{1a}$ comprises a cyclic peptide. In some embodiments, $P_1$, $P_2$, or $P_{1a}$ comprises a linear peptide.

In some embodiments, $P_1$, $P_2$, or $P_{1a}$ or $P_1$, $P_2$, and $P_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments $P_1$, $P_2$, or $P_{1a}$ or $P_1$, $P_2$, and $P_{1a}$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $P_1$, $P_2$, or $P_{1a}$ or $P_1$, $P_2$, and $P_{1a}$ including the peptide backbone, the amino acid side chains, and the terminus.

In some embodiments, $P_1$, $P_2$, or $P_{1a}$ does not comprise albumin or an albumin fragment. In some embodiments, $P_1$, $P_2$, or $P_{1a}$ does not comprise an albumin binding domain.

Linking Moiety ($L_1$, $L_2$, $L_3$, and $L_{1a}$)

In some embodiments, $L_1$, $L_2$, $L_3$, or $L_{1a}$ is a peptide sequence having at least 5 to no more than 50 amino acids. In some embodiments $L_1$, $L_2$, $L_3$, or $L_{1a}$ is a peptide sequence having at least 10 to no more than 30 amino acids. In some embodiments, $L_1$, $L_2$, $L_3$, or $L_{1a}$ is a peptide sequence having at least 10 amino acids. In some embodiments, $L_1$, $L_2$, $L_3$, or $L_{1a}$ is a peptide sequence having at least 18 amino acids. In some embodiments, $L_1$, $L_2$, $L_3$, or $L_{1a}$ is a peptide sequence having at least 26 amino acids. In some embodiments, $L_1$, $L_2$, $L_3$, or $L_{1a}$ has a formula comprising $(G_2S)_n$, wherein n is an integer from 1 to 3 (SEQ ID NO: 118). In some embodiments, $L_1$, $L_2$, $L_3$, or $L_{1a}$ has a formula comprising $(G_2S)_n$, wherein n is an integer of at least 1. In some embodiments, $L_1$, $L_2$, $L_3$, or $L_{1a}$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1. In some embodiments, the tumor specific protease is selected from the group consisting of metalloprotease, serine protease, cysteine protease, threonine protease, and aspartic protease. In some embodiments $L_1$, $L_2$, $L_3$, or $L_{1a}$ comprises a urokinase cleavable amino acid sequence, a matriptase cleavable amino acid sequence, a legumain cleavable amino acid sequence, or a matrix metalloprotease cleavable amino acid sequence. In some embodiments, the matrix metalloprotease comprises MMP2, MMP7, MMP9, MMP13, or MMP14. In some embodiments, the serine protease comprises matriptase (MTSP1), urokinase, or hepsin.

In some embodiments, $L_1$, $L_2$, $L_3$, or $L_{1a}$ comprises a sequence as disclosed in Table 4 or a sequence substantially identical thereto (e.g., a sequence that has 0, 1, or 2 amino acid modifications).

In some embodiments, $L_1$, comprises the sequence of Linker-25 (SEQ ID NO: 45). In some embodiments, $L_1$, comprises the sequence of Linker-26 (SEQ ID NO: 46). In some embodiments, $L_1$, comprises the sequence of Linker-27 (SEQ ID NO: 47). In some embodiments, $L_1$ comprises the sequence of Linker-28 (SEQ ID NO: 48).

In some embodiments, $L_2$, comprises the sequence of Linker-25 (SEQ ID NO: 45). In some embodiments, $L_2$, comprises the sequence of Linker-26 (SEQ ID NO: 46). In some embodiments, $L_2$, comprises the sequence of Linker-27 (SEQ ID NO: 47). In some embodiments, $L_2$, comprises the sequence of Linker-28 (SEQ ID NO: 48).

TABLE 4

$L_1$, $L_2$, $L_3$, and $L_{1a}$ Sequences

| Construct Description | Amino Acid Sequence (N to C) | SEQ ID NO: |
|---|---|---|
| Linker 1 | GGGGSGGGGSGGGGS | 20 |
| Linker 2 | GGGGS | 21 |
| Linker 3 | GGGGSGGGS | 22 |
| Cleavable linker | GGGGSGGGLSGRSDAGSPLGLAGSGGGS | 23 |
| Linker 4 | GGGGSLSGRSDNHGSSGT | 24 |
| Linker 5 | GGGGSSGGSGGSGLSGRSDNHGSSGT | 25 |
| Linker 6 | ASGRSDNH | 26 |
| Linker 7 | LAGRSDNH | 27 |
| Linker 8 | ISSGLASGRSDNH | 28 |
| Linker 9 | ISSGLLAGRSDNH | 29 |
| Linker 10 | LSGRSDNH | 30 |
| Linker 11 | ISSGLLSGRSDNP | 31 |
| Linker 12 | ISSGLLSGRSDNH | 32 |
| Linker 13 | LSGRSDNHSPLGLAGS | 33 |
| Linker 14 | SPLGLAGSLSGRSDNH | 34 |
| Linker 15 | SPLGLSGRSDNH | 35 |
| Linker 16 | LAGRSDNHSPLGLAGS | 36 |
| Linker 17 | LSGRSDNHVPLSLKMG | 37 |
| Linker 18 | LSGRSDNHVPLSLSMG | 38 |
| Linker 19 | GSSGGSGGSGGSGISSGLLSGRSDNHGSSGT | 39 |
| Linker 20 | GSSGGSGGSGGISSGLLSGRSDNHGGGS | 40 |
| Linker 21 | ASGRSDNH | 41 |
| Linker 22 | LAGRSDNH | 42 |
| Linker 23 | ISSGLASGRSDNH | 43 |
| Linker 24 | LSGRSDAG | 44 |
| Linker 25 | ISSGLLSGRSDAG | 45 |
| Linker 26 | AAGLLAPPGGLSGRSDAG | 46 |
| Linker 27 | SPLGLSGRSDAG | 47 |
| Linker 28 | LSGRSDAGSPLGLAG | 48 |
| Non-cleavable linker | GGGGSGGGSGGGSGGASSGAGGSGGGS | 49 |

In some embodiments, $L_1$ is bound to a N-terminus of $A_1$. In some embodiments, $L_1$ is bound to a C-terminus of $A_1$. In some embodiments, $L_2$ is bound to a N-terminus of $A_2$. In some embodiments, $L_2$ is bound to a C-terminus of $A_2$. In some embodiments, $P_1$ becomes unbound from $A_1$ when $L_1$ is cleaved by the tumor specific protease thereby exposing $A_1$ to the effector cell antigen. In some embodiments, $P_2$ becomes unbound from $A_2$ when $L_2$ is cleaved by the tumor specific protease thereby exposing $A_2$ to PSMA.

In some embodiments, $L_1$, $L_2$, $L_3$, or $L_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments, $L_1$, $L_2$, $L_3$, or La comprise a modification including, but not limited, to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $L_1$, $L_2$, $L_3$, or $L_{1a}$ including the peptide backbone, or the amino acid side chains.

In some embodiments, the cleavable linker is cleavable by a protease. In some embodiments, the protease is present in higher levels in a disease-state microenvironment relative to levels in healthy tissue or a microenvironment that is not the disease-state microenvironment. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the matrix metalloprotease is selected from the group consisting of MMP2, MMP7, MMP9, MMP13, and MMP14. In some embodiments, the matrix metalloprotease comprises MMP2. In some embodiments, the matrix metalloprotease comprises MMP7. In some embodiments, the matrix metalloprotease comprises MMP9. In some embodiments, the matrix metalloprotease comprises MMP13. In some embodiments, the matrix metalloprotease comprises MMP14. In some embodiments, the serine protease comprises matriptase (MTSP1), urokinase, or hepsin. In some embodiments, the serine protease is selected from the group consisting of matriptase (MTSP1), urokinase, and hepsin. In some embodiments, the serine protease comprises matriptase (MTSP1). In some embodiments, the serine protease comprises urokinase. In some embodiments, the serine protease comprises hepsin. In some embodiments, the cleavable linker is cleaved by a variety of proteases. In some embodiments, the cleavable linker is cleaved by at least 1, 2, 3, 4, 5, 6, 7, 8, 9, 10, 15, 20, or more than 20 different proteases.

Half-Life Extending Molecule ($H_1$ and $H_{1a}$)

In some embodiments, $H_1$ does not block $A_1$ binding to the effector cell antigen. In some embodiments, $H_1$ comprises a linking moiety ($L_3$) that connects $H_1$ to $P_1$. In some embodiments, $H_{1a}$ does not block the first antigen recognizing molecule binding to the effector cell antigen. In some embodiments, $H_{1a}$ comprises a linking moiety ($L_3$) that connects $H_{1a}$ to $P_{1a}$. In some embodiments, the half-life extending molecule ($H_1$ or $H_{1a}$) does not have binding affinity to antigen recognizing molecule. In some embodiments, the half-life extending molecule ($H_1$ or $H_{1a}$) does not have binding affinity to the effector cell antigen. In some embodiments, the half-life extending molecule ($H_1$ or $H_{1a}$) does not shield antigen recognizing molecule from the effector cell antigen. In some embodiments, the half-life extending molecule ($H_1$ or $H_{1a}$) is not directly linked to antigen recognizing molecule.

In some embodiments, $H_1$ or $H_{1a}$ comprises a sequence as disclosed in Table 5 or a sequence substantially identical thereto (e.g., a sequence that has at least 90%, 95%, 96%, 97%, 98%, or 99% sequence identity).

TABLE 5

$H_1$ and $H_{1a}$ Sequences

| Construct Description | Amino Acid Sequence (N to C) | SEQ ID NO: |
|---|---|---|
| Anti-Albumin: CDR-H1 | GSTFYTAV | 54 |
| Anti-Albumin: CDR-H2 | IRWTALTT | 55 |
| Anti-Albumin: CDR-H3 | AARGTLGLFTTADSYDY | 56 |
| Anti-albumin | EVQLVESGGGLVQPGGSLRLSCAAS**GSTFYTAV**MGWVRQAPGKGLEWVAA**IRWTALTT**SYADSVKGRFTISRDGAKTTLYLQMNSLRPEDTAVYYC**AARGTLGLFTTADSYDY**WGQGTLVTVSS | 57 |
| 10G Anti-Albumin: CDR-H1 | GFTFSKFG | 58 |
| 10G Anti-Albumin: CDR-H2 | ISGSGRDT | 59 |
| 10G Anti-Albumin: CDR-H3 | TIGGSLSV | 60 |
| 10G Anti-albumin | EVQLVESGGGLVQPGNSLRLSCAAS**GFTFSKFG**MSWVRQAPGKGLEWVSS**ISGSGRDT**LYADSVKGRFTISRDNAKTTLYLQMNSLRPEDTAVYYC**TIGGSLSV**SSQGTLVTVSS | 61 |

In some embodiments, $H_1$ or $H_{1a}$ comprise an amino acid sequence that has repetitive sequence motifs. In some embodiments, $H_1$ or $H_{1a}$ comprises an amino acid sequence that has highly ordered secondary structure. "Highly ordered secondary structure," as used in this context, means that at least about 50%, or about 70%, or about 80%, or about 90%, of amino acid residues of $H_1$ or $H_{1a}$ contribute to secondary structure, as measured or determined by means, including, but not limited to, spectrophotometry (e.g. by circular dichroism spectroscopy in the "far-UV" spectral region (190-250 nm), and computer programs or algorithms, such as the Chou-Fasman algorithm and the Garnier-Osguthorpe-Robson ("GOR") algorithm.

In some embodiments, $H_1$ or $H_{1a}$ comprises a polymer. In some embodiments, the polymer is polyethylene glycol (PEG). In some embodiments, $H_1$ or $H_{1a}$ comprises albumin. In some embodiments, $H_1$ or $H_{1a}$ comprises an Fe domain. In some embodiments, the albumin is serum albumin. In some embodiments, the albumin is human serum albumin. In some embodiments, $H_1$ or $H_{1a}$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, slgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the single domain antibody comprises a single domain antibody that binds to albumin. In some embodiments, the single domain antibody is a human or humanized antibody. In some embodiments, the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10E and SA21. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56; and wherein the CDRs comprise from 0-2 amino acid modifications in at least one of the HC-CDR1, HC-CDR2, or HC-CDR3. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60; and wherein the CDRs comprise from 0-2 amino acid modifications in at least one of the HC-CDR1, HC-CDR2, or HC-CDR3.

In some embodiments, $H_1$ comprises an amino acid sequence according to SEQ ID NO: 57. In some embodiments, $H_1$ comprises an amino acid sequence that has at least 80% sequence identity to SEQ ID NO: 57. In some embodiments, $H_1$ comprises an amino acid sequence that has at least 85% sequence identity to SEQ ID NO: 57. In some embodiments, $H_1$ comprises an amino acid sequence that has at least 90% sequence identity to SEQ ID NO: 57. In some embodiments, $H_1$ comprises an amino acid sequence that has at least 95% sequence identity to SEQ ID NO: 57. In some embodiments, $H_1$ comprises an amino acid sequence that has at least 99% sequence identity to SEQ ID NO: 57.

In some embodiments, $H_{1a}$ comprises an amino acid sequence according to SEQ ID NO: 57. In some embodiments, $H_{1a}$ comprises an amino acid sequence that has at least 80% sequence identity to SEQ ID NO: 57. In some embodiments, $H_{1a}$ comprises an amino acid sequence that has at least 85% sequence identity to SEQ ID NO: 57. In some embodiments, $H_{1a}$ comprises an amino acid sequence that has at least 90% sequence identity to SEQ ID NO: 57. In some embodiments, $H_{1a}$ comprises an amino acid sequence that has at least 95% sequence identity to SEQ ID NO: 57. In some embodiments, $H_{1a}$ comprises an amino acid sequence that has at least 99% sequence identity to SEQ ID NO: 57.

In some embodiments, $H_1$ comprises an amino acid sequence according to SEQ ID NO: 61. In some embodiments, $H_1$ comprises an amino acid sequence that has at least 80% sequence identity to SEQ ID NO: 61. In some embodiments, $H_1$ comprises an amino acid sequence that has at least 85% sequence identity to SEQ ID NO: 61. In some embodiments, $H_1$ comprises an amino acid sequence that has at least 90% sequence identity to SEQ ID NO: 61. In some embodiments, $H_1$ comprises an amino acid sequence that has at least 95% sequence identity to SEQ ID NO: 61. In some embodiments, $H_1$ comprises an amino acid sequence that has at least 99% sequence identity to SEQ ID NO: 61.

In some embodiments, $H_{1a}$ comprises an amino acid sequence according to SEQ ID NO: 61. In some embodiments, $H_{1a}$ comprises an amino acid sequence that has at least 80% sequence identity to SEQ ID NO: 61. In some embodiments, $H_{1a}$ comprises an amino acid sequence that has at least 85% sequence identity to SEQ ID NO: 61. In some embodiments, $H_{1a}$ comprises an amino acid sequence that has at least 90% sequence identity to SEQ ID NO: 61. In some embodiments, $H_{1a}$ comprises an amino acid sequence that has at least 95% sequence identity to SEQ ID NO: 61. In some embodiments, $H_{1a}$ comprises an amino acid sequence that has at least 99% sequence identity to SEQ ID NO: 61.

In some embodiments, $H_1$ or $H_{1a}$ or $H_1$ and $H_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments $H_1$ or $H_{1a}$ or $H_1$ and $H_{1a}$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $H_1$ or $H_{1a}$ or $H_1$ and $H_{1a}$ including the peptide backbone, the amino acid side chains, and the terminus.

In some embodiments, $H_1$ comprises a linking moiety ($L_3$) that connects $H_1$ to $P_1$. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$(SEQ ID NO: 53), wherein n is an integer of at least 1. In some embodiments, $L_3$ comprises an amino acid sequence according to SEQ ID NO: 22.

In some embodiments, $H_{1a}$ comprises a linking moiety ($L_{1a}$) that connects $H_{1a}$ to $P_{1a}$. In some embodiments, $L_{1a}$ is a peptide sequence having at least 5 to no more than 50 amino acids. In some embodiments, $L_{1a}$ is a peptide sequence having at least 10 to no more than 30 amino acids. In some embodiments, $L_{1a}$ is a peptide sequence having at least 10 amino acids. In some embodiments, $L_{1a}$ is a peptide sequence having at least 18 amino acids. In some embodiments, $L_{1a}$ is a peptide sequence having at least 26 amino acids. In some embodiments, $L_{1a}$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1. In some embodiments, $L_{1a}$ comprises an amino acid sequence according to SEQ ID NO: 22.

Antibodies that Bind to PSMA and CD3

In some embodiments, the polypeptide or polypeptide complex comprises an amino acid sequence disclosed in Table 6 or a sequence substantially identical thereto (e.g., a sequence that has at least 90%, 95%, 96%, 97%, 98%, or 99% sequence identity). In some embodiments, the polypeptide or polypeptide complex comprises an amino acid sequence with at least 95% sequence identity to any one of SEQ ID NOs: 62-77. In some embodiments, the polypeptide or polypeptide complex comprises an amino acid sequence with at least 95% sequence identity to SEQ ID NO: 72. In some embodiments, the polypeptide or polypeptide complex comprises an amino acid sequence with at least 95% sequence identity to SEQ ID NO: 73.

TABLE 6

Polypeptide complex sequences

| Construct Description | Amino Acid Sequence (N to C) | SEQ ID NO: |
|---|---|---|
| PC1:LC: 006 PSMA Fab LC | DIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 62 |
| PC LHC: SP34.185 scFv Linker 2 006 PSMA Fab HC | EVQLVESGGGLVQPGGSLKLSCAAS**GFTFNKY**AMNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GT**KFLAPGTPARFSGSLLGGKAALTLSGV | 63 |

TABLE 6-continued

Polypeptide complex sequences

| Construct Description | Amino Acid Sequence (N to C) | SEQ ID NO: |
|---|---|---|
| | QPEDEAEYYC**VLWYSNRWV**FGGGTKLTVLGGGGSQVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | |
| PC:2:LC SP34.185 scFv Linker 2 006 PSMA Fab LC | EVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYCV**RHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIGGTKFLAPGTPARFSGSLLGGKAALTLSGVQPEDEAEYYC**VLWYSNRWV**FGGGTKLTVLGGGGSDIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYERHKVYACEVTHQGLSSPVTKSFNRGEC | 64 |
| PC2: HC 006 PSMA Fab HC | QVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 65 |
| PC3:LC 006 PSMA Fab LC | DIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 66 |
| PC3: HC Anti-albumin (SEQ ID NO: 57) + Linker 3 SP34.185 scFv mask (SEQ ID NO: 16) | EVQLVESGGGLVQPGGSLRLSCAAS**GSTFYTAV**MGWVRQAPGKGLEWVAA**IRWTALTT**SYADSVKGRFTISRDGAKTTLYLQMNSLRPEDTAVYYC**AARGTLGLFTTADSYDY**WGQGTLVTVSSGGGGSGGGSGGGSQCLGPEWEVCPYGGGGSGGGLSGRSDAGSPLGLAGSGGGSEVQ | 67 |

TABLE 6-continued

Polypeptide complex sequences

| Construct Description | Amino Acid Sequence (N to C) | SEQ ID NO: |
|---|---|---|
| cleavable linker + SP34.185 scFv (VH-linker 1-VL) + Linker 2 006 PSMA Fab HC | LVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GT**KFLAPGTPARFSGSLLGGKAALTLSGVQPEDEAEYYC**VLWYSNRWV**FGGGTKLTVLGGGGSQVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | |
| PC4: LC Anti-albumin (SEQ ID NO: 57) + Linker 3 + SP34.185 scFv mask (SEQ ID NO: 16) +cleavable linker+ SP34.185 scFv (VH-linker 1 - VL) + Linker 2 006 PSMA Fab LC | EVQLVESGGGLVQPGGSLRLSCAAS**GSTFYTAV**MGWVRQAPGKGLEWVAA**IRWTALTT**SYADSVKGRFTISRDGAKTTLYLQMNSLRPEDTAVYYC**AARGTLGLFTTADSYDY**WGQGTLVTVSSGGGGSGGGSGGGSQCLGPEWEVCPYGGGGSGGGLSGRSDAGSPLGLAGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYCV**RHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GT**KFLAPGTPARFSGSLLGGKAALTLSGVQPEDEAEYYC**VLWYSNRWV**FGGGTKLTVLGGGGSDIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 68 |
| PC4: HC 006 PSMA Fab HC | QVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 69 |

TABLE 6-continued

Polypeptide complex sequences

| Construct Description | Amino Acid Sequence (N to C) | SEQ ID NO: |
|---|---|---|
| PC5:LC 006 PSMA Fab LC | DIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 70 |
| PC5: HC Anti-albumin (SEQ ID NO: 57) + Linker 3 + SP34.185 scFv mask (SEQ ID NO: 17) + cleavable linker + SP34.185 scFv (VH-Linker 1 - VL) + Linker 2 006 PSMA Fab HC | EVQLVESGGGLVQPGGSLRLSCAAS**GSTFYTAV**MGWVRQAPGKGLEWVAA**IRWTALTT**SYADSVKGRFTISRDGAKTTLYLQMNSLRPEDTAVYYC**AARGTLGLFTTADSYDY**WGQGTLVTVSSGGGGSGGGSGGVYCGPEFDESVGCMGGGGSGGGLSGRSDAGSPLGLAGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYCV**RHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GT**KFLAPGTPARFSGSLLGGKAALTLSGVQPEDEAEYYC**VLWYSNRWV**FGGGTKLTVLGGGGSQVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 71 |
| PC6: LC Anti-albumin (SEQ ID NO: 57) +Linker 3 + SP34.185 scFv mask (SEQ ID NO: 17) + cleavable linker+ SP34.185 scFv (VH-linker 1- VL) + Linker 2 006 PSMA Fab LC | EVQLVESGGGLVQPGGSLRLSCAAS**GSTFYTAV**MGWVRQAPGKGLEWVAA**IRWTALTT**SYADSVKGRFTISRDGAKTTLYLQMNSLRPEDTAVYYC**AARGTLGLFTTADSYDY**WGQGTLVTVSSGGGGSGGGSGGVYCGPEFDESVGCMGGGGSGGGLSGRSDAGSPLGLAGSGGGSEVQLVESGGGLVQPGGSLKLSCAAS**GFTFNKYA**MNWVRQAPGKCjLEWVAR**IRSKYNNYAT**YTADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GT**KFLAPGTPARFSGSLLGGKAALTLSGVQPEDEAEYYC**VLWYSNRWV**FGGGTKLTVLGGGGSDIQMTQSPSSLSASVGDRVTITCRAS**QGISNY**LAWYQQKTGKVPKFLIY**EA**STLQSGVPSRFSGGGSGTDFTLTISSLQPEDVATYYC | 72 |

TABLE 6-continued

Polypeptide complex sequences

| Construct Description | Amino Acid Sequence (N to C) | SEQ ID NO: |
|---|---|---|
| | **QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | |
| PC6: HC 006 PSMA Fab HC | QVQLVESGGGVVQPGRSLRLSCAASG**FAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 73 |
| PC7: LC | EVQLVESGGGLVQPGNSLRLSCAAS**GFTFSKFG**MSWVRQAPGKGLEWVSS**ISGSGRDT**LYADSVKGRFTISRDNAKTTLYLQMNSLRPEDTAVYYC**TIGGSLSV**SSQGTLVTVSSGGGGSGGGSGGVYCGPEFDESVGCMGGGGSGGGLSGRSDAGSPLGLAGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSS**TGAVTSGNY**PNWVQQKPGQAPRGLIG**GT**KFLAPGTPARFSGSLLGGKAALTLSGVQPEDEAEYYC**VLWYSNRWV**FGGGTKLTVLGGGGSDIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 74 |
| PC7: HC | QVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 75 |
| PC8: LC | EVQLVESGGGLVQPGNSLRLSCAAS**GFTFSKFG**MSWVRQAPGKGLEWVSS**ISGSGRDT**LYADSVKGRFTISRDNAKTTLYLQMNSLRPEDTAVYYC**TIGGSLSV**SSQGTLVTVSSGGGGSGGGSGGVYCGPEFDESVGCMGGGGSGGGSGGGGSGGASSGAGGSGGGSEVQLVESGGGLVQPGGSLKLSCAAS**GFTFNKYA**MNWVRQAPGKGLEWVAR**IRSKYNNYAT**YYADSVKDRFTISRDDSKNTAYLQMNNLKTEDTAVYYC**VRHGNFGNSYISYWAY**WGQGTLVTVSSGGGGSGGGGSGGGGSQTVVTQEPSLTVSPGGTVTLTCGSSTGAVTSGNYPNWVQQKPGQAPRGLIG**GT**KFLAPGTPARFSGSLLGGKAALTLSGVQPEDEAEYYC**VLWYSNRWV**FGGGTKLTVLGGGGSDIQMTQSPSSLSASVGDRVTITCRAS**QGISNY**LAWYQQKTGKVPKFLIY**EA**STLQSGVPSRFSGGGSGTDFTLTISSLQPEDVATYYC**QNYNSAPFT**FGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 76 |
| PC8: HC | QVQLVESGGGVVQPGRSLRLSCAAS**GFAFSRYG**MHWVRQAPGKGLEWVAV**IWYDGSNK**YYADSVKGRFTISRDNSKNTQYLQMNSLRAEDTAVYYC**ARGGDFLYYYYYGMDV**WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 77 |

In some embodiments, the polypeptide or polypeptide complex comprises amino acid sequences according to SEQ ID NO: 62 and SEQ ID NO: 63. In some embodiments, the polypeptide or polypeptide complex comprises amino acid sequences with at least 90% sequence identity to SEQ ID NO: 62 and SEQ ID NO: 63. In some embodiments, the polypeptide or polypeptide complex comprises amino acid sequences with at least 95% sequence identity to SEQ ID NO: 62 and SEQ ID NO: 63. In some embodiments, the polypeptide or polypeptide complex comprises amino acid sequences with at least 99% sequence identity to SEQ ID NO: 62 and SEQ ID NO: 63.

In some embodiments, the polypeptide or polypeptide complex comprises amino acid sequences according to SEQ ID NO: 64 and SEQ ID NO: 65. In some embodiments, the polypeptide or polypeptide complex comprises amino acid sequences with at least 90% sequence identity to SEQ ID NO: 64 and SEQ ID NO: 65. In some embodiments, the polypeptide or polypeptide complex comprises amino acid sequences with at least 95% sequence identity to SEQ ID NO: 64 and SEQ ID NO: 65. In some embodiments, the polypeptide or polypeptide complex comprises amino acid sequences with at least 99% sequence identity to SEQ ID NO: 64 and SEQ ID NO: 65.

In some embodiments, the polypeptide or polypeptide complex comprises amino acid sequences according to SEQ ID NO: 66 and SEQ ID NO: 67. In some embodiments, the polypeptide or polypeptide complex comprises amino acid sequences with at least 90% sequence identity to SEQ ID NO: 66 and SEQ ID NO: 67. In some embodiments, the polypeptide or polypeptide complex comprises amino acid sequences with at least 95% sequence identity to SEQ ID NO: 66 and SEQ ID NO: 67. In some embodiments, the polypeptide or polypeptide complex comprises amino acid sequences with at least 99% sequence identity to SEQ ID NO: 66 and SEQ ID NO: 67.

In some embodiments, the polypeptide or polypeptide complex comprises amino acid sequences according to SEQ ID NO: 68 and SEQ ID NO: 69. In some embodiments, the polypeptide or polypeptide complex comprises amino acid sequences with at least 90% sequence identity to SEQ ID NO: 68 and SEQ ID NO: 69. In some embodiments, the polypeptide or polypeptide complex comprises amino acid sequences with at least 95% sequence identity to SEQ ID NO: 68 and SEQ ID NO: 69. In some embodiments, the polypeptide or polypeptide complex comprises amino acid sequences with at least 99% sequence identity to SEQ ID NO: 68 and SEQ ID NO: 69.

In some embodiments, the polypeptide or polypeptide complex comprises amino acid sequences according to SEQ ID NO: 70 and SEQ ID NO: 71. In some embodiments, the polypeptide or polypeptide complex comprises amino acid sequences with at least 90% sequence identity to SEQ ID NO: 70 and SEQ ID NO: 71. In some embodiments, the polypeptide or polypeptide complex comprises amino acid sequences with at least 95% sequence identity to SEQ ID NO: 70 and SEQ ID NO: 71. In some embodiments, the polypeptide or polypeptide complex comprises amino acid sequences with at least 99% sequence identity to SEQ ID NO: 70 and SEQ ID NO: 71.

In some embodiments, the polypeptide or polypeptide complex comprises amino acid sequences according to SEQ ID NO: 72 and SEQ ID NO: 73. In some embodiments, the polypeptide or polypeptide complex comprises amino acid sequences with at least 90% sequence identity to SEQ ID NO: 72 and SEQ ID NO: 73. In some embodiments, the polypeptide or polypeptide complex comprises amino acid sequences with at least 95% sequence identity to SEQ ID NO: 72 and SEQ ID NO: 73. In some embodiments, the polypeptide or polypeptide complex comprises amino acid sequences with at least 99% sequence identity to SEQ ID NO: 72 and SEQ ID NO: 73.

In some embodiments, the polypeptide or polypeptide complex comprises amino acid sequences according to SEQ ID NO: 74 and SEQ ID NO: 75. In some embodiments, the polypeptide or polypeptide complex comprises amino acid sequences with at least 90% sequence identity to SEQ ID NO: 74 and SEQ ID NO: 75. In some embodiments, the polypeptide or polypeptide complex comprises amino acid sequences with at least 95% sequence identity to SEQ ID NO: 74 and SEQ ID NO: 75. In some embodiments, the polypeptide or polypeptide complex comprises amino acid sequences with at least 99% sequence identity to SEQ ID NO: 74 and SEQ ID NO: 75.

In some embodiments, the polypeptide or polypeptide complex comprises amino acid sequences according to SEQ ID NO: 76 and SEQ ID NO: 77. In some embodiments, the polypeptide or polypeptide complex comprises amino acid sequences with at least 90% sequence identity to SEQ ID NO: 76 and SEQ ID NO: 77. In some embodiments, the polypeptide or polypeptide complex comprises amino acid sequences with at least 95% sequence identity to SEQ ID NO: 76 and SEQ ID NO: 77. In some embodiments, the polypeptide or polypeptide complex comprises amino acid sequences with at least 99% sequence identity to SEQ ID NO: 76 and SEQ ID NO: 77.

Polypeptides or polypeptide complexes, in some embodiments, comprise a sequence set forth in Table 6. In some embodiments, the sequence comprises at least or about 70%, 80%, 85%, 90%, 91%, 92%, 93%, 94%, 95%, 96%, 97%, 98%, 99%, or 100% sequence identity to any one of SEQ ID NOs: 62-77. In some instances, the sequence comprises at least or about 95% homology to any one of SEQ ID NOs: 62-77. In some instances, the sequence comprises at least or about 97% homology to any one of SEQ ID NOs: 62-77. In some instances, the sequence comprises at least or about 99% homology to any one of SEQ ID NOs: 62-77. In some instances, the sequence comprises at least or about 100% homology to any one of SEQ ID NOs: 62-77. In some instances, the sequence comprises at least a portion having at least or about 10, 20, 30, 40, 50, 60, 70, 80, 90, 100, 110, 120, 130, 140, 150, 160, 170, 180, 190, 200, 210, or more than 210 amino acids of any one of SEQ ID NOs: 62, 65, 66, 69, 70, 73, 75, or 77. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, or more than 450 amino acids of any one of SEQ ID NOs: 63 or 64. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, or more than 640 amino acids of any one of SEQ ID NOs: 67, 68, 71, 72, 74, or 76.

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Figure 1C:
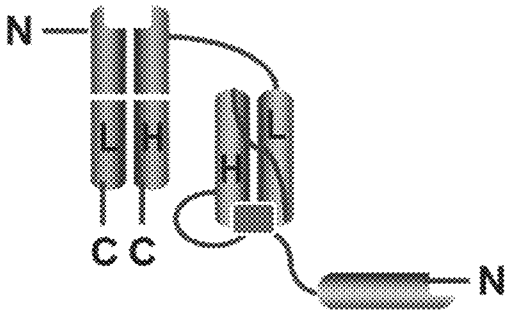

Disclosed herein, in some embodiments, are isolated polypeptides or polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv.

Figure 1D:
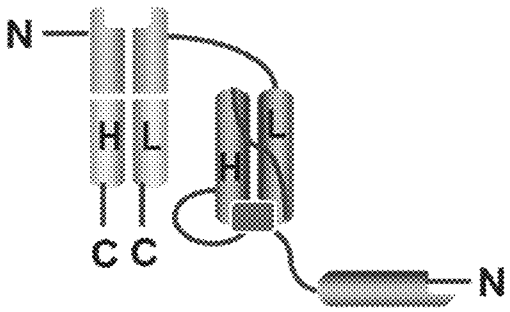

Disclosed herein, in some embodiments, are isolated polypeptides or polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

Figure 1E:
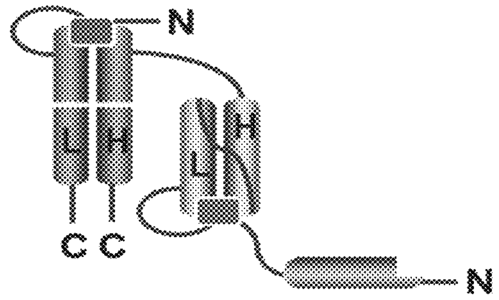

Disclosed herein, in some embodiments, are isolated polypeptides or polypeptide complexes comprising a structural arrangement according to the configuration shown in FIG. 1E, wherein the polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the light chain variable domain of the scFv with a linking moiety ($L_1$) that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab heavy chain polypeptide is linked to a C terminus of the heavy chain variable domain of the scFv, and wherein the Fab is linked to $P_2$ and $L_2$, wherein $P_2$ comprises a peptide that impairs binding of the Fab to PSMA; and $L_2$ comprises a linking moiety that connects the Fab light chain polypeptide to $P_2$ and is a substrate for a tumor specific protease.

Figure 1F:
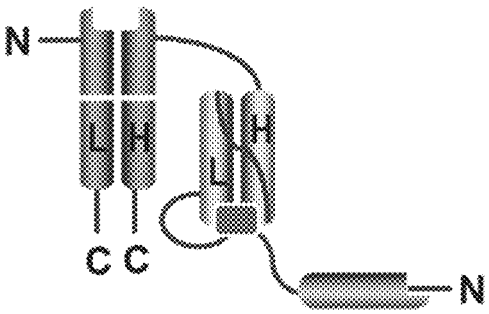

Disclosed herein, in some embodiments, are isolated polypeptides or polypeptide complexes comprising a structural arrangement according to the configuration shown in FIG. 1F, wherein the polypeptide or polypeptide complex comprises a single chain variable fragment (scFv) comprising a light chain variable domain and a heavy chain variable domain, wherein the scFv is linked to a peptide that impairs binding of the scFv to an effector cell antigen and the peptide is linked to the light chain variable domain of the scFv with a linking moiety that is a substrate for a tumor specific protease, and the peptide is further linked to a half-life extending molecule; and a Fab that binds to prostate-specific membrane antigen (PSMA), wherein the Fab comprises a Fab light chain polypeptide chain and a Fab heavy chain polypeptide chain, and wherein the Fab heavy chain polypeptide chain is linked to a C terminus of the heavy chain variable domain of the scFv.

Figure 1G:
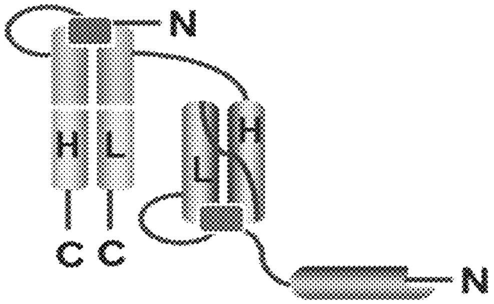

Disclosed herein, in some embodiments, are isolated polypeptides or polypeptide complexes comprising a structural arrangement according to the configuration shown in FIG. 1G, wherein the polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the light chain variable domain of the scFv with a linking moiety that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab light chain polypeptide is linked to a C terminus of the heavy chain variable domain of the scFv, and wherein the Fab is linked to $P_2$ and $L_2$, wherein $P_2$ comprises a peptide that impairs binding to PSMA; and $L_2$ comprises a linking moiety that connects the Fab heavy chain polypeptide to $P_2$ and is a substrate for a tumor specific protease.

Figure 1H:
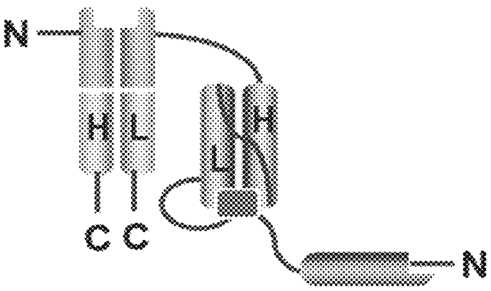

Disclosed herein, in some embodiments, are isolated polypeptides or polypeptide complexes comprising a structural arrangement according to the configuration shown in FIG. 1H, wherein the polypeptide or polypeptide complex comprises a single chain variable fragment (scFv) comprising a light chain variable domain and a heavy chain variable domain, wherein the scFv is further linked to a peptide that impairs binding of the scFv to an effector cell antigen and the peptide is linked to a N-terminus of the light chain variable domain of the scFv with a linking moiety that is a substrate for a tumor specific protease, and the peptide is further linked to a half-life extending molecule; and a Fab that binds to prostate-specific membrane antigen (PSMA), wherein the Fab comprises a Fab light chain polypeptide and a Fab heavy chain polypeptide, wherein the Fab light chain polypeptide is linked to a C terminus of the heavy chain variable domain of the scFv.

Figure 1I:
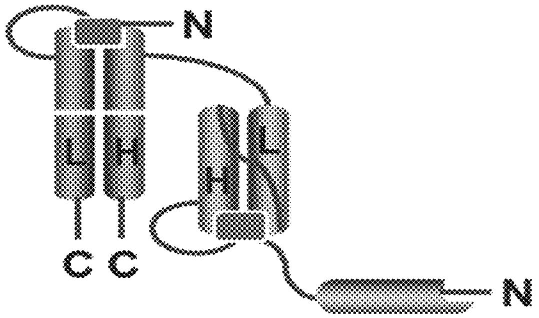

Disclosed herein, in some embodiments, are isolated polypeptides or polypeptide complexes comprising a structural arrangement according to the configuration shown in FIG. 1I, wherein the polypeptide or polypeptide complex comprises a single chain variable fragment (scFv) comprising a light chain variable domain and a heavy chain variable domain, wherein the scFv is linked to a peptide (P i) that impairs binding of the scFv to an effector cell antigen and $P_1$ is linked to a N-terminus of the heavy chain variable domain of the scFv with a linking moiety ($L_1$) that is a substrate for a tumor specific protease, and P, is further linked to a half-life extending molecule; and a Fab that binds to prostate-specific membrane antigen (PSMA), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to PSMA; and $L_2$ comprises a linking moiety that connects the Fab light chain polypeptide to $P_2$ and is a substrate for a tumor specific protease.

Figure 1J:
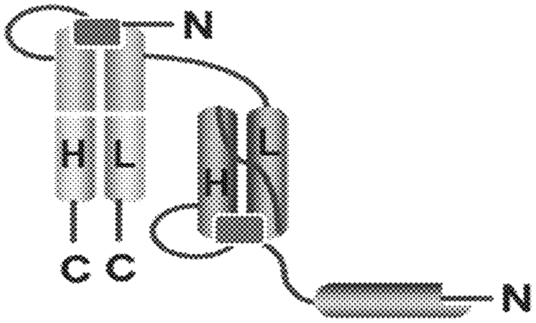

Disclosed herein, in some embodiments, are isolated polypeptides or polypeptide complexes comprising a structural arrangement according to the configuration shown in FIG. 1J, wherein the polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to PSMA; and $L_2$ comprises a linking moiety that connects the Fab heavy chain polypeptide to $P_2$ and is a substrate for a tumor specific protease.

Figure 1K:
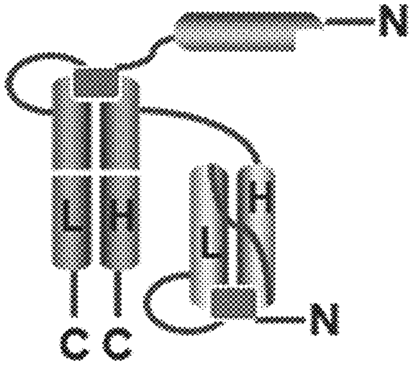

Disclosed herein, in some embodiments, are isolated polypeptides or polypeptide complexes comprising a structural arrangement according to the configuration shown in FIG. 1K, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide ($P_1$) that impairs binding of the Fab to PSMA and $P_1$ is linked to a N terminus of the Fab light chain polypeptide with a linking moiety ($L_1$) that is a substrate for a tumor specific protease, and the $P_1$ is further linked to a half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab heavy chain polypeptide, wherein the scFv is linked to $P_2$ and $L_2$, wherein $P_2$ comprises a peptide that impairs binding of the scFv to the effector cell antigen, and $L_2$ comprises a linking moiety that connects the light chain variable domain of the scFv to $P_2$ and is a substrate for a tumor specific protease.

Figure 1L:
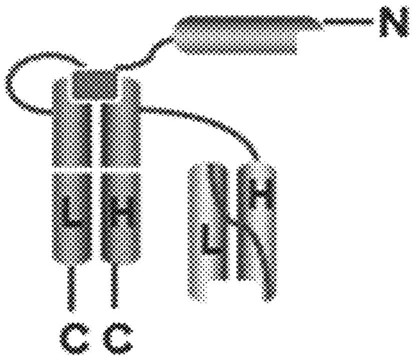

Disclosed herein, in some embodiments, are isolated polypeptides or polypeptide complexes comprising a structural arrangement according to the configuration shown in FIG. 1L, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab light chain polypeptide with a linking moiety that is a substrate for a tumor specific protease, and the peptide is further linked to half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab heavy chain polypeptide.

Figure 1M:
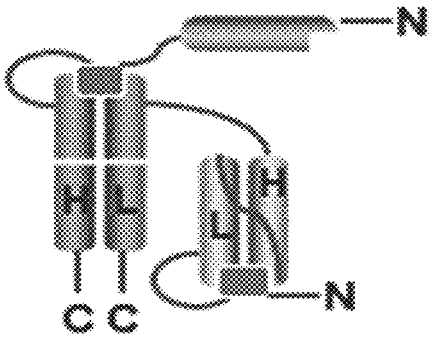

Disclosed herein, in some embodiments, are isolated polypeptides or polypeptide complexes comprising a structural arrangement according to the configuration shown in FIG. 1M, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide ($P_1$) that impairs binding of the Fab to PSMA and $P_1$ is linked to a N terminus of the Fab heavy chain polypeptide with a linking moiety ($L_1$) that is a substrate for a tumor specific protease, and $P_1$ is further linked to a half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab light chain polypeptide, wherein the scFv further is linked to $P_2$ and $L_2$, wherein $P_2$ comprises a peptide that impairs binding of the scFv to the effector cell antigen, and $L_2$ comprises a linking moiety that connects the light chain variable domain of the scFv to $P_2$ and is a substrate for a tumor specific protease.

Figure 1N:
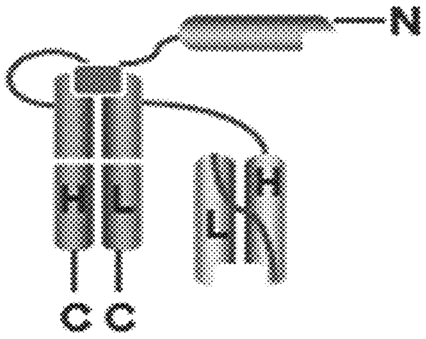

Disclosed herein, in some embodiments, are isolated polypeptides or polypeptide complexes comprising a structural arrangement according to the configuration shown in FIG. 1N, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab heavy chain polypeptide with a linking moiety that is a substrate for a tumor specific protease, and the peptide is further linked to a half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab light chain polypeptide.

Figure 1O:
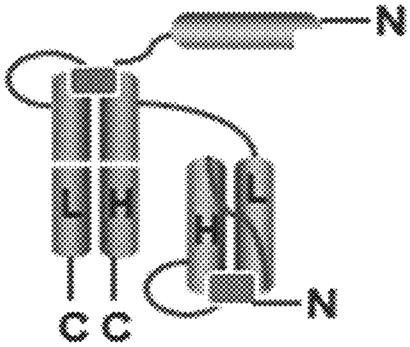

Disclosed herein, in some embodiments, are isolated polypeptides or polypeptide complexes comprising a structural arrangement according to the configuration shown in FIG. 1O, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide ($P_1$) that impairs binding of the Fab to PSMA and $P_1$ is linked to a N terminus of the Fab light chain polypeptide with a linking moiety ($L_1$) that is a substrate for a tumor specific protease, and $P_1$ is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab heavy chain polypeptide, wherein the scFv is linked to $P_2$ and $L_2$, wherein $P_2$ comprises a peptide that impairs binding of the scFv to the effector cell antigen, and $L_2$ comprises a linking moiety that connects the heavy chain variable domain of the scFv to $P_2$ and is a substrate for a tumor specific protease.

Figure 1P:
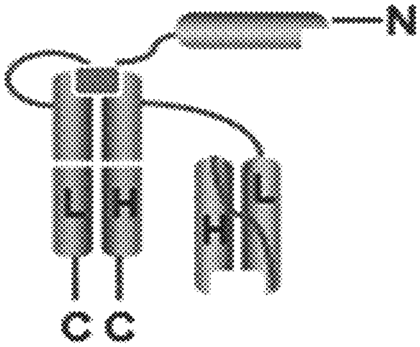

Disclosed herein, in some embodiments, are isolated polypeptides or polypeptide complexes comprising a structural arrangement according to the configuration shown in FIG. 1P, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab light chain polypeptide with a linking moiety that is a substrate for a tumor specific protease, and the peptide is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab heavy chain polypeptide.

Figure 1Q:
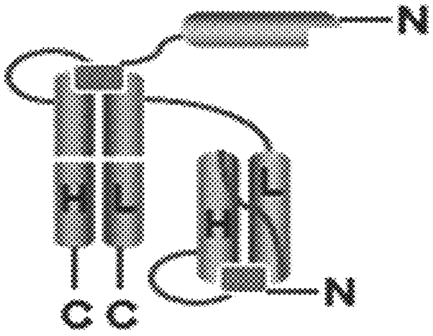

Disclosed herein, in some embodiments, are isolated polypeptides or polypeptide complexes comprising a structural arrangement according to the configuration shown in FIG. 1Q, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a ($P_1$) that impairs binding of the Fab to PSMA and $P_1$ is linked to a N terminus of the Fab heavy chain polypeptide with a linking moiety ($L_1$) that is a substrate for a tumor specific protease, and $P_1$ is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab light chain polypeptide, wherein the scFv is linked to $P_2$ and $L_2$, wherein $P_2$ comprises a peptide that impairs binding of the scFv to the effector cell antigen, and $L_2$ comprises a linking moiety that connects the heavy chain variable domain of the scFv to $P_2$ and is a substrate for a tumor specific protease.

Figure 1R:
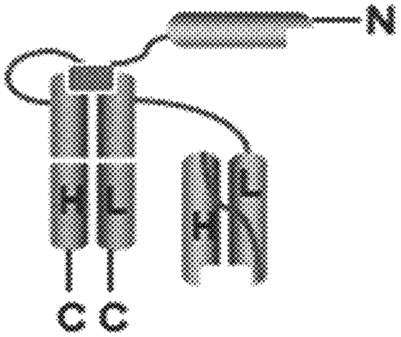

Disclosed herein, in some embodiments, are isolated polypeptides or polypeptide complexes comprising a structural arrangement according to the configuration shown in FIG. 1R, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab heavy chain polypeptide with a linking moiety that is a substrate for a tumor specific protease, and the peptide is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab light chain polypeptide.

Polynucleotides Encoding Polypeptides or Polypeptide Complexes

Disclosed herein, in some embodiments, are isolated recombinant nucleic acid molecules encoding polypeptides or polypeptide complexes as disclosed herein. In some embodiments, the polypeptides or polypeptide complexes comprise an antibody or an antibody fragment. In some embodiments, the polypeptides or polypeptide complexes comprise a Fab and a single chain variable fragment (scFv).

Disclosed herein, in some embodiments, are isolated recombinant nucleic acid molecules encoding polypeptides or polypeptide complexes according to Formula I:

$$A_2\text{-}A_1\text{-}L_1\text{-}P_1\text{-}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Disclosed herein, in some embodiments, are isolated recombinant nucleic acid molecules encoding polypeptides or polypeptide complexes according to Formula I:

$$A_2\text{-}A_1\text{-}L_1\text{-}P_1\text{-}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA).

Disclosed herein, in some embodiments, are isolated recombinant nucleic acid molecules encoding polypeptides or polypeptide complexes comprising Formula I:

$$A_2\text{-}A_1\text{-}L_1\text{-}P_1\text{-}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Disclosed herein, in some embodiments, are isolated recombinant nucleic acid molecules encoding polypeptides or polypeptide complexes comprising Formula I:

$$A_2\text{-}A_1\text{-}L_1\text{-}P_1\text{-}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA).

Disclosed herein, in some embodiments, are isolated recombinant nucleic acid molecules encoding polypeptides or polypeptide complexes according to Formula Ia:

$$P_2\text{-}L_2\text{-}A_2\text{-}A_1\text{-}L_1\text{-}P_1\text{-}H_{1a} \quad \text{(Formula Ia).}$$

Disclosed herein, in some embodiments, are isolated recombinant nucleic acid molecules encoding polypeptides or polypeptide complexes according to Formula II:

$$L_{1a}\text{-}P_{1a}\text{-}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated recombinant nucleic acid molecules encoding polypeptides or polypeptide complexes comprising Formula II:

$$L_{1a}\text{-}P_{1a}\text{-}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated recombinant nucleic acid molecules encoding polypeptides or polypeptide complexes according to Formula II:

$L_{1a}$-$P_{1a}$-$H_{1a}$ (Formula II)

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

Disclosed herein, in some embodiments, are isolated recombinant nucleic acid molecules encoding polypeptides or polypeptide complexes comprising Formula II:

$L_{1a}$-$P_{1a}$-$H_{1a}$ (Formula II)

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

Disclosed herein, in some embodiments, are isolated nucleic acid molecules encoding polypeptides or polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv.

Disclosed herein, in some embodiments, are isolated nucleic acid molecules encoding polypeptides or polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

Pharmaceutical Compositions

Disclosed herein, in some embodiments, are pharmaceutical compositions comprising: (a) the polypeptides or polypeptide complexes as disclosed herein; and (b) a pharmaceutically acceptable excipient.

In some embodiments, the pharmaceutical composition comprises (a) polypeptides or polypeptide complexes according to Formula I:

$A_2$-$A_1$-$L_1$-$P_1$-$H_1$ (Formula I)

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes according to Formula I:

$A_2$-$A_1$-$L_1$-$P_1$-$H_1$ (Formula I)

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes comprising Formula I:

$A_2$-$A_1$-$L_1$-$P_1$-$H_1$ (Formula I)

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes comprising Formula I:

$A_2$-$A_1$-$L_1$-$P_1$-$H_1$ (Formula I)

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes according to Formula Ia:

$P_2$-$L_2$-$A_2$-$A_1$-$L_1$-$P_1$-$H_1$ (Formula Ia);

and (b) a pharmaceutically acceptable excipient.

In some embodiments, the pharmaceutical composition comprises (a) polypeptides or polypeptide complexes according to Formula II:

$L_{1a}$-$P_{1a}$-$H_{1a}$ (Formula II)

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule; and (b) a pharmaceutically acceptable excipient.

In some embodiments, the pharmaceutical composition comprises (a) polypeptides or polypeptide complexes comprising Formula II:

$$L_{1a}\text{-}P_{1a}\text{-}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule; and (b) a pharmaceutically acceptable excipient.

In some embodiments, the pharmaceutical composition comprises (a) polypeptides or polypeptide complexes according to Formula II:

$$L_{1a}\text{-}P_{1a}\text{-}H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule; and (b) a pharmaceutically acceptable excipient.

In some embodiments, the pharmaceutical composition comprises (a) polypeptides or polypeptide complexes comprising Formula II:

$$L_{1a}\text{-}P_{1a}\text{-}H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule; and (b) a pharmaceutically acceptable excipient.

Disclosed herein, in some embodiments, the pharmaceutical composition comprises (a) polypeptides or polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv; and (b) a pharmaceutically acceptable excipient. Disclosed herein, in some embodiments, the pharmaceutical composition comprises (a) polypeptides or polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv; and (b) a pharmaceutically acceptable excipient.

In some embodiments, the polypeptide or polypeptide complex further comprises a detectable label, a therapeutic agent, or a pharmacokinetic modifying moiety. In some embodiments, the detectable label comprises a fluorescent label, a radiolabel, an enzyme, a nucleic acid probe, or a contrast agent.

For administration to a subject, the polypeptide or polypeptide complex as disclosed herein, may be provided in a pharmaceutical composition together with one or more pharmaceutically acceptable carriers or excipients. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

The pharmaceutical composition may be in any suitable form, (depending upon the desired method of administration). It may be provided in unit dosage form, may be provided in a sealed container and may be provided as part of a kit. Such a kit may include instructions for use. It may include a plurality of said unit dosage forms.

The pharmaceutical composition may be adapted for administration by any appropriate route, including a parenteral (e.g., subcutaneous, intramuscular, or intravenous) route. Such compositions may be prepared by any method known in the art of pharmacy, for example by mixing the active ingredient with the carrier(s) or excipient(s) under sterile conditions.

Dosages of the substances of the present disclosure can vary between wide limits, depending upon the disease or disorder to be treated, the age and condition of the individual to be treated, etc. and a physician will ultimately determine appropriate dosages to be used.

Methods of Treatment

In some embodiments, are methods of treating cancer in a subject need in need thereof comprising administering to the subject an isolated polypeptide or polypeptide complex as described herein. In some embodiments, the cancer has cells that express PSMA. In some instances, the cancer is a solid tumor cancer. In some embodiments, the cancer is lung, breast (e.g. HER2+; ER/PR+; TNBC), cervical, ovarian, colorectal, pancreatic or gastric.

In some embodiments, are methods of treating prostate cancer in a subject need in need thereof comprising administering to the subject an isolated polypeptide or polypeptide complex as described herein. In some embodiments, are methods of treating metastatic castrate-resistant prostate cancer (mCRPC) in a subject need in need thereof comprising administering to the subject an isolated polypeptide or polypeptide complex as described herein.

Described herein, in some embodiments, are isolated polypeptides or polypeptide complexes, wherein the polypeptides or polypeptide complexes comprise a long half-life. In some instances, the half-life of the polypeptides or polypeptide complexes is at least or about 12 hours, 24 hours 36 hours, 48 hours, 60 hours, 72 hours, 84 hours, 96 hours, 100 hours, 108 hours, 119 hours, 120 hours, 140 hours, 160 hours, 180 hours, 200 hours, or more than 200 hours. In some instances, the half-life of the polypeptides or polypeptide complexes is in a range of about 12 hours to about 300 hours, about 20 hours to about 280 hours, about 40 hours to about 240 hours, about 60 hours to about 200 hours, or about 80 hours to about 140 hours.

Described herein, in some embodiments, are polypeptide or polypeptide complexes administered as once weekly. In some embodiments, the polypeptide or polypeptide complexes are administered once weekly by intravenous, intramuscular, intralesional, topical, subcutaneous, infusion, or oral. In some embodiments, the polypeptide or polypeptide complexes are administered once weekly by bolus injection. In some embodiments, the polypeptide or polypeptide complexes are administered once weekly by continuous infusion. In some embodiments, the polypeptide or polypeptide complex is administered to the subject once a week as a continuous infusion over a period of no more than 60 minutes. In some embodiments, the polypeptide or polypeptide complex is administered to the subject once a week as a continuous intravenous infusion over a period of no more than 30 minutes. In some embodiments, the polypeptide or polypeptide complex is administered to the subject once a week as a continuous intravenous infusion over a period of at least 10 minutes.

In some embodiments, the polypeptide or polypeptide complex is administered to the subject once a week and the polypeptide or polypeptide complex has a half-life of at least 30 hours. In some embodiments, the polypeptide or polypeptide complex is administered to the subject once a week and the polypeptide or polypeptide complex has a half-life of at least 50 hours. In some embodiments, the polypeptide or polypeptide complex is administered to the subject once a week and the polypeptide or polypeptide complex has a half-life of at least 60 hours. In some embodiments, the polypeptide or polypeptide complex is administered to the subject once a week and the polypeptide or polypeptide complex has a half-life of at least 70 hours. In some embodiments, the polypeptide or polypeptide complex is administered to the subject once a week and the polypeptide or polypeptide complex has a half-life of at least 80 hours. In some embodiments, the polypeptide or polypeptide complex is administered to the subject once a week and the polypeptide or polypeptide complex has a half-life of at least 90 hours. In some embodiments, the polypeptide or polypeptide complex is administered to the subject once a week and the polypeptide or polypeptide complex has a half-life of at least 100 hours. In some embodiments, the polypeptide or polypeptide complex is administered to the subject once a week and the polypeptide or polypeptide complex has a half-life of at least 110 hours. In some embodiments, the polypeptide or polypeptide complex is administered to the subject once a week and the polypeptide or polypeptide complex has a half-life of at least 115 hours. In some embodiments, the polypeptide or polypeptide complex is administered to the subject once a week and the polypeptide or polypeptide complex has a half-life of at least 119 hours.

Production of Antibodies that Bind to PSMA and CD3

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding fragment is optionally generated by immunizing an animal, such as a mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk-, hgprt- or aprt-cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

In some instances, the expression levels of an antibody are increased by vector amplification (for a review, see Bebbington and Hentschel, the use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in the culture of the host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vector derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichia*

*pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors may include pRK5, p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cells include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, Deinococcus-Thermus, Fibrobacteres—Chlorobi/Bacteroidetes (FCB group), Fusobacteria, Gemmatimonadetes, Nitrospirae, Planctomycetes—Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or *Coli bacilli.*

Exemplary prokaryotic host cells include, but are not limited to, BL21, Mach1™, DH10B™, TOP10, DH5α, DH10Bac™, OmniMax™, MegaX™, DH12S™, INV110, TOP10F™, INVαF, TOP10/P3, ccdB Survival, PIR1, PIR2, Stb12™, Stb13™, or Stb14™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. *Schizosaccharomycetes* (fission yeasts)). In some cases, Basidiomycota includes Agaricomycotina (e.g. *Tremellomycetes*) or Pucciniomycotina (e.g. *Microbotryomycetes*).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii.*

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen-binding site that specifically binds to CD3 and a second antigen-binding site that specifically binds to PSMA as defined herein before.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "antibody" is used in the broadest sense and covers fully assembled antibodies, antibody fragments that can bind antigen, for example, Fab, F(ab')2, Fv, single chain antibodies (scFv), diabodies, antibody chimeras, hybrid antibodies, bispecific antibodies, and the like.

The term "complementarity determining region" or "CDR" is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in *Monoclonal Antibodies: Production, Engineering and Clinical Application*, Ritter et al. (eds.), pages 166-179 (Cambridge University Press 1995); and Ward et al., "Genetic Manipulation and Expression of Antibodies," in *Monoclonal Antibodies: Principles and Applications*, Birch et al., (eds.), pages 137-185 (Wiley-Liss, Inc. 1995).

The term "Fab" refers to a protein that contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VII with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Embodiments

Embodiment 1 comprises an isolated polypeptide or polypeptide complex according to Formula I: $A_2$-$A_1$-$L_1$-$P_1$-$H_1$ wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Embodiment 2 comprises an isolated polypeptide or polypeptide complex of embodiment 1, wherein the first antigen recognizing molecule comprises an antibody or antibody fragment.

Embodiment 3 comprises an isolated polypeptide or polypeptide complex of embodiment 1, wherein first antigen recognizing molecule comprises an antibody or antibody fragment that is human or humanized.

Embodiment 4 comprises an isolated polypeptide or polypeptide complex of any one of embodiments 1-3, wherein $L_1$ is bound to N-terminus of the first antigen recognizing molecule.

Embodiment 5 comprises an isolated polypeptide or polypeptide complex of any one of embodiments 1-3, wherein $A_2$ is bound to C-terminus of the first antigen recognizing molecule.

Embodiment 6 comprises an isolated polypeptide or polypeptide complex of any one of embodiments 1-3, wherein $L_1$ is bound to C-terminus of the first antigen recognizing molecule.

Embodiment 7 comprises an isolated polypeptide or polypeptide complex of any one of embodiments 1-3, wherein $A_2$ is bound to N-terminus of the first antigen recognizing molecule.

Embodiment 8 comprises an isolated polypeptide or polypeptide complex of any one of embodiments 2-7, wherein the antibody or antibody fragment comprises a single chain variable fragment, a single domain antibody, or a Fab fragment.

Embodiment 9 comprises an isolated polypeptide or polypeptide complex of embodiment 8, wherein $A_1$ is the single chain variable fragment (scFv).

Embodiment 10 comprises an isolated polypeptide or polypeptide complex of embodiment 9, wherein the scFv comprises a scFv heavy chain polypeptide and a scFv light chain polypeptide.

Embodiment 11 comprises an isolated polypeptide or polypeptide complex of embodiment 8, wherein $A_1$ is the single domain antibody, Embodiment 12 comprises an isolated polypeptide or polypeptide complex of embodiment 8, wherein the antibody or antibody fragment comprises a single chain variable fragment (scFv), a heavy chain variable domain (VH domain), a light chain variable domain (VL domain), or a variable domain (VHH) of a camelid derived single domain antibody.

Embodiment 13 comprises an isolated polypeptide or polypeptide complex of any one of embodiments 1-12, wherein $A_1$ comprises an anti-CD3e single chain variable fragment.

Embodiment 14 comprises an isolated polypeptide or polypeptide complex of any one of embodiments 1-12, wherein $A_1$ comprises an anti-CD3e single chain variable fragment that has a $K_D$ binding of 1 μM or less to CD3 on CD3 expressing cells.

Embodiment 15 comprises an isolated polypeptide or polypeptide complex of any one of embodiments 1-14, wherein the effector cell antigen comprises CD3.

Embodiment 16 comprises an isolated polypeptide or polypeptide complex of embodiment 1, wherein $A_1$ comprises a variable light chain and variable heavy chain each of which is capable of specifically binding to human CD3.

Embodiment 17 comprises an isolated polypeptide or polypeptide complex of embodiment 1, wherein $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

Embodiment 18 comprises an isolated polypeptide or polypeptide complex of embodiment 1, wherein the polypeptide or polypeptide complex of Formula I binds to an effector cell when $L_1$ is cleaved by the tumor specific protease.

Embodiment 19 comprises an isolated polypeptide or polypeptide complex of embodiment 1, wherein the polypeptide or polypeptide complex of Formula I binds to an effector cell when $L_1$ is cleaved by the tumor specific protease and $A_1$ binds to the effector cell.

Embodiment 20 comprises an isolated polypeptide or polypeptide complex of embodiment 19, wherein the effector cell is a T cell.

Embodiment 21 comprises an isolated polypeptide or polypeptide complex of embodiment 1, wherein $A_1$ binds to a polypeptide that is part of a TCR-CD3 complex on the effector cell.

Embodiment 22 comprises an isolated polypeptide or polypeptide complex of embodiment 21, wherein the polypeptide that is part of the TCR-CD3 complex is human CD3.

Embodiment 23 comprises an isolated polypeptide or polypeptide complex of embodiment 1, wherein the effector cell antigen comprises CD3, wherein the scFv comprises complementarity determining regions (CDRs): HC-CDR1, HC-CDR2, and HC-CDR3, wherein the HC-CDR1, the HC-CDR2, and the HC-CDR3 of the scFv comprise: HC-CDR1: SEQ ID NO: 1, HC-CDR2: SEQ ID NO: 2, and HC-CDR3: SEQ ID NO: 3; and the scFv comprises CDRs: LC-CDR1, LC-CDR2, and LC-CDR3, wherein the LC-CDR1, the LC-CDR2, and the LC-CDR3 of the scFv comprise: LC-CDR1: SEQ ID NO: 4, LC-CDR2: SEQ ID NO:5, and LC-CDR3: SEQ ID NO: 6.

Embodiment 24 comprises an isolated polypeptide or polypeptide complex of embodiment 1, wherein the effector cell antigen comprises CD3, and the scFv comprises an amino acid sequence according to SEQ ID NO: 7.

Embodiment 25 comprises an isolated polypeptide or polypeptide complex of any one of embodiments 1-24, wherein second antigen recognizing molecule comprises an antibody or antibody fragment.

Embodiment 26 comprises an isolated polypeptide or polypeptide complex of embodiment 25, wherein the antibody or antibody fragment thereof comprises a single chain variable fragment, a single domain antibody, or a Fab.

Embodiment 27 comprises an isolated polypeptide or polypeptide complex of embodiment 25, wherein the antibody or antibody fragment thereof comprises a single chain variable fragment (scFv), a heavy chain variable domain (VH domain), a light chain variable domain (VL domain), a variable domain (VHH) of a camelid derived single domain antibody.

Embodiment 28 comprises an isolated polypeptide or polypeptide complex of embodiment 25, wherein the antibody or antibody fragment thereof is humanized or human.

Embodiment 29 comprises an isolated polypeptide or polypeptide complex of embodiment 26, wherein $A_2$ is the Fab.

Embodiment 30 comprises an isolated polypeptide or polypeptide complex of embodiment 29, wherein the Fab comprises (a) a Fab light chain polypeptide and (b) a Fab heavy chain polypeptide.

Embodiment 31 comprises an isolated polypeptide or polypeptide complex of embodiment 29, wherein the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO:

9, and HC-CDR3: SEQ ID NO: 10; and the Fab comprises CDRs: LC-CDR1, LC-CDR2, and LC-CDR3, wherein the LC-CDR1, the LC-CDR2, and the LC-CDR3 of the Fab comprise: LC-CDR1: SEQ ID NO: 11, LC-CDR2: SEQ ID NO:12, and LC-CDR3: SEQ ID NO: 13.

Embodiment 32 comprises an isolated polypeptide or polypeptide complex of embodiment 30, wherein the Fab light chain polypeptide comprises an amino acid sequence according to SEQ ID NO: 14.

Embodiment 33 comprises an isolated polypeptide or polypeptide complex of embodiment 30, wherein Fab heavy chain polypeptide comprises an amino acid sequence according to SEQ ID NO: 15.

Embodiment 34 comprises an isolated polypeptide or polypeptide complex of embodiment 30, wherein the Fab light chain polypeptide of $A_2$ is bound to a C-terminus of the single chain variable fragment (scFv) of A.

Embodiment 35 comprises an isolated polypeptide or polypeptide complex of embodiment 30, wherein the Fab heavy chain polypeptide of $A_2$ is bound to a C-terminus of the single chain variable fragment (scFv) $A_1$.

Embodiment 36 comprises an isolated polypeptide or polypeptide complex of embodiment 30, wherein the Fab light chain polypeptide of $A_2$ is bound to a N-terminus of the single chain variable fragment (scFv) of $A_1$.

Embodiment 37 comprises an isolated polypeptide or polypeptide complex of embodiment 30, wherein the Fab heavy chain polypeptide of $A_2$ is bound to a N-terminus of the single chain variable fragment (scFv) $A_1$.

Embodiment 38 comprises a polypeptide or polypeptide complex of embodiment 30, wherein the Fab heavy chain polypeptide of $A_2$ is bound to the scFv heavy chain polypeptide of $A_1$.

Embodiment 39 comprises a polypeptide or polypeptide complex of embodiment 30, wherein the Fab light chain polypeptide of $A_2$ is bound to the scFv heavy chain polypeptide of $A_1$.

Embodiment 40 comprises a polypeptide or polypeptide complex of embodiment 30, wherein the Fab heavy chain polypeptide of $A_2$ is bound to the scFv light chain polypeptide of A.

Embodiment 41 comprises a polypeptide or polypeptide complex of embodiment 30, wherein the Fab light chain polypeptide of $A_2$ is bound to the scFv light chain polypeptide of $A_1$.

Embodiment 42 comprises a polypeptide or polypeptide complex of any one of embodiments 1-41, wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Embodiment 43 comprises a polypeptide or polypeptide complex of embodiment 42, wherein the polypeptide or polypeptide complex is according to Formula Ia: $P_2$-$L_2$-$A_2$-$A_1$-$L_1$-$P_1$-$H_1$.

Embodiment 44 comprises a polypeptide or polypeptide complex of embodiment 43, wherein the Fab heavy chain polypeptide of $A_2$ is bound to the scFv heavy chain polypeptide of $A_1$ and $L_2$ is bound to the Fab light chain polypeptide of $A_2$.

Embodiment 45 comprises a polypeptide or polypeptide complex of embodiment 43, wherein the Fab light chain polypeptide of $A_2$ is bound to the scFv heavy chain polypeptide of $A_1$ and $L_2$ is bound to the Fab heavy chain polypeptide of $A_2$.

Embodiment 46 comprises a polypeptide or polypeptide complex of embodiment 43, wherein the Fab heavy chain polypeptide of $A_2$ is bound to the scFv light chain polypeptide of $A_1$ and $L_2$ is bound to the Fab light chain polypeptide of $A_2$.

Embodiment 47 comprises a polypeptide or polypeptide complex of embodiment 43, wherein the Fab light chain polypeptide of $A_2$ is bound to the scFv light chain polypeptide of $A_1$ and $L_2$ is bound to the Fab heavy chain polypeptide of $A_2$.

Embodiment 48 comprises a polypeptide or polypeptide complex of any one of embodiments 1-47, wherein $P_1$ impairs binding of $A_1$ to the effector cell antigen.

Embodiment 49 comprises a polypeptide or polypeptide complex of any one of embodiments 1-48, wherein $P_1$ is bound to $A_1$ through ionic interactions, electrostatic interactions, hydrophobic interactions, Pi-stacking interactions, or H-bonding interactions, or a combination thereof.

Embodiment 50 comprises a polypeptide or polypeptide complex of any one of embodiments 1-48, wherein $P_1$ has less than 70% sequence homology to the effector cell antigen.

Embodiment 51 comprises a polypeptide or polypeptide complex of any one of embodiments 1-50, wherein $P_2$ impairs binding of $A_2$ to PSMA.

Embodiment 52 comprises a polypeptide or polypeptide complex of any one of embodiments 1-50, wherein $P_2$ is bound to $A_2$ through ionic interactions, electrostatic interactions, hydrophobic interactions, Pi-stacking interactions, or H-bonding interactions, or a combination thereof.

Embodiment 53 comprises a polypeptide or polypeptide complex of any one of embodiments 1-50, wherein $P_2$ is bound to $A_2$ at or near an antigen binding site.

Embodiment 54 comprises a polypeptide or polypeptide complex of any one of embodiments 1-50, wherein $P_2$ has less than 70% sequence homology to PSMA.

Embodiment 55 comprises a polypeptide or polypeptide complex of any one of embodiments 1-54, wherein $P_1$ or $P_2$ comprises a peptide sequence of at least 10 amino acids in length.

Embodiment 56 comprises a polypeptide or polypeptide complex of any one of embodiments 1-54, wherein $P_1$ or $P_2$ comprises a peptide sequence of at least 10 amino acids in length and no more than 20 amino acids in length.

Embodiment 57 comprises a polypeptide or polypeptide complex of any one of embodiments 1-54, wherein $P_1$ or $P_2$ comprises a peptide sequence of at least 16 amino acids in length.

Embodiment 58 comprises a polypeptide or polypeptide complex of any one of embodiments 1-54, wherein $P_1$ or $P_2$ comprises a peptide sequence of no more than 40 amino acids in length.

Embodiment 59 comprises an isolated polypeptide or polypeptide complex of any one of embodiments 1-54, wherein $P_1$ or $P_2$ comprises at least two cysteine amino acid residues.

Embodiment 60 comprises an isolated polypeptide or polypeptide complex of any one of embodiments 1-54, wherein $P_1$ or $P_2$ comprises a cyclic peptide or a linear peptide.

Embodiment 61 comprises an isolated polypeptide or polypeptide complex of any one of embodiments 1-54, wherein $P_1$ or $P_2$ comprises a cyclic peptide.

Embodiment 62 comprises an isolated polypeptide or polypeptide complex of any one of embodiments 1-54, wherein $P_1$ or $P_2$ comprises a linear peptide Embodiment 63 comprises an isolated polypeptide or polypeptide complex of any one of embodiments 1-54, wherein $P_1$ comprises at least two cysteine amino acid residues.

Embodiment 64 comprises a polypeptide or polypeptide complex of any one of embodiments 1-54, wherein $P_1$ comprises an amino acid sequence according to any one of SEQ ID NOs: 16-19 or 78.

Embodiment 65 comprises an isolated polypeptide or polypeptide complex of any one of embodiments 1-64, wherein $L_1$ is bound to N-terminus of $A_1$.

Embodiment 66 comprises an isolated polypeptide or polypeptide complex of any one of embodiments 1-64, wherein $L_1$ is bound to C-terminus of $A_1$.

Embodiment 67 comprises an isolated polypeptide or polypeptide complex of any one of embodiments 1-66, wherein $L_2$ is bound to N-terminus of $A_2$.

Embodiment 68 comprises an isolated polypeptide or polypeptide complex of any one of embodiments 1-66, wherein $L_2$ is bound to C-terminus of $A_2$.

Embodiment 69 comprises an isolated polypeptide or polypeptide complex of any one of embodiments 1-68, wherein $L_1$ or $L_2$ is a peptide sequence having at least 5 to no more than 50 amino acids.

Embodiment 70 comprises an isolated polypeptide or polypeptide complex of any one of embodiments 1-68, wherein $L_1$ or $L_2$ is a peptide sequence having at least 10 to no more than 30 amino acids.

Embodiment 71 comprises an isolated polypeptide or polypeptide complex of any one of embodiments 1-68, wherein $L_1$ or $L_2$ is a peptide sequence having at least 10 amino acids.

Embodiment 72 comprises an isolated polypeptide or polypeptide complex of any one of embodiments 1-68, wherein $L_1$ or $L_2$ is a peptide sequence having at least 18 amino acids.

Embodiment 73 comprises an isolated polypeptide or polypeptide complex of any one of embodiments 1-68, wherein $L_1$ or $L_2$ is a peptide sequence having at least 26 amino acids.

Embodiment 74 comprises an isolated polypeptide or polypeptide complex of any one of embodiments 1-68, wherein $L_1$ or $L_2$ has a formula comprising $(G_2S)_n$, wherein n is an integer from 1 to 3 (SEQ ID NO: 118).

Embodiment 75 comprises an isolated polypeptide or polypeptide complex of any one of embodiments 1-68, wherein $L_1$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1.

Embodiment 76 comprises an isolated polypeptide or polypeptide complex of any one of embodiments 1-68, wherein $P_1$ becomes unbound from $A_1$ when $L_1$ is cleaved by the tumor specific protease thereby exposing $A_1$ to the effector cell antigen.

Embodiment 77 comprises an isolated polypeptide or polypeptide complex of any one of embodiments 1-68, wherein $P_2$ becomes unbound from $A_2$ when $L_2$ is cleaved by the tumor specific protease thereby exposing $A_2$ to PSMA.

Embodiment 78 comprises an isolated polypeptide or polypeptide complex of any one of embodiments 1-68, wherein the tumor specific protease is selected from the group consisting of a matrix metalloprotease (MMP), serine protease, cysteine protease, threonine protease, and aspartic protease.

Embodiment 79 comprises an isolated polypeptide or polypeptide complex of embodiment 78, wherein the matrix metalloprotease comprises MMP2, MMP7, MMP9, MMP13, or MMP14.

Embodiment 80 comprises an isolated polypeptide or polypeptide complex of embodiment 78, wherein the serine protease comprises matriptase (MTSP1), urokinase, or hepsin.

Embodiment 81 comprises an isolated polypeptide or polypeptide complex of any one of embodiments 1-68, wherein $L_1$ or $L_2$ comprises a urokinase cleavable amino acid sequence, a matriptase cleavable amino acid sequence, matrix metalloprotease cleavable amino acid sequence, or a legumain cleavable amino acid sequence.

Embodiment 82 comprises an isolated polypeptide or polypeptide complex of any one of embodiments 1-68, wherein $L_1$ or $L_2$ comprises an amino acid sequence according to SEQ ID NO: 23.

Embodiment 83 comprises an isolated polypeptide or polypeptide complex of any one of embodiments 1-68, wherein $L_1$ or $L_2$ comprises an amino acid sequence according to any one of SEQ ID NOs: 20-49.

Embodiment 84 comprises an isolated polypeptide or polypeptide complex of any one of embodiments 1-68, wherein $L_1$ or $L_2$ comprises an amino acid sequence of Linker 25 (ISSGLLSGRSDAG) (SEQ ID NO: 45), Linker 26 (AAGLLAPPGGLSGRSDAG) (SEQ ID NO: 46), Linker 27 (SPLGLSGRSDAG) (SEQ ID NO: 47), or Linker 28 (LSGRSDAGSPLGLAG) (SEQ ID NO: 48), or an amino acid sequence that has 1, 2, or 3 amino acid substitutions, additions, or deletions relative to the amino acid sequence of Linker 25, Linker 26, Linker 27, or Linker 28.

Embodiment 85 comprises an isolated polypeptide or polypeptide complex of any one of embodiments 1-83, wherein $H_1$ comprises a polymer.

Embodiment 86 comprises an isolated polypeptide or polypeptide complex of any one of embodiments 1-83, wherein the polymer is polyethylene glycol (PEG).

Embodiment 87 comprises an isolated polypeptide or polypeptide complex of any one of embodiments 1-83, wherein $H_1$ comprises albumin.

Embodiment 88 comprises an isolated polypeptide or polypeptide complex of any one of embodiments 1-83, wherein $H_1$ comprises an Fc domain.

Embodiment 89 comprises an isolated polypeptide or polypeptide complex of embodiment 87, wherein the albumin is serum albumin.

Embodiment 90 comprises an isolated polypeptide or polypeptide complex of embodiment 87, wherein the albumin is human serum albumin.

Embodiment 91 comprises an isolated polypeptide or polypeptide complex of any one of embodiments 1-83, wherein $H_1$ comprises a polypeptide, a ligand, or a small molecule.

Embodiment 92 comprises an isolated polypeptide or polypeptide complex of embodiment 91, wherein the polypeptide, the ligand or the small molecule binds serum protein or a fragment thereof, a circulating immunoglobulin or a fragment thereof, or CD35/CR1.

Embodiment 93 comprises an isolated polypeptide or polypeptide complex of embodiment 88, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 94 comprises an isolated polypeptide or polypeptide complex of embodiment 88, wherein the circulating immunoglobulin molecule comprises IgG1, IgG2, IgG3, IgG4, sIgA, IgM or IgD.

Embodiment 95 comprises an isolated polypeptide or polypeptide complex of embodiment 92, wherein the serum protein is albumin.

Embodiment 96 comprises an isolated polypeptide or polypeptide complex of embodiment 91, wherein the polypeptide is an antibody.

Embodiment 97 comprises an isolated polypeptide or polypeptide complex of embodiment 96, wherein the antibody comprises a single domain antibody, a single chain variable fragment, or a Fab.

Embodiment 98 comprises an isolated polypeptide or polypeptide complex of embodiment 97, wherein the single domain antibody comprises a single domain antibody that binds to albumin.

Embodiment 99 comprises an isolated polypeptide or polypeptide complex of embodiment 97, wherein the single domain antibody is a human or humanized antibody.

Embodiment 100 comprises an isolated polypeptide or polypeptide complex of embodiment 97, wherein the single domain antibody is 645gH1gL1.

Embodiment 101 comprises an isolated polypeptide or polypeptide complex of embodiment 97, wherein the single domain antibody is 645dsgH5gL4.

Embodiment 102 comprises an isolated polypeptide or polypeptide complex of embodiment 97, wherein the single domain antibody is 23-13-A01-sc02.

Embodiment 103 comprises an isolated polypeptide or polypeptide complex of embodiment 97, wherein the single domain antibody is A10m3 or a fragment thereof.

Embodiment 104 comprises an isolated polypeptide or polypeptide complex of embodiment 97, wherein the single domain antibody is DOM7r-31.

Embodiment 105 comprises an isolated polypeptide or polypeptide complex of embodiment 97, wherein the single domain antibody is DOM7h-11-15.

Embodiment 106 comprises an isolated polypeptide or polypeptide complex of embodiment 97, wherein the single domain antibody is Alb-1, Alb-8, or Alb-23.

Embodiment 107 comprises an isolated polypeptide or polypeptide complex of embodiment 97, wherein the single domain antibody is 10E.

Embodiment 108 comprises an isolated polypeptide or polypeptide complex of embodiment 97, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56.

Embodiment 109 comprises an isolated polypeptide or polypeptide complex of embodiment 97, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60.

Embodiment 110 comprises an isolated polypeptide or polypeptide complex of embodiment 97, wherein the single domain antibody is SA21.

Embodiment 111 comprises an isolated polypeptide or polypeptide complex of any one of embodiments 1-110, wherein the polypeptide or polypeptide complex comprises a modified amino acid, a non-natural amino acid, a modified non-natural amino acid, or a combination thereof.

Embodiment 112 comprises an isolated polypeptide or polypeptide complex of embodiment 111, wherein the modified amino acid or modified non-natural amino acid comprises a post-translational modification.

Embodiment 113 comprises an isolated polypeptide or polypeptide complex of any one of embodiments 1-112, wherein $H_1$ comprises a linking moiety ($L_3$) that connects $H_1$ to $P_1$.

Embodiment 114 comprises an isolated polypeptide or polypeptide complex of embodiment 113, wherein $L_3$ is a peptide sequence having at least 5 to no more than 50 amino acids.

Embodiment 115 comprises an isolated polypeptide or polypeptide complex of embodiment 113, wherein $L_3$ is a peptide sequence having at least 10 to no more than 30 amino acids.

Embodiment 116 comprises an isolated polypeptide or polypeptide complex of embodiment 113, wherein $L_3$ is a peptide sequence having at least 10 amino acids.

Embodiment 117 comprises an isolated polypeptide or polypeptide complex of embodiment 113, wherein $L_3$ is a peptide sequence having at least 18 amino acids.

Embodiment 118 comprises an isolated polypeptide or polypeptide complex of embodiment 113, wherein $L_3$ is a peptide sequence having at least 26 amino acids.

Embodiment 119 comprises an isolated polypeptide or polypeptide complex of embodiment 113, wherein $L_3$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1.

Embodiment 120 comprises an isolated polypeptide or polypeptide complex of embodiment 113, wherein $L_3$ comprises an amino acid sequence according to SEQ ID NO: 22.

Embodiment 121 comprises an isolated polypeptide or polypeptide complex of embodiment 1, wherein the polypeptide or polypeptide complex comprises an amino acid sequence with at least 95% sequence identity to SEQ ID NOs: 62-77.

Embodiment 122 comprises an isolated polypeptide or polypeptide complex of embodiment 1, wherein the polypeptide or polypeptide complex comprises an amino acid sequence with at least 95% sequence identity to SEQ ID NO: 72.

Embodiment 123 comprises an isolated polypeptide or polypeptide complex of embodiment 1, wherein the polypeptide or polypeptide complex comprises an amino acid sequence with at least 95% sequence identity to SEQ ID NO: 73.

Embodiment 124 comprises an isolated polypeptide or polypeptide complex of embodiment 1, wherein the polypeptide or polypeptide complex comprises an amino acid sequence with at least 95% sequence identity to SEQ ID NO: 62 and SEQ ID NO: 63.

Embodiment 125 comprises an isolated polypeptide or polypeptide complex of embodiment 1, wherein the polypeptide or polypeptide complex comprises an amino acid sequence with at least 95% sequence identity to SEQ ID NO: 64 and SEQ ID NO: 65.

Embodiment 126 comprises an isolated polypeptide or polypeptide complex of embodiment 1, wherein the polypeptide or polypeptide complex comprises an amino acid sequence with at least 95% sequence identity to SEQ ID NO: 66 and SEQ ID NO: 67.

Embodiment 127 comprises an isolated polypeptide or polypeptide complex of embodiment 1, wherein the polypeptide or polypeptide complex comprises an amino acid sequence with at least 95% sequence identity to SEQ ID NO: 68 and SEQ ID NO: 69.

Embodiment 128 comprises an isolated polypeptide or polypeptide complex of embodiment 1, wherein the polypeptide or polypeptide complex comprises an amino acid sequence with at least 95% sequence identity to SEQ ID NO: 70 and SEQ ID NO: 71.

Embodiment 129 comprises an isolated polypeptide or polypeptide complex of embodiment 1, wherein the polypeptide or polypeptide complex comprises an amino acid sequence with at least 95% sequence identity to SEQ ID NO: 72 and SEQ ID NO: 73.

Embodiment 130 comprises an isolated polypeptide or polypeptide complex of embodiment 1, wherein the polypeptide or polypeptide complex comprises an amino acid sequence with at least 95% sequence identity to SEQ ID NO: 74 and SEQ ID NO: 75.

Embodiment 131 comprises an isolated polypeptide or polypeptide complex of embodiment 1, wherein the polypeptide or polypeptide complex comprises an amino acid sequence with at least 95% sequence identity to SEQ ID NO: 76 and SEQ ID NO: 77.

Embodiment 132 comprises a pharmaceutical composition comprising: (a) the polypeptide or polypeptide complex of any one of embodiments 1-131; and (b) a pharmaceutically acceptable excipient.

Embodiment 133 comprises an isolated recombinant nucleic acid molecule encoding the polypeptide or polypeptide complex of any one of embodiments 1-131.

Embodiment 134 comprises an isolated polypeptide or polypeptide complex according to Formula II: $L_{1a}$-$P_{1a}$-$H_{1a}$ wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to PSMA; $P_{1a}$ comprises a peptide that binds to the first antigen recognizing molecule when $L_{1a}$ is uncleaved; and $H_{1a}$ comprises a half-life extending molecule.

Embodiment 135 comprises an isolated polypeptide or polypeptide complex of embodiment 134, wherein $P_{1a}$ when $L_{1a}$ is uncleaved impairs binding of the first antigen recognizing molecule to the effector cell antigen.

Embodiment 136 comprises an isolated polypeptide or polypeptide complex of embodiment 134, wherein the first antigen recognizing molecule comprises an antibody or antibody fragment.

Embodiment 137 comprises an isolated polypeptide or polypeptide complex of embodiment 134, wherein the effector cell antigen is an anti-CD3 effector cell antigen.

Embodiment 138 comprises an isolated polypeptide or polypeptide complex of embodiment 134, wherein $P_{1a}$ has less than 70% sequence homology to the effector cell antigen.

Embodiment 139 comprises an isolated polypeptide or polypeptide complex of embodiment 134, wherein $P_{1a}$ comprises a peptide sequence of at least 10 amino acids in length.

Embodiment 140 comprises an isolated polypeptide or polypeptide complex of embodiment 134, wherein $P_{1a}$ comprises a peptide sequence of at least 10 amino acids in length and no more than 20 amino acids in length.

Embodiment 141 comprises an isolated polypeptide or polypeptide complex of embodiment 134, wherein $P_{1a}$ comprises a peptide sequence of at least 16 amino acids in length.

Embodiment 142 comprises an isolated polypeptide or polypeptide complex of embodiment 134, wherein $P_{1a}$ comprises a peptide sequence of no more than 40 amino acids in length.

Embodiment 143 comprises an isolated polypeptide or polypeptide complex of embodiment 134, wherein $P_{1a}$ comprises at least two cysteine amino acid residues.

Embodiment 144 comprises an isolated polypeptide or polypeptide complex of embodiment 134, wherein $P_{1a}$ comprises a cyclic peptide or a linear peptide.

Embodiment 145 comprises an isolated polypeptide or polypeptide complex of embodiment 134, wherein $P_{1a}$ comprises a cyclic peptide.

Embodiment 146 comprises an isolated polypeptide or polypeptide complex of embodiment 134, wherein $P_{1a}$ comprises a linear peptide.

Embodiment 147 comprises an isolated polypeptide or polypeptide complex of embodiment 134, wherein $P_{1a}$ comprises an amino acid sequence selected from the group consisting of any one of SEQ ID NOs: 16-19.

Embodiment 148 comprises an isolated polypeptide or polypeptide complex of any one of embodiments 132-145, wherein $H_{1a}$ comprises a polymer.

Embodiment 149 comprises an isolated polypeptide or polypeptide complex of embodiment 148, wherein the polymer is polyethylene glycol (PEG).

Embodiment 150 comprises an isolated polypeptide or polypeptide complex of any one of embodiments 134-147, wherein ia comprises albumin.

Embodiment 151 comprises an isolated polypeptide or polypeptide complex of any one of embodiments 134-147, wherein $H_{1a}$ comprises an Fc domain.

Embodiment 152 comprises an isolated polypeptide or polypeptide complex of embodiment 150, wherein the albumin is serum albumin.

Embodiment 153 comprises an isolated polypeptide or polypeptide complex of embodiment 152, wherein the albumin is human serum albumin.

Embodiment 154 comprises an isolated polypeptide or polypeptide complex of any one of embodiments 134-147, wherein $H_{1a}$ comprises a polypeptide, a ligand, or a small molecule.

Embodiment 155 comprises an isolated polypeptide or polypeptide complex of embodiment 154, wherein the polypeptide, the ligand or the small molecule binds a serum protein or a fragment thereof, a circulating immunoglobulin or a fragment thereof, or CD35/CR1.

Embodiment 156 comprises an isolated polypeptide or polypeptide complex of embodiment 155, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 157 comprises an isolated polypeptide or polypeptide complex of embodiment 155, wherein the circulating immunoglobulin molecule comprises IgG1, IgG2, IgG3, IgG4, slgA, IgM or IgD.

Embodiment 158 comprises an isolated polypeptide or polypeptide complex of embodiment 153, wherein the serum protein is albumin.

Embodiment 159 comprises an isolated polypeptide or polypeptide complex of embodiment 154, wherein the polypeptide is an antibody.

Embodiment 160 comprises an isolated polypeptide or polypeptide complex of embodiment 159, wherein the antibody comprises a single domain antibody, a single chain variable fragment or a Fab.

Embodiment 161 comprises an isolated polypeptide or polypeptide complex of embodiment 159, wherein the antibody comprises a single domain antibody that binds to albumin.

Embodiment 162 comprises an isolated polypeptide or polypeptide complex of embodiment 159, wherein the antibody is a human or humanized antibody.

Embodiment 163 comprises an isolated polypeptide or polypeptide complex of embodiment 160, wherein the single domain antibody is 645gH1gL1.

Embodiment 164 comprises an isolated polypeptide or polypeptide complex of embodiment 160, wherein the single domain antibody is 645dsgH5gL4.

Embodiment 165 comprises an isolated polypeptide or polypeptide complex of embodiment 160, wherein the single domain antibody is 23-13-A01-sc02.

Embodiment 166 comprises an isolated polypeptide or polypeptide complex of embodiment 160, wherein the single domain antibody is A10m3 or a fragment thereof.

Embodiment 167 comprises an isolated polypeptide or polypeptide complex of embodiment 160, wherein the single domain antibody is DOM7r-31.

Embodiment 168 comprises an isolated polypeptide or polypeptide complex of embodiment 160, wherein the single domain antibody is DOM7h-11-15.

Embodiment 169 comprises an isolated polypeptide or polypeptide complex of embodiment 160, wherein the single domain antibody is Alb-1, Alb-8, or Alb-23.

Embodiment 170 comprises an isolated polypeptide or polypeptide complex of embodiment 160, wherein the single domain antibody is 10E.

Embodiment 171 comprises an isolated polypeptide or polypeptide complex of embodiment 160, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56.

Embodiment 172 comprises an isolated polypeptide or polypeptide complex of embodiment 158, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60.

Embodiment 173 comprises an isolated polypeptide or polypeptide complex of embodiment 160, wherein the single domain antibody is SA21.

Embodiment 174 comprises an isolated polypeptide or polypeptide complex of any one of embodiments 134-173, wherein $H_{1a}$ comprises a linking moiety ($L_{1a}$) that connects $H_{1a}$ to $P_{1a}$.

Embodiment 175 comprises an isolated polypeptide or polypeptide complex of embodiment 174, wherein $L_{1a}$ is a peptide sequence having at least 5 to no more than 50 amino acids.

Embodiment 176 comprises an isolated polypeptide or polypeptide complex of embodiment 174, wherein $L_{1a}$ is a peptide sequence having at least 10 to no more than 30 amino acids.

Embodiment 177 comprises an isolated polypeptide or polypeptide complex of embodiment 174, wherein $L_{1a}$ is a peptide sequence having at least 10 amino acids.

Embodiment 178 comprises an isolated polypeptide or polypeptide complex of embodiment 174, wherein $L_{1a}$ is a peptide sequence having at least 18 amino acids.

Embodiment 179 comprises an isolated polypeptide or polypeptide complex of embodiment 174, wherein $L_{1a}$ is a peptide sequence having at least 26 amino acids.

Embodiment 180 comprises an isolated polypeptide or polypeptide complex of embodiment 174, wherein $L_{1a}$ has a formula selected from the group consisting of $(G_2S)_n$, $(GS)_n$, $(GSGGS)_n$ (SEQ ID NO: 50), $(GGGS)_n$ (SEQ ID NO: 51), $(GGGGS)_n$ (SEQ ID NO: 52), and $(GSSGGS)_n$ (SEQ ID NO: 53), wherein n is an integer of at least 1.

Embodiment 181 comprises an isolated polypeptide or polypeptide complex of embodiment 174, wherein $L_{1a}$ comprises an amino acid sequence according to SEQ ID NO: 23.

Embodiment 182 comprises an isolated polypeptide or polypeptide complex of any one of embodiments 134-181, wherein $P_{1a}$ comprises an amino acid sequence according to $Z_1$-$Z_2$-C-$Z_4$-P-$Z_6$-$Z_7$-$Z_8$-$Z_9$-$Z_{10}$-$Z_{11}$-$Z_{12}$-C-$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_5$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S.

Embodiment 183 comprises an isolated polypeptide or polypeptide complex of embodiment 182, wherein $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_5$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; and $Z_{14}$ is selected from D, Y, N, F, I, and P;

Embodiment 184 comprises an isolated polypeptide or polypeptide complex of any one of embodiments 182-183, wherein Z, is selected from D, Y, and F; $Z_2$ is selected from D, Y, L, and F; $Z_4$ is selected from G and W; $Z_6$ is selected from E and D; $Z_7$ is selected from W, $L_1$ and F; $Z_5$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N.

Embodiment 185 comprises an isolated polypeptide or polypeptide complex of any one of embodiments 134-181, wherein $P_{1a}$ comprises an amino acid sequence according to Ur-$U_2$-C-$U_4$-P-$U_6$-$U_7$—$U_8$-$U_9$-$U_{10}$-$U_{11}$-$U_{12}$-C-$U_{14}$ and U, is selected from D, Y, F, I, N, V, H, L, A, T, S, and P; $U_2$ is selected from D, Y, L, F, 1, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S.

Embodiment 186 comprises an isolated polypeptide or polypeptide complex of embodiment 185, wherein U, is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, 1, M, and P.

Embodiment 187 comprises an isolated polypeptide or polypeptide complex of embodiment 186, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

Embodiment 188 comprises an isolated polypeptide or polypeptide complex of any one of embodiments 134-181 and 70-88, wherein $P_{1a}$ comprises the amino acid sequences according to SEQ ID NOs: 79-105.

Embodiment 189 comprises an isolated polypeptide or polypeptide complex of any one of embodiments 134-181 and 70-88, wherein $P_{1a}$ comprises an amino acid sequences according to any of the sequences of Table 20.

Embodiment 190 comprises an isolated polypeptide or polypeptide complex of any one of embodiments 134-181, or 189, wherein $P_{1a}$ comprises the amino acid sequences according to any one of SEQ ID NOs: 106-117.

Embodiment 191 comprises an isolated polypeptide or polypeptide complex of any one of embodiments 134-181, wherein $P_{1a}$ comprises the amino acid sequence according to SEQ ID NO: 18 or a peptide sequence that has 1, 2, or 3, amino acid substitutions, additions, or deletions relative to the amino acid sequence of SEQ ID NO: 18.

Embodiment 192 comprises an isolated polypeptide or polypeptide complex of any one of embodiments 134-187, wherein $P_{1a}$ comprises the amino acid sequence according to SEQ ID NO: 19 or a peptide sequence that has 1, 2, or 3, amino acid substitutions, additions, or deletions relative to the amino acid sequence of SEQ ID NO: 19.

Embodiment 193 comprises an isolated polypeptide or polypeptide complex of any one of embodiments 134-187, wherein $P_{1a}$ comprises the amino acid sequence according to SEQ ID NO: 116 or a peptide sequence that has 1, 2, or 3, amino acid substitutions, additions, or deletions relative to the amino acid sequence of SEQ ID NO: 116.

Embodiment 194 comprises an isolated polypeptide or polypeptide complex of embodiment 191, wherein $P_{1a}$ comprises the amino acid sequence according to SEQ ID NO: 18.

Embodiment 195 comprises an isolated polypeptide or polypeptide complex of embodiment 192, wherein $P_{1a}$ comprises the amino acid sequence according to SEQ ID NO: 19.

Embodiment 196 comprises an isolated polypeptide or polypeptide complex of embodiment 193, wherein $P_{1a}$ comprises the amino acid sequence according to SEQ ID NO: 116.

Embodiment 197 comprises a polypeptide complex comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv.

Embodiment 198 comprises a polypeptide complex comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

Embodiment 199 comprises an isolated polypeptide or polypeptide complex of any one of embodiments 1-133, wherein $P_1$ comprises an amino acid sequence according to $Z_1$-$Z_2$-C-$Z_4$-P-$Z_6$-$Z_7$-$Z_8$-$Z_9$-$Z_{10}$-$Z_{11}$-$Z_{12}$-C-$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S.

Embodiment 200 comprises an isolated polypeptide or polypeptide complex of embodiment 199, wherein Z, is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_8$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; and $Z_{14}$ is selected from D, Y, N, F, I, and P.

Embodiment 201 comprises an isolated polypeptide or polypeptide complex of any one of embodiments 199-200, wherein Z, is selected from D, Y, and F; $Z_2$ is selected from D, Y, L, and F; $Z_4$ is selected from G and W; $Z_6$ is selected from E and D; $Z_7$ is selected from W, $L_1$ and F; $Z_8$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N.

Embodiment 202 comprises an isolated polypeptide or polypeptide complex of any one of embodiments 1-133, wherein $P_1$ comprises an amino acid sequence according to $U_1$-$U_2$-C-$U_4$-P-$U_6$-$U_7$-$U_8$-$U_9$-$U_{10}$-$U_{11}$-$U_{12}$-C-$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S.

Embodiment 203 comprises an isolated polypeptide or polypeptide complex of embodiment 202, wherein $U_1$ is selected from D, Y, F, 1, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_1$n is selected from I, Y, F, V, L, and T; $U_{12}$ is selected from F, D, Y, L, I, V, A, G, and N; and $U_{14}$ is selected from D, Y, N, F, I, M, and P.

Embodiment 204 comprises an isolated polypeptide or polypeptide complex of embodiment 203, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

Embodiment 205 comprises an isolated polypeptide or polypeptide complex of any one of embodiments 1-133 and 200-204, wherein $P_1$ comprises the amino acid sequences according to any one of SEQ ID NOs: 79-105.

Embodiment 206 comprises an isolated polypeptide or polypeptide complex of any one of embodiments 1-133 and 200-204, wherein $P_1$ comprises an amino acid sequences according to any of the sequences of Table 20.

Embodiment 207 comprises an isolated polypeptide or polypeptide complex of any one of embodiments 1-133, or 206, wherein $P_1$ comprises the amino acid sequences according to SEQ ID NOs: 106-117.

Embodiment 208 comprises an isolated polypeptide or polypeptide complex of any one of embodiments 1-133, wherein $P_1$ comprises the amino acid sequence according to SEQ ID NO: 18 or a peptide sequence that has 1, 2, or 3, amino acid substitutions, additions, or deletions relative to the amino acid sequence of SEQ ID NO: 18.

Embodiment 209 comprises an isolated polypeptide or polypeptide complex of any one of embodiments 1-133, 200-204, wherein $P_1$ comprises the amino acid sequence according to SEQ ID NO: 19 or a peptide sequence that has 1, 2, or 3, amino acid substitutions, additions, or deletions relative to the amino acid sequence of SEQ ID NO: 19.

Embodiment 210 comprises an isolated polypeptide or polypeptide complex of any one of embodiments 1-133, 200-204, wherein $P_1$ comprises the amino acid sequence according to SEQ ID NO: 116 or a peptide sequence that has 1, 2, or 3, amino acid substitutions, additions, or deletions relative to the amino acid sequence of SEQ ID NO: 116.

Embodiment 211 comprises an isolated polypeptide or polypeptide complex of embodiment 208, wherein $P_1$ comprises the amino acid sequence according to SEQ ID NO: 18.

Embodiment 212 comprises an isolated polypeptide or polypeptide complex of embodiment 209, wherein $P_1$ comprises the amino acid sequence according to SEQ ID NO: 19.

Embodiment 213 comprises an isolated polypeptide or polypeptide complex of embodiment 210, wherein $P_1$ comprises the amino acid sequence according to SEQ ID NO: 116.

Embodiment 214 comprises a pharmaceutical composition comprising: (a) the polypeptide or polypeptide complex of any of embodiments 1-213; and (b) a pharmaceutically acceptable excipient.

Embodiment 215 comprises an isolated recombinant nucleic acid molecule encoding the polypeptide or polypeptide complex of any of embodiments 1-213.

Embodiment 216 comprises a method of treating lung cancer comprising administering to a subject in need thereof an isolated polypeptide or polypeptide complex according to Embodiments 1-213.

Embodiment 217 comprises a method of treating breast cancer comprising administering to a subject in need thereof an isolated polypeptide or polypeptide complex according to Embodiments 1-213.

Embodiment 218 comprises a method of treating cervical cancer comprising administering to a subject in need thereof an isolated polypeptide or polypeptide complex according to Embodiments 1-213.

Embodiment 219 comprises a method of treating ovarian cancer comprising administering to a subject in need thereof an isolated polypeptide or polypeptide complex according to Embodiments 1-213.

Embodiment 220 comprises a method of treating pancreatic cancer comprising administering to a subject in need thereof an isolated polypeptide or polypeptide complex according to Embodiments 1-213.

Embodiment 221 comprises a method of treating colorectal cancer comprising administering to a subject in need thereof an isolated polypeptide or polypeptide complex according to Embodiments 1-213.

Embodiment 222 comprises a method of treating gastric cancer comprising administering to a subject in need thereof an isolated polypeptide or polypeptide complex according to Embodiments 1-213.

Embodiment 223 comprises a method of treating pancreatic cancer comprising administering to a subject in need thereof an isolated polypeptide or polypeptide complex according to Embodiments 1-213.

Embodiment 224 comprises a method of treating metastatic castrate-resistant prostate cancer comprising administering to a subject in need thereof an isolated polypeptide or polypeptide complex according to Embodiments 1-213.

EXAMPLES

Example 1: PSMA Polypeptide Complex Binding

The PSMA-CD3 polypeptide complexes of Table 7 were evaluated for PSMA and CD3s binding.

TABLE 7

| Polypeptide complexes | | | | | | |
|---|---|---|---|---|---|---|
| Polypeptide complex | Form | Fab Mask | CD3 | CD3 Mask | Cleavable linker | sdA |
| PC1 | Vh | — | | | | |
| PC3 | Vh | — | SEQ ID NO. 7 | SEQ ID NO. 16 | LSGRSD AGSPLG LAG (SEQ ID NO: 48) | SEQ ID NO. 57 |
| PC5 | Vh | — | SEQ ID NO. 7 | SEQ ID NO. 17 | LSGRSD AGSPLG LAG (SEQ ID NO: 48) | SEQ ID NO. 57 |
| PC2 | Vl | | | | | |
| PC4 | Vl | — | SEQ ID NO. 7 | SEQ ID NO. 16 | LSGRSD AGSPLG LAG (SEQ ID NO: 48) | SEQ ID NO. 57 |
| PC6 | Vl | — | SEQ ID NO. 7 | SEQ ID NO. 17 | LSGRSD AGSPLG LAG (SEQ ID NO: 48) | SEQ ID NO. 57 |

The polypeptide complex molecules of Table 7 were evaluated for their ability to bind PSMA as well as CD3 in a standard enzyme linked immunosorbent assay (ELISA) format. Polypeptide complex binding of PSMA or CD3 were measured before and after protease treatment. Briefly, biotinylated antigen was captured on neutravidin coated plates. Polypeptide complex molecules were treated with active matriptase (MTSP1) where indicated. Polypeptide complex molecules diluted in buffer were then added to the antigen coated plates. Bound polypeptide complex was detected using a standard horse radish peroxidase conjugate secondary antibody. The concentration of polypeptide complex required to achieve 50% maximal signal ($EC_{50}$) was calculated in Graphpad Prism.

Figure 2A:
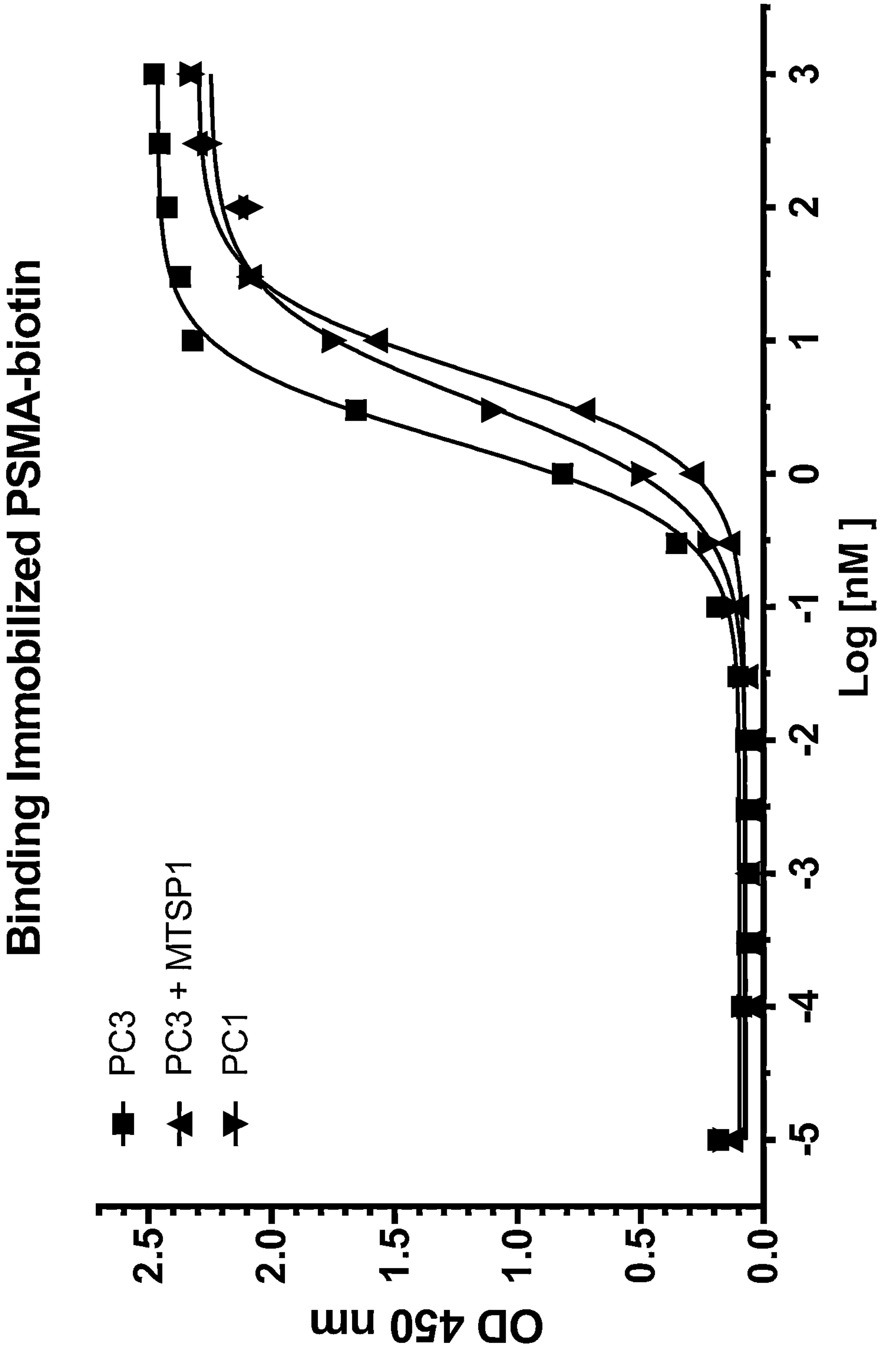
FIG. 2A illustrates titration data for PSMA binding for several polypeptide complexes of this disclosure.
Figure 2B:
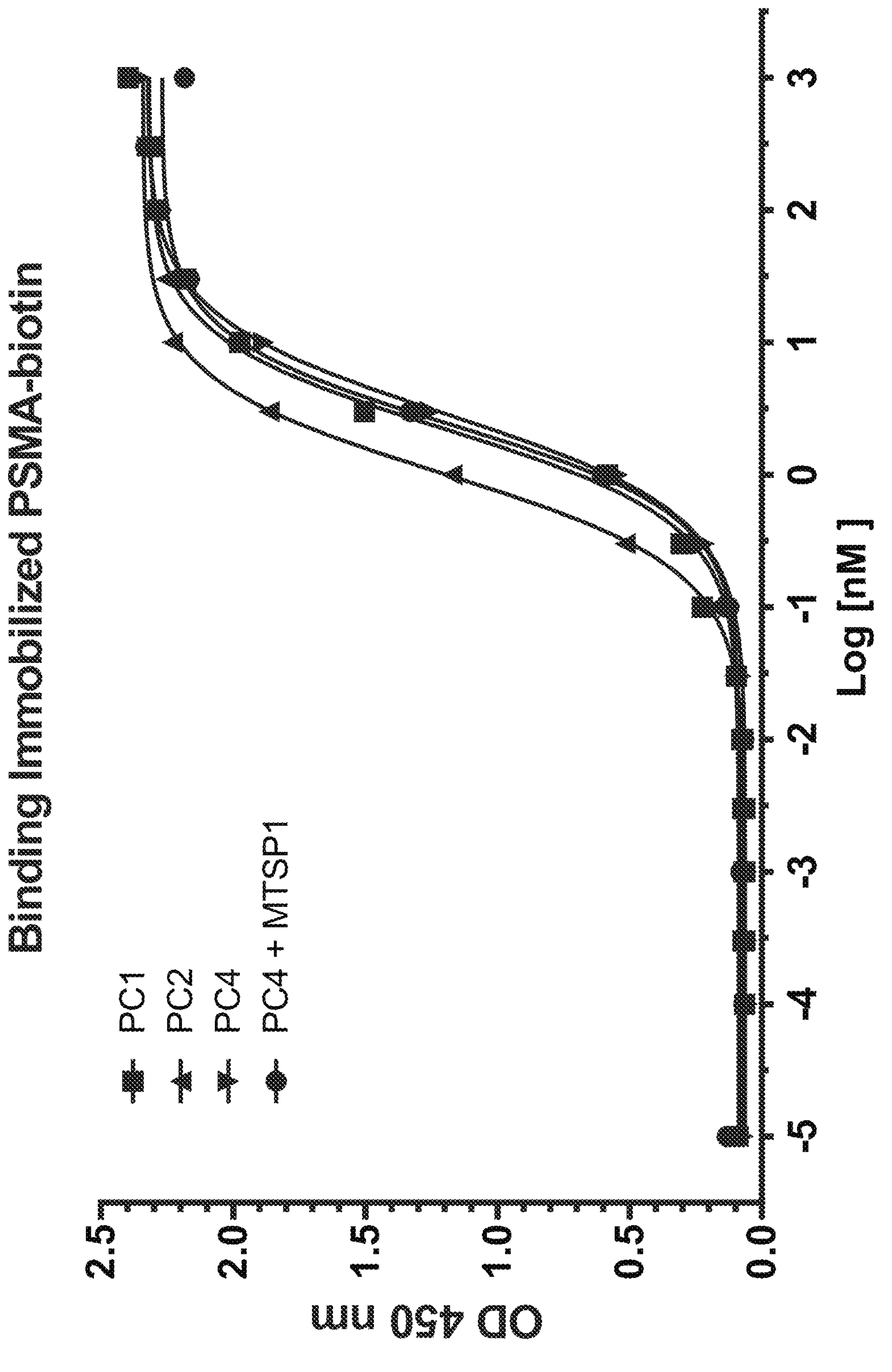
FIG. 2B illustrates titration data for PSMA binding for several polypeptide complexes of this disclosure.
Figure 2C:
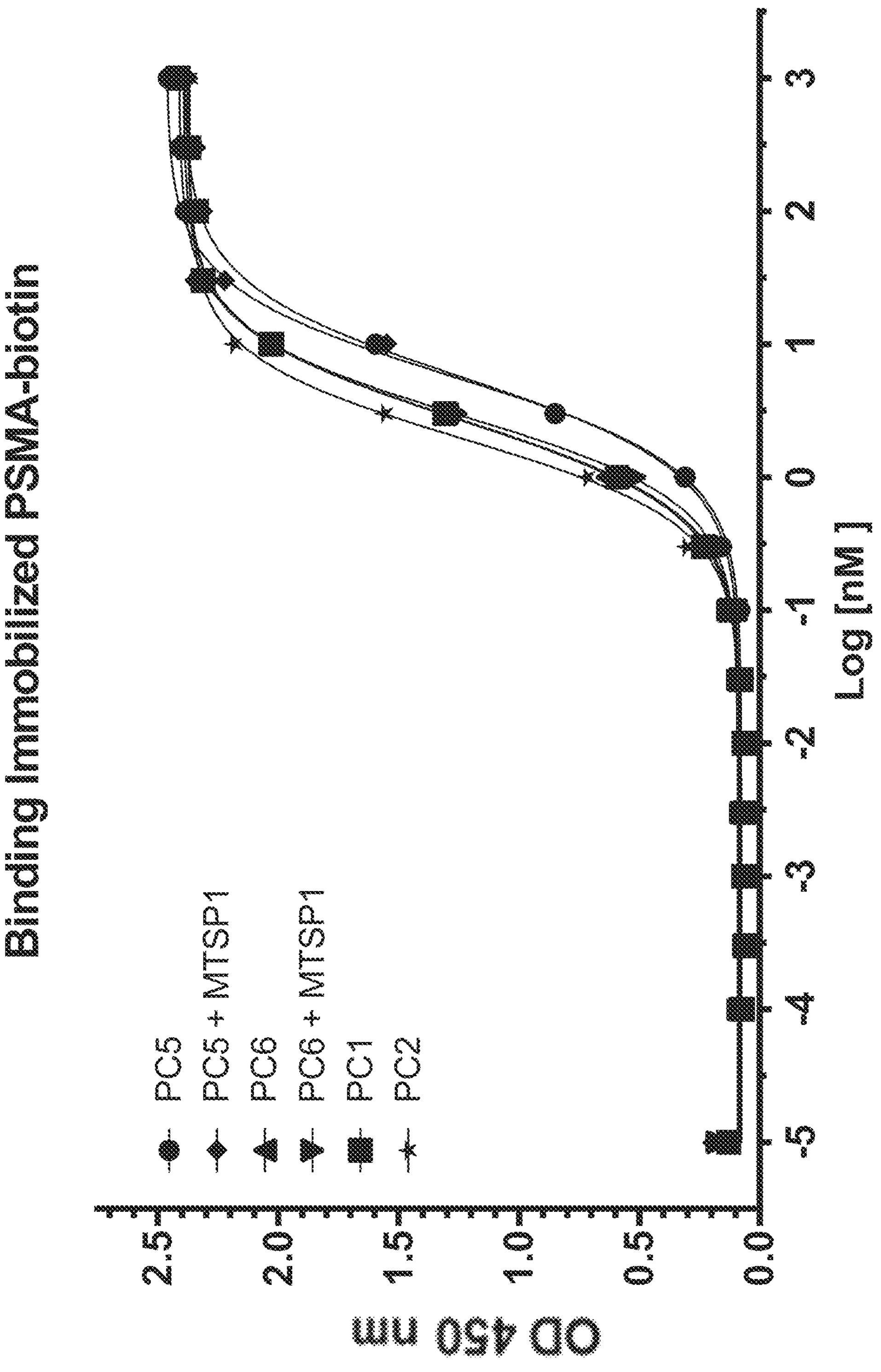
FIG. 2C illustrates titration data for PSMA binding for several polypeptide complexes of this disclosure.
Figure 3A:
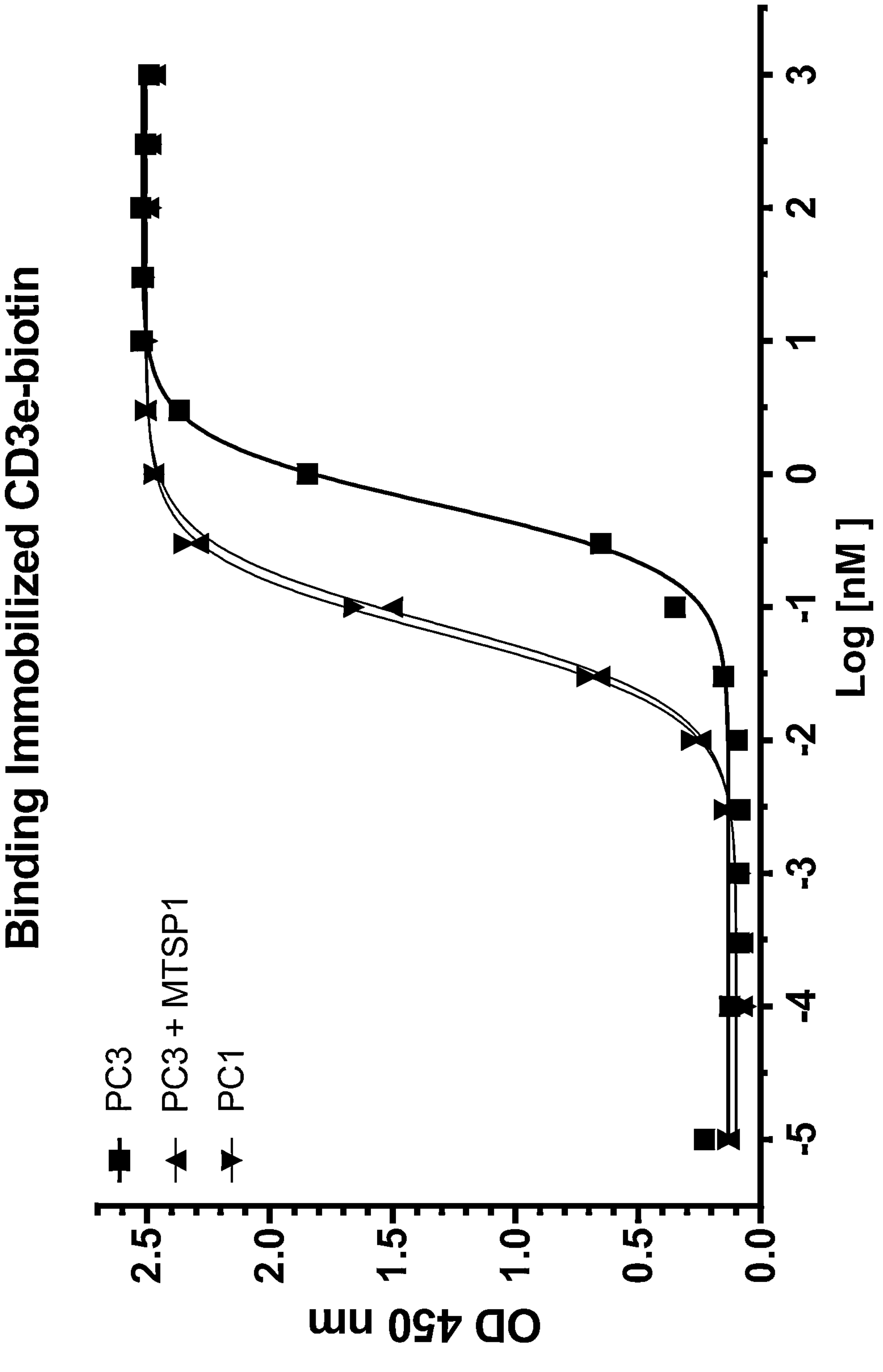
FIG. 3A illustrates titration data for CD3ε binding for several polypeptide complexes of this disclosure.
Figure 3B:
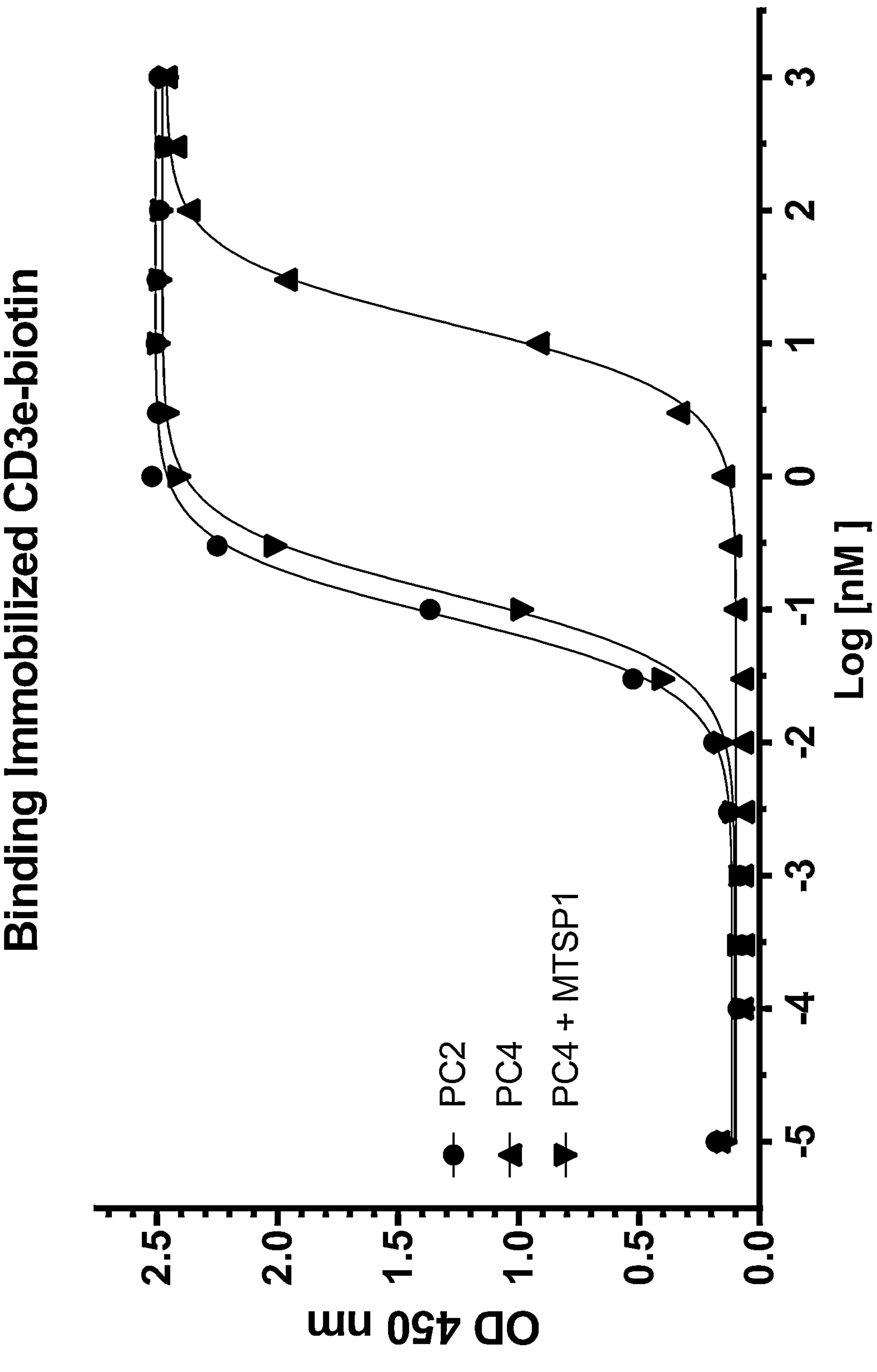
FIG. 3B illustrates titration data for CD3ε binding for several polypeptide complexes of this disclosure.
Figure 3C:
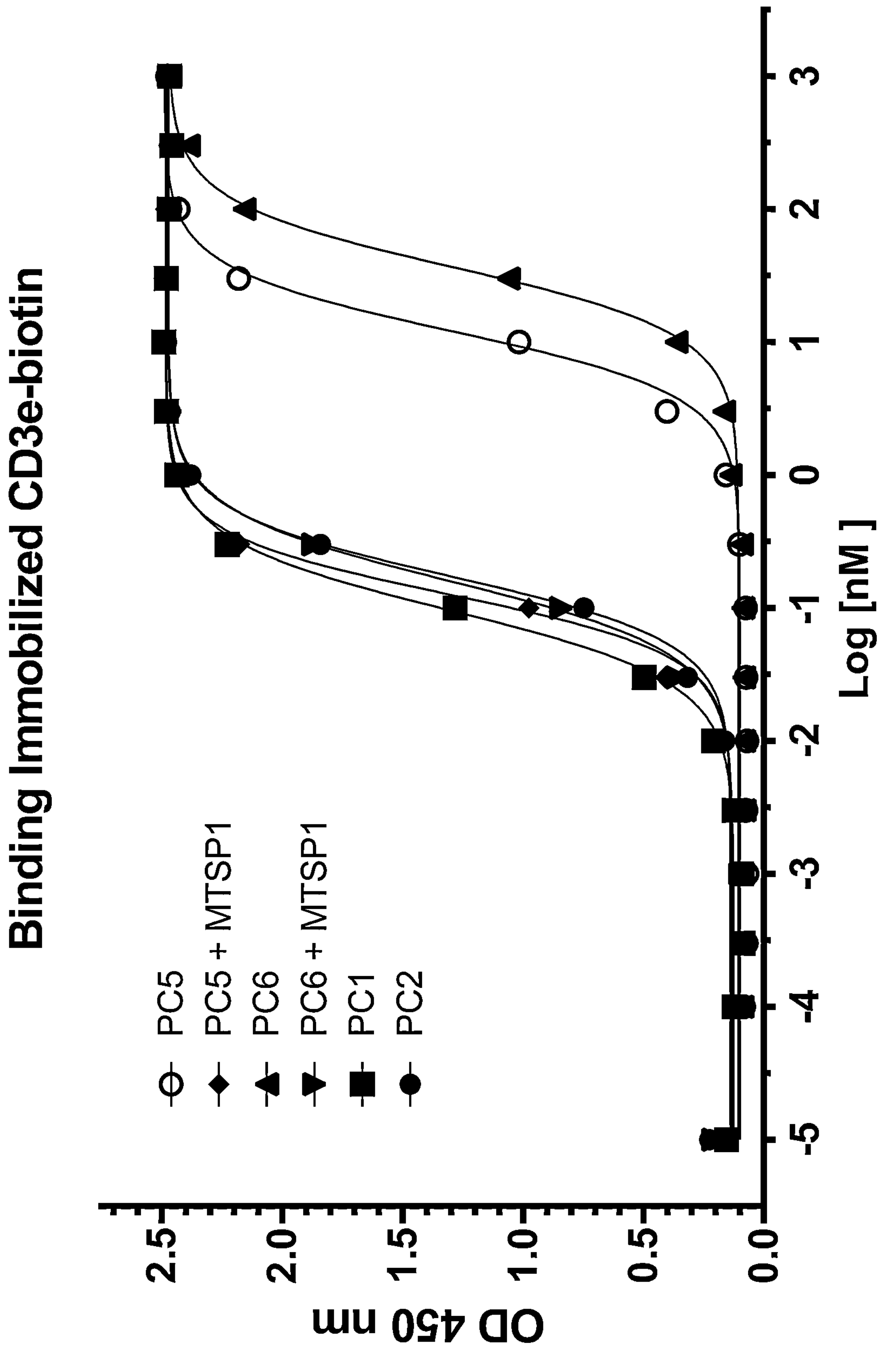
FIG. 3C illustrates titration data for CD3ε binding for several polypeptide complexes of this disclosure.

FIGS. 2A, 2B and 2C show representative PSMA binding ELISAs. This data is summarized in Table 8. FIGS. 3A, 3B and 3C show representative CD3 binding ELISAs. This data is summarized in Table 9. The masked polypeptide complex of PC3 has an $EC_{50}$ about 8 fold higher than the protease treated PC3. The masked polypeptide complex of PC5 has an $EC_{50}$ about 95 fold higher than the protease treated PC3. The masked polypeptide complexes of PC4 and PC6 had $EC_{50}$s about 100 fold and about 230 fold higher than the respective protease treated polypeptide complexes.

TABLE 8

| PSMA binding | | |
|---|---|---|
| EC50 nM | Masked | Cleaved |
| PC1 | — | 2.68 |
| PC3 | 1.78 | 5.73 |
| PC5 | 5.67 | 5.65 |
| PC2 | — | 1.93 |
| PC4 | 2.88 | 2.40 |
| PC6 | 2.70 | 2.89 |

TABLE 9

| CD3 binding | | | |
|---|---|---|---|
| EC50 nM | Masked | Cleaved | Fold shift |
| PC1 | — | 0.08 | — |
| PC3 | 0.5923 | 0.07384 | 8x |
| PC5 | 12.05 | 0.1266 | 95.2x |
| PC2 | — | 0.10 | — |
| PC4 | 13.96 | 0.1313 | 106.3x |
| PC6 | 36.49 | 0.1593 | 229.1x |

Example 2: Polypeptide Complex Mediated Tumor Cytotoxicity and T Cell Activation Polypeptide complexes were evaluated in a functional in vitro tumor cell killing assay using the PSMA positive tumor cell lines 22Rv1 and LNCaP. Tumor cell killing was measured using a real time cell analyzer from Acea Biosciences that relies on sensor impedance measurements (cell index) that increased as tumor cells adhere, spread, and expand on the surface of the sensor. Likewise, as the tumor cells were killed the impedance decreased. 25,000 tumor cells were added per well and allowed to adhere overnight. The following day polypeptide complexes titrated in human serum supplemented medium along with 75,000 CD8+ T cells were added to the wells. Cell index measurements were taken every 10 minutes for an additional 96 hours. The cell index times number of hours (tumor cell growth kinetics) was then plotted versus concentration of polypeptide complex where the concentration required to reduce the tumor growth 50% (IC50) was calculated using Graphpad Prism.

Figure 4:
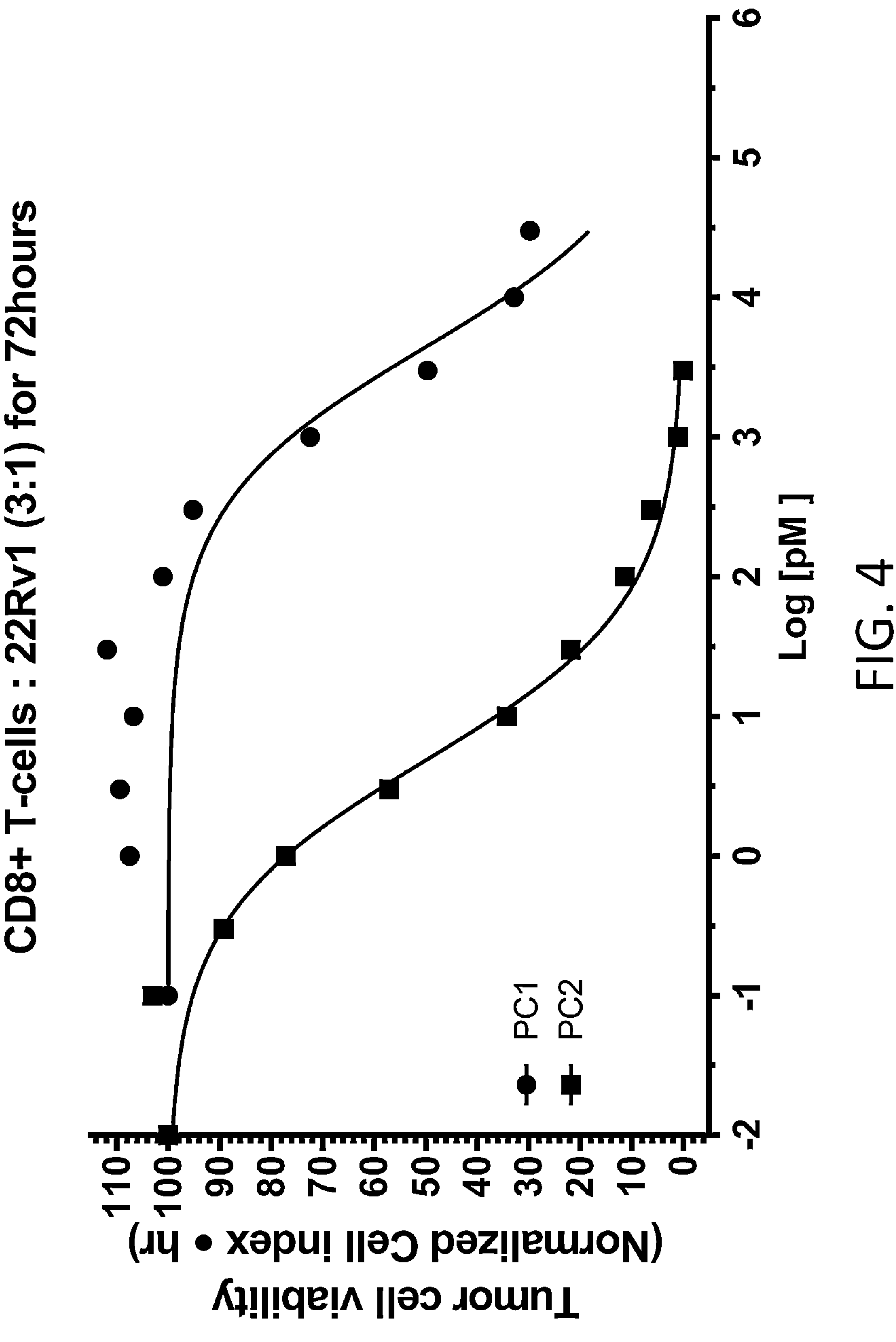
FIG. 4 illustrates cell viability data for 22Rv1 tumor cells treated with PC1 or PC2.
Figure 5A:
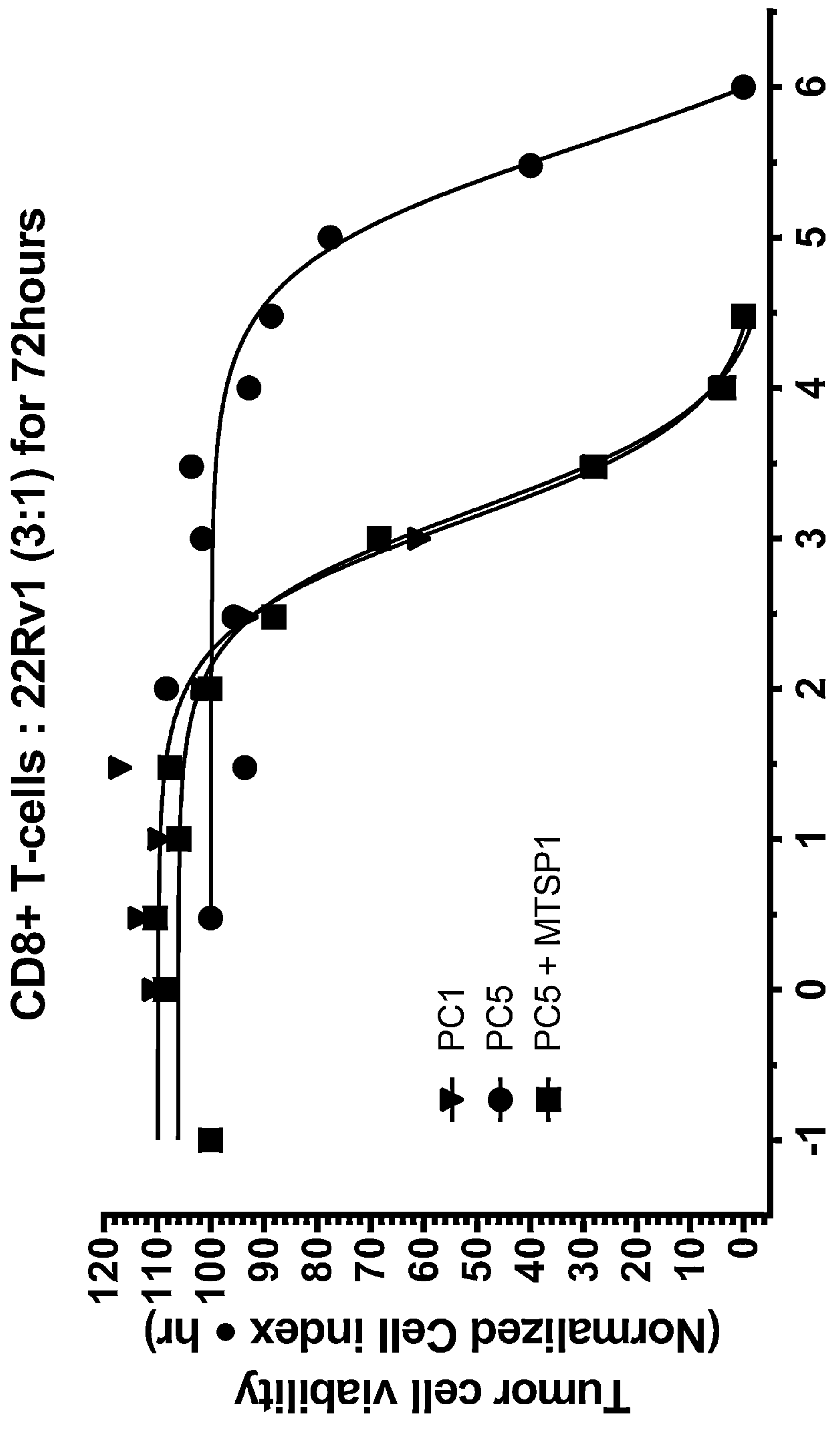
FIG. 5A illustrates cell viability data for 22Rv1 tumor cells treated with PC1, PC5 or MTSP1 treated PC5.
Figure 5B:
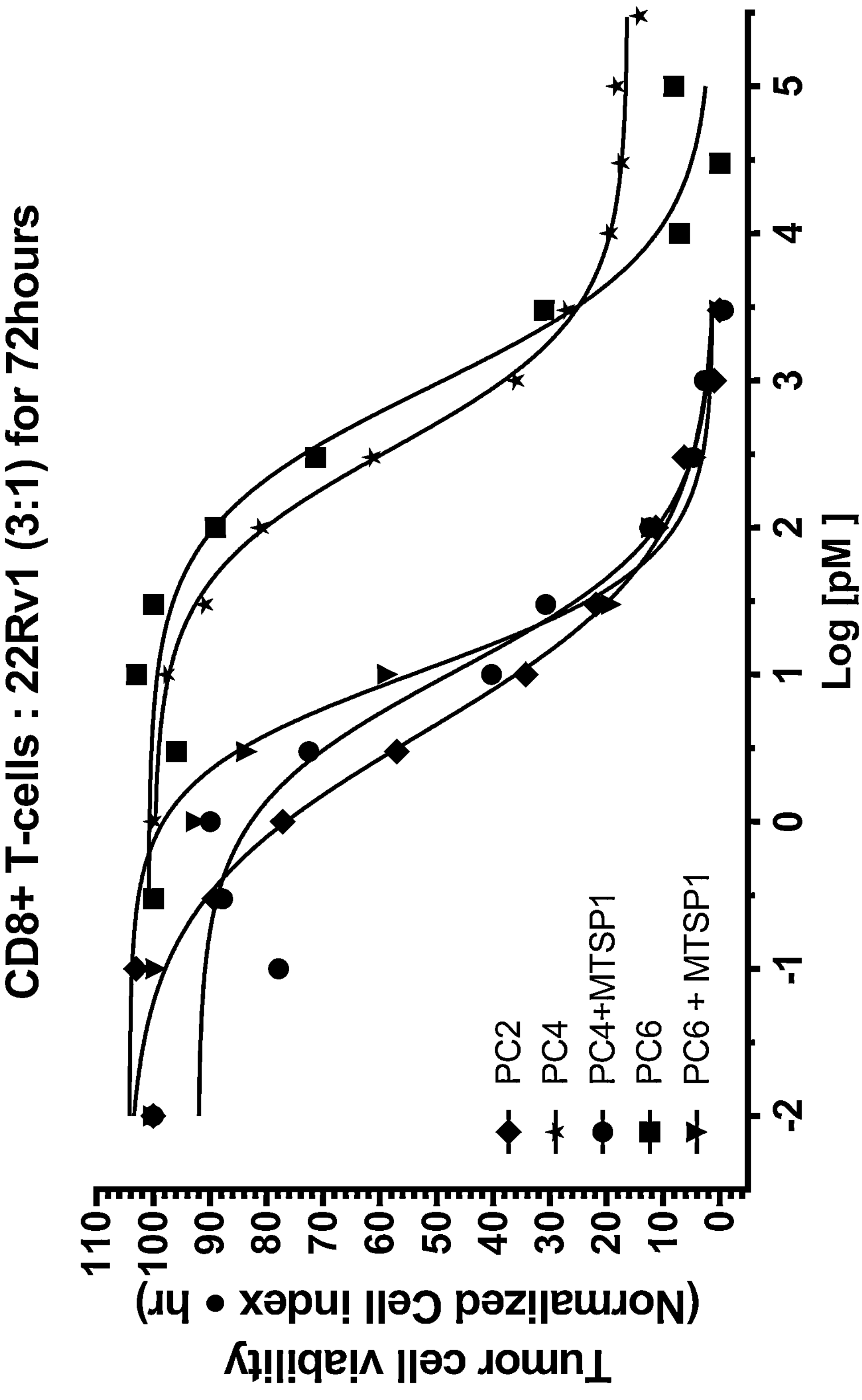
FIG. 5B illustrates cell viability data for 22Rv1 tumor cells treated with PC2, or PC4 or PC6 with and without MTSP1 treatment.

The 22Rv1 tumor cell line has a PSMA density of about 3000 copies per cell. FIG. 4 shows representative viability data for 22Rv1 treated with PC1 or PC2. This data is summarized in Table 10, and shows that PC2 is about 1000 times more potent than PC1. FIGS. 5A and 5B, and Tables 11 and 12, show viability data for 22Rv1 cells treated with masked or cleaved polypeptide complexes. The masked polypeptide complex of PC5 has an IC50 greater than 50 fold higher than the unmasked polypeptide complex of PC1, protease treatment reduced the IC50 to less than the IC50 of PC1. Similarly, the masked polypeptide complexes of PC4 and PC6 had IC50s about 150 and 200 fold higher than PC2 respectively, and protease treatment rescues both to about 1.7 and 2.5 fold higher than PC2.

Figure 6:
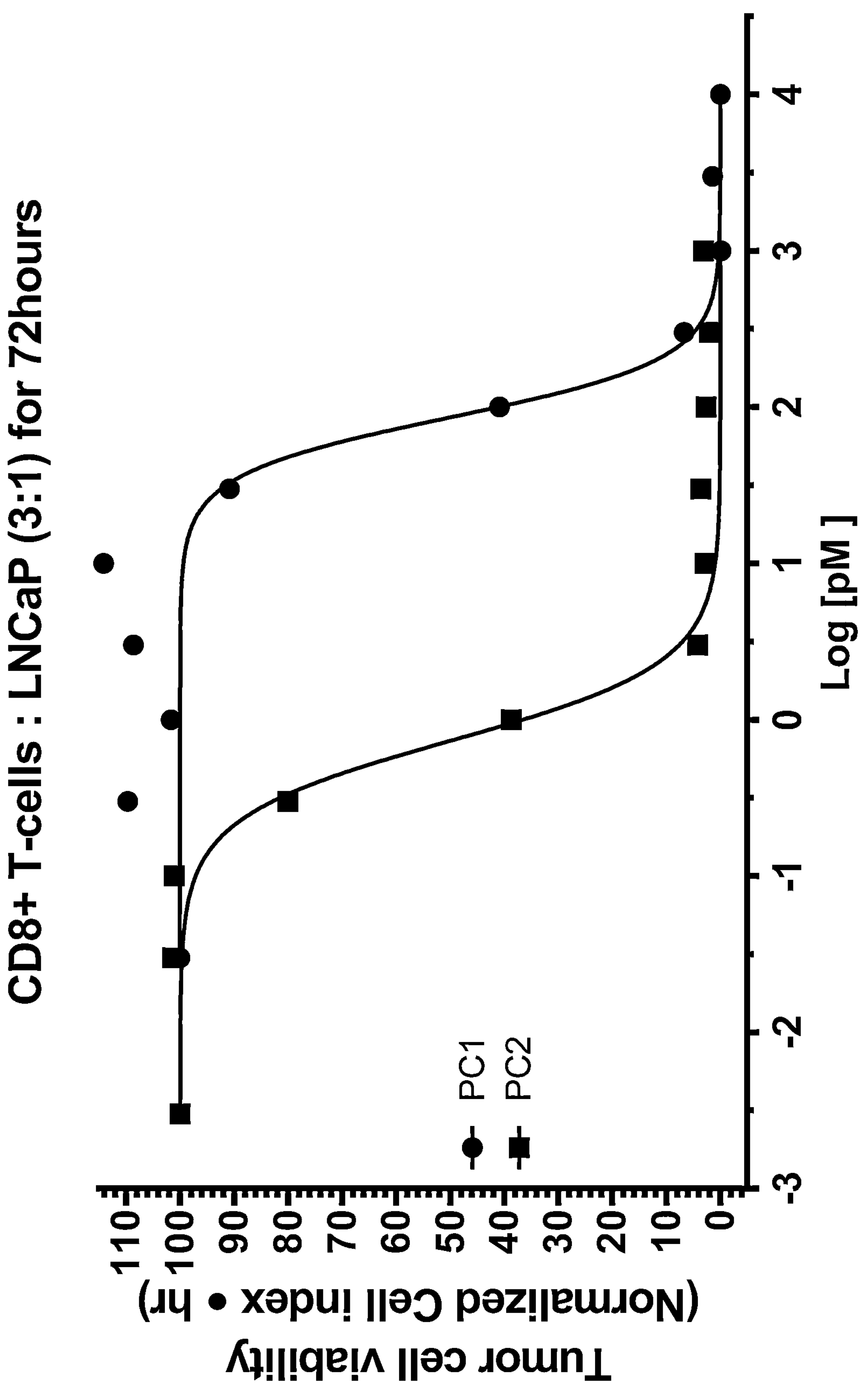
FIG. 6 illustrates cell viability data for LNCaP tumor cells treated with PC1 or PC2.
Figure 7:
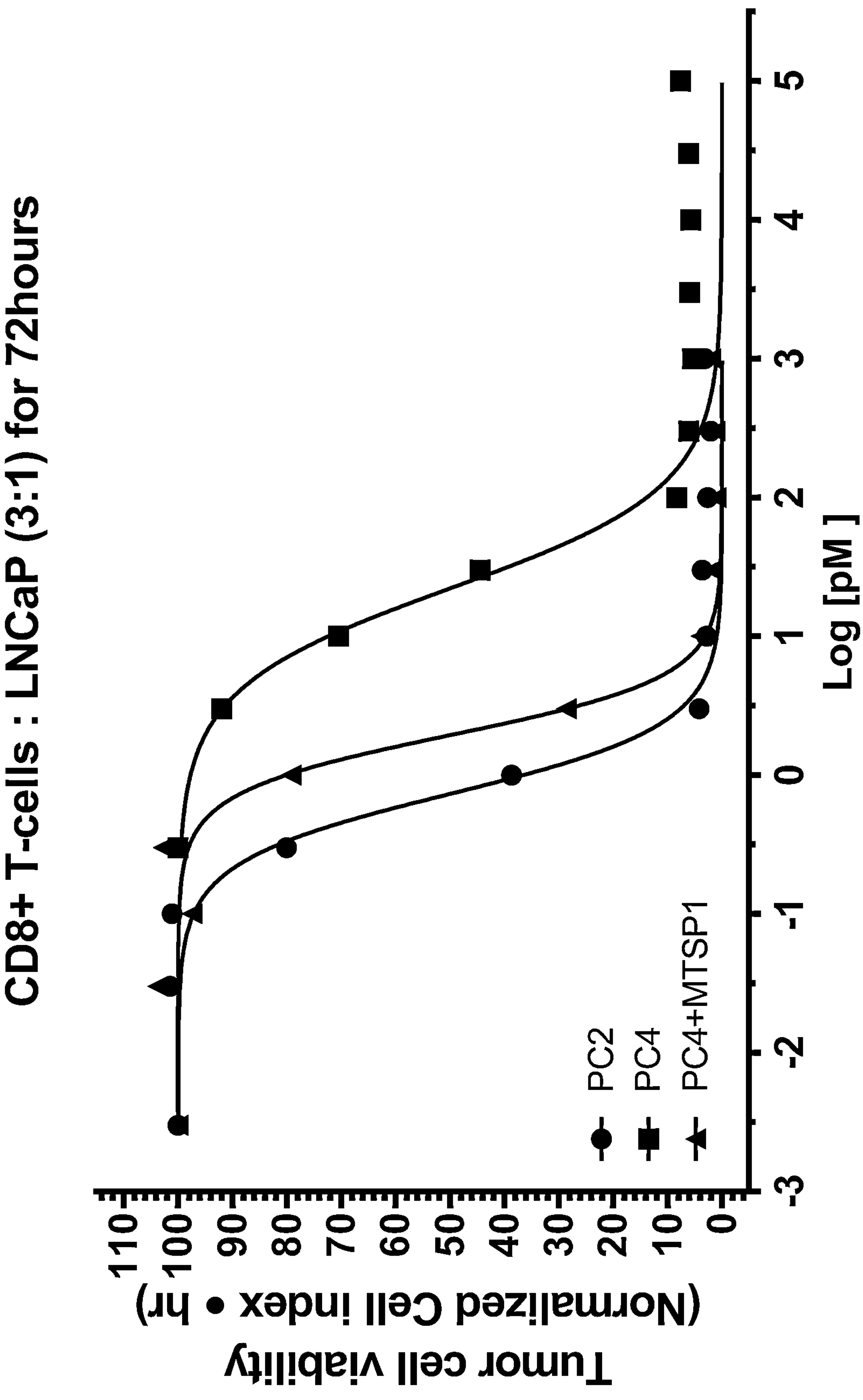
FIG. 7 illustrates cell viability data for LNCaP tumor cells treated with PC2, PC4 or MTSP1 treated PC4.

The LNCaP tumor cell line has a PSMA density of about 350,000 copies per cell. FIG. 6 shows representative viability data for LNCaP. This data is summarized in Table 13 and shows that PC2 is about 100 times more potent than PC1. FIG. 7, and Table 14 show viability data for LNCaP cells treated with masked or cleaved polypeptide complexes. The masked polypeptide complex of PC4 has an IC50 about 30 fold higher than the unmasked polypeptide complex of PC2, protease treatment rescues the IC50 to about 2.5 fold higher than the unmasked polypeptide complex.

TABLE 10

| 22Rv1 cell viability | | |
|---|---|---|
| 22Rv1 IC50 pM | PC1.01 | PC2.01 |
| 72 hr | 4409 | 4.831 |

TABLE 11

| 22Rv1 cell viability | | | |
|---|---|---|---|
| 22Rv1 72 hr | PC1 | PC5 | PC5 + MTSP1 |
| IC50 pM | 3,916 | 212810 | 1591 |
| Fold shift | 1x | 54.3x | 0.4x |

TABLE 12

| 22Rv1 cell viability | | | | | |
|---|---|---|---|---|---|
| 22Rv1 72 hr | PC2 | PC4 | PC4 + MTSP1 | PC6 | PC6 + MTSP1 |
| IC50 pM | 4.831 | 757.3 | 8.169 | 984.9 | 12.03 |
| Fold shift | 1x | 156.8x | 1.7x | 203.9x | 2.5x |

TABLE 13

| LNCaP cell viability | | |
|---|---|---|
| LNCaP IC50 pM | PC1 | PC2 |
| 72 hr | 85.97 | 0.73 |

TABLE 14

| LNCaP cell viability | | | |
|---|---|---|---|
| LNCaP IC50 pM | PC2 | PC4 + MTSP1 | PC4 |
| 72 hr | 0.73 (1x) | 1.94 (2.65x) | 22.1 (30.2x) |

Example 3: Polypeptide Complex Mediated Tumor Cell Killing

Figure 8A:
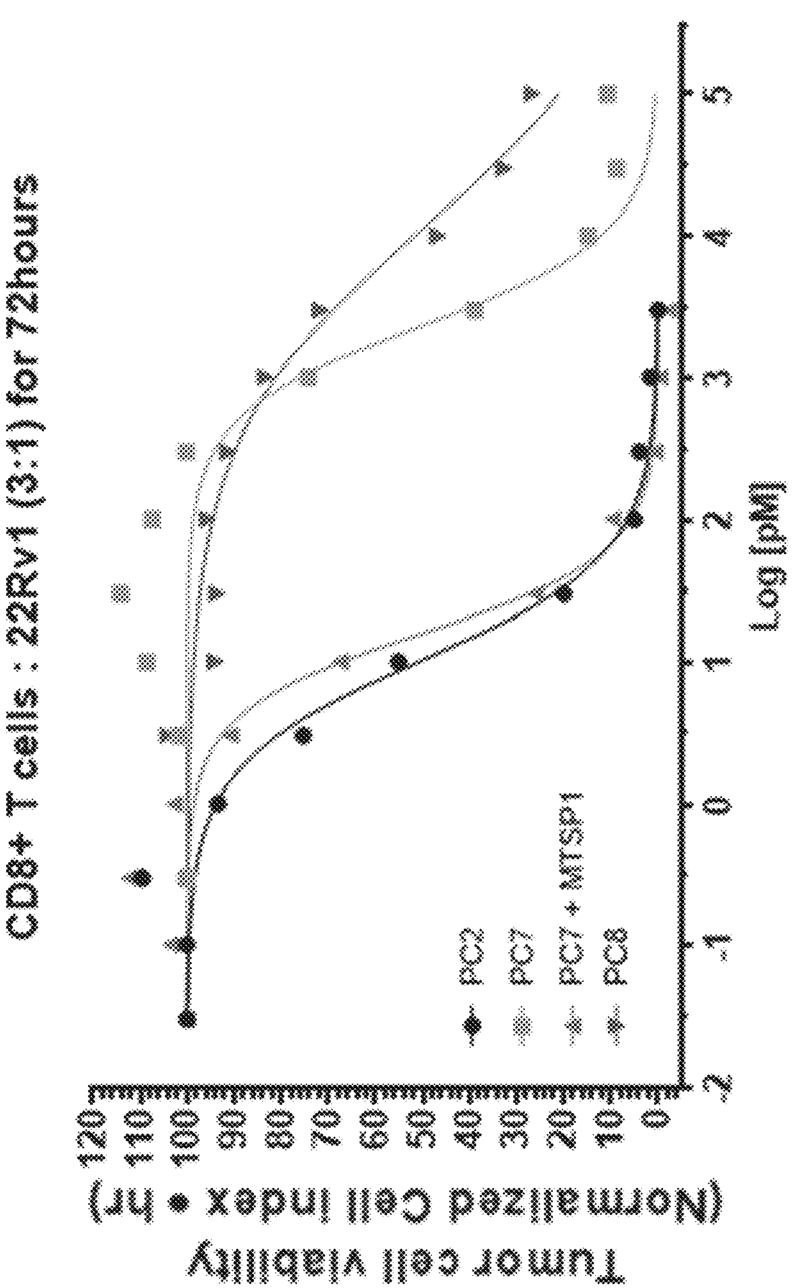
FIGS. 8A-8B illustrates polypeptide complex mediated 22Rv1 tumor cell killing in the presence of CD8+ T cells.
Figure 8B:
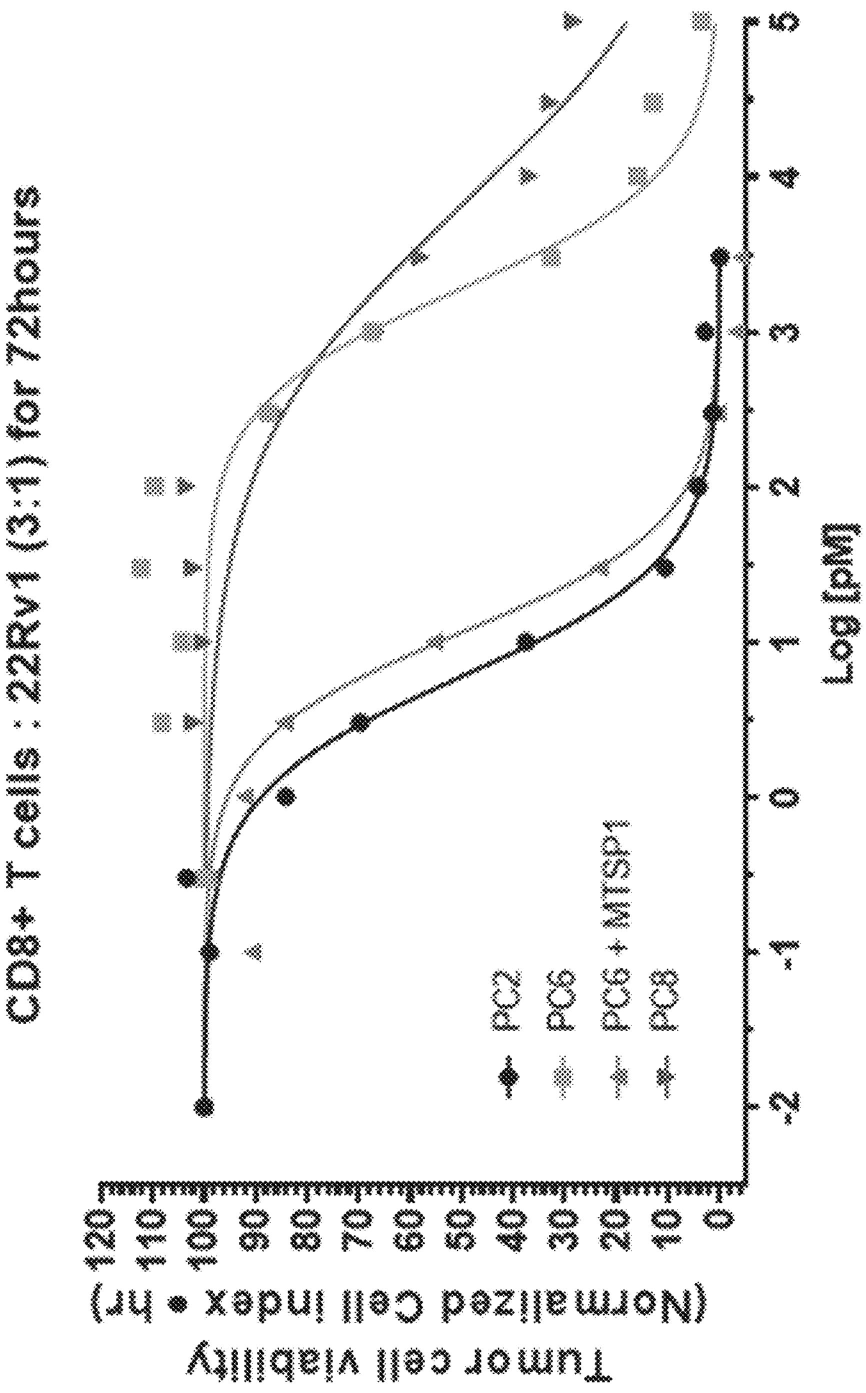

Polypeptide complexes were evaluated in a functional in vitro tumor cell killing assay using the PSMA positive tumor cell lines 22Rv1. Tumor cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. 10,000 tumor cells were added per well and allowed to adhere overnight on a 96 well E-Plate. The following day polypeptide complexes titrated in human serum supplemented medium along with 30,000 CD8+ T cells were added to the wells. Cell index measurements were taken every 10 minutes for an additional 72 hours. The cell index times number of hours (tumor cell growth kinetics) was then plotted versus concentration of polypeptide complex where the concentration required to reduce the tumor growth 50% (IC50) was calculated using Graphpad Prism software. Data is seen in FIGS. 8A-8B.

Example 4: Polypeptide Complex Pharmacokinetics in Cynomolgus Monkey

Figure 9A:
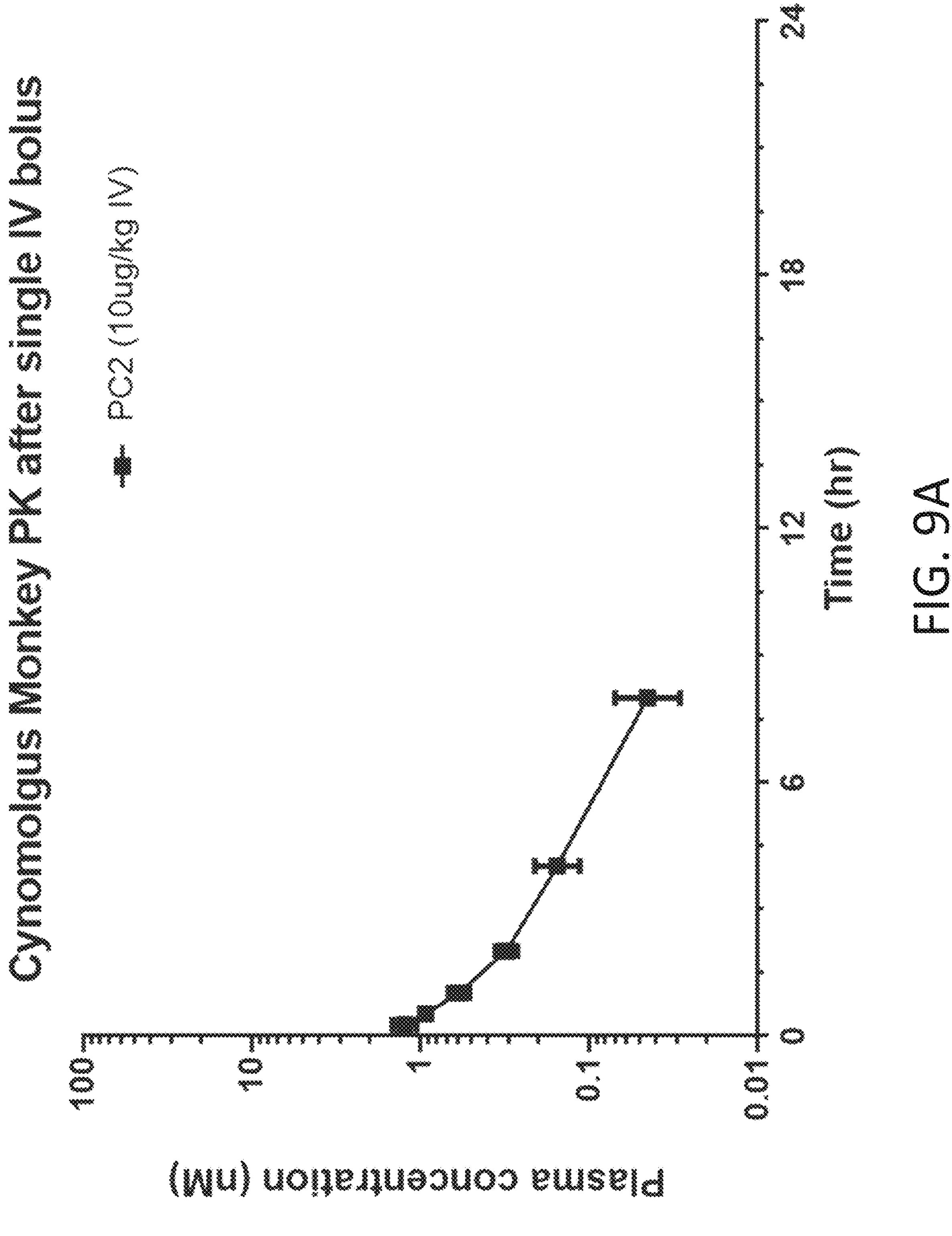
FIG. 9A illustrates polypeptide (PSMA TCEs) pharmacokinetics in cynomolgus monkeys after a single IV bolus injection.
Figure 9B:
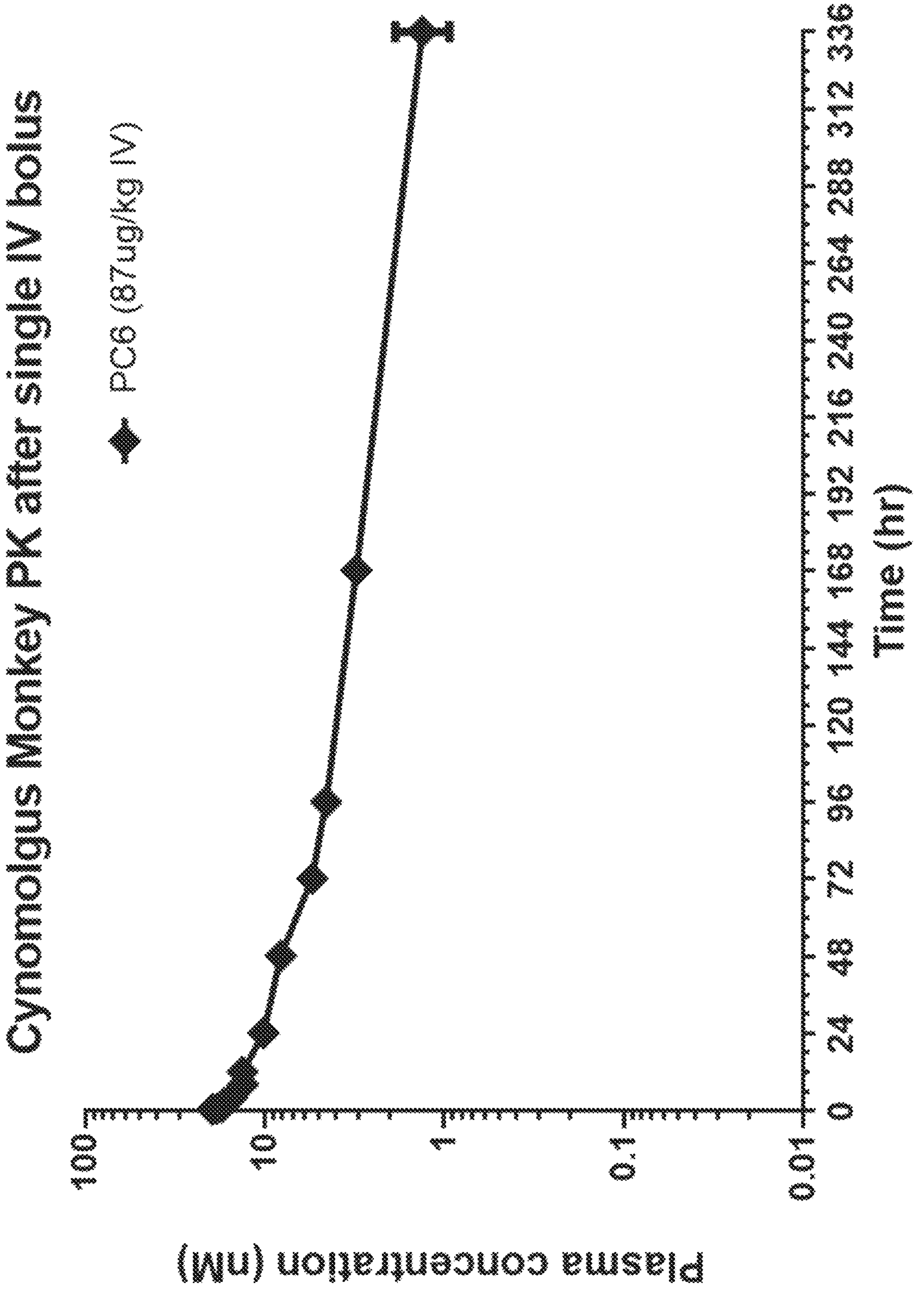
FIG. 9B illustrates polypeptide (PSMA TRACTrs) pharmacokinetics in cynomolgus monkeys after a single IV bolus injection.

Pharmacokinetics and exploratory safety of polypeptide molecules were evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cyno plasma. Plasma concentration curves were fit to a standard two phase exponential equation representing distribution and elimination phases. Fitting of pharmacokinetics enabled the calculation of Cmax, half-life, volume of distribution, clearance, and 7 day area under the curve (AUC) shown in Table 15 for PSMA TCE polypeptide complexes and Table 16 for PSMA TRACTr polypeptide complexes. Data is seen in FIGS. 9A-9B. Measured pharmacokinetics in cyno support once weekly dosing in humans.

TABLE 15

| PSMA TCE | | |
|---|---|---|
| | PC2 10 ug/kg | Units |
| $C_{MAX}$ | 1.69 | nM |
| $t_{1/2}$ | 2.17 | hr |
| Vd | 0.23 | L |
| VSS | 0.67 | L |
| CL | 24.49 | mL/hr/kg |
| BW | 3.00 | kg |
| 7 day AUC | 141 | nM · min |

TABLE 16

| PSMA TRACTr | | |
|---|---|---|
| | PC6 87 ug/kg | Units |
| $C_{MAX}$ | 17.90 | nM |
| $t_{1/2}$ | 118.99 | hr |
| Vd | 0.18 | L |
| VSS | 0.35 | L |
| CL | 0.34 | mL/hr/kg |
| BW | 3.00 | kg |
| 7 day AUC | 63,731 | nM · min |

Example 5: Polypeptide Complexes in Cynomolgus Cytokine Release

Figure 10A:
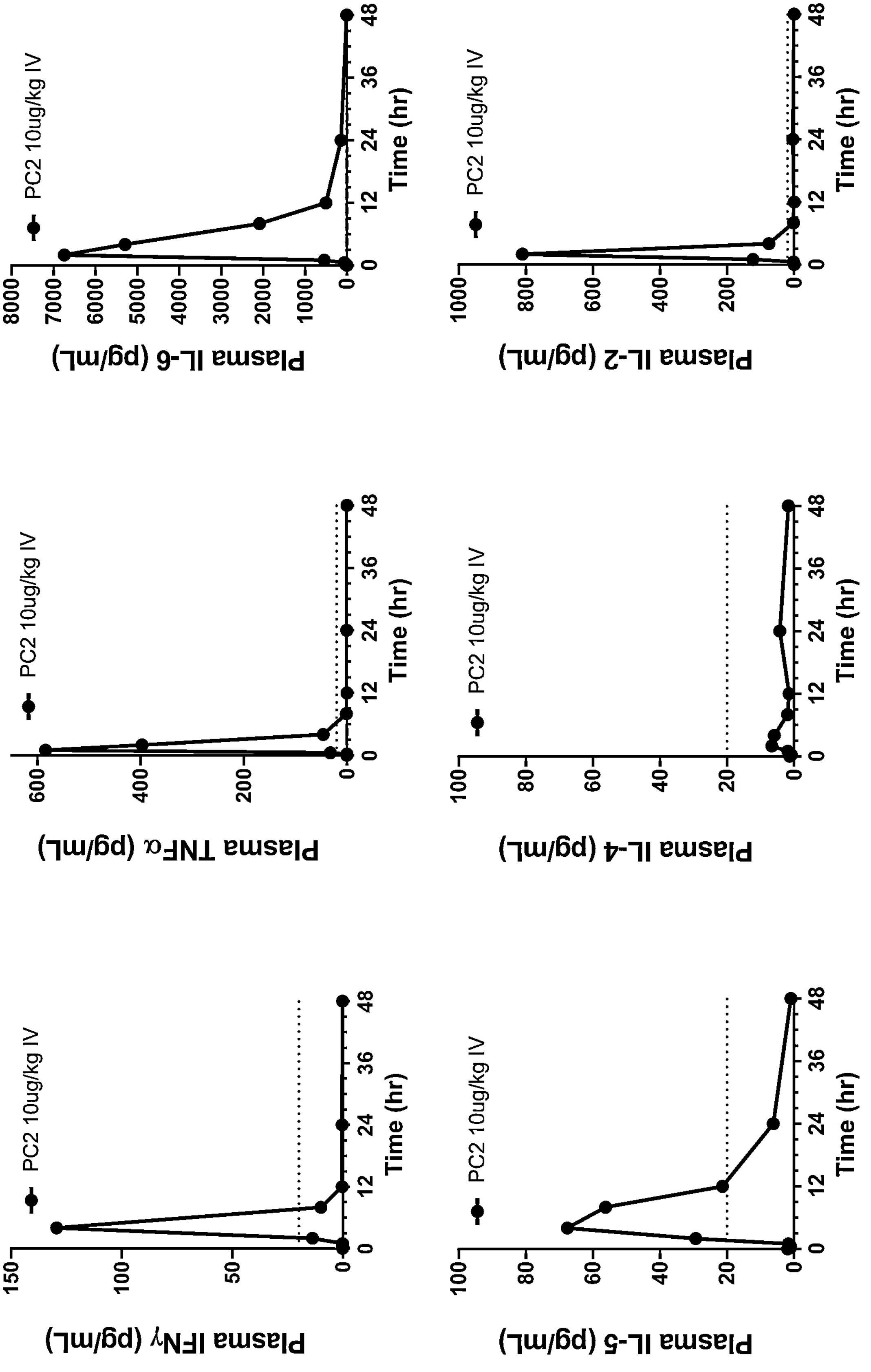
FIG. 10A illustrates cytokine release in cynomolgus monkeys after single IV bolus of PSMA TCE.
Figure 10B:
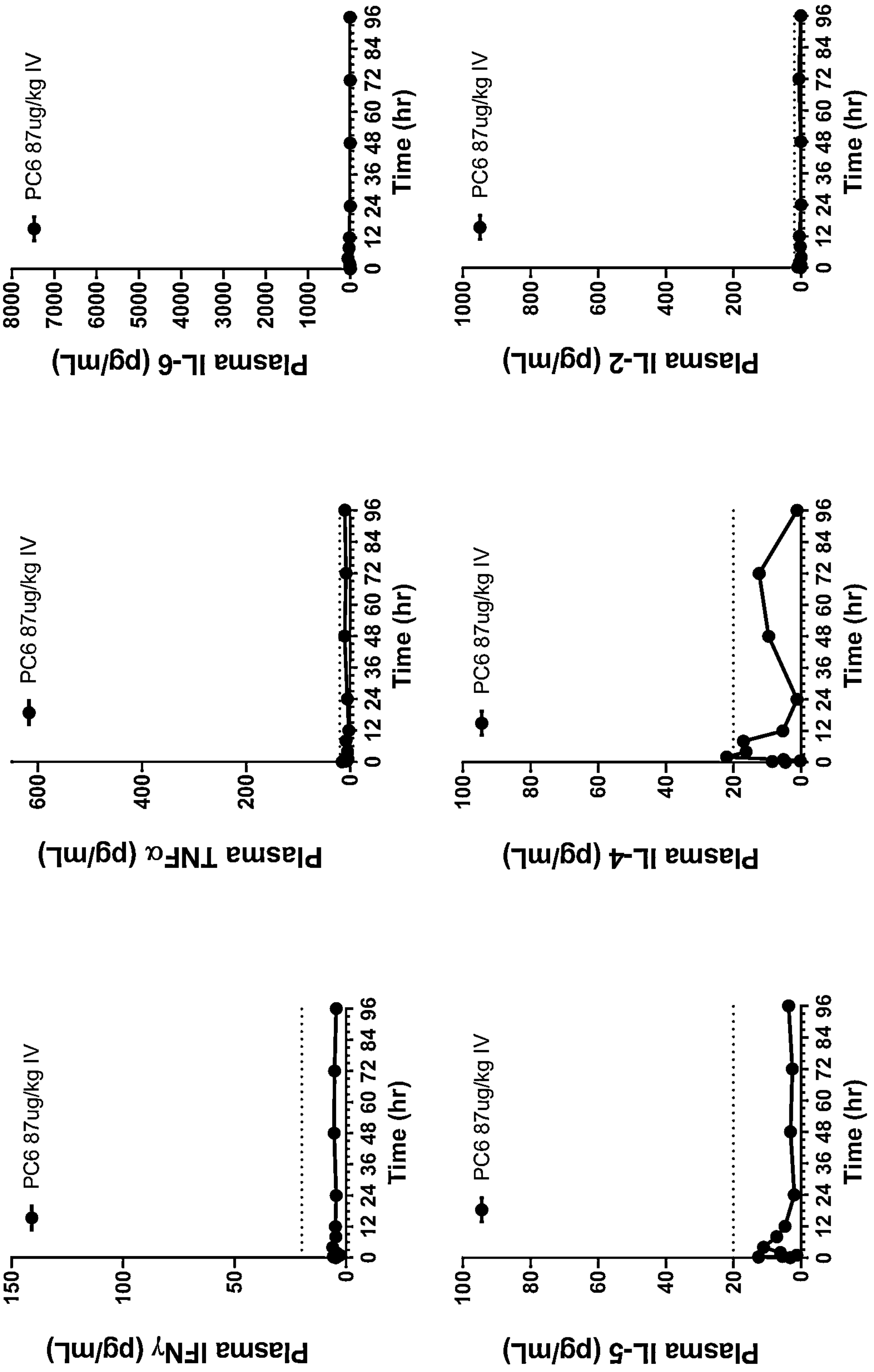
FIG. 10B illustrates cytokine release in cynomolgus monkeys after single IV bolus of PSMA polypeptide TRACTr complex.
Figure 10C:
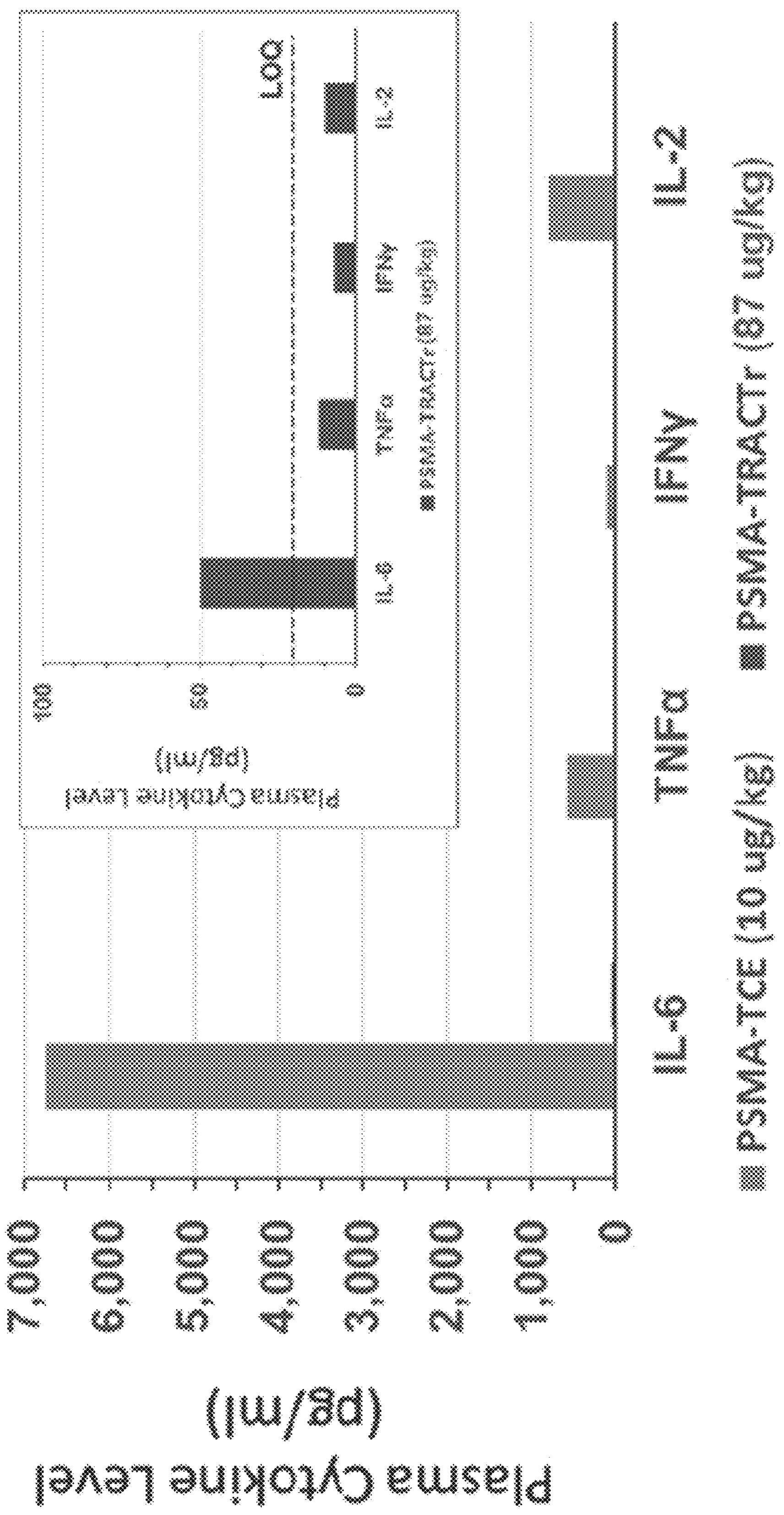
FIG. 10C illustrates cytokine release in cynomolgus monkeys using PSMA TCE versus PSMA TRACTRs.

Cytokine release after polypeptide molecule administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for cytokines using a non-human primate cytometric Th1/Th2 bead array kit from BD biosciences following the manufacturer's instructions. Interferon gamma, tumor necrosis factor alpha, interleukin 6, interleukin 5, interleukin 4, and interleukin 2 levels in plasma were calculated relative to reference standards provided with the bead array kit. Data is seen in FIGS. 10A-10C.

Example 6: Polypeptide Complexes in Cynomolgus Toxicity

Figure 11A:
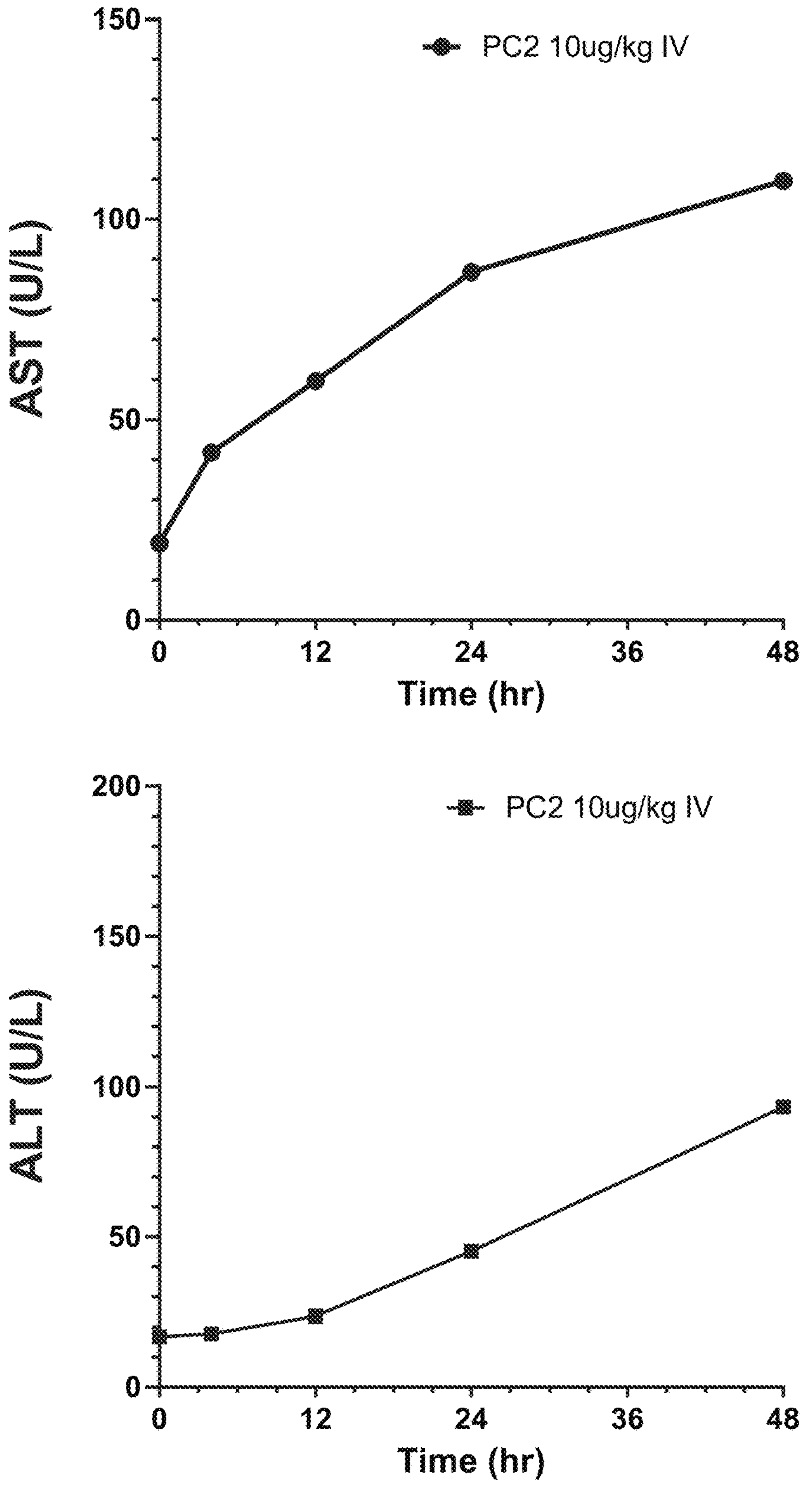
FIG. 11A illustrates serum liver enzymes in cynomolgus monkeys after single IV bolus of PSMA TCE.
Figure 11B:
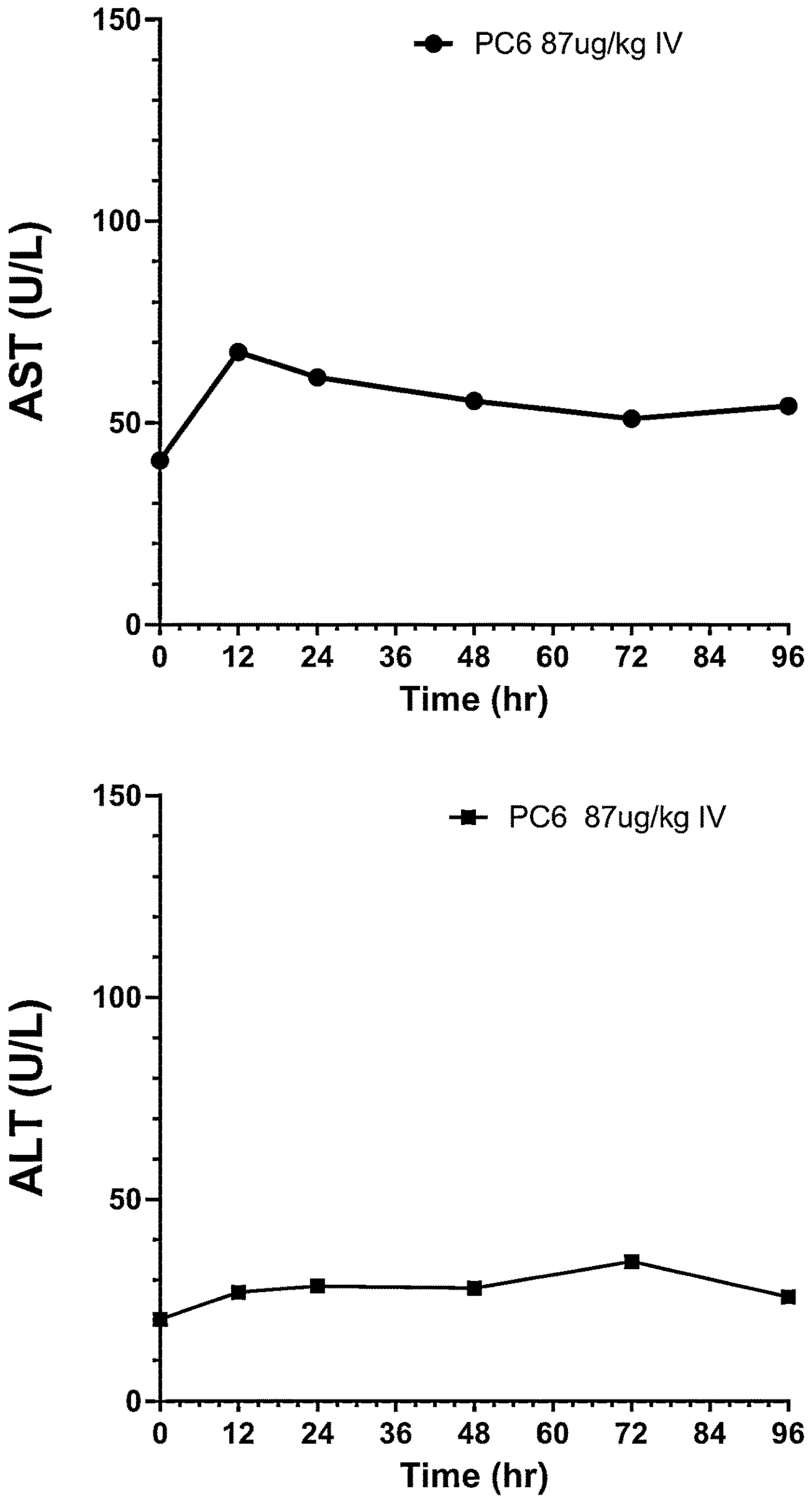
FIG. 11B illustrates serum liver enzymes in cynomolgus monkeys after single IV bolus of PSMA polypeptide TRACTr complex.

Systemic liver enzymes after polypeptide molecule administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for the presence of liver enzymes aspartate transaminase (AST) and alanine aminotransferase (ALT) as signs of potential liver toxicity. AST and ALT levels remained within the normal ranges for all timepoints tested after dosing suggesting a lack of liver toxicity. AST and ALT were quantified following the instructions provided in a commercially available kit from Millipore. AST and ALT levels were calculated according to manufacturer's instructions relative to a positive control reference standard. Data is seen in FIGS. 11A-11B.

Example 7: Optimized Phage Library Construction—CD3 scFv Peptides

Sequence activity relationships (SAR) were established for Peptide-A and Peptide-B by mutating each individual residue within the peptide to alanine and measuring binding and inhibition against SP34.185 scFv. Peptide residues whose alanine mutations significantly weakened binding and inhibition can be considered critical residues where mutations were not tolerated. Peptide residues whose alanine mutations performed similarly to the non-mutated sequence can be considered non-critical sites where mutations were indeed tolerated. Using the peptide SAR, DNA oligo libraries were constructed where codons encoding critical residues within each peptide sequence were minimally mutated and codons encoding non-critical residues were heavily mutated. The resulting oligos were cloned into bacteriophage vectors used to display the SAR guided peptides via fusion to the pIII filament of the bacteriophage. The relevant vectors were then used to produce the phage optimization libraries via amplification in bacteria using standard techniques in the field.

Peptides were evaluated for their ability to bind SP34.185 scFv by standard enzyme linked immunosorbent assays (ELISAs). Briefly, biotinylated peptides were captured on neutravidin coated plates, quenched with biocytin followed by a washing step. SP34.185 scFv was then titrated onto the peptide captured plates. Plates were then washed and bound SP34.185 scFv was detected using a secondary horse radish peroxidase antibody conjugate. After washing again, plates were developed using standard ELISA techniques and stopped using acid. The concentration of SP34.185 scFv required to achieve 50% maximal signal or $EC_{50}$ was calculated using Graphpad prism. Data is shown in FIGS. 12A-12F and summarized in Tables 17A-17D. Peptide Sequences of CD3 Ala Scan Peptides for Peptide A and Peptide-B are shown in Table 19.

TABLE 17A

Figure 12A:
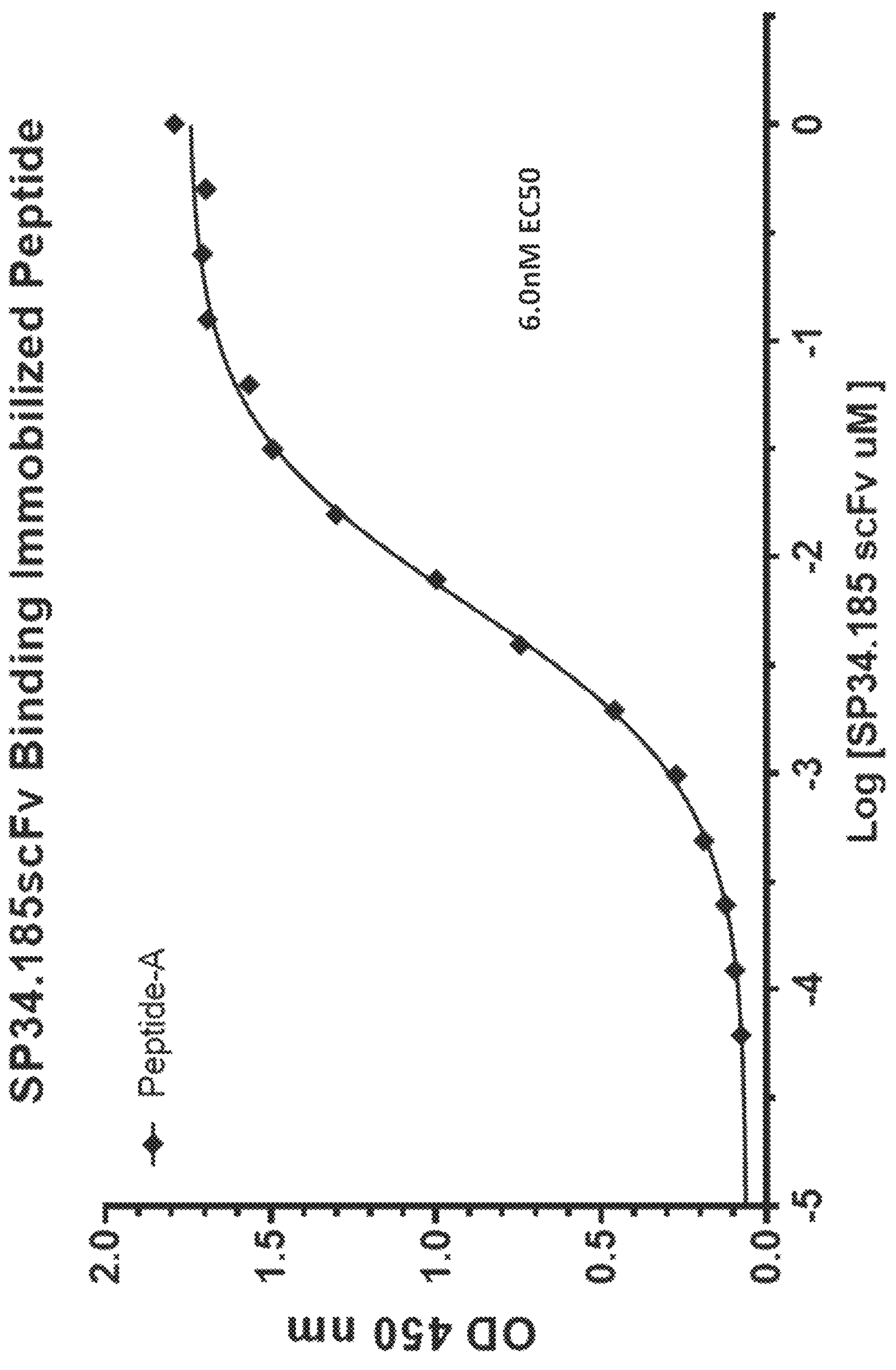
FIGS. 12A-12F illustrate anti-CD3 scFv binding by alanine scanning peptides of anti-CD3 scFv Peptide-A and Peptide-B as measured by ELISA.
Figure 12B:
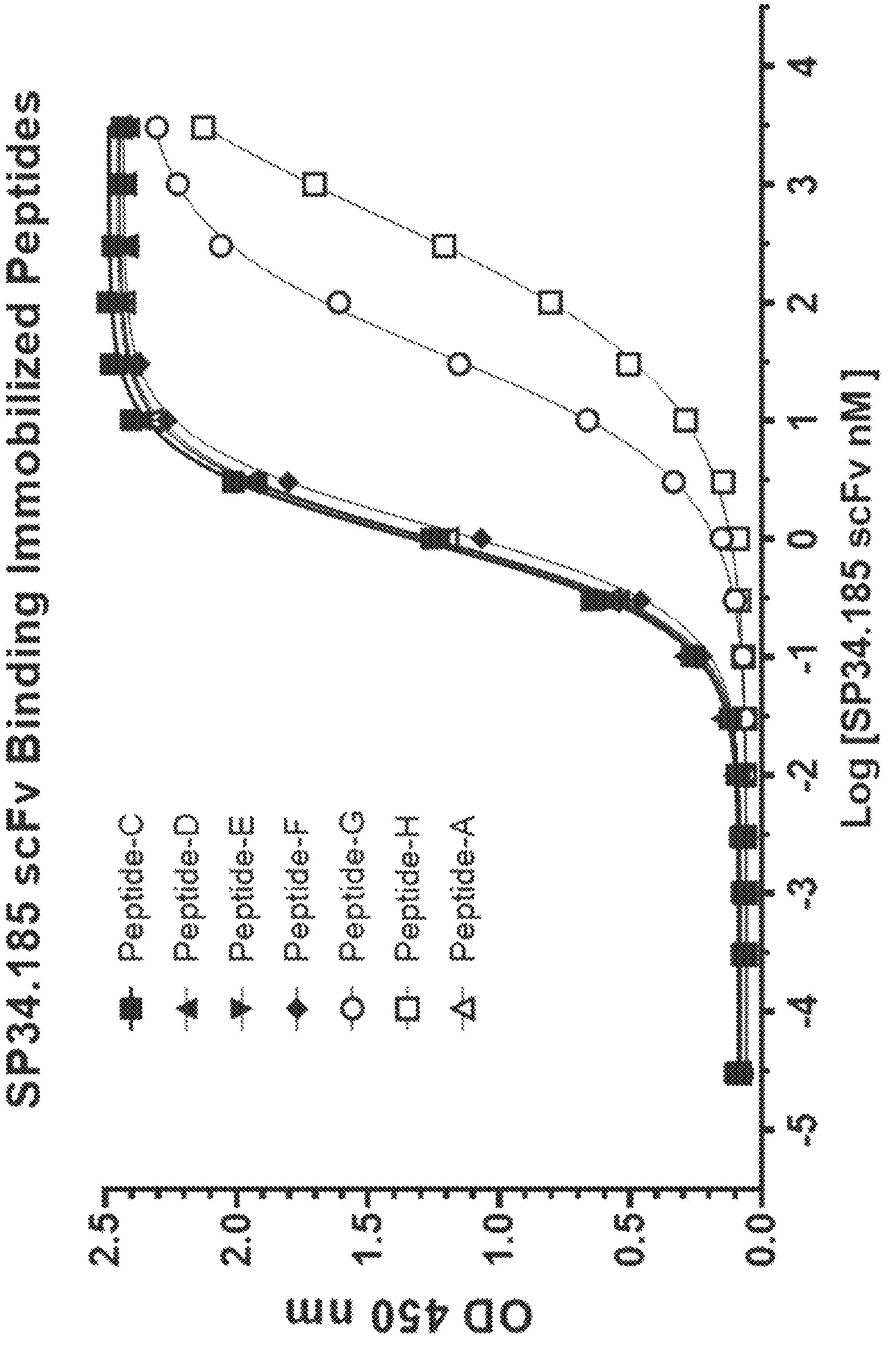

| Summary of FIG. 12B | | | | | | | |
|---|---|---|---|---|---|---|---|
| ELISA | Peptide-A | Peptide-C | Peptide-D | Peptide-E | Peptide-F | Peptide-G | Peptide-H |
| EC50 nM | 1.013 | 0.9429 | 1.018 | 0.9738 | 1.27 | 47.5 | 346.2 |

TABLE 17B

Figure 12C:
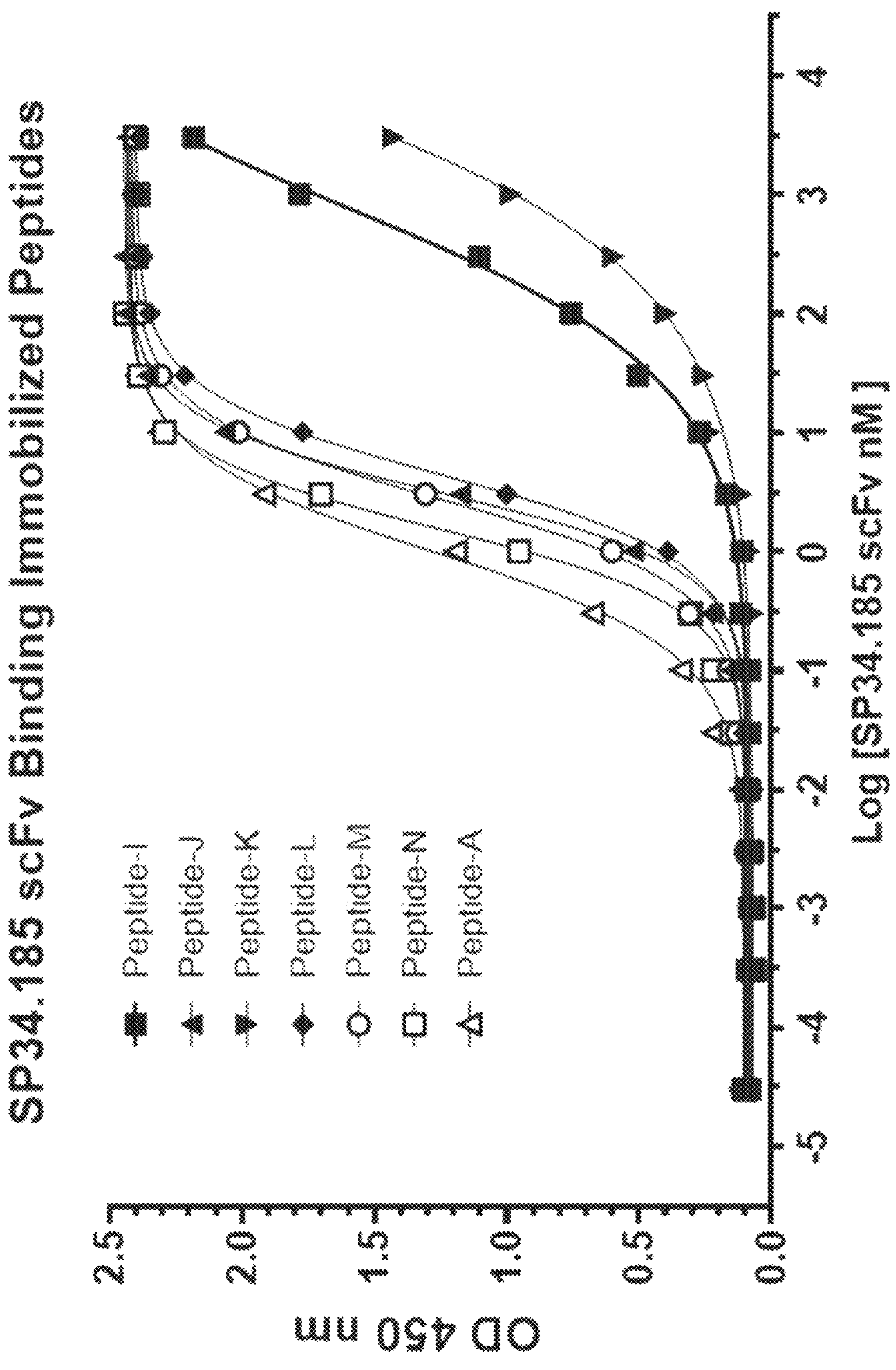
Figure 12D:
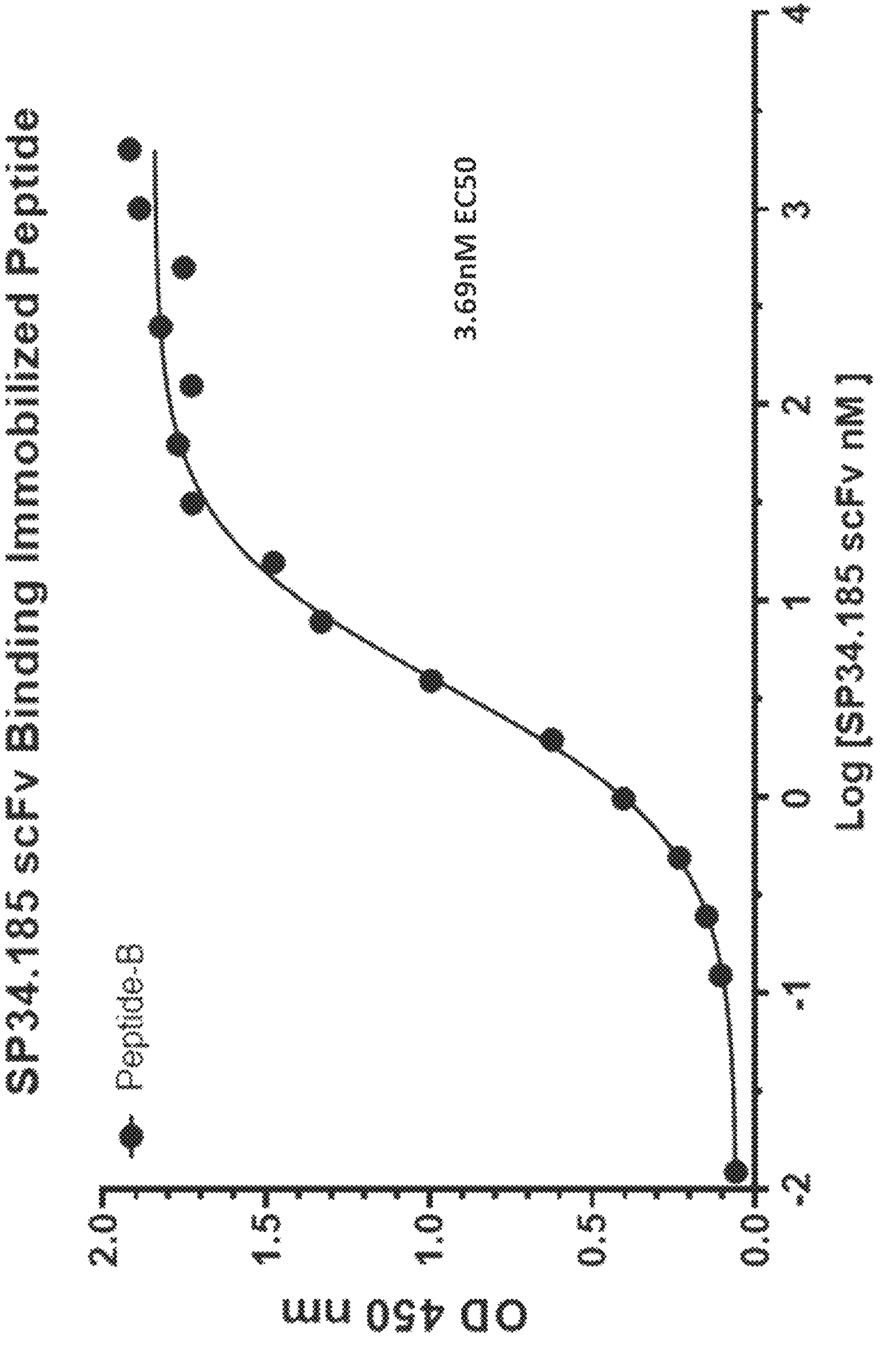

| Summary of FIG. 12C | | | | | | | |
|---|---|---|---|---|---|---|---|
| ELISA | Peptide-A | Peptide-I | Peptide-J | Peptide-K | Peptide-L | Peptide-M | Peptide-N |
| EC50 nM | 0.986 | 310.8 | 3.134 | 1.960 | 4.363 | 2.76 | 1.546 |

TABLE 17C

Figure 12E:
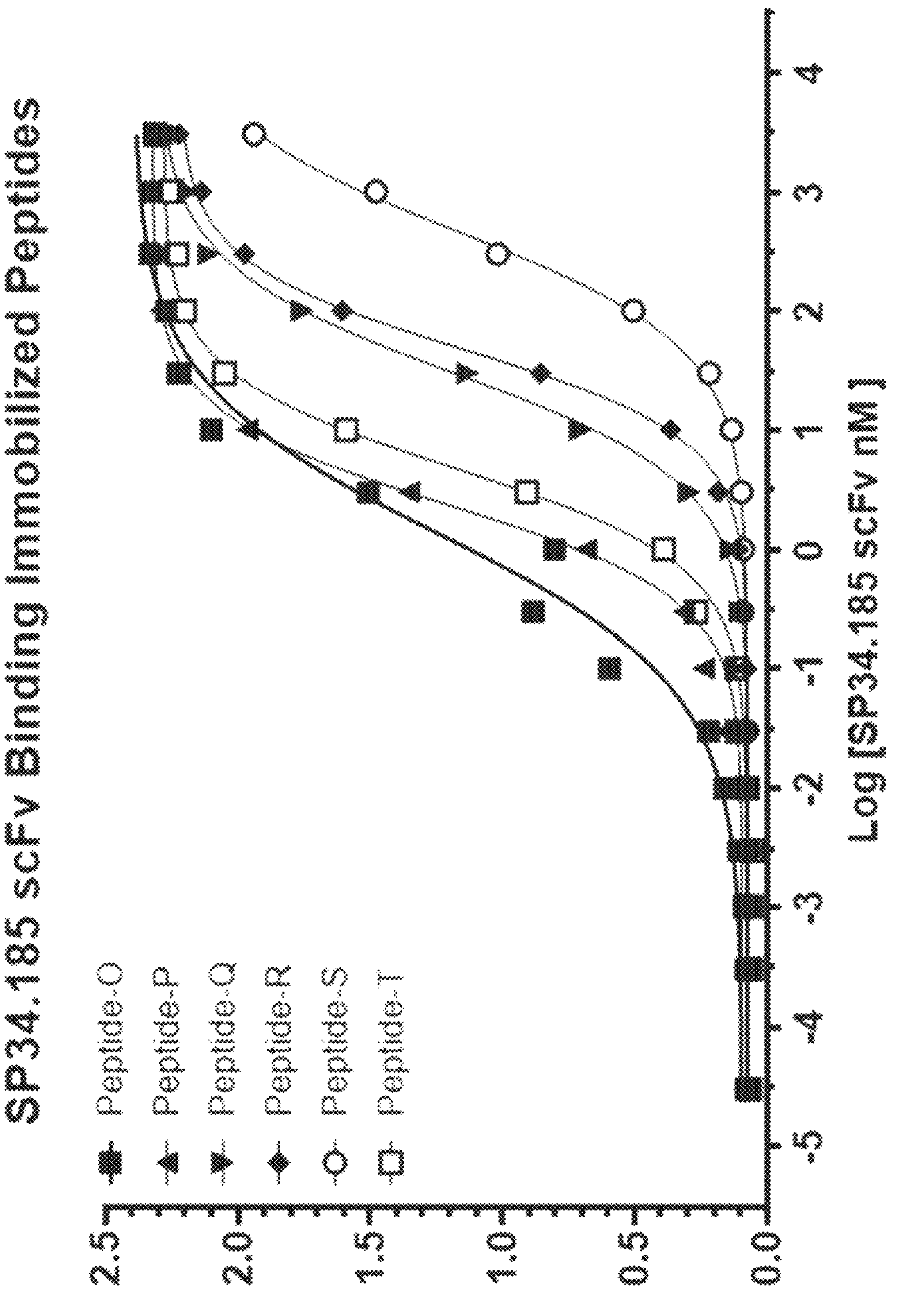

| Summary of FIG. 12E | | | | | | |
|---|---|---|---|---|---|---|
| ELISA | Peptide-O | Peptide-P | Peptide-Q | Peptide-R | Peptide-S | Peptide-T |
| EC50 nM | 1.356 | 2.359 | 30.04 | 47.50 | 457.1 | 4.762 |

TABLE 17D

Figure 12F:
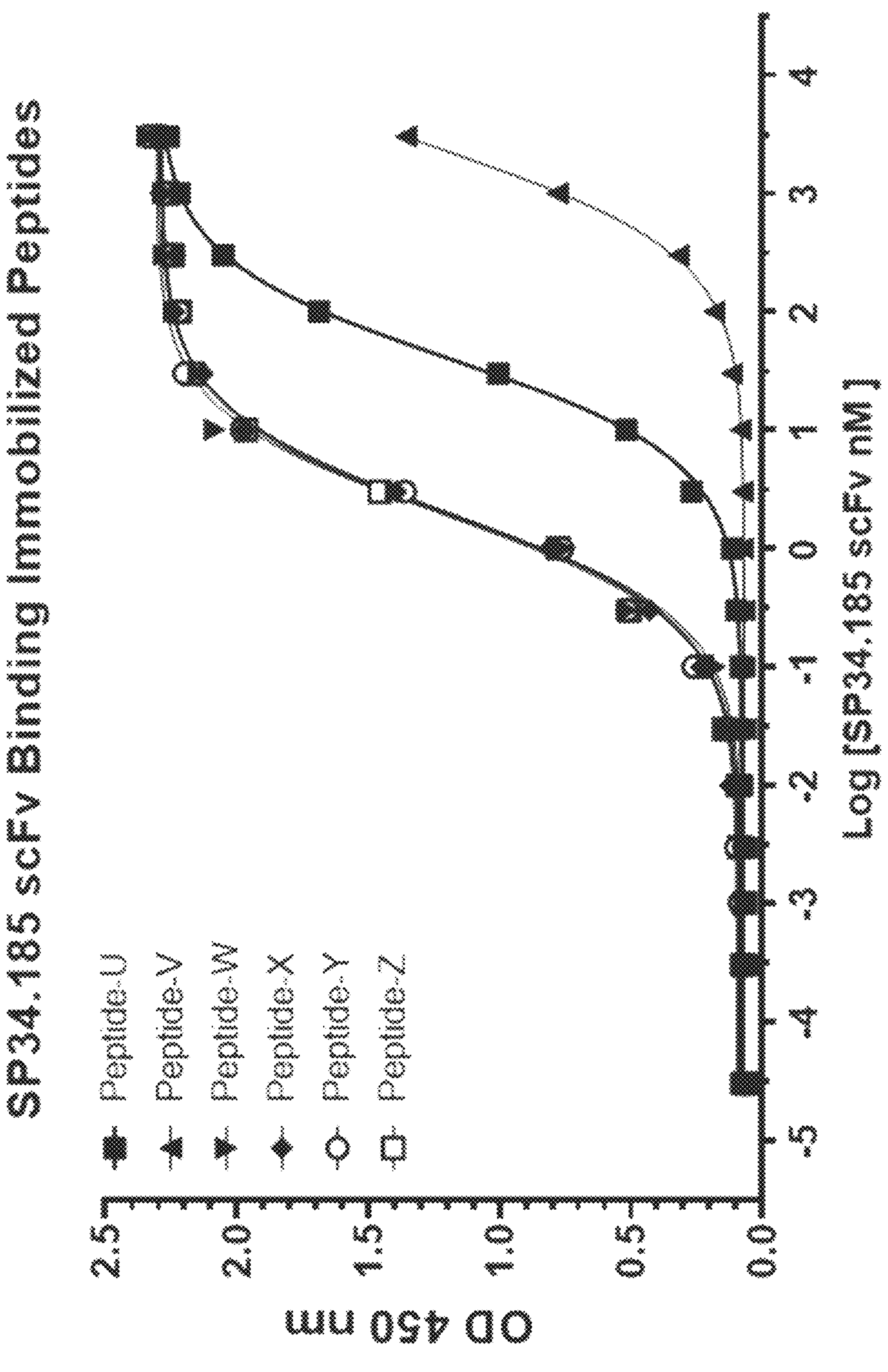

| Summary of FIG. 12F | | | | | | |
|---|---|---|---|---|---|---|
| ELISA | Peptide-U | Peptide-V | Peptide-W | Peptide-X | Peptide-Y | Peptide-Z |
| EC50 nM | 39.90 | 2168 | 1.916 | 1.948 | 2.012 | 1.833 |

Peptides were evaluated for their ability to inhibit SP34.185 scFv from binding CD3e by standard enzyme linked immunosorbent assays (ELISAs). Briefly, a fixed concentration of SP34.185 scFv was incubated with varying concentrations of peptides in solution. SP34.185scFv and peptide solutions were incubated for 1 hr prior to addition to CD3 coated plates. Binding was allowed to proceed for 30 min prior to washing. After washing, bound SP34.185 scFv using a secondary horse radish peroxidase antibody conjugate. After washing again, plates were developed using standard ELISA techniques and stopped using acid. The concentration of peptide required to inhibit 50% of the SP34.185 scFv CD3 binding signal (IC50) was calculated using Graphpad prism. Data is shown in FIGS. 13A-13F and summarized in Tables 18A-18D.

TABLE 18A

Figure 13A:
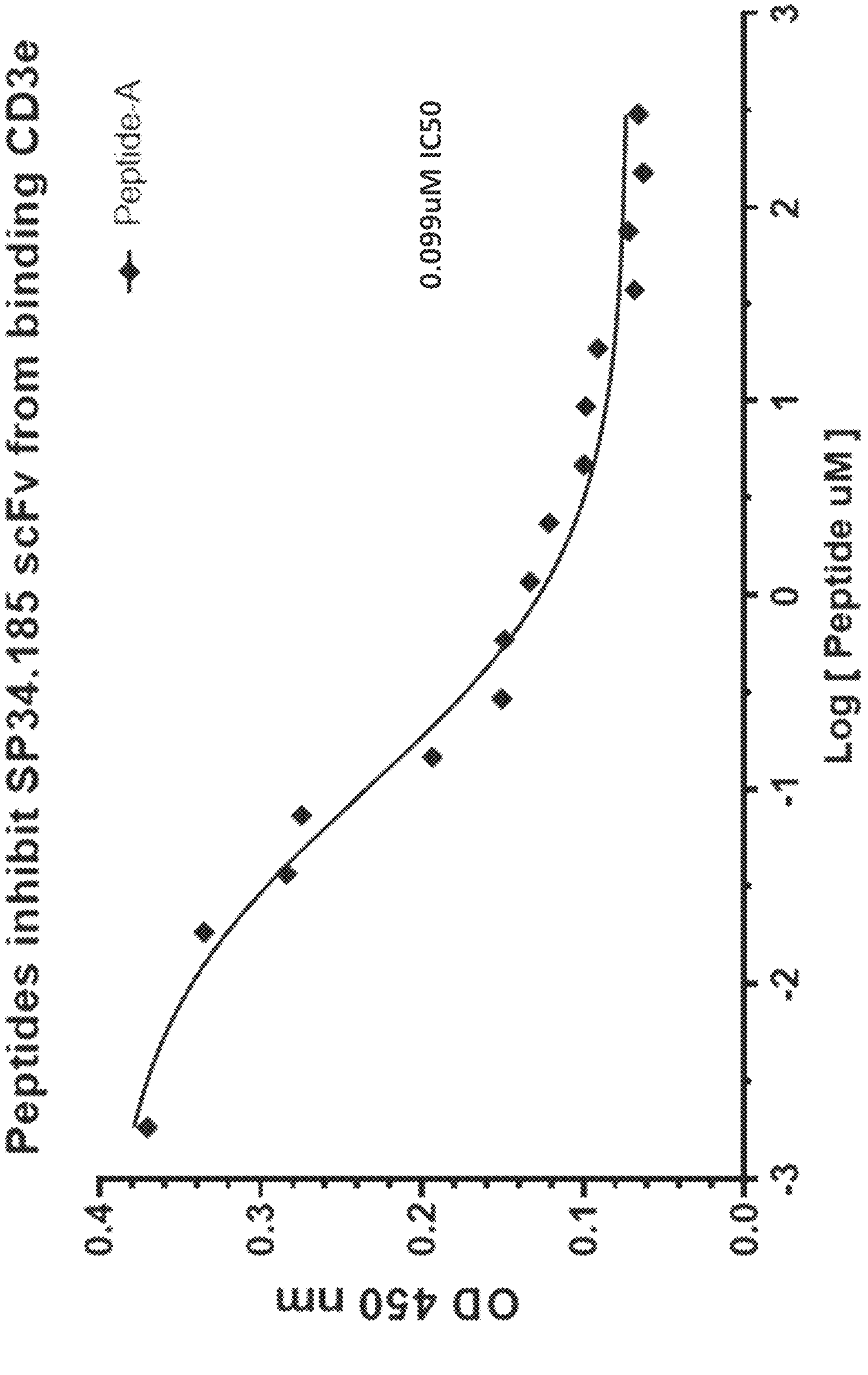
FIGS. 13A-13F illustrate inhibition of anti-CD3 scFv binding to CD3 by alanine scanning peptides of anti-CD3 scFv Peptide-A and Peptide-B as measured by ELISA.
Figure 13B:
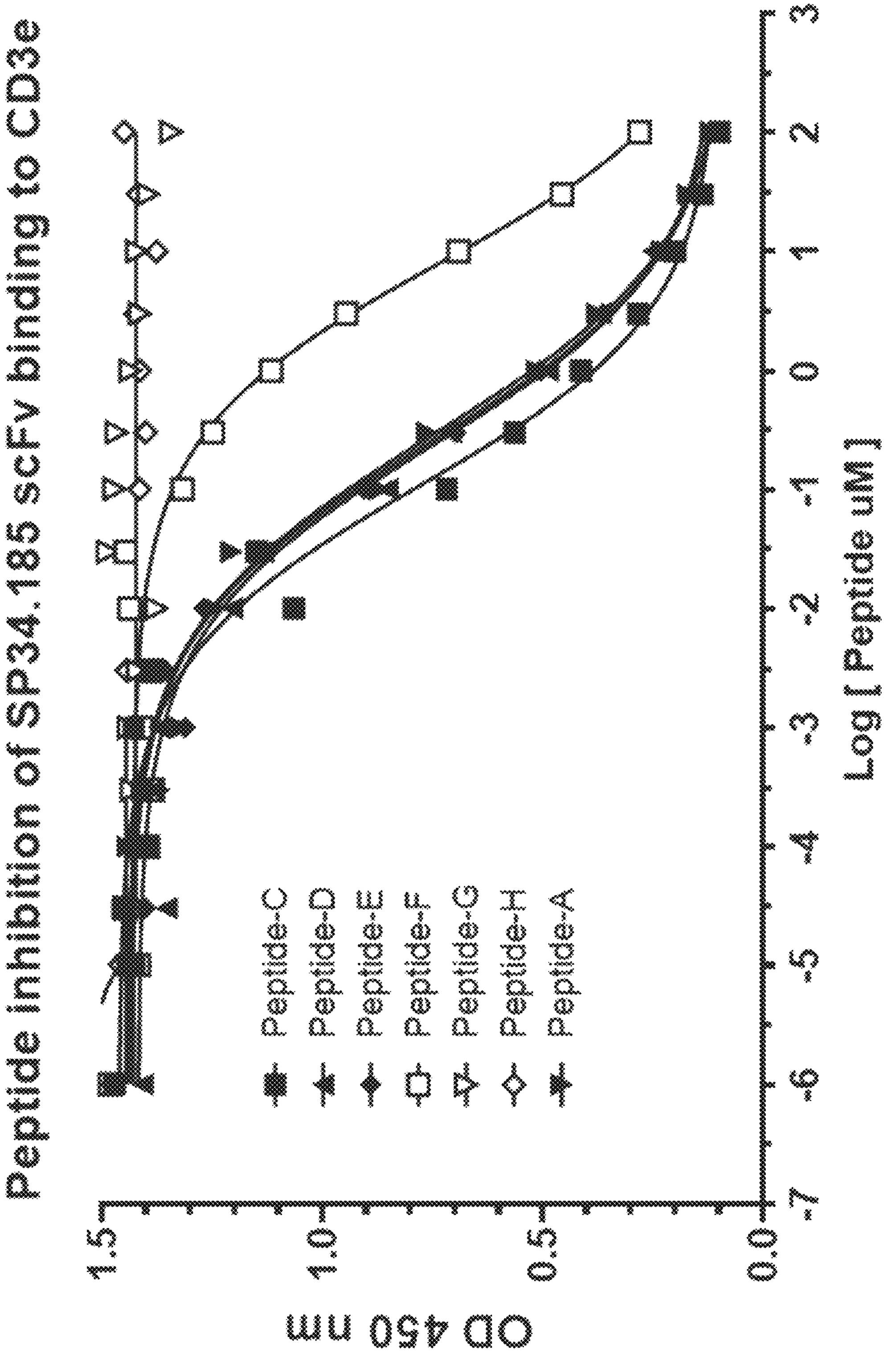

| Summary of FIG. 13B | | | | | | | |
|---|---|---|---|---|---|---|---|
| ELISA | Peptide-A | Peptide-C | Peptide-D | Peptide-E | Peptide-F | Peptide-G | Peptide-H |
| IC50 uM | 0.1926 | 0.1025 | 0.2318 | 0.1905 | 5.484 | >100 | >100 |

TABLE 18B

Figure 13C:
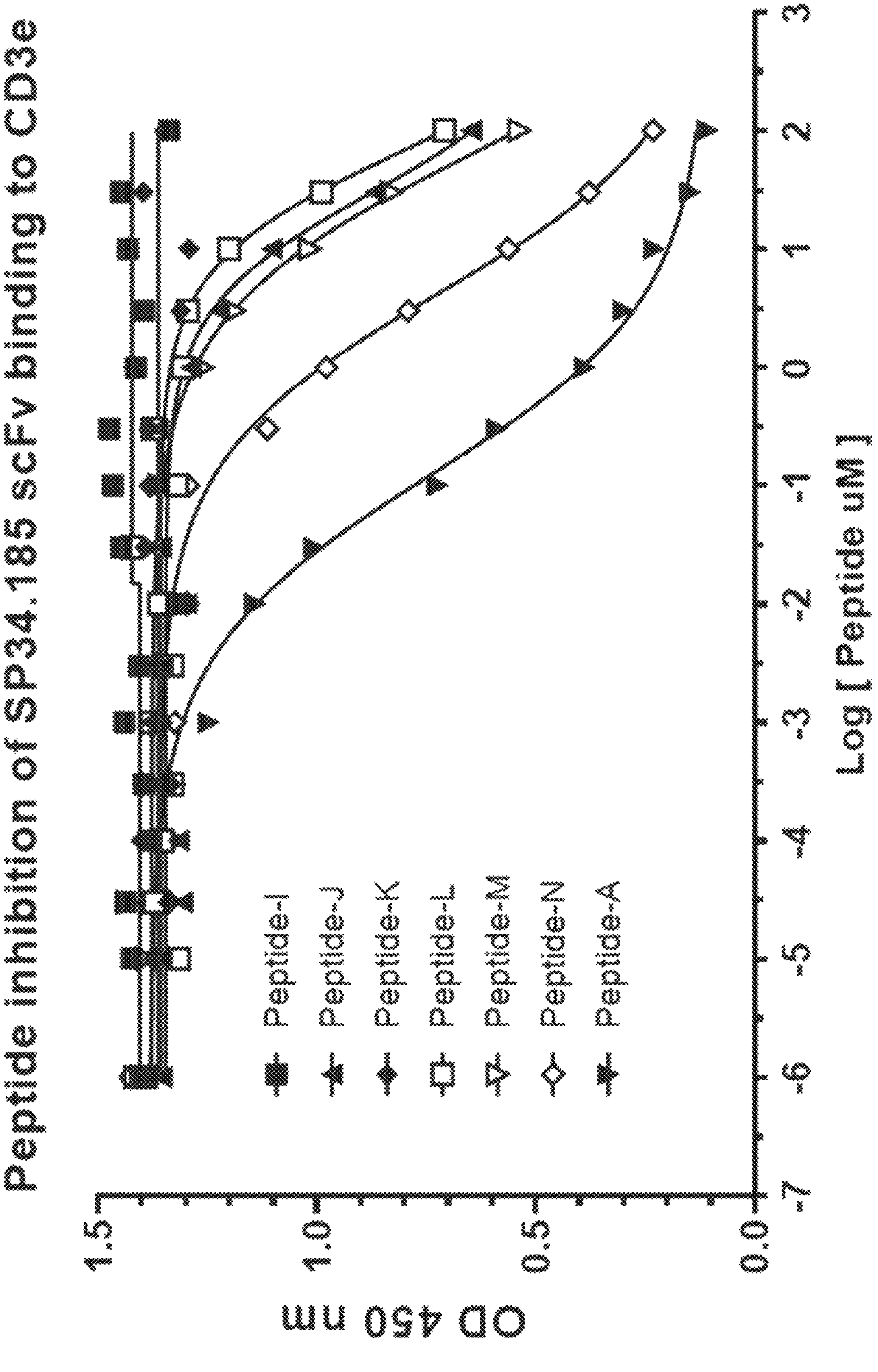
Figure 13D:
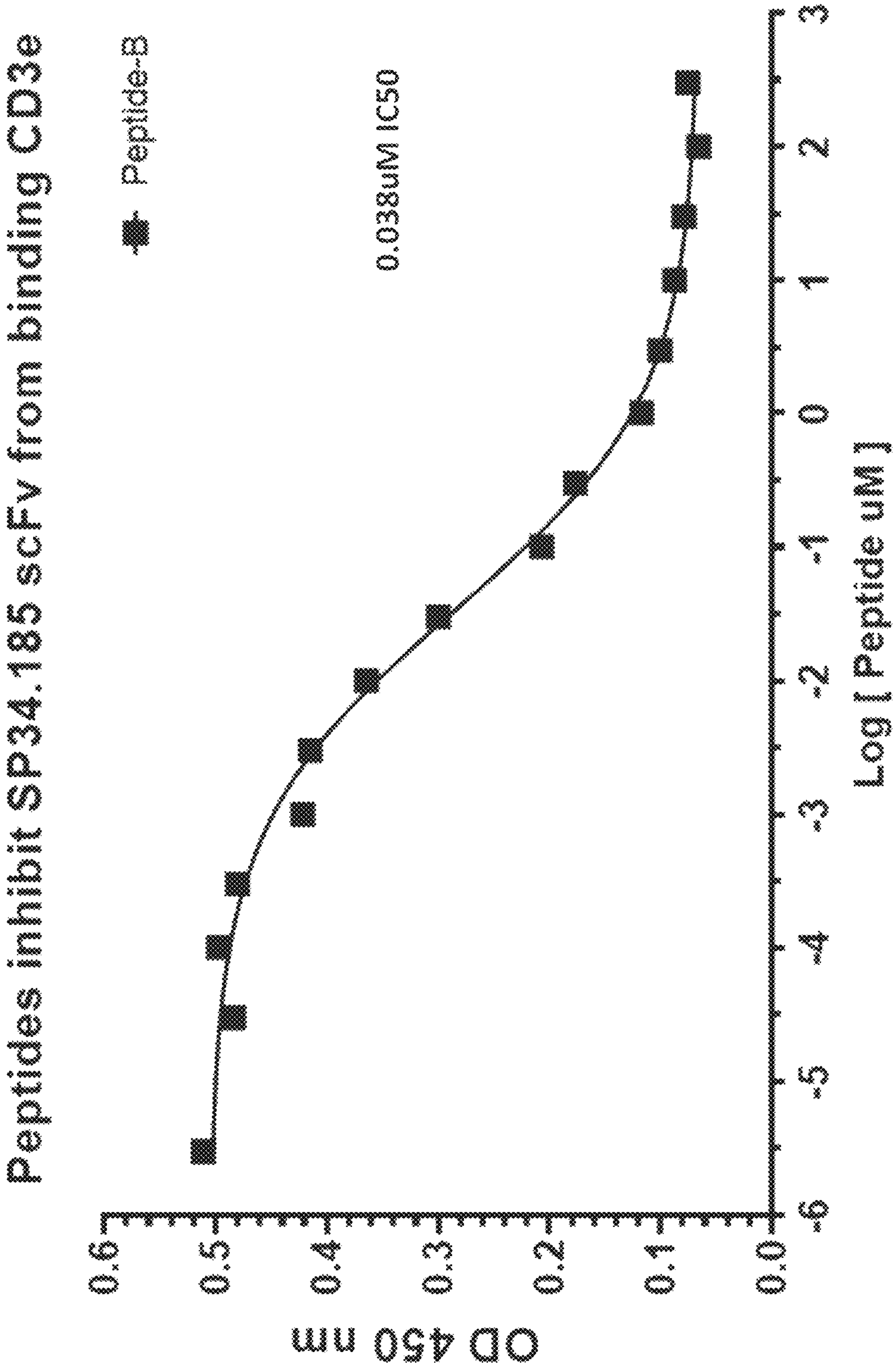

| Summary of FIG. 13C | | | | | | | |
|---|---|---|---|---|---|---|---|
| ELISA | Peptide-A | Peptide-I | Peptide-10 | Peptide-K | Peptide-L | Peptide-M | Peptide-N |
| IC50 uM | 0.1138 | >100 | 63.18 | >100 | 86.78 | 36.66 | 3.009 |

TABLE 18C

Figure 13E:
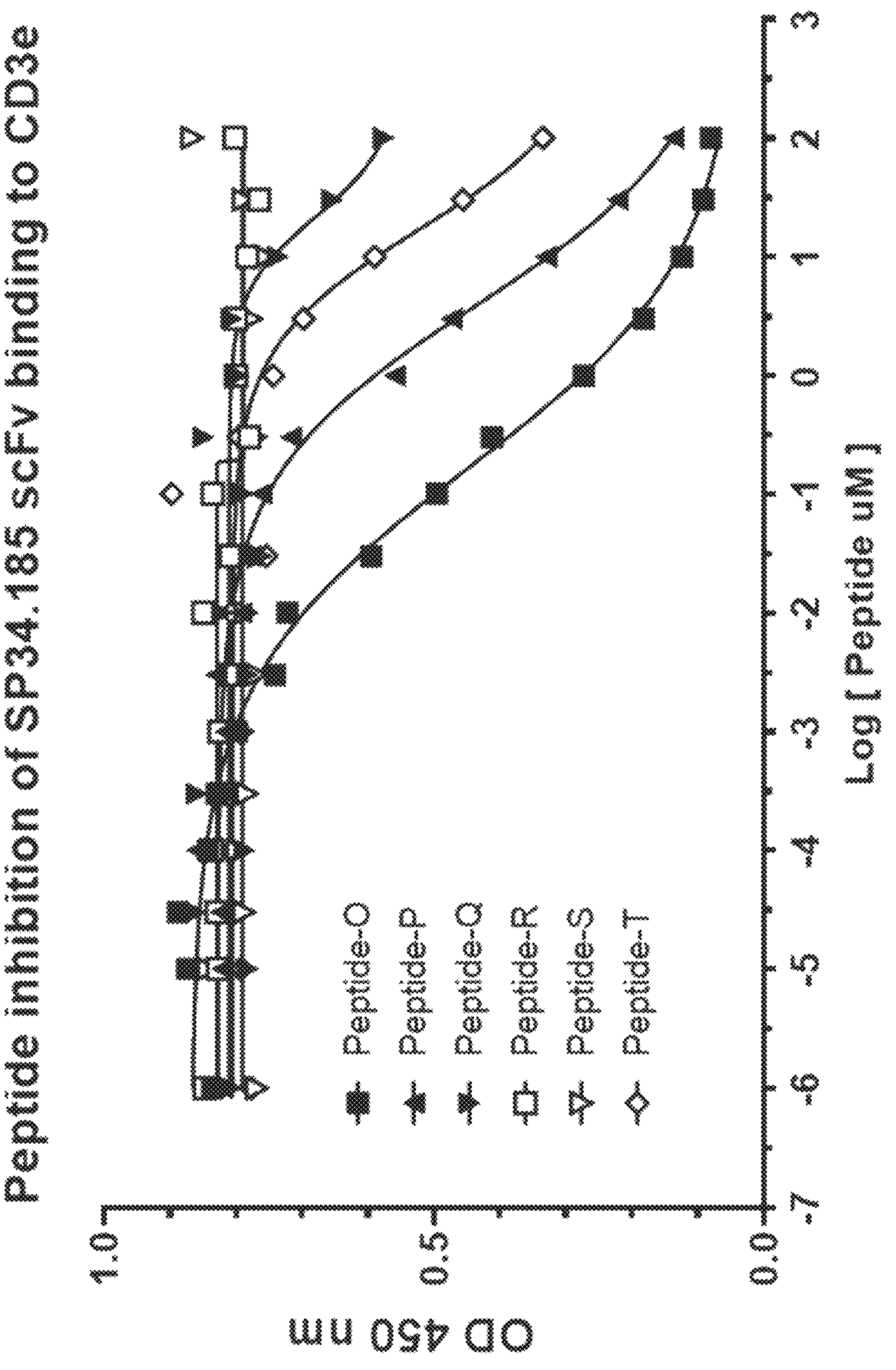

| Summary of FIG. 13E | | | | | | |
|---|---|---|---|---|---|---|
| ELISA | Peptide-O | Peptide-P | Peptide-Q | Peptide-R | Peptide-S | Peptide-T |
| IC50 uM | 0.1473 | 3.333 | >100 | >100 | >100 | 41.46 |

TABLE 18D

Figure 13F:
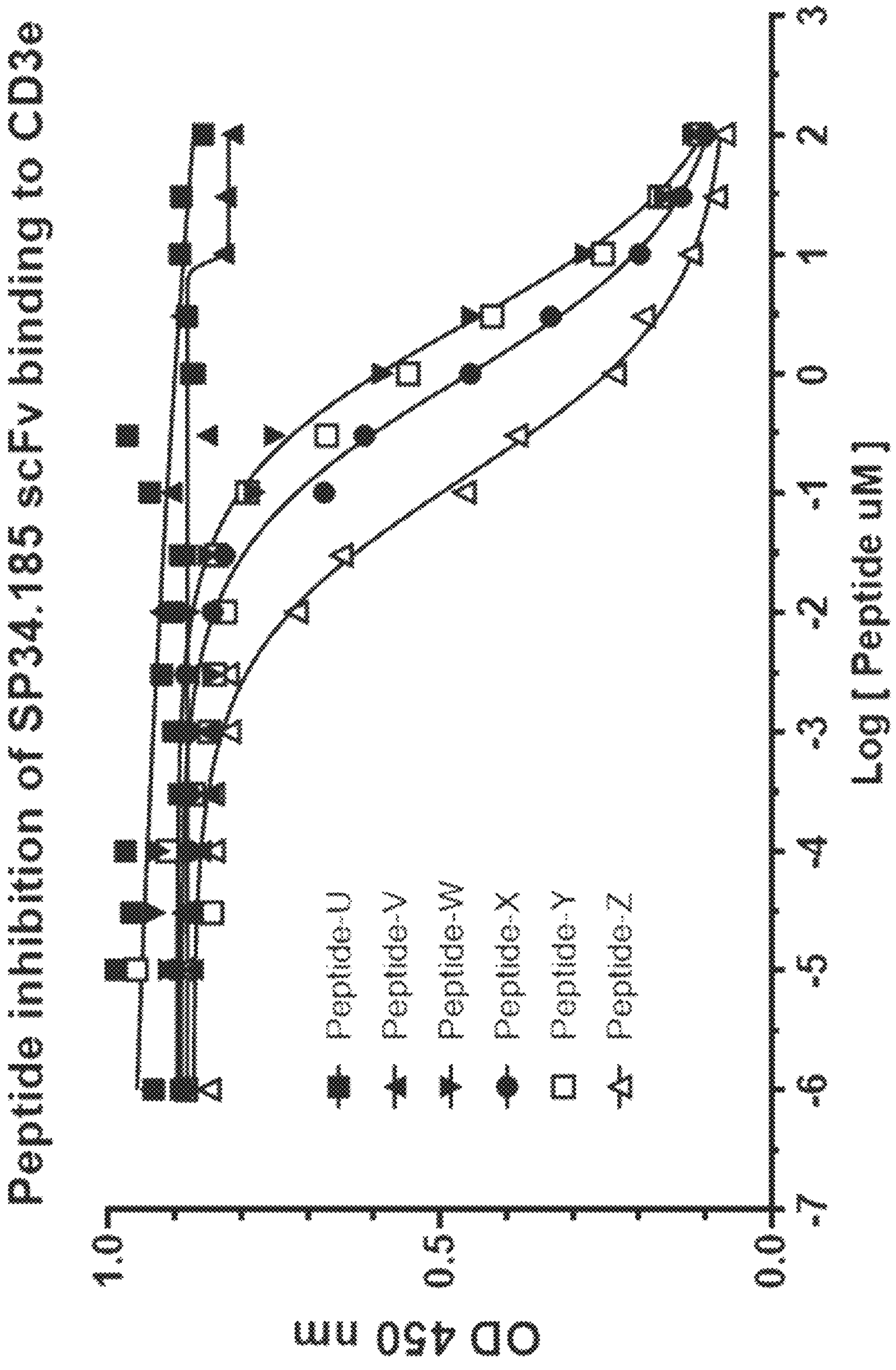

| Summary of FIG. 13F | | | | | | |
|---|---|---|---|---|---|---|
| ELISA | Peptide-U | Peptide-V | Peptide-W | Peptide-X | Peptide-Y | Peptide-Z |
| IC50 uM | >100 | >100 | 1.912 | 0.6992 | 1.456 | 0.1180 |

TABLE 19

CD3 Ala Scan Sequences-Peptide A and Peptide-B

| Peptide-ID | anti-CD3 Panned target | Sequence | SEQ ID NO: |
|---|---|---|---|
| Peptide-A | SP34.185 | GSQCLGPEWEVCPY | 79 |
| Peptide-C | SP34.185 | ASQCLGPEWEVCPY | 80 |
| Peptide-D | SP34.185 | GAQCLGPEWEVCPY | 81 |
| Peptide-E | SP34.185 | GSACLGPEWEVCPY | 82 |
| Peptide-F | SP34.185 | GSQCAGPEWEVCPY | 83 |
| Peptide-G | SP34.185 | GSQCLAPEWEVCPY | 84 |
| Peptide-H | SP34.185 | GSQCLGAEWEVCPY | 85 |
| Peptide-I | SP34.185 | GSQCLGPAWEVCPY | 86 |
| Peptide-J | SP34.185 | GSQCLGPEAEVCPY | 87 |
| Peptide-K | SP34.185 | GSQCLGPEWAVCPY | 88 |
| Peptide-L | SP34.185 | GSQCLGPEWEACPY | 89 |
| Peptide-M | SP34.185 | GSQCLGPEWEVCAY | 90 |
| Peptide-N | SP34.185 | GSQCLGPEWEVCPA | 91 |
| Peptide-A | SP34.185 | GSQCLGPEWEVCPY | 92 |
| Peptide-B | SP34.185 | VYCGPEFDESVGCM | 93 |
| Peptide-O | SP34.185 | AYCGPEFDESVGCM | 94 |
| Peptide-P | SP34.185 | VACGPEFDESVGCM | 95 |
| Peptide-Q | SP34.185 | VYCAPEFDESVGCM | 96 |
| Peptide-R | SP34.185 | VYCGAEFDESVGCM | 97 |
| Peptide-S | SP34.185 | VYCGPAFDESVGCM | 98 |

TABLE 19-continued

CD3 Ala Scan Sequences-Peptide A and Peptide-B

| Peptide-ID | anti-CD3 Panned target | Sequence | SEQ ID NO: |
|---|---|---|---|
| Peptide-T | SP34.185 | VYCGPEADESVGCM | 99 |
| Peptide-U | SP34.185 | VYCGPEFAESVGCM | 100 |
| Peptide-V | SP34.185 | VYCGPEFDASVGCM | 101 |
| Peptide-W | SP34.185 | VYCGPEFDEAVGCM | 102 |
| Peptide-X | SP34.185 | VYCGPEFDESAGCM | 103 |
| Peptide-Y | SP34.185 | VYCGPEFDESVACM | 104 |
| Peptide-Z | SP34.185 | VYCGPEFDESVGCA | 105 |

Example 8: Panning of the Optimized Phage Library Construction—CD3 scFv Peptides Once the phage optimization libraries were completed, phage libraries were bio-panned using SP34.185 scFv loaded beads. Multiple rounds of panning were performed where bacteriophage was allowed to bind to SP34.185 scFv loaded beads, washed, eluted, and amplified. Additional selective pressure was included during each round of panning using a fixed concentration of CD3, Peptide-A, or Peptide-B. After panning, phage infected bacteria were plated out and colonies picked into 96 well blocks. Clonal phage was then amplified and separated from bacterial cells via centrifugation. Phage containing supernatants were tested in binding ELISAs against SP34.185 scFv coated plates in the presence or absence of saturating concentration of CD3. Phage able to bind SP34.185 scFv were selected for sequence analysis if the binding signal was reduced in the presence of CD3.

Example 9: Panning ELISAs—CD3 scFv Peptides

Clonal phages were harvested as crude supernatants and screened via standard enzyme linked immunsorbent assays (ELISAs). Briefly, biotinylated SP34.185 scFv was captured on neutravidin coated plates. Prior to the addition of clonal phage, wells were incubated with blocking buffer and CD3 or blocking buffer alone. Without washing or aspirating, clonal phage supernatants were then added to the wells and incubated for a short time. Wells were then washed followed by detection of bound phage using a horse radish peroxidase conjugated anti-M13 antibody. Clonal phage of interest was then sent for sequence analysis.

Figure 14A:
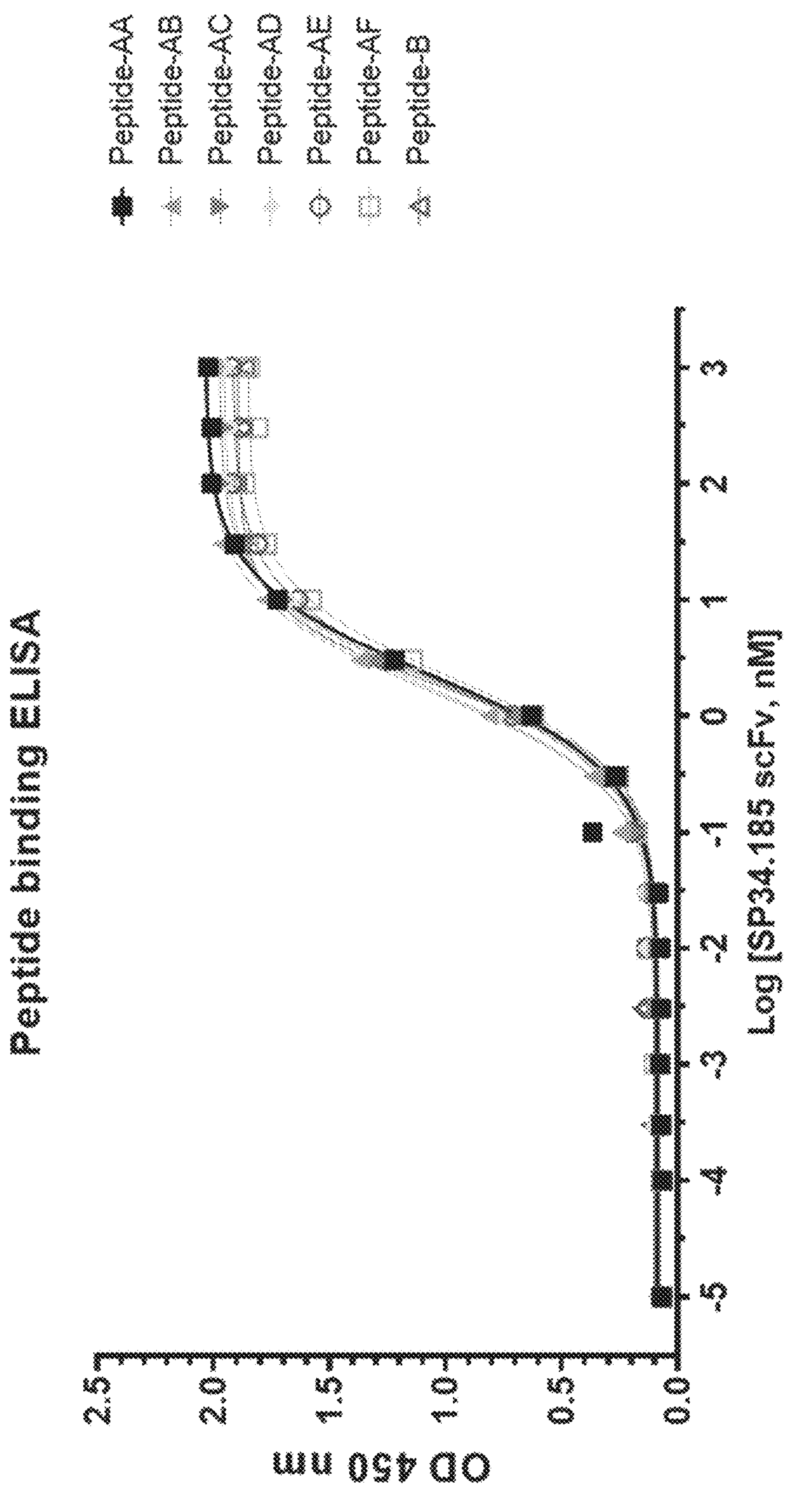
FIGS. 14A-14B illustrate anti-CD3 scFv binding by optimized anti-CD3 scFv Peptide-B sequences as measured by ELISA.
Figure 14B:
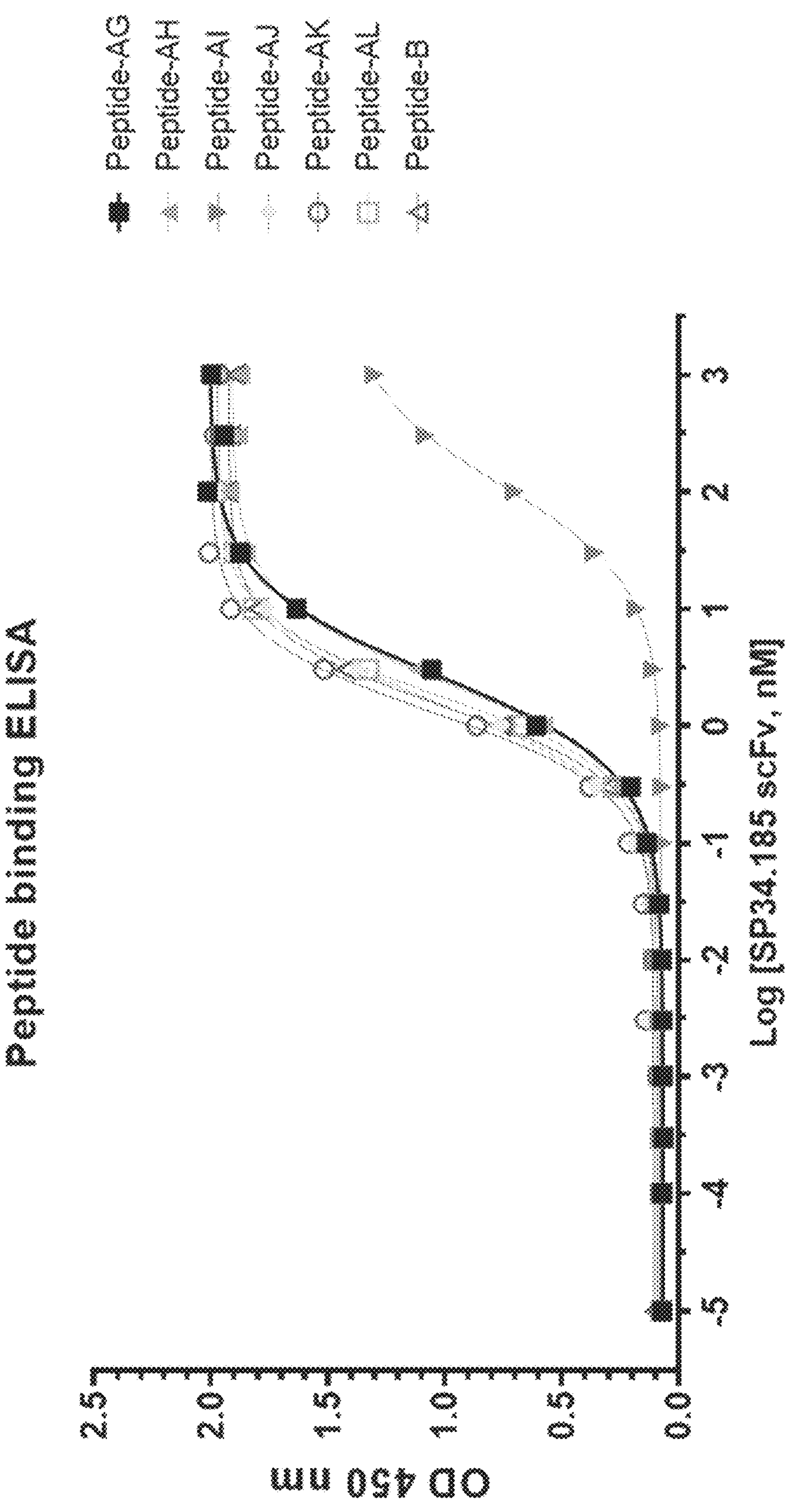
Figure 15A:
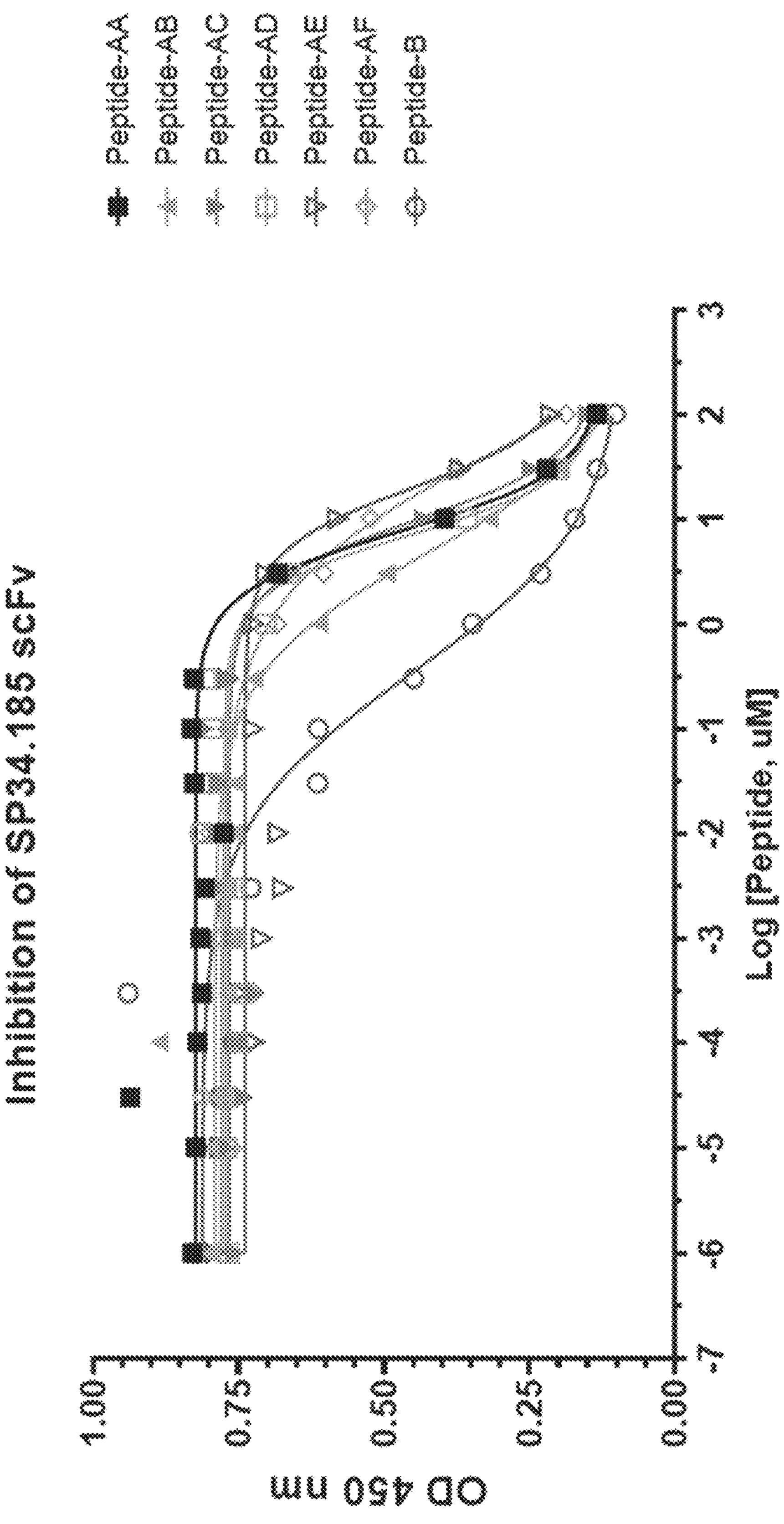
FIGS. 15A-15B illustrate inhibition of anti-CD3 scFv binding to CD3 by optimized anti-CD3 scFv Peptide-B sequences as measured by ELISA.
Figure 15B:
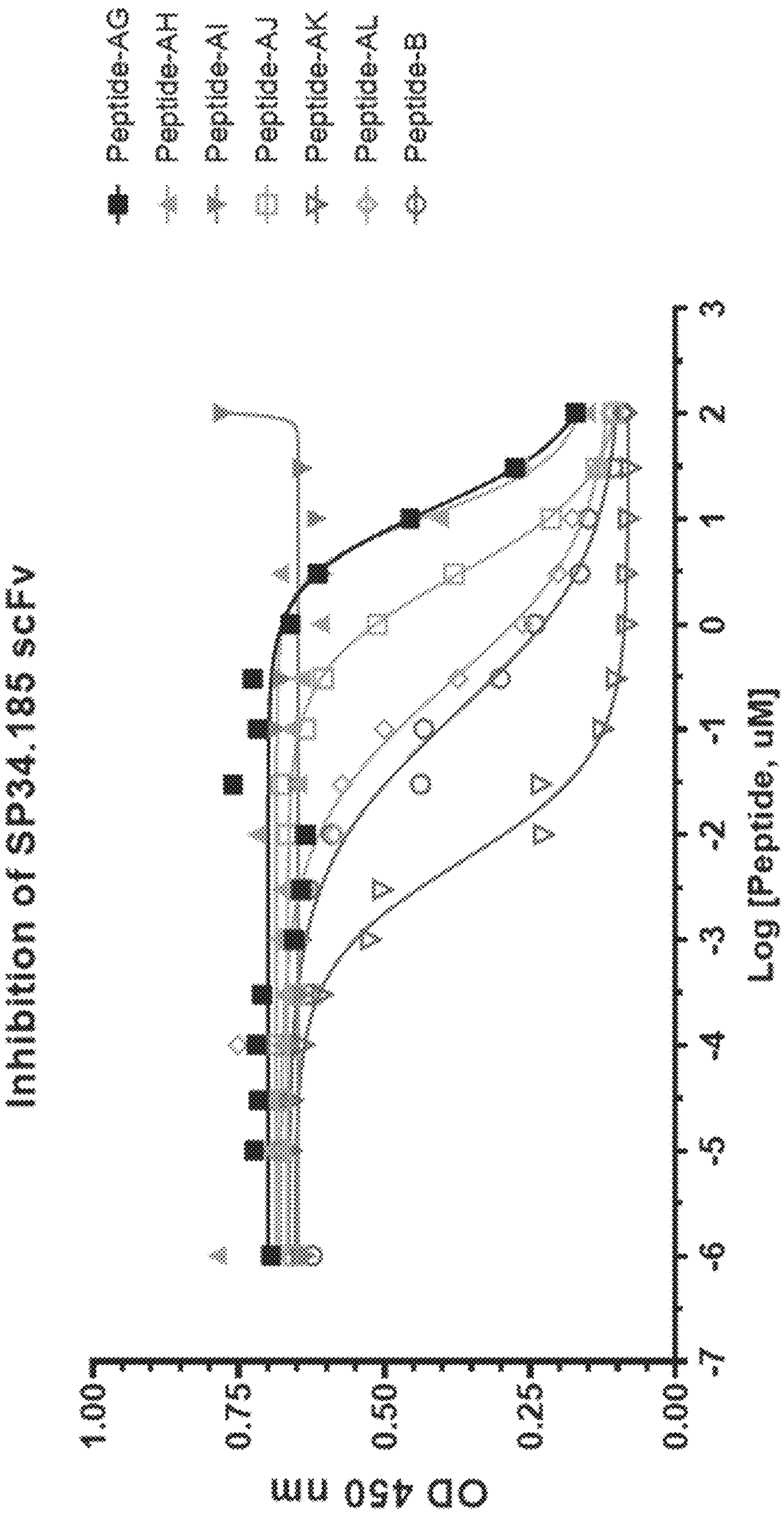
Figure 16:
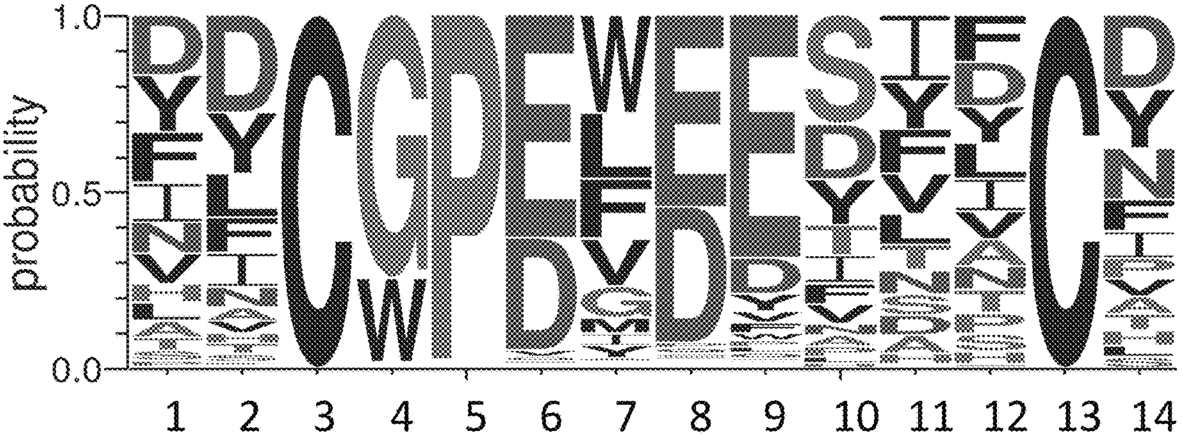
FIG. 16 illustrates the core sequence motif of optimized anti-CD3 scFv Peptide-B sequences generated using WebLogo 3.7.4.

Phage panning results of CD3 scFv Peptide-A library sequences are shown in Table 20. The sequences of those peptides selected for synthesis are shown in Table 21, and further evaluated for binding to anti-CD3 scFv (FIGS. 14A-14B) and inhibition of anti-CD3 scFv binding to CD3 (FIGS. 15A-15B). The consensus sequence shown in FIG. 16 was calculated from all the sequences shown in Table 20 and was generated using WebLogo 3.7.4.

TABLE 20

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA: Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-1/ Peptide B | V | Y | C | G | P | E | F | D | E | S | V | G | C | M | 0.06 | 2.79 | 0.09 | 19 |
| Phage-2 | D | D | — | W | — | D | W | E | F | D | F | A | — | A | 0.08 | 2.75 | 0.09 | 106 |
| Phage-3 | Y | I | — | — | L | D | — | P | D | F | L | Y | — | D | 0.08 | 2.88 | 0.10 | 107 |
| Phage-4 | F | D | — | W | — | D | W | E | — | Y | F | V | — | D | 0.08 | 2.79 | 0.09 | 108 |
| Phage-5 | Y | I | — | W | — | D | W | E | — | Y | F | D | — | D | 0.08 | 2.74 | 0.09 | 109 |
| Phage-6 | N | I | — | W | — | D | W | E | D | D | Y | F | — | F | 0.09 | 2.54 | 0.09 | 110 |
| Phage-7 | N | F | — | W | — | D | W | E | Y | I | Y | P | — | I | 0.07 | 2.77 | 0.09 | 111 |
| Phage-8 | — | D | — | W | — | D | W | E | — | D | F | L | — | I | 0.08 | 2.54 | 0.08 | 112 |
| Phage-9 | H | A | — | W | — | D | W | E | — | Y | F | P | — | N | 0.08 | 2.85 | 0.09 | 113 |
| Phage-10 | Y | D | — | — | — | D | V | — | — | — | Y | V | — | V | 0.09 | 2.63 | 0.10 | 114 |
| Phage-11 | I | D | — | W | — | D | W | E | D | D | T | F | — | Y | 0.09 | 2.73 | 0.08 | 115 |
| Phage-12 | Y | L | — | — | — | D | G | — | — | T | L | A | — | Y | 0.08 | 2.66 | 0.15 | 116 |
| Phage-13 | — | D | — | — | — | D | G | — | — | — | I | L | — | Y | 0.11 | 2.13 | 0.08 | 117 |
| Phage-14 | F | I | — | W | — | D | W | E | — | D | Y | F | — | A | 0.07 | 2.44 | 0.09 | 119 |
| Phage-15 | G | D | — | W | — | D | W | E | W | D | F | Y | — | D | 0.07 | 2.71 | 0.07 | 120 |
| Phage-16 | Y | L | — | W | — | D | W | E | Y | I | D | L | — | D | 0.12 | 2.67 | 0.08 | 121 |
| Phage-17 | S | F | — | W | — | D | W | E | — | Y | F | D | — | D | 0.10 | 2.60 | 0.07 | 122 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34.185 scFv | Sp34.185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-18 | D | D | — | W | — | D | W | E | — | Y | A | S | — | D | 0.09 | 2.57 | 0.07 | 123 |
| Phage-19 | N | L | — | W | — | D | W | E | Y | P | F | F | — | D | 0.09 | 2.52 | 0.09 | 124 |
| Phage-20 | F | D | — | W | — | D | W | E | — | — | F | V | — | D | 0.08 | 2.34 | 0.09 | 125 |
| Phage-21 | D | I | — | | — | D | G | — | — | T | I | I | — | D | 0.13 | 2.3 | 0.1 | 126 |
| Phage-22 | D | D | — | W | — | D | W | E | Y | Y | A | V | — | D | 0.09 | 2.28 | 0.09 | 127 |
| Phage-23 | Y | D | — | W | — | D | W | E | — | Y | S | N | — | D | 0.1 | 2.17 | 0.08 | 128 |
| Phage-24 | I | N | — | W | — | D | W | E | D | Y | F | F | — | D | 0.07 | 2.16 | 0.07 | 129 |
| Phage-25 | N | I | — | W | — | D | W | E | D | D | T | F | — | F | 0.06 | 2.87 | 0.07 | 130 |
| Phage-26 | N | I | — | W | — | D | W | E | P | N | S | F | — | F | 0.09 | 2.87 | 0.08 | 131 |
| Phage-27 | Y | D | — | — | — | — | M | — | — | — | I | D | — | F | 0.09 | 2.39 | 0.08 | 132 |
| Phage-28 | D | F | — | W | — | D | W | E | F | P | F | I | — | H | 0.11 | 2.73 | 0.12 | 133 |
| Phage-29 | D | F | — | — | — | — | M | — | — | — | I | T | — | I | 0.07 | 2.36 | 0.08 | 134 |
| Phage-30 | Y | D | — | — | — | — | — | — | — | — | T | V | — | I | 0.1 | 2.32 | 0.08 | 135 |
| Phage-31 | H | D | — | W | — | D | W | E | W | D | I | F | — | I | 0.07 | 2.26 | 0.08 | 136 |
| Phage-32 | H | A | — | W | — | D | W | E | — | Y | N | P | — | N | 0.11 | 2.71 | 0.11 | 137 |
| Phage-33 | D | V | — | W | — | D | W | E | W | D | F | F | — | N | 0.08 | 2.65 | 0.08 | 138 |
| Phage-34 | N | — | — | W | — | D | W | E | Y | Y | I | P | — | N | 0.1 | 2.57 | 0.08 | 139 |
| Phage-35 | I | I | — | W | — | D | W | E | F | I | D | Y | — | N | 0.08 | 2.1 | 0.07 | 140 |
| Phage-36 | S | L | — | W | — | D | W | E | Y | D | I | A | — | P | 0.07 | 2.53 | 0.08 | 141 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-37 | D | L | — | — | — | — | L | — | — | — | I | F | — | P | 0.08 | 2.49 | 0.09 | 142 |
| Phage-38 | T | N | — | W | — | D | W | E | W | V | L | P | — | P | 0.14 | 2.47 | 0.1 | 143 |
| Phage-39 | I | E | — | W | — | D | W | E | P | N | Y | F | — | P | 0.13 | 2.29 | 0.09 | 144 |
| Phage-40 | I | F | — | W | — | D | W | E | D | Y | — | D | — | P | 0.07 | 2.28 | 0.07 | 145 |
| Phage-41 | I | D | — | W | — | D | W | E | Y | D | F | F | — | P | 0.07 | 2.26 | 0.08 | 146 |
| Phage-42 | L | F | — | W | — | D | W | E | D | — | F | F | — | P | 0.18 | 2.11 | 0.13 | 147 |
| Phage-43 | — | D | — | W | — | D | W | E | D | Y | A | D | — | T | 0.11 | 2.2 | 0.1 | 148 |
| Phage-44 | — | I | — | W | — | D | W | E | 0 | Y | F | P | — | V | 0.11 | 2.34 | 0.09 | 149 |
| Phage-45 | I | E | — | W | — | D | W | E | P | I | Y | P | — | Y | 0.09 | 2.85 | 0.09 | 150 |
| Phage-46 | I | T | — | W | — | D | W | E | V | Y | F | P | — | Y | 0.07 | 2.55 | 0.08 | 151 |
| Phage-47 | I | D | — | W | — | D | W | E | Y | I | H | P | — | Y | 0.06 | 2.51 | 0.09 | 152 |
| Phage-48 | I | D | — | W | — | D | W | E | Y | I | N | P | — | Y | 0.12 | 2.5 | 0.12 | 153 |
| Phage-49 | A | D | — | W | — | D | W | E | — | A | F | P | — | Y | 0.09 | 2.44 | 0.09 | 154 |
| Phage-50 | I | D | — | W | — | D | W | E | Y | I | Y | P | — | Y | 0.09 | 2.31 | 0.07 | 155 |
| Phage-51 | N | I | — | W | — | D | W | E | D | D | N | F | — | F | 0.09 | 2.08 | 0.09 | 156 |
| Phage-52 | Y | D | — | W | — | D | W | E | Y | V | D | A | — | Y | 0.09 | 2.06 | 0.09 | 157 |
| Phage-53 | F | — | — | — | — | D | G | — | — | — | Y | V | — | D | 0.09 | 2.03 | 0.11 | 158 |
| Phage-54 | D | I | — | W | — | D | W | E | Y | I | N | I | — | S | 0.11 | 2.02 | 0.11 | 159 |
| Phage-55 | F | V | — | W | — | D | W | E | D | F | N | F | — | D | 0.07 | 2.01 | 0.08 | 160 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34.185 scFv | Sp34.185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-56 | F | A | — | W | — | D | W | E | D | Y | — | A | — | D | 0.07 | 2.01 | 0.09 | 161 |
| Phage-57 | D | N | — | W | — | D | W | E | Y | D | F | F | — | V | 0.08 | 1.99 | 0.09 | 162 |
| Phage-58 | Y | D | — | W | — | D | W | E | — | Y | N | D | — | A | 0.09 | 1.96 | 0.11 | 163 |
| Phage-59 | D | D | — | — | — | D | G | — | — | T | I | I | — | V | 0.07 | 1.91 | 0.09 | 164 |
| Phage-60 | F | P | — | W | — | D | W | E | — | Y | A | I | — | D | 0.1 | 1.89 | 0.1 | 165 |
| Phage-61 | P | D | — | — | — | D | G | — | — | — | L | F | — | T | 0.12 | 1.86 | 0.07 | 166 |
| Phage-62 | D | N | — | W | — | D | W | E | Y | D | Y | F | — | V | 0.07 | 1.83 | 0.07 | 167 |
| Phage-63 | I | F | — | W | — | D | W | E | — | F | Y | D | — | Y | 0.12 | 1.82 | 0.08 | 168 |
| Phage-64 | A | D | — | W | — | D | W | E | — | Y | F | P | — | N | 0.08 | 1.82 | 0.08 | 169 |
| Phage-65 | H | T | — | W | — | D | W | E | D | D | I | F | — | N | 0.12 | 1.81 | 0.10 | 170 |
| Phage-66 | F | A | — | W | — | D | W | E | — | A | F | L | — | L | 0.09 | 1.80 | 0.09 | 171 |
| Phage-67 | Y | D | — | — | — | — | L | — | — | — | I | A | — | D | 0.08 | 1.77 | 0.08 | 172 |
| Phage-68 | N | S | — | W | — | D | W | E | — | D | I | I | — | D | 0.08 | 1.77 | 0.10 | 173 |
| Phage-69 | F | A | — | W | — | D | W | E | — | V | A | P | — | Y | 0.07 | 1.75 | 0.07 | 174 |
| Phage-70 | L | D | — | — | — | D | G | — | — | T | L | T | — | Y | 0.10 | 1.75 | 0.12 | 175 |
| Phage-71 | — | L | — | W | — | D | W | E | — | F | Y | D | — | P | 0.07 | 1.74 | 0.09 | 176 |
| Phage-72 | H | A | — | W | — | V | W | E | — | Y | F | P | — | N | 0.07 | 1.72 | 0.08 | 177 |
| Phage-73 | N | E | — | W | — | N | G | E | — | T | F | P | — | T | 0.08 | 1.71 | 0.07 | 178 |
| Phage-74 | L | T | — | — | — | D | G | — | — | T | L | Y | — | D | 0.08 | 1.70 | 0.07 | 179 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-75 | Y | D | — | — | — | — | Y | — | — | — | — | P | — | I | 0.13 | 1.67 | 0.09 | 180 |
| Phage-76 | I | E | — | W | — | D | W | E | — | N | S | F | — | D | 0.09 | 1.66 | 0.08 | 181 |
| Phage-77 | Y | D | — | — | — | — | L | — | — | — | I | H | — | Y | 0.12 | 1.66 | 0.09 | 182 |
| Phage-78 | I | — | — | — | — | — | — | — | — | — | T | I | — | N | 0.08 | 1.63 | 0.08 | 183 |
| Phage-79 | I | — | — | — | — | — | V | E | — | A | Y | L | — | Y | 0.09 | 1.62 | 0.10 | 184 |
| Phage-80 | F | D | — | — | — | D | G | — | — | T | — | Y | — | D | 0.09 | 1.61 | 0.08 | 185 |
| Phage-81 | I | D | — | — | — | D | G | — | — | T | I | S | — | Y | 0.08 | 1.57 | 0.11 | 186 |
| Phage-82 | N | | — | — | — | — | — | — | — | — | S | T | — | L | 0.10 | 1.55 | 0.11 | 187 |
| Phage-83 | Y | D | — | — | — | D | G | — | — | — | Y | F | — | D | 0.08 | 1.53 | 0.08 | 188 |
| Phage-84 | N | F | — | W | — | D | W | E | Y | F | N | D | — | N | 0.09 | 1.53 | 0.09 | 189 |
| Phage-85 | — | L | — | W | — | D | W | E | A | F | F | D | — | D | 0.07 | 1.47 | 0.07 | 190 |
| Phage-86 | I | — | — | — | — | — | W | E | W | P | — | A | — | N | 0.16 | 1.47 | 0.10 | 191 |
| Phage-87 | — | F | — | W | — | D | W | E | D | N | F | F | — | N | 0.08 | 1.46 | 0.10 | 192 |
| Phage-88 | — | V | — | W | — | D | W | E | T | F | F | P | — | D | 0.08 | 1.46 | 0.08 | 193 |
| Phage-89 | D | N | — | — | — | D | G | — | — | T | Y | I | — | N | 0.10 | 1.45 | 0.09 | 194 |
| Phage-90 | D | N | — | W | — | D | W | E | Y | N | F | F | — | V | 0.07 | 1.45 | 0.08 | 195 |
| Phage-91 | F | — | — | — | — | — | V | E | — | D | Y | L | — | I | 0.10 | 1.43 | 0.10 | 196 |
| Phage-92 | D | N | — | W | — | D | W | E | Y | D | I | F | — | V | 0.07 | 1.43 | 0.07 | 197 |
| Phage-93 | I | D | — | — | — | — | — | — | — | — | I | A | — | P | 0.08 | 1.42 | 0.08 | 198 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA: Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-94 | Y | F | — | — | — | — | V | E | — | Y | T | L | — | F | 0.10 | 1.42 | 0.10 | 199 |
| Phage-95 | F | — | — | — | — | — | — | — | — | — | A | P | — | N | 0.06 | 1.37 | 0.08 | 200 |
| Phage-96 | F | D | — | — | — | — | V | E | — | Y | F | Y | — | A | 0.11 | 1.36 | 0.08 | 201 |
| Phage-97 | D | F | — | W | — | D | W | E | D | F | F | F | — | A | 0.18 | 1.35 | 0.12 | 202 |
| Phage-98 | F | F | — | — | — | D | G | — | — | T | L | S | — | N | 0.08 | 1.35 | 0.09 | 203 |
| Phage-99 | F | I | — | — | — | — | — | — | — | — | — | A | — | L | 0.14 | 1.35 | 0.09 | 204 |
| Phage-100 | Y | D | — | — | — | — | — | — | — | A | I | — | — | Y | 0.09 | 1.32 | 0.10 | 205 |
| Phage-101 | Y | I | — | W | — | D | W | E | — | Y | L | Y | — | P | 0.10 | 1.32 | 0.15 | 206 |
| Phage-102 | F | D | — | W | — | D | W | E | — | P | T | T | — | H | 0.08 | 1.31 | 0.08 | 207 |
| Phage-103 | Y | D | — | W | — | D | W | E | D | F | P | I | — | D | 0.14 | 1.31 | 0.10 | 208 |
| Phage-104 | — | V | — | W | — | D | W | E | Y | I | D | D | — | S | 0.08 | 1.30 | 0.07 | 209 |
| Phage-105 | I | N | — | W | — | D | W | E | V | I | S | F | — | D | 0.12 | 1.30 | 0.08 | 210 |
| Phage-106 | L | S | — | W | — | D | W | E | — | V | T | P | — | L | 0.10 | 1.29 | 0.10 | 211 |
| Phage-107 | F | A | — | W | — | D | W | E | — | V | D | I | — | Y | 0.09 | 1.28 | 0.08 | 212 |
| Phage-108 | Y | D | — | — | — | — | M | — | — | — | I | V | — | D | 0.10 | 1.25 | 0.08 | 213 |
| Phage-109 | Y | D | — | W | — | D | W | E | V | F | I | V | — | D | 0.06 | 1.25 | 0.07 | 214 |
| Phage-110 | D | N | — | W | — | D | W | E | H | N | F | F | — | V | 0.10 | 1.25 | 0.08 | 215 |
| Phage-111 | Y | D | — | — | — | D | G | — | — | — | I | Y | — | P | 0.07 | 1.23 | 0.08 | 216 |
| Phage-112 | Y | D | — | — | — | — | — | E | F | P | Y | Y | — | F | 0.12 | 1.23 | 0.12 | 217 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-113 | A | D | — | — | — | — | Y | — | — | — | — | P | — | V | 0.11 | 1.22 | 0.09 | 218 |
| Phage-114 | F | L | — | — | — | — | V | E | — | V | H | Y | — | S | 0.08 | 1.22 | 0.10 | 219 |
| Phage-115 | T | D | — | W | — | D | W | E | Y | I | T | S | — | S | 0.08 | 1.22 | 0.08 | 220 |
| Phage-116 | A | F | — | — | — | — | L | — | — | — | I | T | — | D | 0.09 | 1.21 | 0.09 | 221 |
| Phage-117 | N | D | — | W | — | D | W | E | | Y | F | S | — | Y | 0.09 | 1.19 | 0.09 | 222 |
| Phage-118 | F | D | — | — | — | — | W | E | I | V | T | D | — | Y | 0.08 | 1.19 | 0.09 | 223 |
| Phage-119 | N | L | — | — | — | — | M | — | — | — | I | I | — | P | 0.13 | 1.19 | 0.11 | 224 |
| Phage-120 | D | L | — | — | — | — | M | — | — | — | I | Y | — | D | 0.10 | 1.19 | 0.14 | 225 |
| Phage-121 | F | D | — | — | — | D | G | V | — | D | Y | I | — | D | 0.09 | 1.18 | 0.09 | 226 |
| Phage-122 | Y | A | — | W | — | D | W | E | — | D | F | A | — | Y | 0.11 | 1.18 | 0.08 | 227 |
| Phage-123 | H | D | — | — | — | — | M | — | — | — | I | V | — | V | 0.10 | 1.17 | 0.10 | 228 |
| Phage-124 | — | F | — | — | — | — | — | E | F | I | F | L | — | A | 0.07 | 1.17 | 0.08 | 229 |
| Phage-125 | Y | D | — | — | — | — | L | — | — | — | I | L | — | D | 0.08 | 1.16 | 0.09 | 230 |
| Phage-126 | S | V | — | W | — | D | W | E | — | F | Y | S | — | D | 0.11 | 1.16 | 0.10 | 231 |
| Phage-127 | P | | — | — | — | D | G | — | — | T | A | I | — | T | 0.13 | 1.16 | 0.10 | 232 |
| Phage-128 | D | D | — | — | — | — | L | E | W | Y | Y | P | — | Y | 0.09 | 1.16 | 0.08 | 233 |
| Phage-129 | F | I | — | — | — | — | — | — | — | — | L | P | — | N | 0.08 | 1.14 | 0.09 | 234 |
| Phage-130 | I | D | — | — | — | — | — | — | — | — | L | P | — | D | 0.11 | 1.14 | 0.33 | 235 |
| Phage-131 | F | L | — | — | — | — | — | E | — | D | A | P | — | Y | 0.08 | 1.13 | 0.08 | 236 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-132 | I | F | — | — | — | D | G | — | — | T | H | I | — | H | 0.10 | 1.13 | 0.07 | 237 |
| Phage-133 | — | F | — | W | — | D | W | E | Y | I | D | F | — | N | 0.10 | 1.11 | 0.21 | 238 |
| Phage-134 | I | F | — | — | — | — | Y | — | — | — | L | H | — | I | 0.12 | 1.11 | 0.11 | 239 |
| Phage-135 | H | L | — | W | — | D | W | E | W | Y | — | D | — | P | 0.08 | 1.11 | 0.10 | 240 |
| Phage-136 | F | I | — | — | — | — | M | — | — | — | I | A | — | N | 0.08 | 111 | 0.09 | 241 |
| Phage-137 | I | F | — | — | — | — | V | E | M | I | F | L | — | N | 0.09 | 1.10 | 0.08 | 242 |
| Phage-138 | Y | D | — | — | — | — | W | E | F | P | — | D | — | I | 0.11 | 1.09 | 0.11 | 243 |
| Phage-139 | N | L | — | — | — | — | L | — | — | — | I | T | — | F | 0.10 | 1.09 | 0.08 | 244 |
| Phage-140 | F | — | — | — | — | — | V | E | D | F | Y | F | — | Y | 0.08 | 1.09 | 0.08 | 245 |
| Phage-141 | D | — | — | — | — | — | — | — | — | — | L | I | — | N | 0.11 | 1.07 | 0.11 | 246 |
| Phage-142 | D | — | — | — | — | — | — | — | — | — | L | P | — | D | 0.08 | 1.07 | 0.08 | 247 |
| Phage-143 | A | I | — | — | — | — | L | — | — | — | I | A | — | P | 0.09 | 1.07 | 0.09 | 248 |
| Phage-144 | — | I | — | — | — | — | V | E | D | Y | N | L | — | Y | 0.08 | 1.07 | 0.09 | 249 |
| Phage-145 | H | T | — | W | — | D | W | E | D | Y | T | V | — | P | 0.10 | 1.06 | 0.09 | 250 |
| Phage-146 | S | D | — | W | — | D | W | E | Y | F | Y | D | — | N | 0.10 | 1.06 | 0.08 | 251 |
| Phage-147 | — | F | — | — | — | D | G | — | — | T | — | H | — | D | 0.09 | 1.05 | 0.08 | 252 |
| Phage-148 | D | — | — | — | — | — | Y | — | — | — | — | H | — | I | 0.09 | 1.05 | 0.08 | 253 |
| Phage-149 | A | D | — | — | — | D | G | — | — | — | I | I | — | H | 0.07 | 1.05 | 0.08 | 254 |
| Phage-150 | F | — | — | — | — | — | L | — | — | — | L | T | — | V | 0.10 | 1.05 | 0.08 | 255 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA: Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-151 | I | L | — | — | — | — | V | E | — | D | Y | Y | — | Y | 0.11 | 1.04 | 0.09 | 256 |
| Phage-152 | H | L | — | W | — | D | W | E | — | Y | H | S | — | D | 0.09 | 1.04 | 0.09 | 257 |
| Phage-153 | I | F | — | W | — | D | W | E | D | Y | N | F | — | T | 0.08 | 1.04 | 0.11 | 258 |
| Phage-154 | I | V | — | | — | D | G | — | — | T | L | I | — | H | 0.12 | 1.04 | 0.11 | 259 |
| Phage-155 | A | D | — | W | — | D | W | E | W | D | Y | T | — | D | 0.12 | 1.03 | 0.11 | 260 |
| Phage-156 | I | T | — | — | — | — | — | — | — | — | T | T | — | N | 0.20 | 1.02 | 0.21 | 261 |
| Phage-157 | Y | H | — | W | — | D | W | E | — | Y | T | S | — | D | 0.20 | 1.02 | 0.09 | 262 |
| Phage-158 | N | — | — | — | — | — | V | E | — | Y | A | L | — | T | 0.11 | 1.01 | 0.10 | 263 |
| Phage-159 | F | I | — | — | — | — | M | — | — | — | I | H | — | D | 0.15 | 1.00 | 0.19 | 264 |
| Phage-160 | D | N | — | W | — | D | W | E | — | F | A | V | — | P | 0.14 | 1.00 | 0.10 | 265 |
| Phage-161 | Y | D | — | — | — | — | L | — | — | T | — | V | — | D | 0.10 | 1.00 | 0.09 | 266 |
| Phage-162 | Y | D | — | — | — | — | — | — | — | — | I | A | — | Y | 0.08 | 0.99 | 0.08 | 267 |
| Phage-163 | I | D | — | W | — | D | W | E | Y | T | — | H | — | D | 0.07 | 0.97 | 0.09 | 268 |
| Phage-164 | D | D | — | — | — | — | L | — | — | — | I | I | — | I | 0.09 | 0.96 | 0.09 | 269 |
| Phage-165 | — | — | — | — | — | — | Y | — | — | — | S | F | — | F | 0.09 | 0.91 | 0.08 | 270 |
| Phage-166 | F | N | — | W | — | D | W | E | D | P | Y | F | — | V | 0.09 | 0.86 | 0.07 | 271 |
| Phage-167 | Y | D | — | — | — | — | Y | — | — | — | S | Y | — | S | 0.08 | 0.82 | 0.07 | 272 |
| Phage-168 | — | A | — | W | — | D | W | E | Y | T | D | S | — | F | 0.13 | 0.79 | 0.09 | 273 |
| Phage-169 | T | D | — | — | — | — | — | — | — | — | — | A | — | Y | 0.10 | 0.77 | 0.09 | 274 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA: Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-170 | T | D | — | W | — | D | W | E | F | Y | A | D | — | D | 0.07 | 0.75 | 0.08 | 275 |
| Phage-171 | Y | D | — | — | — | — | L | — | — | — | — | I | — | H | 0.09 | 0.69 | 0.09 | 276 |
| Phage-172 | S | D | — | — | — | D | G | — | — | — | I | I | — | T | 0.07 | 0.69 | 0.07 | 277 |
| Phage-173 | Y | — | — | — | — | — | — | — | — | — | I | D | — | D | 0.08 | 0.67 | 0.09 | 278 |
| Phage-174 | F | F | — | — | — | — | I | — | — | — | I | A | — | V | 0.08 | 0.62 | 0.09 | 279 |
| Phage-175 | D | — | — | — | — | — | — | — | — | — | T | F | — | D | 0.16 | 0.60 | 0.10 | 280 |
| Phage-176 | Y | D | — | — | — | — | W | E | W | P | I | D | — | V | 0.10 | 0.59 | 0.10 | 281 |
| Phage-177 | F | — | — | — | — | — | I | E | L | F | S | F | — | Y | 0.13 | 0.59 | 0.11 | 282 |
| Phage-178 | Y | — | — | — | — | — | V | — | — | — | I | T | — | P | 0.15 | 0.42 | 0.11 | 283 |
| Phage-179 | I | L | — | — | — | — | — | — | — | — | I | N | — | N | 0.09 | 0.37 | 0.25 | 284 |
| Phage-180 | — | V | — | — | — | A | M | G | Q | H | Y | L | — | D | 0.08 | 0.09 | 0.08 | 285 |
| Phage-181 | — | V | — | — | — | K | M | G | — | H | Y | L | — | S | 0.08 | 0.08 | 0.08 | 286 |
| Phage-182 | Y | D | — | — | — | D | W | E | Y | V | Y | A | — | Y | 0.08 | 0.98 | 0.08 | 287 |
| Phage-183 | D | L | — | — | — | — | L | — | — | — | — | N | — | D | 0.09 | 0.98 | 0.08 | 288 |
| Phage-184 | Y | — | — | — | — | — | — | — | — | — | T | V | — | Y | 0.14 | 0.97 | 0.16 | 289 |
| Phage-185 | L | D | — | W | — | D | W | E | W | P | Y | s | — | N | 0.08 | 0.96 | 0.09 | 290 |
| Phage-186 | F | I | — | W | — | D | W | E | D | D | F | F | — | Y | 0.08 | 0.96 | 0.09 | 291 |
| Phage-187 | D | L | — | — | — | — | V | E | W | Y | F | F | — | N | 0.11 | 0.95 | 0.10 | 292 |
| Phage-188 | Y | D | — | — | — | — | L | — | — | — | I | V | — | F | 0.07 | 0.94 | 0.08 | 293 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-189 | L | N | — | W | — | V | W | E | D | D | — | F | — | Y | 0.09 | 0.92 | 0.09 | 294 |
| Phage-190 | F | N | — | W | — | D | W | E | D | P | N | F | — | V | 0.09 | 0.91 | 0.09 | 295 |
| Phage-191 | — | I | — | W | — | D | W | E | D | D | Y | F | — | P | 0.10 | 0.91 | 0.13 | 296 |
| Phage-192 | F | L | — | — | — | — | — | — | — | — | S | V | — | Y | 0.10 | 0.91 | 0.08 | 297 |
| Phage-193 | Y | D | — | — | — | — | L | — | — | — | I | F | — | Y | 0.10 | 0.91 | 0.09 | 298 |
| Phage-194 | H | L | — | — | — | D | G | — | — | — | F | T | — | F | 0.11 | 0.90 | 0.10 | 299 |
| Phage-195 | Y | F | — | — | — | — | M | — | — | — | L | Y | — | I | 0.08 | 0.90 | 0.08 | 300 |
| Phage-196 | Y | — | — | — | — | — | V | E | — | Y | A | N | — | Y | 0.07 | 0.90 | 0.07 | 301 |
| Phage-197 | N | T | — | — | — | — | — | — | — | — | T | A | — | Y | 0.16 | 0.90 | 0.58 | 302 |
| Phage-198 | I | D | — | W | — | D | W | E | — | A | F | N | — | Y | 0.09 | 0.90 | 0.08 | 303 |
| Phage-199 | A | — | — | — | — | — | L | E | — | F | F | L | — | T | 0.09 | 0.89 | 0.08 | 304 |
| Phage-200 | I | — | — | — | — | — | V | E | — | V | H | H | — | Y | 0.08 | 0.89 | 0.08 | 305 |
| Phage-201 | F | F | — | — | — | — | — | — | — | — | — | A | — | D | 0.10 | 0.89 | 0.11 | 306 |
| Phage-202 | Y | D | — | — | — | — | L | — | — | T | I | I | — | A | 0.08 | 0.89 | 0.08 | 307 |
| Phage-203 | I | L | — | — | — | — | W | E | Y | P | L | D | — | S | 0.09 | 0.89 | 0.10 | 308 |
| Phage-204 | F | I | — | — | — | — | — | — | — | — | T | T | — | N | 0.09 | 0.88 | 0.10 | 309 |
| Phage-205 | F | — | — | — | — | — | L | — | — | — | — | S | — | D | 0.17 | 0.88 | 0.15 | 310 |
| Phage-206 | H | L | — | — | — | — | L | — | — | — | — | T | — | F | 0.10 | 0.87 | 0.10 | 311 |
| Phage-207 | L | I | — | — | — | — | V | E | D | Y | S | L | — | H | 0.09 | 0.87 | 0.09 | 312 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-208 | Y | F | — | — | — | — | M | — | — | — | — | Y | — | D | 0.08 | 0.87 | 0.08 | 313 |
| Phage-209 | H | — | — | — | — | — | M | — | — | — | I | Y | — | I | 0.13 | 0.87 | 0.09 | 314 |
| Phage-210 | F | D | — | — | — | — | L | — | — | — | I | N | — | D | 0.08 | 0.87 | 0.09 | 315 |
| Phage-211 | Y | — | — | — | — | — | V | E | — | Y | I | Y | — | T | 0.07 | 0.87 | 0.08 | 316 |
| Phage-212 | L | A | — | W | — | V | R | E | — | I | N | A | — | I | 0.08 | 0.85 | 0.07 | 317 |
| Phage-213 | I | D | — | W | — | D | W | E | D | I | T | F | — | D | 0.08 | 0.85 | 0.08 | 318 |
| Phage-214 | I | V | — | | — | — | L | — | — | — | I | T | — | P | 0.11 | 0.85 | 0.15 | 319 |
| Phage-215 | F | — | — | — | — | — | — | E | L | P | A | D | — | D | 0.08 | 0.85 | 0.09 | 320 |
| Phage-216 | F | D | — | — | — | — | — | — | — | — | N | P | — | F | 0.10 | 0.85 | 0.09 | 321 |
| Phage-217 | D | A | — | W | — | D | W | E | — | Y | S | S | — | D | 0.10 | 0.83 | 0.10 | 322 |
| Phage-218 | D | H | — | W | — | D | W | E | P | N | Y | F | — | V | 0.08 | 0.83 | 0.09 | 323 |
| Phage-219 | D | — | — | W | — | D | W | E | I | N | Y | I | — | F | 0.09 | 0.83 | 0.10 | 324 |
| Phage-220 | I | — | — | W | — | D | W | E | Y | V | Y | A | — | N | 0.10 | 0.82 | 0.09 | 325 |
| Phage-221 | D | F | — | — | — | — | V | E | — | D | Y | L | — | D | 0.07 | 0.82 | 0.08 | 326 |
| Phage-222 | H | D | — | — | — | D | G | R | — | D | Y | D | — | A | 0.11 | 0.82 | 0.09 | 327 |
| Phage-223 | L | A | — | W | — | D | W | E | D | D | Y | F | — | V | 0.08 | 0.82 | 0.09 | 328 |
| Phage-224 | D | I | — | W | — | D | W | E | D | Y | L | P | — | V | 0.10 | 0.82 | 0.10 | 329 |
| Phage-225 | I | L | — | — | — | — | I | E | V | Y | A | L | — | P | 0.08 | 0.81 | 0.10 | 330 |
| Phage-226 | I | F | — | — | — | — | W | E | F | — | — | L | — | N | 0.10 | 0.81 | 0.11 | 331 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-227 | T | — | — | — | — | — | V | E | D | F | S | L | — | V | 0.07 | 0.80 | 0.08 | 332 |
| Phage-228 | F | I | — | — | — | — | W | E | F | V | D | A | — | F | 0.11 | 0.80 | 0.09 | 333 |
| Phage-229 | F | A | — | W | — | D | W | E | — | D | S | P | — | D | 0.06 | 0.80 | 0.07 | 334 |
| Phage-230 | I | L | — | — | — | — | V | E | — | L | I | F | — | P | 0.12 | 0.80 | 0.08 | 335 |
| Phage-231 | F | — | — | — | — | — | V | E | — | Y | I | Y | — | Y | 0.08 | 0.80 | 0.08 | 336 |
| Phage-232 | D | S | — | — | — | — | L | — | — | — | I | I | — | D | 0.10 | 0.79 | 0.09 | 337 |
| Phage-233 | F | L | — | — | — | D | G | — | — | T | S | V | — | D | 0.11 | 0.79 | 0.08 | 338 |
| Phage-234 | F | N | — | W | — | N | G | E | P | T | Y | F | — | V | 0.11 | 0.79 | 0.08 | 339 |
| Phage-235 | L | A | — | W | — | V | W | E | Y | P | — | T | — | I | 0.09 | 0.78 | 0.09 | 340 |
| Phage-236 | D | — | — | — | — | — | V | E | — | D | — | Y | — | Y | 0.09 | 0.78 | 0.09 | 341 |
| Phage-237 | I | T | — | W | — | D | W | E | — | Y | A | N | — | T | 0.08 | 0.77 | 0.07 | 342 |
| Phage-238 | F | F | — | — | — | D | G | — | — | T | Y | S | — | I | 0.15 | 0.77 | 0.13 | 343 |
| Phage-239 | T | D | — | W | — | D | W | E | Y | A | T | S | — | D | 0.09 | 0.76 | 0.09 | 344 |
| Phage-240 | F | N | — | — | — | D | G | Y | — | D | Y | L | — | D | 0.10 | 0.76 | 0.11 | 345 |
| Phage-241 | Y | D | — | W | — | D | W | E | V | D | F | H | — | P | 0.11 | 0.76 | 0.08 | 346 |
| Phage-242 | N | I | — | W | — | D | W | E | D | D | S | F | — | F | 0.08 | 0.76 | 0.08 | 347 |
| Phage-243 | A | T | — | — | — | — | — | — | — | — | I | — | — | S | 0.13 | 0.75 | 0.09 | 348 |
| Phage-244 | S | — | — | — | — | — | — | — | — | — | T | F | — | D | 0.10 | 0.74 | 0.09 | 349 |
| Phage-245 | P | I | — | — | — | — | Y | — | — | — | D | V | — | A | 0.08 | 0.74 | 0.08 | 350 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-246 | Y | — | — | — | — | D | G | — | — | Y | N | S | — | I | 0.11 | 0.74 | 0.11 | 351 |
| Phage-247 | — | D | — | W | — | D | W | E | V | F | I | A | — | D | 0.11 | 0.74 | 0.10 | 352 |
| Phage-248 | D | L | — | — | — | — | V | E | — | V | N | L | — | L | 0.12 | 0.74 | 0.10 | 353 |
| Phage-249 | F | D | — | — | — | — | M | — | — | — | T | T | — | F | 0.09 | 0.74 | 0.09 | 354 |
| Phage-250 | N | F | — | W | — | D | W | E | — | I | Y | F | — | T | 0.13 | 0.74 | 0.14 | 355 |
| Phage-251 | — | D | — | — | — | D | G | — | — | — | F | F | — | L | 0.08 | 0.73 | 0.08 | 356 |
| Phage-252 | — | D | — | — | — | D | G | — | — | T | A | F | — | I | 0.10 | 0.73 | 0.09 | 357 |
| Phage-253 | N | I | — | — | — | — | M | — | — | — | L | V | — | I | 0.10 | 0.73 | 0.09 | 358 |
| Phage-254 | I | I | — | — | — | — | — | — | — | — | F | F | — | F | 0.08 | 0.73 | 0.09 | 359 |
| Phage-255 | N | F | — | — | — | — | Y | — | — | — | I | S | — | I | 0.10 | 0.73 | 0.38 | 360 |
| Phage-256 | H | L | — | — | — | — | I | E | — | A | D | I | — | N | 0.11 | 0.73 | 0.51 | 361 |
| Phage-257 | D | — | — | — | — | — | V | E | — | D | Y | L | — | D | 0.08 | 0.72 | 0.09 | 362 |
| Phage-258 | D | — | — | — | — | — | L | — | — | — | I | N | — | D | 0.11 | 0.72 | 0.10 | 363 |
| Phage-259 | F | — | — | — | — | — | L | — | — | — | L | F | — | V | 0.09 | 0.72 | 0.08 | 364 |
| Phage-260 | P | D | — | — | — | — | W | E | F | Y | — | T | — | N | 0.12 | 0.72 | 0.08 | 365 |
| Phage-261 | F | D | — | — | — | — | — | E | Y | I | Y | A | — | T | 0.09 | 0.72 | 0.08 | 366 |
| Phage-262 | D | — | — | — | — | — | — | — | — | — | S | I | — | N | 0.12 | 0.72 | 0.11 | 367 |
| Phage-263 | D | F | — | — | — | — | V | E | — | Y | I | F | — | F | 0.08 | 0.72 | 0.07 | 368 |
| Phage-264 | P | V | — | W | — | D | W | E | — | V | S | S | — | D | 0.08 | 0.71 | 0.08 | 369 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-265 | Y | I | — | — | — | — | R | — | — | — | N | L | — | L | 0.09 | 0.71 | 0.09 | 370 |
| Phage-266 | Y | D | — | — | — | — | L | — | — | — | I | V | — | D | 0.11 | 0.71 | 0.11 | 371 |
| Phage-267 | H | D | — | W | — | D | W | E | D | F | Y | F | — | V | 0.09 | 0.71 | 0.08 | 372 |
| Phage-268 | H | — | — | — | — | — | Y | — | — | — | I | D | — | Y | 0.12 | 0.71 | 0.10 | 373 |
| Phage-269 | L | F | — | — | — | — | M | P | — | D | I | F | — | N | 0.08 | 0.71 | 0.08 | 374 |
| Phage-270 | H | D | — | — | — | — | L | E | — | H | Y | A | — | Y | 0.10 | 0.71 | 0.12 | 375 |
| Phage-271 | D | F | — | — | — | — | L | — | — | — | I | N | — | F | 0.08 | 0.70 | 0.08 | 376 |
| Phage-272 | Y | F | — | — | — | — | L | — | — | — | I | A | — | N | 0.10 | 0.70 | 0.10 | 377 |
| Phage-273 | T | D | — | W | — | D | W | E | D | D | I | I | — | D | 0.10 | 0.70 | 0.08 | 378 |
| Phage-274 | Y | D | — | — | — | — | L | — | — | — | I | Y | — | F | 0.09 | 0.70 | 0.08 | 379 |
| Phage-275 | Y | — | — | W | — | D | W | W | — | Y | — | T | — | D | 0.10 | 0.70 | 0.11 | 380 |
| Phage-276 | P | I | — | — | — | — | L | E | — | — | Y | L | — | N | 0.13 | 0.69 | 0.52 | 381 |
| Phage-277 | F | D | — | — | — | — | — | — | — | — | I | V | — | Y | 0.12 | 0.69 | 0.11 | 382 |
| Phage-278 | — | L | — | — | — | D | G | I | — | F | F | D | — | P | 0.09 | 0.68 | 0.07 | 383 |
| Phage-279 | A | — | — | — | — | — | Y | — | — | — | L | T | — | V | 0.07 | 0.68 | 0.07 | 384 |
| Phage-280 | D | F | — | — | — | — | L | — | — | — | I | I | — | A | 0.14 | 0.68 | 0.14 | 385 |
| Phage-281 | Y | D | — | — | — | — | — | — | — | — | L | D | — | N | 0.08 | 0.68 | 0.08 | 386 |
| Phage-282 | A | I | — | — | — | — | — | — | — | — | — | A | — | D | 0.14 | 0.67 | 0.08 | 387 |
| Phage-283 | L | L | — | — | — | D | G | V | — | D | F | F | — | D | 0.10 | 0.67 | 0.10 | 388 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-284 | N | F | — | — | — | — | L | P | — | D | I | F | — | F | 0.12 | 0.66 | 0.13 | 389 |
| Phage-285 | F | — | — | — | — | — | V | E | — | V | S | L | — | N | 0.08 | 0.66 | 0.08 | 390 |
| Phage-286 | Y | D | — | — | — | D | G | Y | — | A | F | Y | — | H | 0.12 | 0.66 | 0.10 | 391 |
| Phage-287 | N | F | — | — | — | — | I | E | — | D | Y | L | — | D | 0.08 | 0.65 | 0.08 | 392 |
| Phage-288 | D | — | — | — | — | D | G | V | — | D | F | I | — | N | 0.06 | 0.65 | 0.08 | 393 |
| Phage-289 | T | D | — | W | | D | W | E | Y | I | Y | S | — | S | 0.08 | 0.65 | 0.07 | 394 |
| Phage-290 | F | — | — | — | — | — | — | E | — | I | T | N | — | I | 0.14 | 0.65 | 0.11 | 395 |
| Phage-291 | F | D | — | W | — | D | W | E | — | — | F | F | — | H | 0.07 | 0.64 | 0.08 | 396 |
| Phage-292 | D | F | — | — | — | D | G | — | — | — | — | F | — | P | 0.08 | 0.63 | 0.08 | 397 |
| Phage-293 | H | N | — | — | — | — | L | — | — | — | L | V | — | D | 0.13 | 0.63 | 0.09 | 398 |
| Phage-294 | I | — | — | — | — | D | G | A | — | D | Y | T | — | D | 0.07 | 0.63 | 0.07 | 399 |
| Phage-295 | F | D | — | — | — | — | — | E | — | P | — | I | — | F | 0.08 | 0.62 | 0.08 | 400 |
| Phage-296 | Y | N | — | — | — | — | L | — | — | — | — | T | — | D | 0.09 | 0.62 | 0.08 | 401 |
| Phage-297 | F | D | — | — | — | — | L | — | — | — | I | H | — | A | 0.07 | 0.62 | 0.08 | 402 |
| Phage-298 | D | I | — | — | — | — | V | E | — | Y | F | L | — | F | 0.15 | 0.61 | 0.10 | 403 |
| Phage-299 | F | D | — | — | — | — | V | — | — | — | L | T | — | F | 0.10 | 0.61 | 0.09 | 404 |
| Phage-300 | F | D | — | — | — | — | I | E | — | F | H | L | — | F | 0.08 | 0.61 | 0.08 | 405 |
| Phage-301 | A | — | — | — | — | — | L | — | — | — | I | I | — | D | 0.12 | 0.61 | 0.10 | 406 |
| Phage-302 | Y | N | — | — | — | — | L | — | — | — | I | T | — | N | 0.09 | 0.61 | 0.10 | 407 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-303 | F | D | — | W | | D | W | E | — | P | — | D | — | L | 0.08 | 0.61 | 0.07 | 408 |
| Phage-304 | D | V | — | — | — | — | L | — | — | — | — | L | — | P | 0.08 | 0.60 | 0.08 | 409 |
| Phage-305 | N | — | — | — | — | — | L | — | — | — | L | P | — | P | 0.09 | 0.60 | 0.08 | 410 |
| Phage-306 | Y | — | — | W | — | D | W | E | Y | D | I | F | — | S | 0.08 | 0.60 | 0.10 | 411 |
| Phage-307 | D | D | — | — | — | — | — | — | — | — | T | Y | — | N | 0.08 | 0.60 | 0.09 | 412 |
| Phage-308 | F | — | — | — | — | — | — | E | — | V | F | H | — | Y | 0.09 | 0.60 | 0.09 | 413 |
| Phage-309 | T | D | — | W | — | D | W | E | — | Y | F | L | — | D | 0.07 | 0.60 | 0.09 | 414 |
| Phage-310 | — | — | — | — | — | — | W | E | — | — | Y | L | — | P | 0.09 | 0.60 | 0.09 | 415 |
| Phage-311 | D | D | — | — | — | N | G | Y | A | T | F | I | — | Y | 0.06 | 0.59 | 0.08 | 416 |
| Phage-312 | F | L | — | — | — | — | I | E | D | D | T | H | — | Y | 0.16 | 0.59 | 0.38 | 417 |
| Phage-313 | F | A | — | W | — | D | W | E | — | T | I | P | — | H | 0.08 | 0.59 | 0.08 | 418 |
| Phage-314 | — | L | — | — | — | — | — | — | — | — | Y | N | — | Y | 0.10 | 0.58 | 0.08 | 419 |
| Phage-315 | Y | D | — | — | — | — | — | — | — | — | I | S | — | I | 0.09 | 0.58 | 0.09 | 420 |
| Phage-316 | Y | D | — | — | — | — | — | — | — | — | — | N | — | Y | 0.12 | 0.57 | 0.10 | 421 |
| Phage-317 | A | I | — | W | — | D | W | E | — | F | | D | — | Y | 0.10 | 0.57 | 0.09 | 422 |
| Phage-318 | L | T | — | W | — | V | R | E | — | I | F | A | — | D | 0.07 | 0.57 | 0.08 | 423 |
| Phage-319 | — | L | — | — | — | — | — | — | — | — | Y | Y | — | N | 0.09 | 0.57 | 0.09 | 424 |
| Phage-320 | N | V | — | — | — | — | Y | — | — | — | A | P | — | N | 0.07 | 0.56 | 0.08 | 425 |
| Phage-321 | H | D | — | — | — | — | — | — | — | — | I | S | — | V | 0.11 | 0.55 | 0.09 | 426 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34.185 scFv | Sp34.185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-322 | F | D | — | — | — | — | L | — | — | T | — | D | — | N | 0.12 | 0.55 | 0.41 | 427 |
| Phage-323 | Y | F | — | — | — | — | V | E | — | H | F | Y | — | Y | 0.09 | 0.55 | 0.08 | 428 |
| Phage-324 | D | — | — | — | — | — | L | — | — | — | I | I | — | H | 0.09 | 0.54 | 0.09 | 429 |
| Phage-325 | D | D | — | — | — | — | V | P | — | D | I | T | — | Y | 0.11 | 0.54 | 0.08 | 430 |
| Phage-326 | D | N | — | — | — | — | L | — | — | — | — | V | — | D | 0.10 | 0.54 | 0.08 | 431 |
| Phage-327 | — | H | — | W | — | D | W | E | — | N | Y | V | — | D | 0.10 | 0.54 | 0.08 | 432 |
| Phage-328 | D | — | — | — | — | — | L | — | — | — | L | F | — | L | 0.09 | 0.53 | 0.09 | 433 |
| Phage-329 | D | D | — | — | — | — | L | — | — | — | — | V | — | A | 0.08 | 0.53 | 0.11 | 434 |
| Phage-330 | A | A | — | — | — | — | L | — | — | — | I | V | — | D | 0.13 | 0.53 | 0.09 | 435 |
| Phage-331 | D | F | — | — | — | — | — | E | — | I | N | N | — | F | 0.14 | 0.52 | 0.48 | 436 |
| Phage-332 | Y | — | — | — | — | — | — | — | — | — | N | A | — | Y | 0.08 | 0.52 | 0.07 | 437 |
| Phage-333 | — | L | — | — | — | — | — | — | — | — | N | S | — | Y | 0.10 | 0.52 | 0.11 | 438 |
| Phage-334 | Y | D | — | — | — | — | — | — | — | — | I | D | — | D | 0.09 | 0.52 | 0.09 | 439 |
| Phage-335 | D | S | — | — | — | — | — | E | F | Y | Y | V | — | F | O.U | 0.52 | 0.14 | 440 |
| Phage-336 | Y | I | — | — | — | — | L | — | — | — | L | I | — | H | 0.10 | 0.52 | 0.08 | 441 |
| Phage-337 | F | D | — | — | — | — | V | E | — | D | Y | F | — | Y | 0.11 | 0.52 | 0.10 | 442 |
| Phage-338 | F | D | — | — | — | — | Y | — | — | — | L | Y | — | F | 0.08 | 0.52 | 0.07 | 443 |
| Phage-339 | — | L | — | — | — | D | G | — | — | Y | S | F | — | H | 0.10 | 0.51 | 0.10 | 444 |
| Phage-340 | I | P | — | — | — | — | M | — | — | — | — | V | — | N | 0.12 | 0.51 | 0.09 | 445 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-341 | I | I | — | — | — | D | G | Y | — | D | F | T | — | D | 0.12 | 0.51 | 0.09 | 446 |
| Phage-342 | I | F | — | — | — | — | L | — | — | — | I | I | — | Y | 0.11 | 0.51 | 0.08 | 447 |
| Phage-343 | — | D | — | — | — | — | — | — | — | — | Y | D | — | Y | 0.18 | 0.51 | 0.18 | 448 |
| Phage-344 | L | S | — | — | — | — | M | — | — | — | L | Y | — | D | 0.12 | 0.51 | 0.08 | 449 |
| Phage-345 | Y | D | — | W | — | D | W | E | Y | N | I | D | — | T | 0.08 | 0.51 | 0.09 | 450 |
| Phage-346 | N | H | — | — | — | D | G | — | — | T | I | V | — | F | 0.09 | 0.51 | 0.08 | 451 |
| Phage-347 | N | F | — | — | — | — | L | — | — | — | I | P | — | H | 0.11 | 0.50 | 0.12 | 452 |
| Phage-348 | F | H | — | — | — | — | I | E | — | Y | A | L | — | D | 0.08 | 0.50 | 0.09 | 453 |
| Phage-349 | — | — | — | — | — | — | V | E | D | Y | N | L | — | Y | 0.07 | 0.50 | 0.08 | 454 |
| Phage-350 | — | — | — | — | — | D | G | — | — | L | A | N | — | Y | 0.09 | 0.50 | 0.08 | 455 |
| Phage-351 | L | I | — | — | — | V | I | A | — | D | L | P | — | N | 0.17 | 0.50 | 0.26 | 456 |
| Phage-352 | D | I | — | — | — | — | I | P | — | D | — | S | — | D | 0.10 | 0.50 | 0.08 | 457 |
| Phage-353 | I | — | — | — | — | — | W | E | — | A | D | Y | — | D | 0.11 | 0.50 | 0.45 | 458 |
| Phage-354 | I | D | — | W | — | D | W | E | D | D | S | I | — | Y | 0.10 | 0.50 | 0.10 | 459 |
| Phage-355 | — | L | — | — | — | — | V | E | D | F | T | L | — | D | 0.09 | 0.50 | 0.11 | 460 |
| Phage-356 | L | — | — | — | — | V | I | E | — | I | Y | Y | — | Y | 0.09 | 0.49 | 0.09 | 461 |
| Phage-357 | F | F | — | — | — | — | — | E | V | H | S | D | — | N | 0.14 | 0.49 | 0.38 | 462 |
| Phage-358 | N | D | — | — | — | — | V | E | L | V | S | D | — | N | 0.10 | 0.49 | 0.08 | 463 |
| Phage-359 | D | L | — | — | — | — | L | — | — | — | T | V | — | D | 0.09 | 0.49 | 0.08 | 464 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-360 | I | P | — | — | — | — | V | E | D | Y | N | L | — | N | 0.08 | 0.49 | 0.08 | 465 |
| Phage-361 | Y | — | — | — | — | — | L | E | W | P | | V | — | N | 0.10 | 0.49 | 0.10 | 466 |
| Phage-362 | Y | D | — | — | — | — | L | — | — | — | — | I | — | N | 0.08 | 0.49 | 0.10 | 467 |
| Phage-363 | — | — | — | — | — | D | G | — | — | — | F | D | — | A | 0.08 | 0.49 | 0.08 | 468 |
| Phage-364 | N | D | — | — | — | — | W | E | D | T | Y | F | — | L | 0.08 | 0.49 | 0.10 | 469 |
| Phage-365 | P | | — | — | — | — | M | E | — | L | S | N | — | S | 0.13 | 0.48 | 0.16 | 470 |
| Phage-366 | D | D | — | — | — | — | — | E | V | I | S | D | — | Y | 0.15 | 0.48 | 0.10 | 471 |
| Phage-367 | D | L | — | — | — | — | — | P | — | D | — | P | — | D | 0.08 | 0.48 | 0.08 | 472 |
| Phage-368 | I | — | — | — | — | — | — | — | — | — | F | V | — | Y | 0.11 | 0.48 | 0.10 | 473 |
| Phage-369 | A | — | — | — | — | — | Y | E | V | F | A | D | — | N | 0.10 | 0.48 | 0.11 | 474 |
| Phage-370 | I | D | — | — | — | — | Y | — | — | — | — | D | — | L | 0.09 | 0.48 | 0.09 | 475 |
| Phage-371 | H | I | — | W | — | D | W | E | — | F | H | D | — | N | 0.07 | 0.48 | 0.08 | 476 |
| Phage-372 | Y | D | — | — | — | — | L | — | — | T | I | T | — | L | 0.08 | 0.48 | 0.08 | 477 |
| Phage-373 | Y | L | — | — | — | — | L | — | — | T | I | L | — | N | 0.09 | 0.48 | 0.08 | 478 |
| Phage-374 | F | F | — | — | — | — | — | E | | A | F | L | — | F | 0.10 | 0.48 | 0.14 | 479 |
| Phage-375 | I | L | — | — | — | — | L | — | — | — | F | T | — | A | 0.07 | 0.47 | 0.08 | 480 |
| Phage-376 | F | H | — | — | — | — | V | E | L | Y | T | D | — | N | 0.09 | 0.47 | 0.08 | 481 |
| Phage-377 | N | L | — | — | — | — | V | E | — | Y | N | F | — | Y | 0.08 | 0.47 | 0.08 | 482 |
| Phage-378 | F | D | — | — | — | — | V | E | — | T | Y | Y | — | F | 0.21 | 0.47 | 0.09 | 483 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-379 | — | F | — | — | — | — | — | E | — | D | H | Y | — | Y | 0.12 | 0.47 | 0.37 | 484 |
| Phage-380 | A | I | — | — | — | — | W | E | V | V | A | D | — | N | 0.11 | 0.47 | 0.11 | 485 |
| Phage-381 | F | I | — | W | — | D | W | E | — | D | N | Y | — | N | 0.12 | 0.47 | 0.25 | 486 |
| Phage-382 | I | — | — | — | — | — | — | — | — | — | F | I | — | D | 0.08 | 0.47 | 0.10 | 487 |
| Phage-383 | N | L | — | — | — | — | V | E | D | V | Y | D | — | H | 0.12 | 0.47 | 0.43 | 488 |
| Phage-384 | H | — | — | — | — | — | V | E | — | Y | H | N | — | N | 0.09 | 0.47 | 0.09 | 489 |
| Phage-385 | D | I | — | — | — | — | Y | — | — | — | Y | S | — | T | 0.09 | 0.47 | 0.09 | 490 |
| Phage-386 | D | — | — | — | — | — | L | — | — | T | L | I | — | A | 0.13 | 0.46 | 0.10 | 491 |
| Phage-387 | I | A | — | — | — | — | M | P | — | D | I | D | — | Y | 0.12 | 0.46 | 0.09 | 492 |
| Phage-388 | I | D | — | — | — | — | L | — | — | — | I | F | — | D | 0.10 | 0.46 | 0.10 | 493 |
| Phage-389 | Y | F | — | — | — | D | V | E | — | D | F | A | — | D | 0.11 | 0.46 | 0.11 | 494 |
| Phage-390 | Y | N | — | — | — | — | W | E | Y | A | I | L | — | D | 0.12 | 0.46 | 0.34 | 495 |
| Phage-391 | I | | — | — | — | — | V | E | D | Y | I | V | — | N | 0.14 | 0.46 | 0.22 | 496 |
| Phage-392 | Y | D | — | — | — | — | I | — | — | — | T | P | — | A | 0.07 | 0.46 | 0.07 | 497 |
| Phage-393 | D | T | — | W | — | D | W | E | H | I | Y | A | — | D | 0.09 | 0.46 | 0.09 | 498 |
| Phage-394 | D | I | — | — | — | — | M | — | — | — | — | T | — | N | 0.13 | 0.45 | 0.12 | 499 |
| Phage-395 | Y | D | — | W | | D | W | E | R | Y | F | P | — | I | 0.10 | 0.45 | 0.09 | 500 |
| Phage-396 | H | L | — | — | — | — | L | — | — | — | — | A | — | S | 0.13 | 0.45 | 0.11 | 501 |
| Phage-397 | Y | D | — | — | — | D | G | — | — | T | T | I | — | A | 0.09 | 0.45 | 0.09 | 502 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-398 | Y | — | — | — | — | — | Y | E | D | V | L | D | — | F | 0.07 | 0.45 | 0.08 | 503 |
| Phage-399 | D | F | — | — | — | — | M | — | — | T | I | S | — | D | 0.14 | 0.45 | 0.10 | 504 |
| Phage-400 | I | L | — | — | — | — | L | — | — | — | L | V | — | D | 0.08 | 0.44 | 0.07 | 505 |
| Phage-401 | L | I | — | — | — | — | W | E | V | I | T | N | — | D | 0.12 | 0.44 | 0.40 | 506 |
| Phage-402 | Y | D | — | — | — | — | — | — | — | Y | F | | — | P | 0.09 | 0.44 | 0.09 | 507 |
| Phage-403 | A | L | — | — | — | — | V | E | V | Y | D | V | — | V | 0.08 | 0.44 | 0.08 | 508 |
| Phage-404 | Y | H | — | W | — | D | W | E | D | V | N | F | — | Y | 0.10 | 0.44 | 0.09 | 509 |
| Phage-405 | F | L | — | — | — | M | G | G | L | T | F | Y | — | Y | 0.09 | 0.44 | 0.08 | 510 |
| Phage-406 | I | I | — | — | — | — | — | — | — | Y | — | — | — | F | 0.09 | 0.43 | 0.19 | 511 |
| Phage-407 | F | F | — | — | — | — | M | — | — | — | — | H | — | F | 0.11 | 0.43 | 0.09 | 512 |
| Phage-408 | A | F | — | — | — | — | — | — | — | — | L | F | — | A | 0.09 | 0.43 | 0.09 | 513 |
| Phage-409 | N | — | — | — | — | D | G | — | — | T | N | I | — | D | 0.08 | 0.43 | 0.08 | 514 |
| Phage-410 | Y | L | — | — | — | — | W | E | W | V | H | N | — | L | 0.13 | 0.43 | 0.09 | 515 |
| Phage-411 | A | T | — | — | — | D | G | — | — | — | H | I | — | A | 0.08 | 0.43 | 0.09 | 516 |
| Phage-412 | | | — | — | — | — | V | E | V | L | D | Y | — | D | 0.07 | 0.42 | 0.08 | 517 |
| Phage-413 | I | H | — | — | — | — | W | E | F | Y | T | D | — | D | 0.08 | 0.42 | 0.08 | 518 |
| Phage-414 | D | D | — | — | — | — | L | — | — | T | — | A | — | D | 0.13 | 0.42 | 0.32 | 519 |
| Phage-415 | Y | L | — | — | — | — | — | — | — | — | I | D | — | N | 0.11 | 0.42 | 0.17 | 520 |
| Phage-416 | L | L | — | — | — | — | V | E | D | V | F | A | — | Y | 0.09 | 0.42 | 0.09 | 521 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-417 | Y | D | — | — | — | — | L | — | — | — | L | T | — | D | 0.08 | 0.42 | 0.08 | 522 |
| Phage-418 | F | D | — | — | — | — | L | — | — | T | — | N | — | Y | 0.09 | 0.41 | 0.09 | 523 |
| Phage-419 | F | A | — | W | — | D | W | E | — | I | N | D | — | H | 0.08 | 0.41 | 0.09 | 524 |
| Phage-420 | Y | — | — | — | — | — | Y | E | — | D | I | Y | — | N | 0.09 | 0.41 | 0.09 | 525 |
| Phage-421 | N | V | — | — | — | — | V | E | D | Y | T | F | — | Y | 0.09 | 0.40 | 0.08 | 526 |
| Phage-422 | A | — | — | — | — | — | L | E | — | Y | D | F | — | T | 0.12 | 0.40 | 0.08 | 527 |
| Phage-423 | F | D | — | — | — | — | I | — | — | — | T | I | — | T | 0.08 | 0.40 | 0.09 | 528 |
| Phage-424 | N | L | — | — | — | — | L | — | — | T | L | V | — | A | 0.10 | 0.40 | 0.09 | 529 |
| Phage-425 | Y | S | — | W | — | D | W | E | — | Y | L | A | — | N | 0.08 | 0.40 | 0.08 | 530 |
| Phage-426 | G | I | — | — | — | — | V | E | D | Y | N | Y | — | D | 0.09 | 0.40 | 0.10 | 531 |
| Phage-427 | F | F | — | — | — | — | L | — | — | — | — | N | — | H | 0.07 | 0.40 | 0.07 | 532 |
| Phage-428 | Y | — | — | — | — | — | Y | E | — | D | F | Y | — | F | 0.11 | 0.40 | 0.09 | 533 |
| Phage-429 | L | — | — | — | — | — | Y | — | — | — | T | D | — | Y | 0.11 | 0.40 | 0.10 | 534 |
| Phage-430 | D | — | — | — | — | — | V | E | — | D | F | L | — | Y | 0.10 | 0.40 | 0.08 | 535 |
| Phage-431 | T | L | — | — | — | — | V | E | L | Y | I | F | — | D | 0.08 | 0.40 | 0.09 | 536 |
| Phage-432 | F | — | — | — | — | — | — | E | D | I | A | D | — | Y | 0.11 | 0.40 | 0.09 | 537 |
| Phage-433 | D | D | — | — | — | — | V | E | — | Y | H | L | — | D | O.U | 0.40 | 0.18 | 538 |
| Phage-434 | D | — | — | — | — | — | L | E | D | V | T | L | — | H | 0.13 | 0.39 | 0.09 | 539 |
| Phage-435 | — | L | — | — | — | — | V | E | D | V | N | L | — | Y | 0.09 | 0.39 | 0.08 | 540 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-436 | D | I | — | — | — | — | L | — | — | T | I | D | — | Y | 0.09 | 0.39 | 0.09 | 541 |
| Phage-437 | T | — | — | — | — | — | V | E | — | D | I | N | — | Y | 0.08 | 0.39 | 0.08 | 542 |
| Phage-438 | I | V | — | W | — | D | W | E | — | Y | P | N | — | D | 0.08 | 0.39 | 0.08 | 543 |
| Phage-439 | S | D | — | — | — | — | L | — | — | — | I | I | — | T | 0.11 | 0.39 | 0.10 | 544 |
| Phage-440 | Y | D | — | — | — | — | L | P | — | D | Y | D | — | N | 0.15 | 0.39 | 0.10 | 545 |
| Phage-441 | N | L | — | W | | D | W | E | — | Y | Y | A | — | D | 0.12 | 0.39 | 0.17 | 546 |
| Phage-442 | D | D | — | — | — | — | L | — | — | | L | P | — | H | 0.10 | 0.39 | 0.08 | 547 |
| Phage-443 | S | L | — | — | — | D | G | Q | — | D | Y | T | — | F | 0.08 | 0.39 | 0.08 | 548 |
| Phage-444 | L | I | — | W | — | D | W | E | — | Y | N | F | — | T | 0.13 | 0.39 | 0.11 | 549 |
| Phage-445 | F | H | — | — | — | D | G | — | — | T | | P | — | I | 0.08 | 0.39 | 0.08 | 550 |
| Phage-446 | F | D | — | — | — | — | W | E | W | I | Y | D | — | F | 0.08 | 0.38 | 0.08 | 551 |
| Phage-447 | I | — | — | — | — | — | W | — | — | — | L | D | — | D | 0.08 | 0.38 | 0.09 | 552 |
| Phage-448 | L | I | — | — | — | — | I | — | — | — | A | S | — | N | 0.10 | 0.38 | 0.11 | 553 |
| Phage-449 | T | S | — | W | V | D | W | E | — | F | S | D | — | I | 0.11 | 0.38 | 0.34 | 554 |
| Phage-450 | Y | — | — | — | — | — | V | E | — | D | Y | V | — | D | 0.10 | 0.38 | 0.08 | 555 |
| Phage-451 | D | D | — | — | — | — | Q | E | F | I | Y | A | — | I | 0.09 | 0.38 | 0.08 | 556 |
| Phage-452 | A | D | — | W | | D | W | E | — | Y | A | D | — | Y | 0.11 | 0.38 | 0.10 | 557 |
| Phage-453 | Y | — | — | — | — | — | — | — | — | — | I | H | — | I | 0.08 | 0.38 | 0.07 | 558 |
| Phage-454 | S | E | — | W | — | D | W | E | P | F | F | D | — | N | 0.08 | 0.37 | 0.09 | 559 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-455 | Y | H | — | — | — | — | M | — | — | — | L | I | — | T | 0.07 | 0.37 | 0.07 | 560 |
| Phage-456 | S | D | — | W | — | D | W | E | D | A | Y | F | — | I | 0.09 | 0.37 | 0.07 | 561 |
| Phage-457 | — | D | — | — | — | — | V | E | — | Y | Y | H | — | D | 0.08 | 0.37 | 0.08 | 562 |
| Phage-458 | D | N | — | — | — | — | Y | — | — | — | I | A | — | N | 0.10 | 0.37 | 0.10 | 563 |
| Phage-459 | L | — | — | — | — | V | — | E | F | Y | D | Y | — | Y | 0.08 | 0.37 | 0.10 | 564 |
| Phage-460 | Y | T | — | — | — | — | M | — | — | — | — | T | — | I | 0.09 | 0.37 | 0.08 | 565 |
| Phage-461 | N | F | — | W | — | D | W | E | V | N | S | F | — | D | 0.09 | 0.37 | 0.08 | 566 |
| Phage-462 | N | A | — | W | — | D | W | E | Y | I | D | F | — | N | 0.12 | 0.36 | 0.09 | 567 |
| Phage-463 | Y | N | — | — | — | — | M | — | — | — | I | F | — | S | 0.09 | 0.36 | 0.07 | 568 |
| Phage-464 | L | D | — | — | — | — | L | — | — | — | I | T | — | Y | 0.08 | 0.36 | 0.09 | 569 |
| Phage-465 | H | — | — | — | — | — | — | — | — | — | I | N | — | D | 0.11 | 0.36 | 0.08 | 570 |
| Phage-466 | I | I | — | — | — | — | L | P | — | D | Y | V | — | T | 0.08 | 0.36 | 0.08 | 571 |
| Phage-467 | D | I | — | — | — | — | — | — | — | — | I | D | — | S | 0.08 | 0.36 | 0.08 | 572 |
| Phage-468 | P | — | — | — | — | — | — | — | — | — | — | L | — | F | 0.10 | 0.36 | 0.09 | 573 |
| Phage-469 | — | F | — | — | — | — | — | — | — | — | — | D | — | Y | 0.07 | 0.36 | 0.08 | 574 |
| Phage-470 | Y | D | — | W | — | D | W | E | — | A | L | P | — | A | 0.08 | 0.36 | 0.08 | 575 |
| Phage-471 | D | D | — | W | — | D | W | E | D | Y | — | F | — | F | 0.10 | 0.36 | 0.10 | 576 |
| Phage-472 | H | F | — | — | — | — | W | E | L | F | S | D | — | Y | 0.11 | 0.36 | 0.11 | 577 |
| Phage-473 | I | T | — | W | — | D | W | E | V | N | F | P | — | Y | 0.07 | 0.35 | 0.07 | 578 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-474 | P | D | — | — | — | — | L | — | — | — | I | T | — | N | 0.20 | 0.35 | 0.16 | 579 |
| Phage-475 | N | L | — | W | — | D | W | E | A | F | F | P | — | Y | 0.08 | 0.35 | 0.07 | 580 |
| Phage-476 | F | — | — | — | — | — | — | E | Y | I | R | D | — | Y | 0.08 | 0.35 | 0.07 | 581 |
| Phage-477 | F | F | — | — | — | — | — | — | — | — | I | I | — | D | 0.09 | 0.35 | 0.10 | 582 |
| Phage-478 | — | L | — | — | — | K | G | G | P | T | Y | N | — | S | 0.08 | 0.35 | 0.10 | 583 |
| Phage-479 | L | A | — | W | — | V | W | E | — | P | G | H | — | D | 0.11 | 0.35 | 0.10 | 584 |
| Phage-480 | D | — | — | — | — | — | V | E | D | V | N | D | — | Y | 0.07 | 0.35 | 0.08 | 585 |
| Phage-481 | D | — | — | — | — | — | — | E | — | A | H | Y | — | N | 0.08 | 0.35 | 0.07 | 586 |
| Phage-482 | — | L | — | — | — | — | L | — | — | T | L | T | — | I | 0.08 | 0.35 | 0.07 | 587 |
| Phage-483 | Y | — | — | — | — | — | I | E | D | Y | N | L | — | N | 0.10 | 0.34 | 0.09 | 588 |
| Phage-484 | Y | I | — | — | — | — | V | E | — | Y | Y | N | — | F | 0.13 | 0.34 | 0.14 | 589 |
| Phage-485 | D | I | — | — | — | — | L | — | — | — | I | F | — | F | 0.08 | 0.34 | 0.09 | 590 |
| Phage-486 | D | I | — | — | — | — | V | E | — | D | Y | L | — | Y | 0.07 | 0.34 | 0.08 | 591 |
| Phage-487 | T | L | — | — | — | — | — | E | — | D | A | P | — | I | 0.10 | 0.34 | 0.08 | 592 |
| Phage-488 | N | — | — | W | — | D | W | E | Y | I | N | S | — | V | 0.14 | 0.34 | 0.09 | 593 |
| Phage-489 | N | D | — | — | — | — | V | E | — | Y | Y | Y | — | T | 0.07 | 0.34 | 0.09 | 594 |
| Phage-490 | I | T | — | — | — | — | M | — | — | — | I | D | — | N | 0.08 | 0.34 | 0.08 | 595 |
| Phage-491 | Y | — | — | — | — | — | M | A | — | D | L | I | — | D | 0.10 | 0.34 | 0.29 | 596 |
| Phage-492 | I | D | — | — | — | — | L | — | — | — | I | V | — | T | 0.11 | 0.33 | 0.09 | 597 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34.185 scFv signal | Sp34.185 scFv signal in Pre-sence Of CD3 | SEQ ID NO: |
|---|---|---|---|---|---|---|---|---|---|---|---|---|---|---|---|---|---|---|
| Phage-493 | H | T | — | W | — | D | W | E | W | D | — | Y | — | D | 0.08 | 0.33 | 0.07 | 598 |
| Phage-494 | I | H | — | — | — | — | W | E | L | I | D | D | — | L | 0.08 | 0.33 | 0.10 | 599 |
| Phage-495 | Y | T | — | — | — | — | L | — | — | — | I | T | — | T | 0.08 | 0.33 | 0.08 | 600 |
| Phage-496 | F | H | — | — | — | — | V | E | — | T | — | Y | — | F | 0.11 | 0.33 | 0.09 | 601 |
| Phage-497 | D | — | — | — | — | — | L | — | — | — | L | I | — | N | 0.07 | 0.33 | 0.08 | 602 |
| Phage-498 | I | — | — | — | — | — | — | — | — | — | D | Y | — | I | 0.08 | 0.33 | 0.10 | 603 |
| Phage-499 | D | L | — | — | — | — | I | E | — | D | L | V | — | T | 0.09 | 0.33 | 0.09 | 604 |
| Phage-500 | N | I | — | — | — | — | L | O | — | D | I | V | — | P | 0.09 | 0.33 | 0.09 | 605 |
| Phage-501 | N | N | — | — | — | — | M | — | — | — | I | T | — | Y | 0.08 | 0.33 | 0.08 | 606 |
| Phage-502 | H | T | — | — | — | — | L | — | — | — | I | V | — | V | 0.08 | 0.33 | 0.08 | 607 |
| Phage-503 | Y | — | — | — | — | — | I | E | D | I | L | V | — | T | 0.12 | 0.33 | 0.23 | 608 |
| Phage-504 | N | T | — | — | — | — | — | E | F | V | H | L | — | P | 0.07 | 0.33 | 0.11 | 609 |
| Phage-505 | D | I | — | — | — | — | M | — | — | — | T | V | — | D | 0.10 | 0.33 | 0.09 | 610 |
| Phage-506 | A | I | — | — | — | — | V | E | I | V | N | Y | — | Y | 0.09 | 0.32 | 0.07 | 611 |
| Phage-507 | H | L | — | — | — | — | V | E | D | P | T | A | — | V | 0.10 | 0.32 | 0.28 | 612 |
| Phage-508 | A | D | — | — | — | — | L | — | — | — | I | S | — | T | 0.10 | 0.32 | 0.09 | 613 |
| Phage-509 | F | D | — | — | — | — | L | — | — | — | — | I | — | D | 0.07 | 0.32 | 0.09 | 614 |
| Phage-510 | D | V | — | — | — | — | — | — | — | — | I | D | — | N | 0.10 | 0.32 | 0.08 | 615 |
| Phage-511 | Y | L | — | — | — | — | V | E | — | I | S | I | — | F | 0.08 | 0.32 | 0.07 | 616 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-512 | S | A | — | — | — | — | — | — | — | — | L | H | — | V | 0.10 | 0.31 | 0.30 | 617 |
| Phage-513 | H | L | — | W | — | D | W | E | — | D | S | A | — | N | 0.08 | 0.31 | 0.08 | 618 |
| Phage-514 | H | T | — | W | — | D | W | E | Y | D | Y | D | — | F | 0.10 | 0.31 | 0.08 | 619 |
| Phage-515 | Y | D | — | — | — | — | W | E | — | V | A | L | — | N | 0.10 | 0.31 | 0.10 | 620 |
| Phage-516 | T | L | — | — | — | — | I | E | — | Y | I | V | — | Y | 0.09 | 0.31 | 0.23 | 621 |
| Phage-517 | S | — | — | — | — | — | — | — | — | — | I | F | — | T | 0.09 | 0.31 | 0.09 | 622 |
| Phage-518 | D | I | — | — | — | — | — | — | — | — | L | H | — | Y | 0.08 | 0.31 | 0.08 | 623 |
| Phage-519 | L | F | — | — | — | — | — | E | — | A | Y | L | — | I | 0.08 | 0.31 | 0.08 | 624 |
| Phage-520 | I | F | — | — | — | — | I | E | — | D | F | V | — | T | 0.10 | 0.31 | 0.10 | 625 |
| Phage-521 | D | D | — | — | — | — | W | E | Y | Y | — | A | — | V | 0.08 | 0.31 | 0.08 | 626 |
| Phage-522 | D | D | — | — | — | — | L | — | — | T | T | I | — | Y | 0.10 | 0.31 | 0.09 | 627 |
| Phage-523 | A | S | — | — | — | — | L | — | — | — | I | A | — | D | 0.10 | 0.31 | 0.09 | 628 |
| Phage-524 | Y | L | — | — | — | — | V | E | D | Y | D | Y | — | Y | 0.08 | 0.31 | 0.09 | 629 |
| Phage-525 | D | L | — | — | — | — | W | E | — | T | I | F | — | A | 0.12 | 0.30 | 0.09 | 630 |
| Phage-526 | D | F | — | — | — | D | G | E | — | F | Y | I | — | P | 0.12 | 0.30 | 0.11 | 631 |
| Phage-527 | — | — | — | — | — | — | V | E | — | N | I | L | — | H | 0.15 | 0.30 | 0.17 | 632 |
| Phage-528 | D | — | — | — | — | — | V | E | — | N | Y | F | — | F | 0.12 | 0.30 | 0.21 | 633 |
| Phage-529 | N | D | — | W | — | D | W | Y | — | F | L | S | — | D | 0.10 | 0.30 | 0.10 | 634 |
| Phage-530 | R | D | — | W | — | D | W | E | V | P | Y | F | — | D | 0.08 | 0.30 | 0.09 | 635 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34.185 scFv | Sp34.185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-531 | N | L | — | — | — | — | V | E | — | A | — | Y | — | Y | 0.10 | 0.30 | 0.13 | 636 |
| Phage-532 | F | D | — | W | — | D | G | E | L | N | Y | L | — | T | 0.23 | 0.30 | 0.08 | 637 |
| Phage-533 | Y | — | — | — | — | — | V | E | D | V | N | L | — | I | 0.18 | 0.30 | 0.10 | 638 |
| Phage-534 | D | N | — | — | — | — | Y | — | — | — | I | T | — | L | 0.11 | 0.29 | 0.09 | 639 |
| Phage-535 | L | N | — | W | — | D | W | E | — | D | Y | S | — | N | 0.09 | 0.29 | 0.09 | 640 |
| Phage-536 | P | T | — | — | — | — | V | E | — | L | L | S | — | N | 0.12 | 0.29 | 0.26 | 641 |
| Phage-537 | D | H | — | — | — | — | V | E | L | I | F | Y | — | H | 0.11 | 0.29 | 0.08 | 642 |
| Phage-538 | F | H | — | — | — | — | L | — | — | — | I | F | — | Y | 0.08 | 0.29 | 0.08 | 643 |
| Phage-539 | F | D | — | — | — | — | L | E | — | — | — | V | — | P | 0.16 | 0.29 | 0.16 | 644 |
| Phage-540 | D | F | — | — | — | — | L | — | — | — | L | P | — | A | 0.08 | 0.29 | 0.08 | 645 |
| Phage-541 | D | S | — | — | — | — | L | — | — | — | I | Y | — | D | 0.09 | 0.29 | 0.09 | 646 |
| Phage-542 | A | D | — | W | — | D | W | E | — | F | L | L | — | F | 0.12 | 0.29 | 0.10 | 647 |
| Phage-543 | I | L | — | — | — | — | V | E | — | L | D | F | — | N | 0.10 | 0.28 | 0.08 | 648 |
| Phage-544 | F | F | — | — | — | — | — | E | — | I | F | L | — | Y | 0.09 | 0.28 | 0.07 | 649 |
| Phage-545 | Y | N | — | — | — | D | G | — | — | — | Y | D | — | H | 0.07 | 0.28 | 0.07 | 650 |
| Phage-546 | D | N | — | — | — | — | L | — | — | T | I | T | — | F | 0.11 | 0.28 | 0.11 | 651 |
| Phage-547 | H | N | — | — | — | D | G | — | — | A | F | I | — | N | 0.09 | 0.28 | 0.23 | 652 |
| Phage-548 | D | — | — | — | — | — | V | E | — | D | L | V | — | P | 0.10 | 0.28 | 0.23 | 653 |
| Phage-549 | D | — | — | — | — | — | L | — | — | — | L | N | — | F | 0.08 | 0.28 | 0.07 | 654 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-550 | D | — | — | — | — | — | — | Q | — | D | F | H | — | H | 0.11 | 0.28 | 0.27 | 655 |
| Phage-551 | Y | D | — | — | — | — | W | E | — | T | D | D | — | I | 0.10 | 0.28 | 0.18 | 656 |
| Phage-552 | D | I | — | — | — | — | Y | E | — | D | I | I | — | Y | 0.14 | 0.28 | 0.19 | 657 |
| Phage-553 | F | D | — | — | — | — | L | — | — | T | — | P | — | P | 0.11 | 0.28 | 0.08 | 658 |
| Phage-554 | N | — | — | — | — | — | L | — | — | T | S | V | — | D | 0.09 | 0.28 | 0.26 | 659 |
| Phage-555 | Y | — | — | — | — | — | W | E | F | — | F | D | — | D | 0.17 | 0.28 | 0.11 | 660 |
| Phage-556 | Y | A | — | — | — | — | L | — | — | — | — | T | — | D | 0.09 | 0.28 | 0.08 | 661 |
| Phage-557 | F | L | — | — | — | — | V | E | Q | D | Y | F | — | V | 0.08 | 0.28 | 0.10 | 662 |
| Phage-558 | D | N | — | — | — | — | — | — | — | — | — | R | — | D | 0.09 | 0.27 | 0.26 | 663 |
| Phage-559 | N | D | — | — | — | D | G | I | — | T | — | D | — | Y | 0.10 | 0.27 | 0.24 | 664 |
| Phage-560 | Y | F | — | — | — | — | V | E | D | Y | N | D | — | F | 0.08 | 0.27 | 0.09 | 665 |
| Phage-561 | N | L | — | — | — | — | — | — | — | — | I | F | — | Y | 0.10 | 0.27 | 0.07 | 666 |
| Phage-562 | I | D | — | W | — | D | W | E | — | Y | I | P | — | T | 0.10 | 0.27 | 0.08 | 667 |
| Phage-563 | I | — | — | — | — | D | G | — | — | — | F | I | — | A | 0.07 | 0.27 | 0.08 | 668 |
| Phage-564 | D | — | — | — | — | — | — | — | — | — | — | V | — | Y | 0.08 | 0.27 | 0.07 | 669 |
| Phage-565 | — | F | — | — | — | — | W | E | D | I | T | D | — | D | 0.13 | 0.27 | 0.09 | 670 |
| Phage-566 | L | D | — | — | — | — | V | — | — | T | F | T | — | H | 0.08 | 0.26 | 0.08 | 671 |
| Phage-567 | D | D | — | — | — | — | Y | — | — | — | F | A | — | H | 0.13 | 0.26 | 0.10 | 672 |
| Phage-568 | I | — | — | — | — | — | Y | Q | — | D | L | P | — | N | 0.12 | 0.26 | 0.11 | 673 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Background signal | Sp34.185 scFv signal | Sp34.185 scFv signal in Presence Of CD3 | SEQ ID NO: |
|---|---|---|---|---|---|---|---|---|---|---|---|---|---|---|---|---|---|---|
| Phage-569 | L | D | — | — | — | — | V | E | — | Y | N | Y | — | V | 0.09 | 0.26 | 0.08 | 674 |
| Phage-570 | Y | V | — | — | — | — | — | — | — | — | S | A | — | N | 0.14 | 0.26 | 0.08 | 675 |
| Phage-571 | T | P | — | — | — | — | L | E | — | A | I | — | — | Y | 0.10 | 0.26 | 0.10 | 676 |
| Phage-572 | Y | F | — | — | — | — | — | — | — | — | A | D | — | N | 0.08 | 0.26 | 0.08 | 677 |
| Phage-573 | D | D | — | — | — | — | — | E | — | D | I | I | — | D | 0.12 | 0.26 | 0.25 | 678 |
| Phage-574 | L | — | — | — | — | V | V | E | — | L | N | H | — | N | 0.08 | 0.26 | 0.09 | 679 |
| Phage-575 | — | I | — | — | — | D | G | E | — | L | I | A | — | A | 0.09 | 0.26 | 0.27 | 680 |
| Phage-576 | F | A | — | W | — | D | W | Q | — | T | Y | V | — | N | 0.09 | 0.25 | 0.08 | 681 |
| Phage-577 | Y | I | — | — | — | — | V | E | F | L | F | F | — | N | 0.08 | 0.25 | 0.08 | 682 |
| Phage-578 | T | Q | — | — | — | K | G | E | P | T | Y | H | — | Y | 0.12 | 0.25 | 0.12 | 683 |
| Phage-579 | N | — | — | — | — | — | V | E | — | Y | H | N | — | D | 0.10 | 0.25 | 0.17 | 684 |
| Phage-580 | — | — | — | — | — | — | W | E | F | F | S | D | — | A | 0.08 | 0.25 | 0.07 | 685 |
| Phage-581 | F | — | — | — | — | — | L | E | — | — | F | F | — | Y | 0.10 | 0.25 | 0.22 | 686 |
| Phage-582 | D | — | — | — | — | — | I | E | — | N | F | Y | — | Y | 0.13 | 0.25 | 0.09 | 687 |
| Phage-583 | Y | A | — | — | — | — | V | E | — | Y | — | Y | — | A | 0.08 | 0.25 | 0.09 | 688 |
| Phage-584 | — | D | — | — | — | — | L | — | — | — | I | I | — | D | 0.08 | 0.25 | 0.07 | 689 |
| Phage-585 | N | D | — | — | — | — | M | — | — | — | I | A | — | Y | 0.07 | 0.25 | 0.07 | 690 |
| Phage-586 | — | — | — | — | — | — | — | — | — | Y | L | A | — | A | 0.09 | 0.25 | 0.21 | 691 |
| Phage-587 | — | I | — | — | — | — | — | — | — | — | A | N | — | D | 0.08 | 0.25 | 0.09 | 692 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Background signal | Sp34.185 scFv signal | Sp34.185 scFv signal in Presence Of CD3 | SEQ ID NO: |
|---|---|---|---|---|---|---|---|---|---|---|---|---|---|---|---|---|---|---|
| Phage-588 | L | T | — | W | — | D | W | E | — | D | F | F | — | N | 0.07 | 0.24 | 0.07 | 693 |
| Phage-589 | F | — | — | — | — | — | Q | E | — | I | N | Y | — | Y | 0.10 | 0.24 | 0.23 | 694 |
| Phage-590 | T | — | — | — | — | — | L | E | — | F | F | L | — | Y | 0.13 | 0.24 | 0.08 | 695 |
| Phage-591 | P | D | — | — | — | — | L | — | — | — | — | A | — | H | 0.12 | 0.24 | 0.09 | 696 |
| Phage-592 | N | D | — | — | — | — | — | E | — | I | I | F | — | V | 0.09 | 0.24 | 0.24 | 697 |
| Phage-593 | Y | I | — | — | — | — | — | — | — | — | F | Y | — | N | 0.25 | 0.24 | 0.08 | 698 |
| Phage-594 | H | A | — | — | — | — | L | — | — | — | L | L | — | N | 0.20 | 0.24 | 0.07 | 699 |
| Phage-595 | Y | — | — | — | — | — | W | E | — | A | — | L | — | A | 0.09 | 0.24 | 0.21 | 700 |
| Phage-596 | A | F | — | — | — | — | V | E | — | Y | D | L | — | N | 0.10 | 0.24 | 0.16 | 701 |
| Phage-597 | Y | N | — | — | — | — | — | — | — | — | — | A | — | S | 0.15 | 0.23 | 0.09 | 702 |
| Phage-598 | Y | L | — | — | — | — | V | E | D | D | T | L | — | A | 0.08 | 0.23 | 0.09 | 703 |
| Phage-599 | A | V | — | — | — | — | — | — | — | — | — | N | — | D | 0.08 | 0.23 | 0.08 | 704 |
| Phage-600 | N | — | — | — | — | — | W | E | V | Y | S | L | — | P | 0.13 | 0.23 | 0.08 | 705 |
| Phage-601 | D | F | — | — | — | — | V | E | — | D | T | Y | — | H | 0.07 | 0.23 | 0.07 | 706 |
| Phage-602 | I | S | — | — | — | — | Y | E | w | D | Y | A | — | N | 0.08 | 0.23 | 0.10 | 707 |
| Phage-603 | | N | — | — | — | — | L | — | — | — | I | I | — | Y | 0.08 | 0.23 | 0.08 | 708 |
| Phage-604 | Y | D | — | — | — | — | — | — | — | T | A | P | — | Y | 0.07 | 0.23 | 0.08 | 709 |
| Phage-605 | Y | L | — | — | — | — | — | E | — | N | F | L | — | T | 0.09 | 0.23 | 0.22 | 710 |
| Phage-606 | F | D | — | — | — | — | V | — | — | — | — | D | — | A | 0.08 | 0.22 | 0.09 | 711 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Background signal | Sp34.185 scFv signal | Sp34.185 scFv signal in Presence Of CD3 | SEQ ID NO: |
|---|---|---|---|---|---|---|---|---|---|---|---|---|---|---|---|---|---|---|
| Phage-607 | Y | D | — | — | — | — | — | E | — | I | S | F | — | N | 0.09 | 0.22 | 0.09 | 712 |
| Phage-608 | I | D | — | — | — | — | I | E | L | Y | D | D | — | F | 0.09 | 0.22 | 0.09 | 713 |
| Phage-609 | T | F | — | — | — | — | L | — | — | — | — | Y | — | Y | 0.08 | 0.22 | 0.07 | 714 |
| Phage-610 | F | F | — | — | — | — | I | — | — | — | N | A | — | V | 0.09 | 0.22 | 0.07 | 715 |
| Phage-611 | Y | H | — | W | — | D | W | E | P | I | Y | I | — | I | 0.12 | 0.22 | 0.10 | 716 |
| Phage-612 | A | I | — | — | — | — | Y | E | — | D | H | Y | — | Y | 0.08 | 0.22 | 0.08 | 717 |
| Phage-613 | P | L | — | — | — | D | G | F | — | N | Y | N | — | F | 0.12 | 0.22 | 0.08 | 718 |
| Phage-614 | F | P | — | W | — | D | W | E | W | D | N | N | — | H | 0.09 | 0.22 | 0.09 | 719 |
| Phage-615 | — | D | — | — | — | D | G | — | — | L | A | A | — | H | 0.10 | 0.22 | 0.11 | 720 |
| Phage-616 | — | D | — | W | | D | W | E | — | Y | Y | S | — | D | 0.08 | 0.22 | 0.07 | 721 |
| Phage-617 | — | — | — | — | — | — | Y | — | — | | Y | D | — | T | 0.07 | 0.21 | 0.10 | 722 |
| Phage-618 | N | L | — | — | — | — | W | E | N | F | A | D | — | F | 0.08 | 0.21 | 0.08 | 723 |
| Phage-619 | Y | L | — | — | — | — | L | E | V | F | F | V | — | D | 0.12 | 0.21 | 0.10 | 724 |
| Phage-620 | I | F | — | — | — | — | L | E | D | Y | S | I | — | F | 0.09 | 0.21 | 0.08 | 725 |
| Phage-621 | D | — | — | — | — | — | L | E | Q | Y | D | L | — | F | 0.09 | 0.21 | 0.08 | 726 |
| Phage-622 | L | L | — | — | — | V | N | E | D | P | L | D | — | Y | 0.11 | 0.21 | 0.13 | 727 |
| Phage-623 | I | D | — | — | — | — | — | — | — | — | — | F | — | Y | 0.08 | 0.21 | 0.08 | 728 |
| Phage-624 | I | I | — | — | — | — | V | E | — | I | D | I | — | S | 0.08 | 0.21 | 0.08 | 729 |
| Phage-625 | I | A | — | W | — | D | W | E | D | Y | S | S | — | P | 0.08 | 0.21 | 0.11 | 730 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-626 | Y | — | — | — | — | V | V | E | D | I | N | D | — | I | 0.09 | 0.21 | 0.07 | 731 |
| Phage-627 | N | I | — | — | — | — | M | — | — | — | I | D | — | I | 0.08 | 0.21 | 0.07 | 732 |
| Phage-628 | F | D | — | W | — | D | w | E | — | L | — | S | — | Y | 0.07 | 0.21 | 0.08 | 733 |
| Phage-629 | Y | F | — | — | — | — | w | E | D | H | F | F | — | D | 0.09 | 0.21 | 0.19 | 734 |
| Phage-630 | T | | — | — | — | — | — | E | — | D | S | Y | — | D | 0.12 | 0.20 | 0.09 | 735 |
| Phage-631 | N | L | — | — | — | — | V | E | L | I | D | I | — | S | 0.11 | 0.20 | 0.09 | 736 |
| Phage-632 | D | N | — | — | — | — | W | E | — | V | Y | L | — | N | 0.08 | 0.20 | 0.08 | 737 |
| Phage-633 | F | L | — | — | — | — | — | — | — | — | D | L | — | F | 0.08 | 0.20 | 0.09 | 738 |
| Phage-634 | H | I | — | — | — | — | Q | — | — | — | I | — | — | T | 0.09 | 0.20 | 0.19 | 739 |
| Phage-635 | F | D | — | W | — | D | W | E | D | N | S | Y | — | D | 0.10 | 0.20 | 0.09 | 740 |
| Phage-636 | T | A | — | — | — | — | W | E | F | D | F | N | — | D | 0.08 | 0.20 | 0.07 | 741 |
| Phage-637 | H | H | — | W | — | D | W | E | D | Y | S | T | — | P | 0.10 | 0.20 | 0.11 | 742 |
| Phage-638 | Y | — | — | — | — | — | — | — | — | — | — | N | — | F | 0.07 | 0.20 | 0.08 | 743 |
| Phage-639 | L | H | — | W | — | D | W | E | — | I | D | I | — | D | 0.08 | 0.20 | 0.09 | 744 |
| Phage-640 | D | I | — | — | — | D | G | Q | — | D | F | V | — | S | 0.08 | 0.20 | 0.09 | 745 |
| Phage-641 | D | V | — | W | — | D | W | E | V | N | Y | F | — | D | 0.09 | 0.20 | 0.07 | 746 |
| Phage-642 | — | N | — | — | — | — | M | — | — | — | I | D | — | A | 0.12 | 0.20 | 0.10 | 747 |
| Phage-643 | D | N | — | — | — | — | — | — | — | A | T | V | — | N | O.U | 0.19 | 0.19 | 748 |
| Phage-644 | D | L | — | — | — | — | — | E | — | V | H | N | — | N | 0.08 | 0.19 | 0.08 | 749 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-645 | — | N | — | — | — | — | — | — | — | — | S | Y | — | F | 0.13 | 0.19 | 0.09 | 750 |
| Phage-646 | N | I | — | W | — | D | W | E | — | D | N | F | — | S | 0.08 | 0.19 | 0.08 | 751 |
| Phage-647 | F | V | — | — | — | — | W | E | V | Y | D | D | — | D | 0.08 | 0.19 | 0.08 | 752 |
| Phage-648 | A | — | — | — | — | — | L | E | V | V | H | L | — | V | 0.10 | 0.19 | 0.17 | 753 |
| Phage-649 | P | F | — | — | — | — | M | — | — | T | I | D | — | Y | 0.07 | 0.19 | 0.09 | 754 |
| Phage-650 | L | L | — | — | — | V | M | E | D | V | F | A | — | Y | 0.08 | 0.19 | 0.08 | 755 |
| Phage-651 | D | L | — | — | — | — | — | — | — | — | T | N | — | Y | 0.07 | 0.19 | 0.08 | 756 |
| Phage-652 | H | D | — | — | — | — | M | E | — | Y | Y | L | — | P | 0.10 | 0.18 | 0.10 | 757 |
| Phage-653 | T | D | — | — | — | — | Y | — | — | — | I | I | — | P | 0.08 | 0.18 | 0.09 | 758 |
| Phage-654 | — | L | — | W | — | D | W | E | D | Y | A | D | — | N | 0.09 | 0.18 | 0.08 | 759 |
| Phage-655 | N | D | — | — | — | — | L | — | — | — | L | T | — | D | 0.07 | 0.18 | 0.09 | 760 |
| Phage-656 | I | — | — | — | — | — | L | — | — | — | I | A | — | Y | 0.11 | 0.18 | 0.08 | 761 |
| Phage-657 | N | — | — | — | — | — | V | E | — | F | N | F | — | H | 0.11 | 0.18 | 0.14 | 762 |
| Phage-658 | D | V | — | — | — | — | I | E | — | Y | S | F | — | I | 0.08 | 0.18 | 0.09 | 763 |
| Phage-659 | D | L | — | — | — | — | V | E | — | I | T | D | — | A | 0.10 | 0.18 | 0.12 | 764 |
| Phage-660 | H | D | — | — | — | — | — | — | — | — | — | F | — | I | 0.12 | 0.18 | 0.12 | 765 |
| Phage-661 | P | L | — | — | — | V | L | E | — | D | I | Y | — | Y | 0.10 | 0.18 | 0.13 | 766 |
| Phage-662 | D | L | — | — | — | — | — | E | D | I | I | D | — | N | 0.10 | 0.18 | 0.11 | 767 |
| Phage-663 | D | — | — | — | — | — | V | E | V | P | S | N | — | N | 0.10 | 0.18 | 0.18 | 768 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-664 | I | I | — | — | — | — | L | — | — | — | T | A | — | D | 0.10 | 0.18 | 0.09 | 769 |
| Phage-665 | D | H | — | — | — | — | — | — | — | — | — | N | — | D | 0.10 | 0.18 | 0.14 | 770 |
| Phage-666 | F | D | — | — | — | — | — | — | — | — | L | Y | — | S | 0.07 | 0.18 | 0.07 | 771 |
| Phage-667 | F | A | — | W | — | D | W | E | — | V | Y | I | — | Y | 0.08 | 0.18 | 0.08 | 772 |
| Phage-668 | L | — | — | — | — | — | — | — | — | — | L | D | — | S | 0.08 | 0.18 | 0.09 | 773 |
| Phage-669 | D | L | — | — | — | — | L | E | | A | F | L | — | A | 0.09 | 0.18 | 0.08 | 774 |
| Phage-670 | F | A | — | — | — | — | L | — | — | T | L | T | — | L | 0.10 | 0.18 | 0.08 | 775 |
| Phage-671 | F | D | — | — | — | — | V | E | — | — | S | N | — | D | 0.17 | 0.18 | 0.10 | 776 |
| Phage-672 | — | H | — | — | — | — | L | E | Y | P | F | D | — | N | 0.09 | 0.17 | 0.16 | 777 |
| Phage-673 | A | — | — | — | — | — | — | E | — | — | T | T | — | N | 0.10 | 0.17 | 0.15 | 778 |
| Phage-674 | L | — | — | — | — | V | S | E | Q | F | T | F | — | I | 0.08 | 0.17 | 0.08 | 779 |
| Phage-675 | D | — | — | — | — | — | L | — | — | — | Y | D | — | N | 0.10 | 0.17 | 0.09 | 780 |
| Phage-676 | F | — | — | — | — | — | W | E | — | F | D | V | — | I | 0.13 | 0.17 | 0.15 | 781 |
| Phage-677 | F | T | — | — | — | — | V | E | — | Y | D | H | — | I | 0.08 | 0.17 | 0.09 | 782 |
| Phage-678 | Y | N | — | — | — | — | — | — | — | — | — | T | — | F | 0.12 | 0.17 | 0.11 | 783 |
| Phage-679 | A | V | — | — | — | — | N | — | — | — | N | S | — | A | 0.08 | 0.17 | 0.08 | 784 |
| Phage-680 | I | — | — | W | — | D | W | E | V | P | N | D | — | A | 0.10 | 0.17 | 0.09 | 785 |
| Phage-681 | Y | F | — | — | — | — | — | E | — | F | F | H | — | Y | 0.12 | 0.17 | 0.12 | 786 |
| Phage-682 | Y | V | — | — | — | D | G | — | — | — | S | F | — | D | 0.12 | 0.17 | 0.12 | 787 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-683 | I | S | — | — | — | — | V | E | — | F | F | Y | — | Y | 0.10 | 0.17 | 0.08 | 788 |
| Phage-684 | L | I | — | — | — | V | — | — | — | D | — | Y | — | D | 0.17 | 0.17 | 0.15 | 789 |
| Phage-685 | — | — | — | — | — | — | V | E | D | H | N | Y | — | A | 0.14 | 0.17 | 0.16 | 790 |
| Phage-686 | L | D | — | — | — | — | — | E | F | V | Y | I | — | A | 0.08 | 0.17 | 0.10 | 791 |
| Phage-687 | Y | D | — | — | — | — | — | E | — | D | L | P | — | I | 0.17 | 0.17 | 0.11 | 792 |
| Phage-688 | D | V | — | — | — | — | V | E | — | D | Y | Y | — | D | 0.10 | 0.17 | 0.14 | 793 |
| Phage-689 | N | D | — | W | — | D | W | E | Y | D | N | V | — | V | 0.08 | 0.17 | 0.10 | 794 |
| Phage-690 | D | L | — | — | — | — | — | E | V | A | N | D | — | N | 0.10 | 0.16 | 0.16 | 795 |
| Phage-691 | H | D | — | — | — | — | L | — | — | — | I | S | — | N | 0.09 | 0.16 | 0.07 | 796 |
| Phage-692 | L | D | — | W | | D | W | E | — | T | T | H | — | D | 0.08 | 0.16 | 0.08 | 797 |
| Phage-693 | I | I | — | — | — | — | V | E | — | D | D | Y | — | L | 0.09 | 0.16 | 0.09 | 798 |
| Phage-694 | Y | — | — | W | | D | W | E | — | V | I | I | — | D | 0.09 | 0.16 | 0.09 | 799 |
| Phage-695 | F | D | — | — | — | — | I | — | — | Y | T | N | — | N | 0.12 | 0.16 | 0.09 | 800 |
| Phage-696 | I | T | — | — | — | — | L | — | — | T | I | N | — | D | 0.08 | 0.16 | 0.11 | 801 |
| Phage-697 | D | S | — | — | — | — | V | E | — | D | I | Y | — | I | 0.07 | 0.16 | 0.08 | 802 |
| Phage-698 | Y | L | — | — | — | — | — | — | — | — | G | N | — | H | 0.07 | 0.16 | 0.08 | 803 |
| Phage-699 | D | N | — | — | — | — | L | P | — | D | Y | F | — | D | 0.08 | 0.16 | 0.10 | 804 |
| Phage-700 | — | L | — | — | — | — | — | E | — | V | S | N | — | N | 0.11 | 0.16 | 0.08 | 805 |
| Phage-701 | — | D | — | W | — | D | W | E | — | D | I | V | — | D | 0.10 | 0.16 | 0.09 | 806 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-702 | — | — | — | W | — | — | W | E | D | N | F | P | — | Y | 0.07 | 0.16 | 0.07 | 807 |
| Phage-703 | D | — | — | — | — | — | V | E | — | H | F | N | — | H | 0.08 | 0.16 | 0.08 | 808 |
| Phage-704 | A | D | — | — | — | — | I | E | — | D | A | Y | — | Y | 0.12 | 0.16 | 0.09 | 809 |
| Phage-705 | I | L | — | W | — | D | W | E | D | A | T | F | — | Y | 0.09 | 0.16 | 0.07 | 810 |
| Phage-706 | I | H | — | W | — | D | W | E | D | F | N | I | — | P | 0.09 | 0.16 | 0.08 | 811 |
| Phage-707 | T | I | — | — | — | — | V | E | D | Y | N | D | — | I | 0.07 | 0.16 | 0.07 | 812 |
| Phage-708 | D | D | — | — | — | — | L | — | — | — | — | A | — | I | 0.08 | 0.16 | 0.08 | 813 |
| Phage-709 | D | D | — | W | — | D | W | E | D | H | I | F | — | F | 0.13 | 0.16 | 0.08 | 814 |
| Phage-710 | — | N | — | — | — | — | V | E | — | I | I | F | — | D | 0.12 | 0.15 | 0.12 | 815 |
| Phage-711 | I | F | — | W | — | D | W | E | D | D | T | V | — | I | 0.08 | 0.15 | 0.09 | 816 |
| Phage-712 | I | I | — | — | — | — | — | E | — | I | S | D | — | L | 0.12 | 0.15 | 0.15 | 817 |
| Phage-713 | F | D | — | — | — | — | V | E | — | Y | N | D | — | D | O.U | 0.15 | 0.09 | 818 |
| Phage-714 | N | D | — | — | — | — | L | | — | T | L | Y | — | I | 0.08 | 0.15 | 0.10 | 819 |
| Phage-715 | A | I | — | — | — | — | L | E | — | D | I | S | — | N | 0.12 | 0.15 | 0.17 | 820 |
| Phage-716 | H | L | — | — | — | — | — | — | — | — | T | N | — | Y | 0.07 | 0.15 | 0.07 | 821 |
| Phage-717 | S | — | — | — | — | — | L | — | — | — | — | A | — | I | 0.10 | 0.15 | 0.11 | 822 |
| Phage-718 | L | — | — | — | — | — | — | E | Q | L | A | D | — | T | 0.08 | 0.15 | 0.08 | 823 |
| Phage-719 | I | D | — | — | — | — | L | — | — | — | I | A | — | N | 0.07 | 0.15 | 0.08 | 824 |
| Phage-720 | F | D | — | — | — | D | G | Q | — | D | L | V | — | N | 0.10 | 0.15 | 0.08 | 825 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-721 | N | L | — | — | — | — | | E | — | F | F | D | — | Y | 0.09 | 0.15 | 0.15 | 826 |
| Phage-722 | S | I | — | — | — | — | L | Q | — | D | I | V | — | P | 0.09 | 0.14 | 0.14 | 827 |
| Phage-723 | N | P | — | — | — | — | Y | — | — | | A | H | — | D | 0.08 | 0.14 | 0.08 | 828 |
| Phage-724 | Y | D | — | — | — | — | L | — | — | Y | Y | N | — | N | 0.12 | 0.14 | 0.11 | 829 |
| Phage-725 | — | D | — | — | — | — | L | — | — | — | I | F | — | D | 0.07 | 0.14 | 0.08 | 830 |
| Phage-726 | D | N | — | — | — | — | L | — | — | — | — | T | — | T | 0.09 | 0.14 | 0.10 | 831 |
| Phage-727 | — | D | — | — | — | — | L | — | — | — | S | Y | — | D | 0.10 | 0.14 | 0.13 | 832 |
| Phage-728 | Y | — | — | — | — | — | | E | F | I | D | F | — | F | 0.07 | 0.14 | 0.07 | 833 |
| Phage-729 | Y | D | — | W | — | D | W | E | V | I | T | Y | — | N | 0.08 | 0.14 | 0.09 | 834 |
| Phage-730 | F | D | — | — | — | — | I | E | — | D | F | F | — | V | 0.06 | 0.14 | 0.07 | 835 |
| Phage-731 | I | F | — | W | — | D | W | | D | I | N | F | — | D | 0.10 | 0.14 | 0.14 | 836 |
| Phage-732 | N | F | — | — | — | — | L | P | — | D | I | T | — | Y | 0.37 | 0.14 | 0.09 | 837 |
| Phage-733 | S | L | — | — | — | — | | E | — | Y | Y | H | — | L | 0.09 | 0.14 | 0.07 | 838 |
| Phage-734 | A | S | — | — | — | — | L | — | — | — | L | D | — | L | 0.12 | 0.14 | 0.13 | 839 |
| Phage-735 | S | F | — | — | — | — | R | E | W | D | L | A | — | Y | 0.09 | 0.14 | 0.08 | 840 |
| Phage-736 | H | L | — | — | — | — | — | E | D | V | L | D | — | I | 0.08 | 0.14 | 0.12 | 841 |
| Phage-737 | L | D | — | — | — | D | G | — | — | F | Y | Y | — | L | 0.20 | 0.14 | 0.09 | 842 |
| Phage-738 | D | N | — | W | — | D | W | E | — | D | I | A | — | T | 0.16 | 0.14 | 0.11 | 843 |
| Phage-739 | S | D | — | — | — | — | L | — | — | T | I | H | — | I | 0.09 | 0.14 | 0.08 | 844 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-740 | N | S | — | — | — | D | G | — | — | — | — | D | — | L | 0.08 | 0.14 | 0.08 | 845 |
| Phage-741 | D | L | — | — | — | — | L | — | — | — | T | L | — | I | 0.07 | 0.14 | 0.08 | 846 |
| Phage-742 | F | D | — | — | — | — | S | — | — | — | F | N | — | Y | 0.09 | 0.14 | 0.11 | 847 |
| Phage-743 | D | L | — | — | — | — | — | E | — | D | D | I | — | Y | 0.12 | 0.14 | 0.13 | 848 |
| Phage-744 | H | A | — | — | — | — | — | E | — | D | T | Y | — | F | 0.10 | 0.14 | 0.14 | 849 |
| Phage-745 | S | D | — | — | — | — | L | — | — | — | — | A | — | I | 0.11 | 0.14 | 0.08 | 850 |
| Phage-746 | I | V | — | — | — | — | L | P | — | D | Y | N | — | Y | 0.09 | 0.13 | 0.11 | 851 |
| Phage-747 | D | L | — | — | — | — | — | — | — | — | F | I | — | F | 0.09 | 0.13 | 0.08 | 852 |
| Phage-748 | Y | D | — | — | — | — | — | — | — | T | L | T | — | N | 0.13 | 0.13 | 0.08 | 853 |
| Phage-749 | Y | D | — | — | — | — | V | E | — | I | — | N | — | D | 0.11 | 0.13 | 0.12 | 854 |
| Phage-750 | — | F | — | — | — | — | I | E | D | D | H | V | — | I | 0.07 | 0.13 | 0.07 | 855 |
| Phage-751 | F | I | — | — | — | — | W | E | D | D | Y | A | — | S | 0.12 | 0.13 | 0.12 | 856 |
| Phage-752 | N | F | — | — | — | — | — | — | — | — | — | — | — | N | 0.10 | 0.13 | 0.09 | 857 |
| Phage-753 | N | L | — | — | — | — | V | E | — | I | L | I | — | D | 0.07 | 0.13 | 0.07 | 858 |
| Phage-754 | D | S | — | — | — | — | V | E | — | Y | D | L | — | N | 0.11 | 0.13 | 0.08 | 859 |
| Phage-755 | T | L | — | — | — | — | — | E | — | I | T | D | — | N | 0.09 | 0.13 | 0.08 | 860 |
| Phage-756 | T | V | — | — | — | K | M | E | M | N | S | T | — | D | 0.09 | 0.13 | 0.09 | 861 |
| Phage-757 | — | H | — | w | — | D | W | E | D | A | — | S | — | N | 0.10 | 0.12 | 0.11 | 862 |
| Phage-758 | D | L | — | — | — | D | G | N | — | L | D | F | — | F | 0.08 | 0.12 | 0.08 | 863 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA: Background signal | Sp34.185 scFv signal | Sp34.185 scFv signal in Presence Of CD3 | SEQ ID NO: |
|---|---|---|---|---|---|---|---|---|---|---|---|---|---|---|---|---|---|---|
| Phage-759 | D | L | — | — | — | D | G | E | — | H | Y | Y | — | D | 0.09 | 0.12 | 0.07 | 864 |
| Phage-760 | F | N | — | — | — | — | V | E | — | I | L | L | — | T | 0.11 | 0.12 | 0.12 | 865 |
| Phage-761 | H | — | — | — | — | — | V | E | N | I | N | D | — | I | 0.09 | 0.12 | 0.07 | 866 |
| Phage-762 | I | D | — | — | — | — | L | — | — | — | — | I | — | D | 0.09 | 0.12 | 0.08 | 867 |
| Phage-763 | I | F | — | — | — | — | I | E | Q | P | A | L | — | Y | 0.08 | 0.12 | 0.09 | 868 |
| Phage-764 | Y | D | — | — | — | — | — | Q | — | D | L | V | — | P | 0.10 | 0.12 | 0.08 | 869 |
| Phage-765 | H | A | — | w | — | D | W | E | — | P | N | Y | — | D | 0.13 | 0.12 | 0.09 | 870 |
| Phage-766 | N | V | — | w | — | D | w | E | — | D | Y | N | — | Y | 0.11 | 0.12 | 0.10 | 871 |
| Phage-767 | S | F | — | — | Q | — | L | G | D | N | Y | D | — | I | 0.09 | 0.12 | 0.12 | 872 |
| Phage-768 | D | D | — | — | — | — | L | — | — | T | T | V | — | Y | 0.08 | 0.12 | 0.09 | 873 |
| Phage-769 | N | F | — | — | — | — | W | E | V | A | T | L | — | L | 0.09 | 0.12 | 0.14 | 874 |
| Phage-770 | D | L | — | — | — | — | V | E | — | D | T | Y | — | N | 0.09 | 0.11 | 0.07 | 875 |
| Phage-771 | A | L | — | — | — | — | V | E | Q | V | D | L | — | T | 0.08 | 0.11 | 0.08 | 876 |
| Phage-772 | D | D | — | — | — | — | L | — | — | — | — | N | — | N | 0.08 | 0.11 | 0.08 | 877 |
| Phage-773 | I | F | — | — | — | — | — | E | Q | I | I | Y | — | D | 0.09 | 0.11 | 0.11 | 878 |
| Phage-774 | S | D | — | W | — | D | W | E | — | V | Y | Y | — | S | 0.09 | 0.11 | 0.10 | 879 |
| Phage-775 | F | F | — | — | — | D | G | — | — | V | A | I | — | D | 0.09 | 0.11 | 0.07 | 880 |
| Phage-776 | D | D | — | W | — | D | W | E | D | D | — | Y | — | Y | 0.11 | 0.11 | 0.07 | 881 |
| Phage-777 | Y | D | — | — | — | — | — | — | — | T | — | V | — | P | 0.08 | 0.11 | 0.08 | 882 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Background signal | Sp34.185 scFv signal | Sp34.185 scFv signal in Presence Of CD3 | SEQ ID NO: |
|---|---|---|---|---|---|---|---|---|---|---|---|---|---|---|---|---|---|---|
| Phage-778 | S | — | — | — | — | — | L | — | — | — | — | N | — | V | 0.10 | 0.11 | 0.08 | 883 |
| Phage-779 | A | F | — | V | S | F | Q | Q | S | L | P | H | — | D | 0.09 | 0.11 | 0.10 | 884 |
| Phage-780 | — | N | — | — | — | — | V | E | — | Y | F | V | — | F | 0.09 | 0.11 | 0.09 | 885 |
| Phage-781 | T | N | — | W | — | D | W | E | — | D | F | A | — | V | 0.07 | 0.11 | 0.08 | 886 |
| Phage-782 | D | D | — | — | — | — | — | E | — | I | I | L | — | F | 0.08 | 0.10 | 0.08 | 887 |
| Phage-783 | N | S | — | — | — | — | L | E | D | Y | H | L | — | P | 0.08 | 0.10 | 0.10 | 888 |
| Phage-784 | I | H | — | — | — | D | S | — | G | F | D | F | — | D | 0.09 | 0.10 | 0.08 | 889 |
| Phage-785 | F | D | — | — | — | — | L | E | — | D | H | L | — | F | 0.08 | 0.10 | 0.08 | 890 |
| Phage-786 | T | V | — | W | — | D | — | E | — | Y | A | D | — | D | 0.10 | 0.10 | 0.08 | 891 |
| Phage-787 | Y | F | — | W | — | D | W | E | — | A | A | D | — | L | 0.09 | 0.10 | 0.09 | 892 |
| Phage-788 | — | S | — | — | — | — | — | — | — | — | — | D | — | I | 0.08 | 0.10 | 0.07 | 893 |
| Phage-789 | A | V | — | — | — | — | L | P | — | D | I | V | — | Y | 0.08 | 0.10 | 0.08 | 894 |
| Phage-790 | — | L | — | — | — | — | V | E | — | Y | H | L | — | A | 0.08 | 0.10 | 0.30 | 895 |
| Phage-791 | S | L | — | W | — | D | W | E | — | V | D | N | — | F | 0.12 | 0.10 | 0.11 | 896 |
| Phage-792 | T | I | — | — | — | D | G | Q | — | D | Y | N | — | H | 0.07 | 0.10 | 0.07 | 897 |
| Phage-793 | F | L | — | — | — | — | G | E | P | T | Y | L | — | T | 0.12 | 0.10 | 0.09 | 898 |
| Phage-794 | D | D | — | W | L | — | Q | H | D | I | Y | V | — | A | 0.10 | 0.10 | 0.08 | 899 |
| Phage-795 | I | F | — | — | — | — | V | E | — | V | A | F | — | F | 0.07 | 0.10 | 0.08 | 900 |
| Phage-796 | A | L | — | — | — | — | V | E | D | D | Y | D | — | L | 0.09 | 0.10 | 0.09 | 901 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA: Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-797 | D | D | — | — | — | — | I | E | L | Y | L | T | — | A | 0.08 | 0.10 | 0.08 | 902 |
| Phage-798 | T | D | — | W | — | D | W | E | D | D | S | I | — | D | 0.07 | 0.10 | 0.07 | 903 |
| Phage-799 | S | I | — | — | — | — | L | E | — | I | F | L | — | N | 0.08 | 0.10 | 0.08 | 904 |
| Phage-800 | N | D | — | — | — | — | L | E | — | D | I | L | — | F | 0.07 | 0.10 | 0.09 | 905 |
| Phage-801 | D | D | — | — | — | — | L | — | — | T | Y | S | — | Y | 0.09 | 0.09 | 0.08 | 906 |
| Phage-802 | F | V | — | — | — | — | W | E | — | I | D | L | — | I | 0.10 | 0.09 | 0.09 | 907 |
| Phage-803 | Y | D | — | — | — | — | L | — | — | — | L | S | — | P | 0.07 | 0.09 | 0.07 | 908 |
| Phage-804 | N | L | — | — | — | — | L | — | — | — | I | I | — | P | 0.08 | 0.09 | 0.08 | 909 |
| Phage-805 | I | D | — | W | — | D | W | E | — | F | N | N | — | F | 0.08 | 0.09 | 0.09 | 910 |
| Phage-806 | A | — | — | — | — | — | L | E | — | H | D | Y | — | Y | 0.08 | 0.09 | 0.09 | 911 |
| Phage-807 | D | D | — | S | — | — | — | — | Q | I | D | L | — | D | 0.14 | 0.09 | 0.09 | 912 |
| Phage-808 | S | — | — | — | — | — | S | — | — | — | I | Y | — | Y | 0.08 | 0.09 | 0.07 | 913 |
| Phage-809 | S | L | — | — | — | — | — | Q | — | D | A | P | — | N | 0.07 | 0.09 | 0.07 | 914 |
| Phage-810 | D | A | — | — | — | — | L | — | — | T | T | H | — | D | 0.09 | 0.09 | 0.08 | 915 |
| Phage-811 | N | D | — | — | — | — | V | E | — | V | A | D | — | F | 0.07 | 0.09 | 0.08 | 916 |
| Phage-812 | Y | I | — | — | — | — | — | E | Q | D | Y | F | — | F | 0.08 | 0.09 | 0.08 | 917 |
| Phage-813 | T | D | — | — | — | D | G | — | — | T | N | Y | — | F | 0.11 | 0.09 | 0.08 | 918 |
| Phage-814 | Y | D | — | — | — | — | V | — | — | — | — | L | — | P | 0.08 | 0.09 | 0.08 | 919 |
| Phage-815 | I | D | — | — | — | — | — | — | — | — | A | Y | — | T | 0.08 | 0.09 | 0.08 | 920 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | SEQ ID |
| ID | 1 | 2 | 3 | 4 | 5 | 6 | 7 | 8 | 9 | 10 | 11 | 12 | 13 | 14 | signal | signal | Of CD3 | NO: |
| Phage-816 | F | D | — | — | — | — | | E | — | F | F | H | — | Y | 0.09 | 0.09 | 0.09 | 921 |
| Phage-817 | F | P | — | — | — | — | I | E | — | Y | D | Y | — | V | 0.09 | 0.09 | 0.08 | 922 |
| Phage-818 | A | D | — | — | — | I | | E | S | I | D | I | — | V | 0.09 | 0.09 | 0.07 | 923 |
| Phage-819 | I | S | — | — | — | D | L | W | P | T | D | I | — | T | 0.10 | 0.09 | 0.10 | 924 |
| Phage-820 | D | D | — | — | — | D | G | — | — | V | H | T | — | N | 0.09 | 0.09 | 0.07 | 925 |
| Phage-821 | I | D | — | W | — | D | W | E | G | — | F | A | — | N | 0.09 | 0.09 | 0.08 | 926 |
| Phage-822 | L | N | — | — | — | D | G | — | — | T | F | Y | — | D | 0.08 | 0.08 | 0.07 | 927 |
| Phage-823 | I | H | — | — | — | — | L | G | A | Y | I | S | — | S | 0.08 | 0.08 | 0.09 | 928 |
| Phage-824 | T | I | — | W | — | D | W | E | — | D | Y | F | — | Y | 0.08 | 0.08 | 0.08 | 929 |
| Phage-825 | H | S | — | L | A | — | — | — | Q | D | L | V | — | I | 0.07 | 0.08 | 0.07 | 930 |
| Phage-826 | N | N | — | A | S | D | L | S | — | D | N | S | — | I | 0.07 | 0.08 | 0.08 | 931 |
| Phage-827 | — | N | — | W | — | D | W | E | — | D | — | A | — | N | 0.09 | 0.08 | 0.07 | 932 |
| Phage-828 | — | — | — | — | — | — | L | — | — | — | F | Y | — | F | 0.08 | 0.08 | 0.07 | 933 |
| Phage-829 | L | F | — | — | T | V | L | — | — | F | F | D | — | D | 0.07 | 0.08 | 0.07 | 934 |
| Phage-830 | F | D | — | — | — | — | L | — | — | — | — | S | — | A | 0.08 | 0.08 | 0.07 | 935 |
| Phage-831 | Y | — | — | — | — | — | V | E | — | N | — | Y | — | I | 0.07 | 0.08 | 0.08 | 936 |
| Phage-832 | D | — | — | — | — | — | L | — | D | — | T | I | — | H | 0.12 | 0.08 | 0.10 | 937 |
| Phage-833 | — | F | — | — | — | Q | W | A | — | A | N | A | — | F | 0.09 | 0.08 | 0.07 | 938 |
| Phage-834 | F | T | — | — | — | — | Y | — | — | — | I | T | — | P | 0.09 | 0.08 | 0.09 | 939 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Back-ground signal | Sp34. 185 scFv signal | Sp34. 185 scFv signal in Pre-sence Of CD3 | SEQ ID NO: |
|---|---|---|---|---|---|---|---|---|---|---|---|---|---|---|---|---|---|---|
| Phage-835 | L | N | — | — | — | V | N | — | — | — | S | V | — | I | 0.07 | 0.08 | 0.08 | 940 |
| Phage-836 | A | I | — | W | — | D | W | E | — | F | S | D | — | H | 0.07 | 0.08 | 0.07 | 941 |
| Phage-837 | Y | — | — | — | V | D | L | G | A | N | — | Y | — | Y | 0.10 | 0.08 | 0.09 | 942 |
| Phage-838 | H | — | — | — | — | — | V | E | — | D | Y | H | — | D | 0.07 | 0.08 | 0.07 | 943 |
| Phage-839 | N | D | — | — | S | L | Q | Y | D | I | P | T | — | V | 0.08 | 0.08 | 0.07 | 944 |
| Phage-840 | Y | V | — | R | — | Q | L | — | V | Y | H | Y | — | N | 0.15 | 0.08 | 0.07 | 945 |
| Phage-841 | H | D | — | — | — | D | G | — | — | — | I | I | — | S | 0.08 | 0.08 | 0.07 | 946 |
| Phage-842 | F | D | — | — | — | — | L | — | — | T | I | I | — | P | 0.08 | 0.08 | 0.08 | 947 |
| Phage-843 | — | D | — | — | S | D | R | G | — | N | A | A | — | H | 0.07 | 0.08 | 0.07 | 948 |
| Phage-844 | N | I | — | L | A | Q | — | N | — | D | P | T | — | N | 0.07 | 0.08 | 0.08 | 949 |
| Phage-845 | T | N | — | — | S | K | S | Q | V | — | D | H | — | I | 0.10 | 0.08 | 0.09 | 950 |
| Phage-846 | N | H | — | H | — | — | — | w |  | L | T | N | — | N | 0.09 | 0.07 | 0.07 | 951 |
| Phage-847 | L | L | — | H | — | — | G |  | L | Y | H | L | — | H | 0.09 | 0.07 | 0.08 | 952 |
| Phage-848 | T | N | — | D | S | K | L | E | G | D | D | N | — | F | 0.09 | 0.07 | 0.07 | 953 |
| Phage-849 | N | D | — | — | — | — | M | — | — | — | L | L | — | D | 0.08 | 0.07 | 0.07 | 954 |
| Phage-850 | F | H | — | — | — | — | V | — | — | — | I | N | — | N | 0.07 | 0.07 | 0.07 | 955 |
| Phage-851 | D | F | — | — | — | D | G | — | — | T | Y | V | — | S | 0.07 | 0.07 | 0.08 | 956 |
| Phage-852 | — | S | — | — | — | Q | — | — | — | N | N | T | — | N | 0.07 | 0.07 | 0.08 | 957 |
| Phage-853 | — | — | — | H | L | — | S | E | Q | F | D | I | — | I | 0.08 | 0.07 | 0.08 | 958 |

TABLE 20-continued

Clonal Phage Peptide Sequences from the Peptide-B OptimizationLibrary Panning (—) indicates same amino acid as in CD3 scFv Peptide-B corresponding position (e.g. Phage-1 position).

| Phage | Amino acid position sequence | | | | | | | | | | | | | | Phage binding ELISA | | | SEQ ID |
|---|---|---|---|---|---|---|---|---|---|---|---|---|---|---|---|---|---|---|
| | | | | | | | | | | | | | | | Back-ground | Sp34. 185 scFv | Sp34. 185 scFv signal in Pre-sence | |
| ID | 1 | 2 | 3 | 4 | 5 | 6 | 7 | 8 | 9 | 10 | 11 | 12 | 13 | 14 | signal | signal | Of CD3 | NO: |
| Phage-854 | D | D | — | — | — | — | w | E | F | V | F | F | — | D | 0.08 | 0.07 | 0.08 | 959 |
| Phage-855 | Y | N | — | E | Q | Q | Q | — | — | D | P | S | — | I | 0.07 | 0.07 | 0.07 | 960 |
| Phage-856 | N | T | — | — | T | — | Q | H | — | F | N | | — | L | 0.08 | 0.07 | 0.08 | 961 |
| Phage-857 | H | P | — | q | — | G | — | E | — | V | D | Y | — | V | 0.08 | 0.07 | 0.08 | 962 |
| Phage-858 | — | A | — | s | R | Q | L | G | — | D | A | Y | — | N | 0.07 | 0.07 | 0.07 | 963 |
| Phage-859 | D | I | — | — | A | Q | E | V | H | V | Y | T | — | P | 0.07 | 0.07 | 0.07 | 964 |
| Phage-860 | F | F | — | E | G | N | L | — | A | Y | L | L | — | L | 0.08 | 0.07 | 0.08 | 965 |
| Phage-861 | Y | — | — | — | — | D | G | E | — | N | I | V | — | D | 0.07 | 0.07 | 0.07 | 966 |

TABLE 21

Sequences of those peptides selected for synthesis (CD3 scFv Peptide-B Optimization)

| Peptide-ID | Sequence | SEQ ID NO: |
|---|---|---|
| Peptide-AA | DDCWPDWEFDFACA | 106 |
| Peptide-AB | YICGLDFPDFLYCD | 107 |
| Peptide-AC | FDCWPDWEEYFVCD | 108 |
| Peptide-AD | YICWPDWEEYFDCD | 109 |
| Peptide-AE | NICWPDWEDDYFCF | 110 |
| Peptide-AF | NFCWPDWEYIYPCI | 111 |
| Peptide-AG | VDCWPDWEEDFLCI | 112 |
| Peptide-AH | HACWPDWEEYFPCN | 113 |
| Peptide-AI | YDCGPDVDESYVCV | 114 |
| Peptide-AJ | IDCWPDWEDDTFCY | 115 |
| Peptide-AK | YLCGPDGDETLACY | 116 |
| Peptide-AL | VDCGPDGDESILCY | 117 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A polypeptide or polypeptide complex according to Formula I:

$A_2$-$A_1$-$L_1$-$P_1$-$H_1$ (Formula I)

wherein:

$A_1$ comprises a first antigen recognizing molecule that binds to an effector cell antigen, wherein $A_1$ comprises an anti-CD3 binding molecule comprising complementarity determining regions (CDRs): HC-CDR1, HC-CDR2, and HC-CDR3, wherein the HC-CDR1, the HC-CDR2, and the HC-CDR3 of $A_1$ comprise: HC-CDR1: SEQ ID NO: 1, HC-CDR2: SEQ ID NO: 2, and HC-CDR3: SEQ ID NO: 3; and $A_1$ comprises CDRs: LC-CDR1, LC-CDR2, and LC-CDR3, wherein the LC-CDR1, the LC-CDR2, and the LC-CDR3 of $A_1$ comprise LC-CDR1: SEQ ID NO: 4, LC-CDR2: SEQ ID NO:5, and LC-CDR3: SEQ ID NO: 6;

$P_1$ comprises a peptide that binds to $A_1$, wherein $P_1$ comprises an amino acid sequence according to $U_1$-$U_2$-C-$U_4$-P-$U_6$-$U_7$-$U_8$-$U_9$-$U_{10}$-$U_{11}$-$U_{12}$-C-$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S;

$L_1$ comprises a linking moiety that connects $A_1$ to $P_1$ and is a substrate for a tumor specific protease;

$H_1$ comprises a half-life extending molecule; and $A_2$ comprises a second antigen recognizing molecule that binds to prostate-specific membrane antigen (PSMA).

2. The polypeptide or polypeptide complex of claim 1, wherein $A_2$ comprises complementarity determining regions (CDRs): HC-CDR1, HC-CDR2, and HC-CDR3, wherein the HC-CDR1, the HC-CDR2, and the HC-CDR3 comprise: HC-CDR1: SEQ ID NO: 8, HC-CDR2: SEQ ID NO: 9, and HC-CDR3: SEQ ID NO: 10; and $A_2$ comprises CDRs: LC-CDR1, LC-CDR2, and LC-CDR3, wherein the LC-CDR1, the LC-CDR2, and the LC-CDR3 of $A_2$ comprise LC-CDR1: SEQ ID NO: 11, LC-CDR2: SEQ ID NO: 12, and LC-CDR3: SEQ ID NO: 13.

3. The polypeptide or polypeptide complex of claim 1, wherein the effector cell antigen comprises cluster of differentiation 3 (CD3).

4. The polypeptide or polypeptide complex of claim 1, wherein $A_1$ comprises an antibody format selected from single chain variable fragment and a Fab or Fab' fragment.

5. The polypeptide or polypeptide complex of claim 1, wherein $A_2$ comprises an antibody format selected from single chain variable fragment, a single domain antibody, and a Fab or Fab' fragment.

6. The polypeptide or polypeptide complex of claim 1, wherein $A_1$ comprises an antibody format of a single chain variable fragment (scFv), and $A_2$ comprises an antibody format of a Fab or Fab'.

7. The polypeptide or polypeptide complex of claim 1, wherein $P_1$ becomes unbound from $A_1$ when $L_1$ is cleaved by the tumor specific protease thereby exposing $A_1$ to the effector cell antigen.

8. The polypeptide or polypeptide complex of claim 1, wherein the tumor specific protease is selected from the group consisting of a matrix metalloprotease (MMP), serine protease, cysteine protease, threonine protease, and aspartic protease.

9. The polypeptide or polypeptide complex of claim 8, wherein the matrix metalloprotease comprises MMP2, MMP7, MMP9, MMP13, or MMP14.

10. The polypeptide or polypeptide complex of claim 8, wherein the serine protease comprises matriptase (MTSP1), urokinase, or hepsin.

11. The polypeptide or polypeptide complex of claim 1, wherein $L_1$ comprises a urokinase cleavable amino acid sequence, a matriptase cleavable amino acid sequence, a matrix metalloprotease cleavable amino acid sequence, or a legumain cleavable amino acid sequence.

12. The polypeptide or polypeptide complex of claim 1, wherein $L_1$ comprises an amino acid sequence according to SEQ ID NO: 23.

13. The polypeptide or polypeptide complex of claim 1, wherein $L_1$ comprises an amino acid sequence according to any one of SEQ ID NOs: 20-49.

14. The polypeptide or polypeptide complex of claim 1, wherein $L_1$ comprises an amino acid sequence of Linker 25 (ISSGLLSGRSDAG) (SEQ ID NO: 45), Linker 26 (AAGLLAPPGGLSGRSDAG) (SEQ ID NO: 46), Linker 27 (SPLGLSGRSDAG) (SEQ ID NO: 47), or Linker 28 (LSGRSDAGSPLGLAG) (SEQ ID NO: 48), or an amino acid sequence that has 1, 2, or 3 amino acid substitutions, additions, or deletions relative to the amino acid sequences of Linker 25, Linker 26, Linker 27, or Linker 28.

15. The polypeptide or polypeptide complex of claim 1, wherein $H_1$ comprises serum albumin.

16. The polypeptide or polypeptide complex of claim 15, wherein the albumin is human serum albumin.

17. The polypeptide or polypeptide complex of claim 1, wherein $H_1$ comprises a single domain antibody.

18. The polypeptide or polypeptide complex of claim 1, wherein $H_1$ comprises complementarity determining regions (CDRs): HC-CDR1, HC-CDR2, and HC-CDR3, wherein the HC-CDR1, the HC-CDR2, and the HC-CDR3 of $H_1$ comprise: HC-CDR1: SEQ ID NO: 54, HC-CDR2: SEQ ID NO: 55, and HC-CDR3: SEQ ID NO: 56.

19. The polypeptide or polypeptide complex of claim 1, wherein $H_1$ comprises complementarity determining regions (CDRs): HC-CDR1, HC-CDR2, and HC-CDR3, wherein the HC-CDR1, the HC-CDR2, and the HC-CDR3 of $H_1$ comprise: HC-CDR1: SEQ ID NO: 58, HC-CDR2: SEQ ID NO: 59, and HC-CDR3: SEQ ID NO: 60.

20. The polypeptide or polypeptide complex of claim 1, wherein $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P.

21. The polypeptide or polypeptide complex of claim 20, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; $U_{14}$ is selected from D, Y, M, and N.

22. The polypeptide or polypeptide complex of claim 1, wherein $P_1$ comprises the amino acid sequences according to any one of SEQ ID NOs: 93-95 and 102-105.

23. The polypeptide or polypeptide complex of claim 1, wherein $P_1$ comprises the amino acid sequences according to any one of SEQ ID NOs: 106 and 108-117.

24. The polypeptide or polypeptide complex of claim 1, wherein $P_1$ comprises the amino acid sequence according to SEQ ID NO: 19.

25. The polypeptide or polypeptide complex of claim 1, wherein $P_1$ comprises the amino acid sequence according to SEQ ID NO: 116.

26. The polypeptide or polypeptide complex of claim 1, wherein the polypeptide or polypeptide complex comprises the amino acid sequences according to SEQ ID NO: 72 and SEQ ID NO: 73.

* * * * *